US012760099B2

(12) United States Patent
Jarjour et al.

(10) Patent No.: US 12,760,099 B2
(45) Date of Patent: Oct. 13, 2026

(54) MULTIPARTITE SIGNALING PROTEINS AND USES THEREOF

(71) Applicant: Regeneron Pharmaceuticals, Inc., Tarrytown, NY (US)

(72) Inventors: Jordan Jarjour, Seattle, WA (US); Alexander Astrakhan, Seattle, WA (US); Michael Certo, Medford, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1008 days.

(21) Appl. No.: 18/054,223

(22) Filed: Nov. 10, 2022

(65) Prior Publication Data

US 2023/0287111 A1 Sep. 14, 2023

Related U.S. Application Data

(60) Division of application No. 16/573,254, filed on Sep. 17, 2019, now Pat. No. 11,530,265, which is a continuation of application No. 16/219,640, filed on Dec. 13, 2018, now Pat. No. 10,457,731, which is a continuation of application No. 14/908,734, filed as application No. PCT/US2014/047852 on Jul. 23, 2014, now Pat. No. 10,196,444.

(60) Provisional application No. 61/934,092, filed on Jan. 31, 2014, provisional application No. 61/859,697, filed on Jul. 29, 2013.

(51) Int. Cl.

| | |
|---|---|
| ***C07K 16/28*** | (2006.01) |
| ***A61K 39/00*** | (2006.01) |
| ***A61K 40/11*** | (2025.01) |
| ***A61K 40/31*** | (2025.01) |
| ***A61K 40/42*** | (2025.01) |
| ***A61K 45/06*** | (2006.01) |
| ***C07K 14/705*** | (2006.01) |
| ***C07K 16/40*** | (2006.01) |
| ***C12N 9/06*** | (2006.01) |
| ***C12N 9/12*** | (2006.01) |
| ***C12N 9/16*** | (2006.01) |
| ***C12N 9/90*** | (2006.01) |
| ***C12N 15/85*** | (2006.01) |
| *C07H 21/04* | (2006.01) |

(52) U.S. Cl.

CPC ...... *C07K 16/2803* (2013.01); *A61K 39/0005* (2013.01); *A61K 40/11* (2025.01); *A61K 40/31* (2025.01); *A61K 40/4211* (2025.01); *A61K 40/4217* (2025.01); *A61K 40/4221* (2025.01); *A61K 45/06* (2013.01); *C07K 14/70503* (2013.01); *C07K 14/7051* (2013.01); *C07K 14/70514* (2013.01); *C07K 14/70517* (2013.01); *C07K 14/70521* (2013.01); *C07K 14/70535* (2013.01); *C07K 14/7056* (2013.01); *C07K 14/70578* (2013.01); *C07K 14/70596* (2013.01); *C07K 16/2896* (2013.01); *C07K 16/40* (2013.01); *C12N 9/003* (2013.01); *C12N 9/12* (2013.01); *C12N 9/16* (2013.01); *C12N 9/90* (2013.01); *C12N 15/85* (2013.01); *C12Y 207/11001* (2013.01); *C12Y 502/01008* (2013.01); *C07H 21/04* (2013.01); *C07K 2317/622* (2013.01); *C07K 2319/00* (2013.01); *C07K 2319/03* (2013.01); *C07K 2319/70* (2013.01); *C12N 2510/00* (2013.01)

(58) Field of Classification Search

CPC . C07K 16/2803; C07K 14/7051; A61K 40/31
See application file for complete search history.

(56) References Cited

U.S. PATENT DOCUMENTS

| | | | |
|---|---|---|---|
| 5,871,753 | A | 2/1999 | Crabtree et al. |
| 5,910,573 | A | 6/1999 | Pluckthun et al. |
| 6,291,158 | B1 | 9/2001 | Winter et al. |
| 6,291,161 | B1 | 9/2001 | Lerner et al. |
| 6,423,498 | B1 | 7/2002 | Markland et al. |
| 6,649,595 | B2 | 11/2003 | Clackson et al. |
| 6,972,193 | B1 | 12/2005 | Crabtree et al. |
| 9,587,020 | B2 | 3/2017 | Wu et al. |
| 10,196,444 | B2 | 2/2019 | Jarjour et al. |
| 10,287,354 | B2 | 5/2019 | Brogdon et al. |
| 10,428,142 | B2 | 10/2019 | Clackson et al. |
| 10,457,731 | B2 | 10/2019 | Jarjour et al. |
| 11,530,265 | B2 | 12/2022 | Jarjour et al. |
| 2007/0065431 | A1 | 3/2007 | Coia et al. |
| 2011/0286980 | A1 | 11/2011 | Brenner |
| 2012/0100160 | A1 | 4/2012 | Lucas et al. |
| 2013/0287752 | A1 | 10/2013 | Davila et al. |

(Continued)

FOREIGN PATENT DOCUMENTS

| | | |
|---|---|---|
| JP | 2002-503667 A | 2/2002 |
| JP | 2002-508971 A | 3/2002 |

(Continued)

OTHER PUBLICATIONS

Abate-Daga et al., CAR models: next-generation CAR modifications for enhanced T-cell function. Mol Ther Oncolytics. May 18, 2016;3:16014, 7 pages.

(Continued)

*Primary Examiner* — Thane Underdahl
(74) *Attorney, Agent, or Firm* — McCarter & English, LLP; Marcie B. Clarke; Dylan M. Blumenthal

(57) ABSTRACT

The present disclosure relates to compositions and methods for using cells having chemically-induced fusion protein complexes to spatially and temporally control immune cell signal initiation and downstream responses for treating disease.

28 Claims, 27 Drawing Sheets

Specification includes a Sequence Listing.

(56) References Cited

U.S. PATENT DOCUMENTS

2015/0266973 A1 9/2015 Jarjour et al.
2016/0017302 A1 1/2016 Dotti et al.
2016/0185862 A1 6/2016 Wu et al.
2020/0071399 A1 3/2020 Jarjour et al.

FOREIGN PATENT DOCUMENTS

WO WO-1999/036553 A2 7/1999
WO WO-1999/041258 A1 8/1999
WO WO-2006/072620 A1 7/2006
WO WO-2006/095164 A1 9/2006
WO WO-2007/098934 A1 9/2007
WO WO-2012/082841 A2 6/2012
WO WO-2014/127261 A1 8/2014
WO WO-2015/017214 A1 2/2015
WO WO-2015/150771 A1 10/2015
WO WO-2016/014553 A1 1/2016

OTHER PUBLICATIONS

Alder et al., Antibody responses of variable lymphocyte receptors in the lamprey. Nat Immunol. Mar. 2008;9(3):319-27.
Banaszynski et al., Characterization of the FKBP.Rapamycin.FRB Ternary Complex. J Am Chem Soc. 2005;127(13):4715-4721.
Baral et al., Experimental therapy of African trypanosomiasis with a nanobody-conjugated human trypanolytic factor. Nat Med. May 2006;12(5):580-4.
Barthelemy et al., Comprehensive analysis of the factors contributing to the stability and solubility of autonomous human VH domains. J Biol Chem. Feb. 8, 2008;283(6):3639-3654.
Bayle et al., Rapamycin analogs with differential binding specificity permit orthogonal control of protein activity. Chem Biol. Jan. 2006;13(1):99-107.
Beavil et al., Alpha-helical coiled-coil stalks in the low-affinity receptor for IgE (Fc epsilon RII/CD23) and related C-type lectins. Proc Natl Acad Sci U S A. Jan. 15, 1992;89(2):753-7.
Belshaw et al., Controlling protein association and subcellular localization with a synthetic ligand that induces heterodimerization of proteins. Proc Natl Acad Sci U S A. May 14, 1996;93(10):4604-7.
Beste et al., Small antibody-like proteins with prescribed ligand specificities derived from the lipocalin fold. Proc Natl Acad Sci U S A. Mar. 2, 1999;96(5):1898-903.
Binz et al., Designing repeat proteins: well-expressed, soluble and stable proteins from combinatorial libraries of consensus ankyrin repeat proteins. J Mol Biol. Sep. 12, 2003;332(2):489-503.
Binz et al., Engineering novel binding proteins from nonimmunoglobulin domains. Nat Biotechnol. Oct. 2005;23(10):1257-68.
Brentjens et al., CD19-targeted T cells rapidly induce molecular remissions in adults with chemotherapy-refractory acute lymphoblastic leukemia. Sci Transl Med. Mar. 20, 2013;5(177):177ra38.
Brentjens et al., Safety and persistence of adoptively transferred autologous CD19-targeted T cells in patients with relapsed or chemotherapy refractory B-cell leukemias. Blood. Nov. 3, 2011;118(18):4817-28.
Brown et al., A mammalian protein targeted by G1-arresting rapamycin-receptor complex. Nature. Jun. 30, 1994;369(6483):756-8.
Capon et al. Designing CD4 immunoadhesins for AIDS therapy. Nature. Feb. 9, 1989;337(6207):525-31.
Carpenito et al., Control of large, established tumor xenografts with genetically retargeted human T cells containing CD28 and CD137 domains. Proc Natl Acad Sci U S A. Mar. 3, 2009;106(9):3360-5.
Challita et al., Multiple modifications in cis elements of the long terminal repeat of retroviral vectors lead to increased expression and decreased DNA methylation in embryonic carcinoma cells. J Virol. Feb. 1995;69(2):748-55.
Cortez-Retamozo et al., Efficient cancer therapy with a nanobody-based conjugate. Cancer Res. Apr. 15, 2004;64(8):2853-7.
Craik et al., Plant cyclotides: A unique family of cyclic and knotted proteins that defines the cyclic cystine knot structural motif. J Mol Biol. Dec. 17, 1999;294(5):1327-36.
Curran et al., Chimeric antigen receptors for T cell immunotherapy: current understanding and future directions. J Gene Med. Jun. 2012;14(6):405-15.
Donnelly et al., The 'cleavage' activities of foot-and-mouth disease virus 2A site-directed mutants and naturally occurring '2A-like' sequences. J Gen Virol. May 2001;82(Pt 5):1027-1041.
Dotti et al., Design and development of therapies using chimeric antigen receptor-expressing T cells. Immunol Rev. Jan. 2014;257(1):107-26.
Duong et al., Enhancing the specificity of T-cell cultures for adoptive immunotherapy of cancer. Immunotherapy. Jan. 2011;3(1):33-48.
Fegan et al., Chemically controlled protein assembly: techniques and applications. Chem Rev. Jun. 9, 2010;110(6):3315-36.
Ghahroudi et al., Selection and identification of single domain antibody fragments from camel heavy-chain antibodies. FEBS Lett. Sep. 15, 1997;414(3):521-6.
Grunberg et al., Building blocks for protein interaction devices. Nucleic Acids Res. May 2010;38(8):2645-62.
Grupp et al., Chimeric antigen receptor-modified T cells for acute lymphoid leukemia. N Engl J Med. Apr. 18, 2013;368(16):1509-1518.
Hackel et al., Picomolar affinity fibronectin domains engineered utilizing loop length diversity, recursive mutagenesis, and loop shuffling. J Mol Biol. Sep. 19, 2008;381(5):1238-52.
Hamers-Casterman et al., Naturally occurring antibodies devoid of light chains. Nature. Jun. 3, 1993;363(6428):446-8.
Herrin et al., Structure and specificity of lamprey monoclonal antibodies. Proc Natl Acad Sci U S A. Feb. 12, 2008;105(6):2040-5.
Hoet et al., Generation of high-affinity human antibodies by combining donor-derived and synthetic complementarity-determining-region diversity. Nat Biotechnol. Mar. 2005;23(3):344-8.
Hsu et al., Primary human T lymphocytes engineered with a codon-optimized IL-15 gene resist cytokine withdrawal-induced apoptosis and persist long-term in the absence of exogenous cytokine. J Immunol. Dec. 1, 2005;175(11):7226-34.
Hu et al., Minibody: A novel engineered anti-carcinoembryonic antigen antibody fragment (single-chain Fv-CH3) which exhibits rapid, high-level targeting of xenografts. Cancer Res. Jul. 1, 1996;56(13):3055-61.
Huang et al., Scorpion-toxin mimics of CD4 in complex with human immunodeficiency virus gp120 crystal structures, molecular mimicry, and neutralization breadth. Structure. May 2005;13(5):755-68.
Irion et al., Identification and targeting of the ROSA26 locus in human embryonic stem cells. Nat Biotechnol. Dec. 2007;25(12):1477-82.
Janeway et al., Immunobiology: The Immune System in Health and Disease, 4th Edition. Current Biology Publications. pp. 148, 149 and 172, (1999).
Jespers et al., Aggregation-resistant domain antibodies selected on phage by heat denaturation. Nat Biotechnol. Sep. 2004;22(9):1161-5.
June et al., T-cell therapy at the threshold. Nat Biotechnol. Jul. 10, 2012;30(7):611-4.
Kalos et al., T cells with chimeric antigen receptors have potent antitumor effects and can establish memory in patients with advanced leukemia. Sci Transl Med. Aug. 10, 2011;3(95):95ra73.
Kay. Structure-function relationships in the FK506-binding protein (FKBP) family of peptidylprolyl cis-trans isomerases. Biochem J. Mar. 1, 1996;314 ( Pt 2)(Pt 2):361-85.
Klemm et al., Dimerization as a regulatory mechanism in signal transduction. Annu Rev Immunol. 1998;16:569-92.
Kochenderfer et al., B-cell depletion and remissions of malignancy along with cytokine-associated toxicity in a clinical trial of anti-CD19 chimeric-antigen-receptor-transduced T cells. Blood. Mar. 22, 2012;119(12):2709-20.
Kochenderfer et al., Treating B-cell cancer with T cells expressing anti-CD19 chimeric antigen receptors. Nat Rev Clin Oncol. May 2013;10(5):267-76.

(56) References Cited

OTHER PUBLICATIONS

Kowolik et al., D28 costimulation provided through a CD19-specific chimeric antigen receptor enhances in vivo persistence and antitumor efficacy of adoptively transferred T cells. Cancer Res. Nov. 15, 2006;66(22):10995-1004.
Lee et al., Design of a binding scaffold based on variable lymphocyte receptors of jawless vertebrates by module engineering. Proc Natl Acad Sci U S A. Feb. 28, 2012;109(9):3299-304.
Leung et al., Small Molecule-Regulated Antigen Recognition System for Inducible T Cell Targeting of CAncer Cells. Mol Ther. 2016;24:S110, Abstract No. 277.
Main et al., Design of stable alpha-helical arrays from an idealized TPR motif. Structure. May 2003;11(5):497-508.
Manzke et al., CD3X anti-nitrophenyl bispecific diabodies: universal immunotherapeutic tools for retargeting T cells to tumors. Int J Cancer. Aug. 27, 1999;82(5):700-8.
Martin et al., Rational design of a CD4 mimic that inhibits HIV-1 entry and exposes cryptic neutralization epitopes. Nat Biotechnol. Jan. 2003;21(1):71-6.
Milone et al., Chimeric receptors containing CD137 signal transduction domains mediate enhanced survival of T cells and increased antileukemic efficacy in vivo. Mol Ther. Aug. 2009;17(8):1453-64.
Nguyen et al., Heavy-chain antibodies in Camelidae; a case of evolutionary innovation. Immunogenetics. Apr. 2002;54(1):39-47.
Nguyen et al., The specific variable domain of camel heavy-chain antibodies is encoded in the germline. J Mol Biol. Jan. 23, 1998;275(3):413-8.
Nord et al., A combinatorial library of an alpha-helical bacterial receptor domain. Protein Eng. Jun. 1995;8(6):601-8.
Nord et al., Binding proteins selected from combinatorial libraries of an alpha-helical bacterial receptor domain. Nat Biotechnol. Aug. 1997;15(8):772-7.
Nord et al., Recombinant human factor VIII-specific affinity ligands selected from phage-displayed combinatorial libraries of protein A. Eur J Biochem. Aug. 2001;268(15):4269-77.
Parker et al., Antibody mimics based on human fibronectin type three domain engineered for thermostability and high-affinity binding to vascular endothelial growth factor receptor two. Protein Eng Des Sel. Sep. 2005;18(9):435-44.
Pule et al., A chimeric T cell antigen receptor that augments cytokine release and supports clonal expansion of primary human T cells. Mol Ther. Nov. 2005;12(5):933-41.
Quintarelli et al., Co-expression of cytokine and suicide genes to enhance the activity and safety of tumor-specific cytotoxic T lymphocytes. Blood. Oct. 15, 2007;110(8):2793-802.
Restifo et al., Adoptive immunotherapy for cancer: harnessing the T cell response. Nat Rev Immunol. Mar. 22, 2012;12(4):269-81.
Richards et al., Engineered fibronectin type III domain with a RGDWXE sequence binds with enhanced affinity and specificity to human alphavbeta3 integrin. J Mol Biol. Mar. 7, 2003;326(5):1475-88.
Roux et al., Structural analysis of the nurse shark (new) antigen receptor (NAR): molecular convergence of NAR and unusual mammalian immunoglobulins. Proc Natl Acad Sci U S A. Sep. 29, 1998;95(20):11804-9.
Ryan et al., Virus-encoded proteinases of the picornavirus super-group. J Gen Virol. Apr. 1997;78 ( Pt 4):699-723.
Sato et al., Genes encoding putative natural killer cell C-type lectin receptors in teleostean fishes. Proc Natl Acad Sci U S A. Jun. 24, 2003;100(13):7779-84.
Schlessinger. Cell signaling by receptor tyrosine kinases. Cell. Oct. 13, 2000;103(2):211-25.
Schonfeld et al., An engineered lipocalin specific for CTLA-4 reveals a combining site with structural and conformational features similar to antibodies. Proc Natl Acad Sci U S A. May 19, 2009;106(20):8198-203.
Skerra, Alternative binding proteins: anticalins—harnessing the structural plasticity of the lipocalin ligand pocket to engineer novel binding activities. FEBS J. Jun. 2008;275(11):2677-83.
Spencer et al., Controlling signal transduction with synthetic ligands. Science. Nov. 12, 1993;262(5136):1019-24.
Standaert et al., Molecular cloning and overexpression of the human FK506-binding protein FKBP. Nature. Aug. 16, 1990;346(6285):671-4.
Stephan et al., T cell-encoded CD80 and 4-1BBL induce auto- and transcostimulation, resulting in potent tumor rejection. Nat Med. Dec. 2007;13(12):1440-9.
Stumpp et al., Designing repeat proteins: modular leucine-rich repeat protein libraries based on the mammalian ribonuclease inhibitor family. J Mol Biol. Sep. 12, 2003;332(2):471-87.
Tal et al., An NCR1-based chimeric receptor endows T-cells with multiple anti-tumor specificities. Oncotarget. Nov. 15, 2014;5(21):10949-58.
Till et al., CD20-specific adoptive immunotherapy for lymphoma using a chimeric antigen receptor with both CD28 and 4-1BB domains: pilot clinical trial results. Blood. Apr. 26, 2012;119(17):3940-50.
Varadamsetty et al., Designed Armadillo repeat proteins: library generation, characterization and selection of peptide binders with high specificity. J Mol Biol. Nov. 23, 2012;424(1-2):68-87.
Vincke et al., General strategy to humanize a camelid single-domain antibody and identification of a universal humanized nanobody scaffold. J Biol Chem. Jan. 30, 2009;284(5):3273-3284.
Vita et al., Scorpion toxins as natural scaffolds for protein engineering. Proc Natl Acad Sci U S A. Jul. 3, 1995;92(14):6404-8.
Weisel et al., A model for fibrinogen: domains and sequence. Science. Dec. 20, 1985;230(4732):1388-91.
White et al., Comparison of the glycosyl-phosphatidylinositol cleavage/attachment site between mammalian cells and parasitic protozoa. J Cell Sci. Feb. 2000;113 ( Pt 4):721-7.
Wilkie et al., Dual targeting of ErbB2 and MUC1 in breast cancer using chimeric antigen receptors engineered to provide complementary signaling. J Clin Immunol. Oct. 2012;32(5):1059-70.
Zelensky et al., The C-type lectin-like domain superfamily. FEBS J. Dec. 2005;272(24):6179-217.
Extended European Search Report for Application No. 21162954.8, dated Nov. 18, 2021, 8 pages.
Extended European Search Report for European Application No. 14832043.5, dated Feb. 10, 2017, 11 pages.
International Preliminary Report on Patentability for Application No. PCT/US2014/047852, dated Feb. 2, 2016, 9 pages.
International Search Report and Written Opinion for Application No. PCT/US2014/047852, dated Nov. 21, 2014, 11 pages.

SEQUENCE LISTING

```
Sequence total quantity: 75
SEQ ID NO: 1            moltype = AA  length = 363
FEATURE                 Location/Qualifiers
REGION                  1..363
                        note = scFvCD19-DmrA protein
source                  1..363
                        mol_type = protein
                        organism = synthetic construct
SEQUENCE: 1
MGSDIQMTQT TSSLSASLGD RVTISCRASQ DISKYLNWYQ QKPDGTVKLL IYHTSRLHSG  60
VPSRFSGSGS GTDYSLTISN LEQEDIATYF CQQGNTLPYT FGGGTKLEIT GSTSGSGKPG  120
SGEGSTKGEV KLQESGPGLV APSQSLSVTC TVSGVSLPDY GVSWIRQPPR KGLEWLGVIW  180
GSETTYYNSA LKSRLTIIKD NSKSQVFLKM NSLQTDDTAI YYCAKHYYYG GSYAMDYWGQ  240
GTSVTVSSAS GGGGSGVQVE TISPGDGRTF PKRGQTCVVH YTGMLEDGKK FDSSRDRNKP  300
FKFMLGKQEV IRGWEEGVAQ MSVGQRAKLT ISPDYAYGAT GHPGIIPPHA TLVFDVELLK  360
LEG                                                                363

SEQ ID NO: 2            moltype = RNA  length = 1149
FEATURE                 Location/Qualifiers
misc_feature            1..1149
                        note = SS-scFvCD19-DmrA mRNA
source                  1..1149
                        mol_type = other RNA
                        organism = synthetic construct
SEQUENCE: 2
atgcccctgg gcctgctgtg gctgggcctg gccctgctgg gcgccctgca cgcccaggcc  60
ggatccgata tccagatgac ccagaccacc agcagcctga gcgccagcct gggcgataga  120
gtgaccatca gctgcagagc cagccaggac atcagcaagt acctgaactg gtatcagcag  180
aaacccgacg gcaccgtgaa gctgctgatc taccacacca gcagactgca cagcggcgtg  240
cccagcagat tttctggcag cggctccggc accgactaca gcctgaccat ctccaacctg  300
gaacaggaag atatcgctac ctacttctgt cagcaaggca acaccctgcc ctacaccttc  360
ggcggaggca ccaagctgga aatcaccggc agcacaagcg gcagcggcaa gcctggatct  420
ggcgagggaa gcaccaaggg cgaagtgaaa ctgcaggaaa gcggccctgg actggtggcc  480
ccaagccagt ctctgagcgt gacctgtacc gtgtccggcg tgtccctgcc tgactatggc  540
gtgtcctgga tcagacagcc ccccagaaag ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tactgcgcca agcactacta ctacggcggc agctacgcca tggactactg gggccagggc  780
acaagcgtga ccgtgtccag cgctagcggc ggaggtggga gcggagtgca ggtggaaacc  840
atctccccag gagacgggcg caccttcccc aagcgcggcc agacctgcgt ggtgcactac  900
accgggatgc ttgaagatgg aaagaaattt gattcctccc gggacagaaa caagcccttt  960
aagtttatgc taggcaagca ggaggtgatc cgaggctggg aagaaggggt tgcccagatg  1020
agtgtgggtc agagagccaa actgactata tctccagatt atgcctatgg tgccactggg  1080
cacccaggca tcatcccacc acatgccact ctcgtcttcg atgtggagct tctaaaactg  1140
gaaggctga                                                          1149

SEQ ID NO: 3            moltype = DNA  length = 1149
FEATURE                 Location/Qualifiers
misc_feature            1..1149
                        note = SS-scFvCD19-DmrA DNA
source                  1..1149
                        mol_type = other DNA
                        organism = synthetic construct
SEQUENCE: 3
atgcccctgg gcctgctgtg gctgggcctg gccctgctgg gcgccctgca cgcccaggcc  60
ggatccgata tccagatgac ccagaccacc agcagcctga gcgccagcct gggcgataga  120
gtgaccatca gctgcagagc cagccaggac atcagcaagt acctgaactg gtatcagcag  180
```

-continued

```
aaacccgacg gcaccgtgaa gctgctgatc taccacacca gcagactgca cagcggcgtg  240
cccagcagat tttctggcag cggctccggc accgactaca gcctgaccat ctccaacctg  300
gaacaggaag atatcgctac ctacttctgt cagcaaggca acaccctgcc ctacaccttc  360
ggcggaggca ccaagctgga aatcaccggc agcacaagcg gcagcggcaa gcctggatct  420
ggcgagggaa gcaccaaggg cgaagtgaaa ctgcaggaaa gcggccctgg actggtggcc  480
ccaagccagt ctctgagcgt gacctgtacc gtgtccggcg tgtccctgcc tgactatggc  540
gtgtcctgga tcagacagcc ccccagaaag ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tactgcgcca agcactacta ctacggcggc agctacgcca tggactactg gggccagggc  780
acaagcgtga ccgtgtccag cgctagcggc ggaggtggga gcggagtgca ggtggaaacc  840
atctccccag gagacgggcg caccttcccc aagcgcggcc agacctgcgt ggtgcactac  900
accgggatgc ttgaagatgg aaagaaattt gattcctccc gggacagaaa caagcccttt  960
aagtttatgc taggcaagca ggaggtgatc cgaggctggg aagaaggggt tgcccagatg  1020
agtgtgggtc agagagccaa actgactata tctccagatt atgcctatgg tgccactggg  1080
cacccaggca tcatcccacc acatgccact ctcgtcttcg atgtggagct tctaaaactg  1140
gaaggctga                                                          1149

SEQ ID NO: 4            moltype = AA  length = 363
FEATURE                 Location/Qualifiers
REGION                  1..363
                        note = scFvCD19-DmrB protein
source                  1..363
                        mol_type = protein
                        organism = synthetic construct
SEQUENCE: 4
MGSDIQMTQT TSSLSASLGD RVTISCRASQ DISKYLNWYQ QKPDGTVKLL IYHTSRLHSG  60
VPSRFSGSGS GTDYSLTISN LEQEDIATYF CQQGNTLPYT FGGGTKLEIT GSTSGSGKPG  120
SGEGSTKGEV KLQESGPGLV APSQSLSVTC TVSGVSLPDY GVSWIRQPPR KGLEWLGVIW  180
GSETTYYNSA LKSRLTIIKD NSKSQVFLKM NSLQTDDTAI YYCAKHYYYG GSYAMDYWGQ  240
GTSVTVSSAS GGGGSGVQVE TISPGDGRTF PKRGQTCVVH YTGMLEDGKK VDSSRDRNKP  300
FKFMLGKQEV IRGWEEGVAQ MSVGQRAKLT ISPDYAYGAT GHPGIIPPHA TLVFDVELLK  360
LEG                                                                363

SEQ ID NO: 5            moltype = RNA  length = 1149
FEATURE                 Location/Qualifiers
misc_feature            1..1149
                        note = SS-scFvCD19-DmrB mRNA
source                  1..1149
                        mol_type = other RNA
                        organism = synthetic construct
SEQUENCE: 5
atgcccctgg gcctgctgtg gctgggcctg gccctgctgg gcgccctgca cgcccaggcc  60
ggatccgata tccagatgac ccagaccacc agcagcctga gcgccagcct gggcgataga  120
gtgaccatca gctgcagagc cagccaggac atcagcaagt acctgaactg gtatcagcag  180
aaacccgacg gcaccgtgaa gctgctgatc taccacacca gcagactgca cagcggcgtg  240
cccagcagat tttctggcag cggctccggc accgactaca gcctgaccat ctccaacctg  300
gaacaggaag atatcgctac ctacttctgt cagcaaggca acaccctgcc ctacaccttc  360
ggcggaggca ccaagctgga aatcaccggc agcacaagcg gcagcggcaa gcctggatct  420
ggcgagggaa gcaccaaggg cgaagtgaaa ctgcaggaaa gcggccctgg actggtggcc  480
ccaagccagt ctctgagcgt gacctgtacc gtgtccggcg tgtccctgcc tgactatggc  540
gtgtcctgga tcagacagcc ccccagaaag ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tactgcgcca agcactacta ctacggcggc agctacgcca tggactactg gggccagggc  780
acaagcgtga ccgtgtccag cgctagcggc ggaggtggga gcggagtgca ggtggaaacc  840
atctccccag gagacgggcg caccttcccc aagcgcggcc agacctgcgt ggtgcactac  900
accgggatgc ttgaagatgg aaagaaagtt gattcctccc gggacagaaa caagcccttt  960
aagtttatgc taggcaagca ggaggtgatc cgaggctggg aagaaggggt tgcccagatg  1020
agtgtgggtc agagagccaa actgactata tctccagatt atgcctatgg tgccactggg  1080
cacccaggca tcatcccacc acatgccact ctcgtcttcg atgtggagct tctaaaactg  1140
gaaggctga                                                          1149

SEQ ID NO: 6            moltype = DNA  length = 1149
FEATURE                 Location/Qualifiers
misc_feature            1..1149
                        note = SS-scFvCD19-DmrB DNA
source                  1..1149
                        mol_type = other DNA
                        organism = synthetic construct
SEQUENCE: 6
atgcccctgg gcctgctgtg gctgggcctg gccctgctgg gcgccctgca cgcccaggcc  60
ggatccgata tccagatgac ccagaccacc agcagcctga gcgccagcct gggcgataga  120
gtgaccatca gctgcagagc cagccaggac atcagcaagt acctgaactg gtatcagcag  180
aaacccgacg gcaccgtgaa gctgctgatc taccacacca gcagactgca cagcggcgtg  240
cccagcagat tttctggcag cggctccggc accgactaca gcctgaccat ctccaacctg  300
gaacaggaag atatcgctac ctacttctgt cagcaaggca acaccctgcc ctacaccttc  360
ggcggaggca ccaagctgga aatcaccggc agcacaagcg gcagcggcaa gcctggatct  420
ggcgagggaa gcaccaaggg cgaagtgaaa ctgcaggaaa gcggccctgg actggtggcc  480
```

```
ccaagccagt ctctgagcgt gacctgtacc gtgtccggcg tgtccctgcc tgactatggc  540
gtgtcctgga tcagacagcc ccccagaaag ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tactgcgcca agcactacta ctacggcggc agctacgcca tggactactg gggccagggc  780
acaagcgtga ccgtgtccag cgctagcggc ggaggtggga gcggagtgca ggtggaaacc  840
atctccccag gagacgggcg caccttcccc aagcgcggcc agacctgcgt ggtgcactac  900
accgggatgc ttgaagatgg aaagaaagtt gattcctccc gggacagaaa caagcccttt  960
aagtttatgc taggcaagca ggaggtgatc cgaggctggg aagaaggggt tgcccagatg  1020
agtgtgggtc agagagccaa actgactata tctccagatt atgcctatgg tgccactggg  1080
cacccaggca tcatcccacc acatgccact ctcgtcttcg atgtggagct tctaaaactg  1140
gaaggctga                                                         1149
```

```
SEQ ID NO: 7           moltype = AA  length = 349
FEATURE                Location/Qualifiers
REGION                 1..349
                       note = scFvCD19-DmrC protein
source                 1..349
                       mol_type = protein
                       organism = synthetic construct
SEQUENCE: 7
MGSDIQMTQT TSSLSASLGD RVTISCRASQ DISKYLNWYQ QKPDGTVKLL IYHTSRLHSG  60
VPSRFSGSGS GTDYSLTISN LEQEDIATYF CQQGNTLPYT FGGGTKLEIT GSTSGSGKPG  120
SGEGSTKGEV KLQESGPGLV APSQSLSVTC TVSGVSLPDY GVSWIRQPPR KGLEWLGVIW  180
GSETTYYNSA LKSRLTIIKD NSKSQVFLKM NSLQTDDTAI YYCAKHYYYG GSYAMDYWGQ  240
GTSVTVSSAS GGGGSILWHE MWHEGLEEAS RLYFGERNVK GMFEVLEPLH AMMERGPQTL  300
KETSFNQAYG RDLMEAQEWC RKYMKSGNVK DLLQAWDLYY HVFRRISKG              349
```

```
SEQ ID NO: 8           moltype = RNA  length = 1107
FEATURE                Location/Qualifiers
misc_feature           1..1107
                       note = SS-scFvCD19-DmrC mRNA
source                 1..1107
                       mol_type = other RNA
                       organism = synthetic construct
SEQUENCE: 8
atgcccctgg gcctgctgtg gctgggcctg gccctgctgg gcgccctgca cgcccaggcc  60
ggatccgata tccagatgac ccagaccacc agcagcctga gcgccagcct gggcgataga  120
gtgaccatca gctgcagagc cagccaggac atcagcaagt acctgaactg gtatcagcag  180
aaacccgacg gcaccgtgaa gctgctgatc taccacacca gcagactgca cagcggcgtg  240
cccagcagat ttctggcag cggctccggc accgactaca gcctgaccat ctccaacctg  300
gaacaggaag atatcgctac ctacttctgt cagcaaggca acaccctgcc ctacaccttc  360
ggcggaggca ccaagctgga aatcaccggc agcacaagcg gcagcggcaa gcctggatct  420
ggcgagggaa gcaccaaggg cgaagtgaaa ctgcaggaaa gcggccctgg actggtggcc  480
ccaagccagt ctctgagcgt gacctgtacc gtgtccggcg tgtccctgcc tgactatggc  540
gtgtcctgga tcagacagcc ccccagaaag ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tactgcgcca agcactacta ctacggcggc agctacgcca tggactactg gggccagggc  780
acaagcgtga ccgtgtccag cgctagcggc ggaggtggga gcatcctctg gcatgagatg  840
tggcatgaag gcctggaaga ggcatctcgt ttgtactttg gggaaaggaa cgtgaaaggc  900
atgtttgagg tgctggagcc cttgcatgct atgatggaac ggggccccca gactctgaag  960
gaaacatcct ttaatcaggc ctatggtcga gatttaatgg aggcccaaga gtggtgcagg  1020
aagtacatga aatcagggaa tgtcaaggac ctcctccaag cctgggacct ctattatcat  1080
gtgttccgac gaatctcaaa gggctga                                     1107
```

```
SEQ ID NO: 9           moltype = DNA  length = 1107
FEATURE                Location/Qualifiers
misc_feature           1..1107
                       note = SS-scFvCD19-DmrC DNA
source                 1..1107
                       mol_type = other DNA
                       organism = synthetic construct
SEQUENCE: 9
atgcccctgg gcctgctgtg gctgggcctg gccctgctgg gcgccctgca cgcccaggcc  60
ggatccgata tccagatgac ccagaccacc agcagcctga gcgccagcct gggcgataga  120
gtgaccatca gctgcagagc cagccaggac atcagcaagt acctgaactg gtatcagcag  180
aaacccgacg gcaccgtgaa gctgctgatc taccacacca gcagactgca cagcggcgtg  240
cccagcagat ttctggcag cggctccggc accgactaca gcctgaccat ctccaacctg  300
gaacaggaag atatcgctac ctacttctgt cagcaaggca acaccctgcc ctacaccttc  360
ggcggaggca ccaagctgga aatcaccggc agcacaagcg gcagcggcaa gcctggatct  420
ggcgagggaa gcaccaaggg cgaagtgaaa ctgcaggaaa gcggccctgg actggtggcc  480
ccaagccagt ctctgagcgt gacctgtacc gtgtccggcg tgtccctgcc tgactatggc  540
gtgtcctgga tcagacagcc ccccagaaag ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tactgcgcca agcactacta ctacggcggc agctacgcca tggactactg gggccagggc  780
acaagcgtga ccgtgtccag cgctagcggc ggaggtggga gcatcctctg gcatgagatg  840
tggcatgaag gcctggaaga ggcatctcgt ttgtactttg gggaaaggaa cgtgaaaggc  900
```

```
atgtttgagg tgctggagcc cttgcatgct atgatggaac ggggccccca gactctgaag  960
gaaacatcct ttaatcaggc ctatggtcga gatttaatgg aggcccaaga gtggtgcagg  1020
aagtacatga aatcagggaa tgtcaaggac ctcctccaag cctgggacct ctattatcat  1080
gtgttccgac gaatctcaaa gggctga                                      1107

SEQ ID NO: 10          moltype = DNA  length = 7255
FEATURE                Location/Qualifiers
misc_feature           1..7255
                       note = pCVL_T7_scFvCD19-DmrA-BFP lentiviral vector
source                 1..7255
                       mol_type = other DNA
                       organism = synthetic construct
SEQUENCE: 10
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatgccc ctgggcctgc  2280
tgtggctggg cctggccctg ctgggcgccc tgcacgccca ggccggatcc gatatccaga  2340
tgacccagac caccagcagc ctgagcgcca gcctgggcga tagagtgacc atcagctgca  2400
gagccagcca ggacatcagc aagtacctga actggtatca gcagaaaccc gacggcaccg  2460
tgaagctgct gatctaccac accagcagac tgcacagcgg cgtgcccagc agattttctg  2520
gcagcggctc cggcaccgac tacagcctga ccatctccaa cctggaacag gaagatatcg  2580
ctacctactt ctgtcagcaa ggcaacaccc tgccctacac cttcggcgga ggcaccaagc  2640
tggaaatcac cggcagcaca agcggcagcg gcaagcctgg atctggcgag ggaagcacca  2700
agggcgaagt gaaactgcag gaaagcggcc ctggactggt ggccccaagc cagtctctga  2760
gcgtgacctg taccgtgtcc ggcgtgtccc tgcctgacta tggcgtgtcc tggatcagac  2820
agccccccag aaagggcctg gaatggctgg gagtgatctg gggcagcgag acaacctact  2880
acaacagcgc cctgaagtcc cggctgacca tcatcaagga caactccaag agccaggtgt  2940
tcctgaagat gaacagcctg cagaccgacg acaccgccat ctactactgc gccaagcact  3000
actactacgg cggcagctac gccatggact actggggcca gggcacaagc gtgaccgtgt  3060
ccagcgctag cggcggaggt gggagcggag tgcaggtgga aaccatctcc ccaggagacg  3120
ggcgcacctt ccccaagcgc ggccagacct gcgtggtgca ctacaccggg atgcttgaag  3180
atggaaagaa atttgattcc tcccgggaca gaaacaagcc ctttaagttt atgctaggca  3240
agcaggaggt gatccgaggc tgggaagaag gggttgccca gatgagtgtg ggtcagagag  3300
ccaaactgac tatatctcca gattatgcct atggtgccac tgggcaccca ggcatcatcc  3360
caccacatgc cactctcgtc ttcgatgtgg agcttctaaa actggaaggc ggccgctccg  3420
gtgagggcag aggaagtctt ctaacatgcg gtgacgtgga ggagaatccg ggcccctcta  3480
gaagcgagct gattaaggag aacatgcaca tgaagctgta catggagggc accgtggaca  3540
accatcactt caagtgcaca tccgagggcg aaggcaagcc ctacgagggc acccagacca  3600
tgagaatcaa ggtggtcgag ggcggccctc tccccttcgc cttcgacatc ctggctacta  3660
gcttcctcta cggcagcaag accttcatca accacaccca gggcatcccc gacttcttca  3720
agcagtcctt ccctgagggc ttcacatggg agagagtcac cacatacgaa gacgggggcg  3780
tgctgaccgc tacccaggac accagcctcc aggacggctg cctcatctac aacgtcaaga  3840
tcagaggggt gaacttcaca tccaacggcc ctgtgatgca gaagaaaaca ctcggctggg  3900
aggccttcac cgagacgctg taccccgctg acggcggcct ggaaggcaga aacgacatgg  3960
```

```
ccctgaagct cgtgggcggg agccatctga tcgcaaacat caagaccaca tatagatcca  4020
agaaacccgc taagaacctc aagatgcctg gcgtctacta tgtggactac agactggaaa  4080
gaatcaagga ggccaacaac gagacctacg tcgagcagca cgaggtggca gtggccagat  4140
actgcgacct ccctagcaaa ctggggcaca agcttaattg agtcgaccga gcatcttacc  4200
gccatttata cccatatttg ttctgttttt cttgatttgg gtatacattt aaatgttaat  4260
agaacaaaat ggtggggcaa tcatttacat ttttagggat atgtaattac tagttcaggt  4320
gtattgccac aagacaaaca tgttaagaaa ctttcccgtt atttacgctc tgttcctgtt  4380
aatcaacctc tggattacaa aatttgtgaa agattgactg atattcttaa ctatgttgct  4440
ccttttacgc tgtgtggata tgctgcttta tagcctctgt atctagctat tgcttcccgt  4500
acggctttcg ttttctcctc cttgtataaa tcctggttgc tgtctctttt agaggagttg  4560
tggcccgttg tccgtcaacg tggcgtggtg tgctctgtgt ttgctgacgc aacccccact  4620
ggctggggca ttgccaccac ctgtcaactc ctttctggga ctttcgcttt ccccctcccg  4680
atcgccacgg cagaactcat cgccgcctgc cttgcccgct gctggacagg ggctaggttg  4740
ctgggcactg ataattccgt ggtgttgtca tcgaattcgg taccttttta aaagaaaagg  4800
ggggactgga agggctaatt cactcccaac gaagacaaga tatcataact tcgtatagca  4860
tacattatac gaagttataa tttatttgtg aaatttgtga tgctattgct ttatttgtaa  4920
ccatatgttt atttgtgaaa tttgtgatgc tattgcttta tttgtaacca ttgcttttg  4980
cttgtactgg gtctctctgg ttagaccaga tctgagcctg ggagctctct ggctaactag  5040
ggaacccact gcttaagcct caataaagct tgcctcgacc agcctcgact gtgccttcta  5100
gttgccagcc atctgttgtt tgcccctccc ccgtgccttc cttgaccctg gaaggtgcca  5160
ctcccactgt cctttcctaa taaaatgagg aaattgcatc gcattgtctg agtaggtgtc  5220
attctattct ggggggtggg gtggggcagg acagcaaggg ggaggattgg gaagacaata  5280
gcaggcatgc tggggatgcg gtgggctcta tggcctgcag ctgcattaat gaatcggcca  5340
acgcgcgggg agaggcggtt tgcgtattgg gcgctcttcc gcttcctcgc tcactgactc  5400
gctgcgctcg gtcgttcggc tgcggcgagc ggtatcagct cactcaaagg cggtaatacg  5460
gttatccaca gaatcagggg ataacgcagg aaagaacatg tgagcaaaag gccagcaaaa  5520
ggccaggaac cgtaaaaagg ccgcgttgct ggcgtttttc cataggctcc gcccccctga  5580
cgagcatcac aaaaatcgac gctcaagtca gaggtggcga aacccgacag gactataaag  5640
ataccaggcg tttccccctg gaagctccct cgtgcgctct cctgttccga ccctgccgct  5700
taccggatac ctgtccgcct ttctcccttc gggaagcgtg gcgctttctc atagctcacg  5760
ctgtaggtat ctcagttcgg tgtaggtcgt tcgctccaag ctgggctgtg tgcacgaacc  5820
ccccgttcag cccgaccgct gcgccttatc cggtaactat cgtcttgagt ccaacccggt  5880
aagacacgac ttatcgccac tggcagcagc cactggtaac aggattagca gagcgaggta  5940
tgtaggcggt gctacagagt tcttgaagtg gtggcctaac tacggctaca ctagaaggac  6000
agtatttggt atctgcgctc tgctgaagcc agttaccttc ggaaaaagag ttggtagctc  6060
ttgatccggc aaacaaacca ccgctggtag cggtggtttt tttgtttgca agcagcagat  6120
tacgcgcaga aaaaaaggat ctcaagaaga tcctttgatc ttttctacgg ggtctgacgc  6180
tcagtggaac gaaaactcac gttaagggat tttggtcatg agattatcaa aaaggatctt  6240
cacctagatc cttttaaatt aaaaatgaag ttttaaatca atctaaagta tatatgagta  6300
aacttggtct gacagttacc aatgcttaat cagtgaggca cctatctcag cgatctgtct  6360
atttcgttca tccatagttg cctgactccc cgtcgtgtag ataactacga tacgggaggg  6420
cttaccatct ggccccagtg ctgcaatgat accgcgagac ccacgctcac cggctccaga  6480
tttatcagca ataaaccagc cagccggaag ggccgagcgc agaagtggtc ctgcaacttt  6540
atccgcctcc atccagtcta ttaattgttg ccgggaagct agagtaagta gttcgccagt  6600
taatagtttg cgcaacgttg ttgccattgc tacaggcatc gtggtgtcac gctcgtcgtt  6660
tggtatggct tcattcagct ccggttccca acgatcaagg cgagttacat gatcccccat  6720
gttgtgcaaa aaagcggtta gctccttcgg tcctccgatc gttgtcagaa gtaagttggc  6780
cgcagtgtta tcactcatgg ttatggcagc actgcataat tctcttactg tcatgccatc  6840
cgtaagatgc ttttctgtga ctggtgagta ctcaaccaag tcattctgag aatagtgtat  6900
gcggcgaccg agttgctctt gcccggcgtc aatacgggat aataccgcgc cacatagcag  6960
aactttaaaa gtgctcatca ttggaaaacg ttcttcgggg cgaaaactct caaggatctt  7020
accgctgttg agatccagtt cgatgtaacc cactcgtgca cccaactgat cttcagcatc  7080
ttttactttc accagcgttt ctgggtgagc aaaaacagga aggcaaaatg ccgcaaaaaa  7140
gggaataagg gcgacacgga aatgttgaat actcatactc ttcctttttc aatattattg  7200
aagcatttat cagggttatt gtctcatgag cggatacata tttgaatgta tttag       7255

SEQ ID NO: 11          moltype = DNA  length = 7255
FEATURE                Location/Qualifiers
misc_feature           1..7255
                       note = pCVL_T7_scFvCD19-DmrB-BFP lentiviral vector
source                 1..7255
                       mol_type = other DNA
                       organism = synthetic construct
SEQUENCE: 11
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
```

-continued

```
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatgccc ctgggcctgc  2280
tgtggctggg cctggccctg ctgggcgccc tgcacgccca ggccggatcc gatatccaga  2340
tgacccagac caccagcagc ctgagcgcca gcctgggcga tagagtgacc atcagctgca  2400
gagccagcca ggacatcagc aagtacctga actggtatca gcagaaaccc gacggcaccg  2460
tgaagctgct gatctaccac accagcagac tgcacagcgg cgtgcccagc agattttctg  2520
gcagcggctc cggcaccgac tacagcctga ccatctccaa cctggaacag gaagatatcg  2580
ctacctactt ctgtcagcaa ggcaacaccc tgccctacac cttcggcgga ggcaccaagc  2640
tggaaatcac cggcagcaca agcggcagcg gcaagcctgg atctggcgag ggaagcacca  2700
agggcgaagt gaaactgcag gaaagcggcc ctggactggt ggccccaagc cagtctctga  2760
gcgtgacctg taccgtgtcc ggcgtgtccc tgcctgacta tggcgtgtcc tggatcagac  2820
agccccccag aaagggcctg gaatggctgg gagtgatctg gggcagcgag acaacctact  2880
acaacagcgc cctgaagtcc cggctgacca tcatcaagga caactccaag agccaggtgt  2940
tcctgaagat gaacagcctg cagaccgacg acaccgccat ctactactgc gccaagcact  3000
actactacgg cggcagctac gccatggact actggggcca gggcacaagc gtgaccgtgt  3060
ccagcgctag cggcggaggt gggagcggag tgcaggtgga aaccatctcc ccaggagacg  3120
ggcgcacctt ccccaagcgc ggccagacct gcgtggtgca ctacaccggg atgcttgaag  3180
atggaaagaa agttgattcc tcccgggaca gaaacaagcc ctttaagttt atgctaggca  3240
agcaggaggt gatccgaggc tgggaagaag gggttgccca gatgagtgtg ggtcagagag  3300
ccaaactgac tatatctcca gattatgcct atggtgccac tgggcaccca ggcatcatcc  3360
caccacatgc cactctcgtc ttcgatgtgg agcttctaaa actggaaggc ggccgctccg  3420
gtgagggcag aggaagtctt ctaacatgcg gtgacgtgga ggagaatccg ggcccctcta  3480
gaagcgagct gattaaggag aacatgcaca tgaagctgta catggagggc accgtggaca  3540
accatcactt caagtgcaca tccgagggcg aaggcaagcc ctacgagggc acccagacca  3600
tgagaatcaa ggtggtcgag ggcggccctc tcccctcgc cttcgacatc ctggctacta  3660
gcttcctcta cggcagcaag accttcatca accacaccca gggcatcccc gacttcttca  3720
agcagtcctt ccctgagggc ttcacatggg agagagtcac cacatacgaa gacgggggcg  3780
tgctgaccgc tacccaggac accagcctcc aggacggctg cctcatctac aacgtcaaga  3840
tcagaggggt gaacttcaca tccaacggcc ctgtgatgca gaagaaaaca ctcggctggg  3900
aggccttcac cgagacgctg taccccgctg acggcggcct ggaaggcaga aacgacatgg  3960
ccctgaagct cgtgggcggg agccatctga tcgcaaacat caagaccaca tatagatcca  4020
agaaacccgc taagaacctc aagatgcctg gcgtctacta tgtggactac agactggaaa  4080
gaatcaagga ggccaacaac gagacctacg tcgagcagca cgaggtggca gtggccagat  4140
actgcgacct ccctagcaaa ctggggcaca agcttaattg agtcgaccga gcatcttacc  4200
gccatttata cccatatttg ttctgttttt cttgatttgg gtatacattt aaatgttaat  4260
agaacaaaat ggtggggcaa tcatttacat ttttagggat atgtaattac tagttcaggt  4320
gtattgccac aagacaaaca tgttaagaaa ctttcccgtt atttacgctc tgttcctgtt  4380
aatcaacctc tggattacaa aatttgtgaa agattgactg atattcttaa ctatgttgct  4440
ccttttacgc tgtgtggata tgctgcttta tagcctctgt atctagctat tgcttcccgt  4500
acggctttcg ttttctcctc cttgtataaa tcctggttgc tgtctctttt agaggagttg  4560
tggcccgttg tccgtcaacg tggcgtggtg tgctctgtgt ttgctgacgc aacccccact  4620
ggctggggca ttgccaccac ctgtcaactc ctttctggga ctttcgcttt ccccctcccg  4680
atcgccacgg cagaactcat cgccgcctgc cttgcccgct gctggacagg ggctaggttg  4740
ctgggcactg ataattccgt ggtgttgtca tcgaattcgg taccttttta aaagaaaagg  4800
ggggactgga agggctaatt cactcccaac gaagacaaga tatcataact tcgtatagca  4860
tacattatac gaagttataa tttatttgtg aaatttgtga tgctattgct ttatttgtaa  4920
ccatatgttt atttgtgaaa tttgtgatgc tattgcttta tttgtaacca ttgcttttg  4980
cttgtactgg gtctctctgg ttagaccaga tctgagcctg ggagctctct ggctaactag  5040
ggaacccact gcttaagcct caataaagct tgcctcgacc agcctcgact gtgccttcta  5100
gttgccagcc atctgttgtt tgcccctccc ccgtgccttc cttgaccctg gaaggtgcca  5160
ctcccactgt cctttcctaa taaaatgagg aaattgcatc gcattgtctg agtaggtgtc  5220
attctattct ggggggtggg gtggggcagg acagcaaggg ggaggattgg gaagacaata  5280
gcaggcatgc tggggatgcg gtgggctcta tggcctgcag ctgcattaat gaatcggcca  5340
acgcgcgggg agaggcggtt tgcgtattgg gcgctcttcc gcttcctcgc tcactgactc  5400
gctgcgctcg gtcgttcggc tgcggcgagc ggtatcagct cactcaaagg cggtaatacg  5460
gttatccaca gaatcagggg ataacgcagg aaagaacatg tgagcaaaag gccagcaaaa  5520
ggccaggaac cgtaaaaagg ccgcgttgct ggcgtttttc cataggctcc gccccctga  5580
cgagcatcac aaaaatcgac gctcaagtca gaggtggcga aacccgacag gactataaag  5640
```

```
ataccaggcg tttccccctg gaagctccct cgtgcgctct cctgttccga ccctgccgct  5700
taccggatac ctgtccgcct ttctcccttc gggaagcgtg gcgctttctc atagctcacg  5760
ctgtaggtat ctcagttcgg tgtaggtcgt tcgctccaag ctgggctgtg tgcacgaacc  5820
ccccgttcag cccgaccgct gcgccttatc cggtaactat cgtcttgagt ccaacccggt  5880
aagacacgac ttatcgccac tggcagcagc cactggtaac aggattagca gagcgaggta  5940
tgtaggcggt gctacagagt tcttgaagtg gtggcctaac tacggctaca ctagaaggac  6000
agtatttggt atctgcgctc tgctgaagcc agttaccttc ggaaaaagag ttggtagctc  6060
ttgatccggc aaacaaacca ccgctggtag cggtggtttt tttgtttgca agcagcagat  6120
tacgcgcaga aaaaaaggat ctcaagaaga tcctttgatc ttttctacgg ggtctgacgc  6180
tcagtggaac gaaaactcac gttaagggat tttggtcatg agattatcaa aaaggatctt  6240
cacctagatc cttttaaatt aaaaatgaag ttttaaatca atctaaagta tatatgagta  6300
aacttggtct gacagttacc aatgcttaat cagtgaggca cctatctcag cgatctgtct  6360
atttcgttca tccatagttg cctgactccc cgtcgtgtag ataactacga tacgggaggg  6420
cttaccatct ggccccagtg ctgcaatgat accgcgagac ccacgctcac cggctccaga  6480
tttatcagca ataaaccagc cagccggaag ggccgagcgc agaagtggtc ctgcaacttt  6540
atccgcctcc atccagtcta ttaattgttg ccgggaagct agagtaagta gttcgccagt  6600
taatagtttg cgcaacgttg ttgccattgc tacaggcatc gtggtgtcac gctcgtcgtt  6660
tggtatggct tcattcagct ccggttccca acgatcaagg cgagttacat gatcccccat  6720
gttgtgcaaa aaagcggtta gctccttcgg tcctccgatc gttgtcagaa gtaagttggc  6780
cgcagtgtta tcactcatgg ttatggcagc actgcataat tctcttactg tcatgccatc  6840
cgtaagatgc ttttctgtga ctggtgagta ctcaaccaag tcattctgag aatagtgtat  6900
gcggcgaccg agttgctctt gcccggcgtc aatacgggat aataccgcgc cacatagcag  6960
aactttaaaa gtgctcatca ttggaaaacg ttcttcgggg cgaaaactct caaggatctt  7020
accgctgttg agatccagtt cgatgtaacc cactcgtgca cccaactgat cttcagcatc  7080
ttttactttc accagcgttt ctgggtgagc aaaaacagga aggcaaaatg ccgcaaaaaa  7140
gggaataagg gcgacacgga aatgttgaat actcatactc ttcctttttc aatattattg  7200
aagcatttat cagggttatt gtctcatgag cggatacata tttgaatgta tttag       7255

SEQ ID NO: 12           moltype = DNA  length = 7213
FEATURE                 Location/Qualifiers
misc_feature            1..7213
                        note = pCVL_T7_scFvCD19-DmrC-BFP lentiviral vector
source                  1..7213
                        mol_type = other DNA
                        organism = synthetic construct
SEQUENCE: 12
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tgggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatgccc ctgggcctgc  2280
tgtggctggg cctggccctg ctgggcgccc tgcacgccca ggccggatcc gatatccaga  2340
tgacccagac caccagcagc ctgagcgcca gcctgggcga tagagtgacc atcagctgca  2400
gagccagcca ggacatcagc aagtacctga actggtatca gcagaaaccc gacggcaccg  2460
tgaagctgct gatctaccac accagcagac tgcacagcgg cgtgcccagc agatttctg   2520
gcagcggctc cggcaccgac tacagcctga ccatctccaa cctggaacag gaagatatcg  2580
```

```
ctacctactt ctgtcagcaa ggcaacaccc tgccctacac cttcggcgga ggcaccaagc  2640
tggaaatcac cggcagcaca agcggcagcg gcaagcctgg atctggcgag ggaagcacca  2700
agggcgaagt gaaactgcag gaaagcggcc ctggactggt ggccccaagc cagtctctga  2760
gcgtgacctg taccgtgtcc ggcgtgtccc tgcctgacta tggcgtgtcc tggatcagac  2820
agcccccag aaagggcctg gaatggctgg gagtgatctg gggcagcgag acaacctact  2880
acaacagcgc cctgaagtcc cggctgacca tcatcaagga caactccaag agccaggtgt  2940
tcctgaagat gaacagcctg cagaccgacg acaccgccat ctactactgc gccaagcact  3000
actactacgg cggcagctac gccatggact actggggcca gggcacaagc gtgaccgtgt  3060
ccagcgctag cggcggaggt gggagcatcc tctggcatga gatgtggcat gaaggcctgg  3120
aagaggcatc tcgtttgtac tttggggaaa ggaacgtgaa aggcatgttt gaggtgctgg  3180
agcccttgca tgctatgatg gaacggggcc cccagactct gaaggaaaca tcctttaatc  3240
aggcctatgg tcgagattta atggaggccc aagagtggtg caggaagtac atgaaatcag  3300
ggaatgtcaa ggacctcctc caagcctggg acctctatta tcatgtgttc cgacgaatct  3360
caaagggcgg ccgctccggt gagggcagag gaagtcttct aacatgcggt gacgtggagg  3420
agaatccggg cccctctaga agcgagctga ttaaggagaa catgcacatg aagctgtaca  3480
tggagggcac cgtggacaac catcacttca agtgcacatc cgagggcgaa ggcaagccct  3540
acgagggcac ccagaccatg agaatcaagg tggtcgaggg cggccctctc cccttcgcct  3600
tcgacatcct ggctactagc ttcctctacg gcagcaagac cttcatcaac cacacccagg  3660
gcatccccga cttcttcaag cagtccttcc ctgagggctt cacatgggag agagtcacca  3720
catacgaaga cgggggcgtg ctgaccgcta cccaggacac cagcctccag gacggctgcc  3780
tcatctacaa cgtcaagatc agaggggtga acttcacatc caacggccct gtgatgcaga  3840
agaaaacact cggctgggag gccttcaccg agacgctgta ccccgctgac ggcggcctgg  3900
aaggcagaaa cgacatggcc ctgaagctcg tgggcgggag ccatctgatc gcaaacatca  3960
agaccacata tagatccaag aaacccgcta agaacctcaa gatgcctggc gtctactatg  4020
tggactacag actggaaaga atcaaggagg ccaacaacga gacctacgtc gagcagcacg  4080
aggtggcagt ggccagatac tgcgacctcc ctagcaaact ggggcacaag cttaattgag  4140
tcgaccgagc atcttaccgc catttatacc catatttgtt ctgtttttct tgatttgggt  4200
atacatttaa atgttaatag aacaaaatgg tggggcaatc atttacattt ttagggatat  4260
gtaattacta gttcaggtgt attgccacaa gacaaacatg ttaagaaact ttcccgttat  4320
ttacgctctg ttcctgttaa tcaacctctg gattacaaaa tttgtgaaag attgactgat  4380
attcttaact atgttgctcc ttttacgctg tgtggatatg ctgctttata gcctctgtat  4440
ctagctattg cttcccgtac ggctttcgtt ttctcctcct tgtataaatc ctggttgctg  4500
tctcttttag aggagttgtg gcccgttgtc cgtcaacgtg gcgtggtgtg ctctgtgttt  4560
gctgacgcaa cccccactgg ctggggcatt gccaccacct gtcaactcct ttctgggact  4620
ttcgctttcc ccctcccgat cgccacggca gaactcatcg ccgcctgcct tgcccgctgc  4680
tggacagggg ctaggttgct gggcactgat aattccgtgg tgttgtcatc gaattcggta  4740
ccttttttaaa agaaaagggg ggactggaag ggctaattca ctcccaacga agacaagata  4800
tcataacttc gtatagcata cattatacga agttataatt tatttgtgaa atttgtgatg  4860
ctattgcttt atttgtaacc atatgtttat ttgtgaaatt tgtgatgcta ttgctttatt  4920
tgtaaccatt gctttttgct tgtactgggt ctctctggtt agaccagatc tgagcctggg  4980
agctctctgg ctaactaggg aacccactgc ttaagcctca ataaagcttg cctcgaccag  5040
cctcgactgt gccttctagt tgccagccat ctgttgtttg cccctccccc gtgccttcct  5100
tgaccctgga aggtgccact cccactgtcc tttcctaata aaatgaggaa attgcatcgc  5160
attgtctgag taggtgtcat tctattctgg ggggtggggt ggggcaggac agcaaggggg  5220
aggattggga agacaatagc aggcatgctg gggatgcggt gggctctatg gcctgcagct  5280
gcattaatga atcggccaac gcgcggggag aggcggtttg cgtattgggc gctcttccgc  5340
ttcctcgctc actgactcgc tgcgctcggt cgttcggctg cggcgagcgg tatcagctca  5400
ctcaaaggcg gtaatacggt tatccacaga atcaggggat aacgcaggaa agaacatgtg  5460
agcaaaaggc cagcaaaagg ccaggaaccg taaaaaggcc gcgttgctgg cgtttttcca  5520
taggctccgc ccccctgacg agcatcacaa aaatcgacgc tcaagtcaga ggtggcgaaa  5580
cccgacagga ctataaagat accaggcgtt tccccctgga agctccctcg tgcgctctcc  5640
tgttccgacc ctgccgctta ccggatacct gtccgccttt ctcccttcgg gaagcgtggc  5700
gctttctcat agctcacgct gtaggtatct cagttcggtg taggtcgttc gctccaagct  5760
gggctgtgtg cacgaacccc ccgttcagcc cgaccgctgc gccttatccg gtaactatcg  5820
tcttgagtcc aacccggtaa gacacgactt atcgccactg gcagcagcca ctggtaacag  5880
gattagcaga gcgaggtatg taggcggtgc tacagagttc ttgaagtggt ggcctaacta  5940
cggctacact agaaggacag tatttggtat ctgcgctctg ctgaagccag ttaccttcgg  6000
aaaaagagtt ggtagctctt gatccggcaa acaaaccacc gctggtagcg gtggtttttt  6060
tgtttgcaag cagcagatta cgcgcagaaa aaaaggatct caagaagatc ctttgatctt  6120
ttctacgggg tctgacgctc agtggaacga aaactcacgt taagggattt tggtcatgag  6180
attatcaaaa aggatcttca cctagatcct tttaaattaa aaatgaagtt ttaaatcaat  6240
ctaaagtata tatgagtaaa cttggtctga cagttaccaa tgcttaatca gtgaggcacc  6300
tatctcagcg atctgtctat ttcgttcatc catagttgcc tgactccccg tcgtgtagat  6360
aactacgata cgggagggct taccatctgg ccccagtgct gcaatgatac cgcgagaccc  6420
acgctcaccg gctccagatt tatcagcaat aaaccagcca gccggaaggg ccgagcgcag  6480
aagtggtcct gcaactttat ccgcctccat ccagtctatt aattgttgcc gggaagctag  6540
agtaagtagt tcgccagtta atagtttgcg caacgttgtt gccattgcta caggcatcgt  6600
ggtgtcacgc tcgtcgtttg gtatggcttc attcagctcc ggttcccaac gatcaaggcg  6660
agttacatga tcccccatgt tgtgcaaaaa agcggttagc tccttcggtc ctccgatcgt  6720
tgtcagaagt aagttggccg cagtgttatc actcatggtt atggcagcac tgcataattc  6780
tcttactgtc atgccatccg taagatgctt ttctgtgact ggtgagtact caaccaagtc  6840
attctgagaa tagtgtatgc ggcgaccgag ttgctcttgc ccggcgtcaa tacgggataa  6900
taccgcgcca catagcagaa ctttaaaagt gctcatcatt ggaaaacgtt cttcggggcg  6960
aaaactctca aggatcttac cgctgttgag atccagttcg atgtaaccca ctcgtgcacc  7020
caactgatct tcagcatctt ttactttcac cagcgtttct gggtgagcaa aaacaggaag  7080
gcaaaatgcc gcaaaaaagg gaataagggc gacacggaaa tgttgaatac tcatactctt  7140
cctttttcaa tattattgaa gcatttatca gggttattgt ctcatgagcg gatacatatt  7200
tgaatgtatt tag                                                    7213
```

```
SEQ ID NO: 13           moltype = RNA  length = 2259
FEATURE                 Location/Qualifiers
misc_feature            1..2259
                        note = scFvCD19-TM-41BB-CD3z-BFP mRNA
source                  1..2259
                        mol_type = other RNA
                        organism = synthetic construct
SEQUENCE: 13
atggctctgc ctgtgacagc tctgctgctg cctctggccc tgctgctcca tgccgccaga  60
cccggatccg atatccagat gacccagacc accagcagcc tgagcgccag cctgggcgat  120
agagtgacca tcagctgcag agccagccag gacatcagca agtacctgaa ctggtatcag  180
cagaaacccg acggcaccgt gaagctgctg atctaccaca ccagcagact gcacagcggc  240
gtgcccagca gatttctgg cagcggctcc ggcaccgact acagcctgac catctccaac  300
ctggaacagg aagatatcgc tacctacttc tgtcagcaag gcaacaccct gccctacacc  360
ttcggcggag gcaccaagct ggaaatcacc ggcagcacaa gcggcagcgg caagcctgga  420
tctggcgagg gaagcaccaa gggcgaagtg aaactgcagg aaagcggccc tggactggtg  480
gccccaagcc agtctctgag cgtgacctgt accgtgtccg gcgtgtccct gcctgactat  540
ggcgtgtcct ggatcagaca gccacccaga aagggcctgg aatggctggg agtgatctgg  600
ggcagcgaga caacctacta caacagcgcc ctgaagtccc ggctgaccat catcaaggac  660
aactccaaga gccaggtgtt cctgaagatg aacagcctgc agaccgacga caccgccatc  720
tactactgcg ccaagcacta ctactacggc ggcagctacg ccatggacta ctggggccag  780
ggcacaagcg tgaccgtgtc cagcgctagc gccaagccta ccaccacccc tgcccctaga  840
cctccaacac ccgccccaac aatcgccagc cagcctctgt ctctgaggcc cgaggcttgt  900
agaccagctg ctggcggagc cgtgcacacc agaggactgg atttcgcctg cgacatctac  960
atctgggccc ctctggccgg cacatgtggc gtgctgctgc tgagcctcgt gatcaccatg  1020
cataaacggg gcagaaagaa actcctgtat atattcaaac aaccatttat gagaccagta  1080
caaactactc aagaggaaga tggctgtagc tgccgatttc cagaagaaga agaaggagga  1140
tgtgaactgc gggtgaagtt cagcagaagc gccgacgccc ctgcctacca gcagggccag  1200
aatcagctgt acaacgagct gaacctgggc agaagggaag agtacgacgt cctggataag  1260
cggagaggcc gggaccctga gatgggcggc aagcctcggc ggaagaaccc ccaggaaggc  1320
ctgtataacg aactgcagaa agacaagatg gccgaggcct acagcgagat cggcatgaag  1380
ggcgagcgga ggcggggcaa gggccacgac ggcctgtatc agggcctgtc caccgccacc  1440
aaggatacct acgacgccct gcacatgcag gccctgcccc caaggggcgg ccgctccggt  1500
gagggcagag gaagtcttct aacatgcggt gacgtggagg agaatccggg cccctctaga  1560
agcgagctga ttaaggagaa catgcacatg aagctgtaca tggagggcac cgtggacaac  1620
catcacttca agtgcacatc cgagggcgaa ggcaagccct acgagggcac ccagaccatg  1680
agaatcaagg tggtcgaggg cggccctctc cccttcgcct tcgacatcct ggctactagc  1740
ttcctctacg gcagcaagac cttcatcaac cacacccagg gcatccccga cttcttcaag  1800
cagtccttcc ctgagggctt cacatgggag agagtcacca catacgaaga cgggggcgtg  1860
ctgaccgcta cccaggacac cagcctccag gacggctgcc tcatctacaa cgtcaagatc  1920
agaggggtga acttcacatc caacggccct gtgatgcaga agaaaacact cggctgggag  1980
gccttcaccg agacgctgta ccccgctgac ggcggcctgg aaggcagaaa cgacatggcc  2040
ctgaagctcg tgggcgggag ccatctgatc gcaaacatca agaccacata tagatccaag  2100
aaacccgcta agaacctcaa gatgcctggc gtctactatg tggactacag actggaaaga  2160
atcaaggagg ccaacaacga gacctacgtc gagcagcacg aggtggcagt ggccagatac  2220
tgcgacctcc ctagcaaact ggggcacaag cttaattga                        2259

SEQ ID NO: 14           moltype = DNA  length = 7597
FEATURE                 Location/Qualifiers
misc_feature            1..7597
                        note = pCVL_T7_scFvCD19-TM-41BB-CD3z-BFP lentiviral vector
source                  1..7597
                        mol_type = other DNA
                        organism = synthetic construct
SEQUENCE: 14
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
```

-continued

```
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatggct ctgcctgtga  2280
cagctctgct gctgcctctg gccctgctgc tccatgccgc cagacccgga tccgatatcc  2340
agatgaccca gaccaccagc agcctgagcg ccagcctggg cgatagagtg accatcagct  2400
gcagagccag ccaggacatc agcaagtacc tgaactggta tcagcagaaa cccgacggca  2460
ccgtgaagct gctgatctac cacaccagca gactgcacag cggcgtgccc agcagatttt  2520
ctggcagcgg ctccggcacc gactacagcc tgaccatctc caacctggaa caggaagata  2580
tcgctaccta cttctgtcag caaggcaaca ccctgcccta caccttcggc ggaggcacca  2640
agctggaaat caccggcagc acaagcggca gcggcaagcc tggatctggc gagggaagca  2700
ccaagggcga agtgaaactg caggaaagcg gccctggact ggtggcccca agccagtctc  2760
tgagcgtgac ctgtaccgtg tccggcgtgt ccctgcctga ctatggcgtg tcctggatca  2820
gacagccacc cagaaagggc ctggaatggc tgggagtgat ctggggcagc gagacaacct  2880
actacaacag cgccctgaag tcccggctga ccatcatcaa ggacaactcc aagagccagg  2940
tgttcctgaa gatgaacagc ctgcagaccg acgacaccgc catctactac tgcgccaagc  3000
actactacta cggcggcagc tacgccatgg actactgggg ccagggcaca agcgtgaccg  3060
tgtccagcgc tagcgccaag cctaccacca cccctgcccc tagacctcca acacccgccc  3120
caacaatcgc cagccagcct ctgtctctga ggcccgaggc ttgtagacca gctgctggcg  3180
gagccgtgca caccagagga ctggatttcg cctgcgacat ctacatctgg gcccctctgg  3240
ccggcacatg tggcgtgctg ctgctgagcc tcgtgatcac catgcataaa cggggcagaa  3300
agaaactcct gtatatattc aaacaaccat ttatgagacc agtacaaact actcaagagg  3360
aagatggctg tagctgccga tttccagaag aagaagaagg aggatgtgaa ctgcgggtga  3420
agttcagcag aagcgccgac gcccctgcct accagcaggg ccagaatcag ctgtacaacg  3480
agctgaacct gggcagaagg gaagagtacg acgtcctgga taagcggaga ggccgggacc  3540
ctgagatggg cggcaagcct cggcggaaga acccccagga aggcctgtat aacgaactgc  3600
agaaagacaa gatggccgag gcctacagcg agatcggcat gaagggcgag cggaggcggg  3660
gcaagggcca cgacggcctg tatcagggcc tgtccaccgc caccaaggat acctacgacg  3720
ccctgcacat gcaggccctg cccccaaggg gcggccgctc cggtgagggc agaggaagtc  3780
ttctaacatg cggtgacgtg gaggagaatc cgggcccctc tagaagcgag ctgattaagg  3840
agaacatgca catgaagctg tacatggagg gcaccgtgga caaccatcac ttcaagtgca  3900
catccgaggg cgaaggcaag ccctacgagg gcacccagac catgagaatc aaggtggtcg  3960
agggcggccc tctccccttc gccttcgaca tcctggctac tagcttcctc tacggcagca  4020
agaccttcat caaccacacc cagggcatcc ccgacttctt caagcagtcc ttccctgagg  4080
gcttcacatg ggagagagtc accacatacg aagacggggg cgtgctgacc gctacccagg  4140
acaccagcct ccaggacggc tgcctcatct acaacgtcaa gatcagaggg gtgaacttca  4200
catccaacgg ccctgtgatg cagaagaaaa cactcggctg ggaggccttc accgagacgc  4260
tgtaccccgc tgacggcggc ctggaaggca gaaacgacat ggccctgaag ctcgtgggcg  4320
ggagccatct gatcgcaaac atcaagacca catatagatc caagaaaccc gctaagaacc  4380
tcaagatgcc tggcgtctac tatgtggact acagactgga aagaatcaag gaggccaaca  4440
acgagaccta cgtcgagcag cacgaggtgg cagtggccag atactgcgac ctccctagca  4500
aactggggca caagcttaat tgagtcgacc gagcatctta ccgccattta tacccatatt  4560
tgttctgttt ttcttgattt gggtatacat ttaaatgtta atagaacaaa atggtggggc  4620
aatcatttac atttttaggg atatgtaatt actagttcag gtgtattgcc acaagacaaa  4680
catgttaaga aactttcccg ttatttacgc tctgttcctg ttaatcaacc tctggattac  4740
aaaatttgtg aaagattgac tgatattctt aactatgttg ctccttttac gctgtgtgga  4800
tatgctgctt tatagcctct gtatctagct attgcttccc gtacggcttt cgttttctcc  4860
tccttgtata aatcctggtt gctgtctctt ttagaggagt tgtggcccgt tgtccgtcaa  4920
cgtggcgtgg tgtgctctgt gtttgctgac gcaaccccca ctggctgggg cattgccacc  4980
acctgtcaac tcctttctgg gactttcgct ttccccctcc cgatcgccac ggcagaactc  5040
atcgccgcct gccttgcccg ctgctggaca ggggctaggt tgctgggcac tgataattcc  5100
gtggtgttgt catcgaattc ggtacctttt taaaagaaaa ggggggactg gaagggctaa  5160
ttcactccca acgaagacaa gatatcataa cttcgtatag catacattat acgaagttat  5220
aatttatttg tgaaatttgt gatgctattg ctttatttgt aaccatatgt ttatttgtga  5280
aatttgtgat gctattgctt tatttgtaac cattgctttt tgcttgtact gggtctctct  5340
ggttagacca gatctgagcc tgggagctct ctggctaact agggaaccca ctgcttaagc  5400
ctcaataaag cttgcctcga ccagcctcga ctgtgccttc tagttgccag ccatctgttg  5460
tttgcccctc ccccgtgcct tccttgaccc tggaaggtgc cactcccact gtcctttcct  5520
aataaaatga ggaaattgca tcgcattgtc tgagtaggtg tcattctatt ctggggggtg  5580
gggtggggca ggacagcaag ggggaggatt gggaagacaa tagcaggcat gctggggatg  5640
cggtgggctc tatggcctgc agctgcatta atgaatcggc caacgcgcgg ggagaggcgg  5700
tttgcgtatt gggcgctctt ccgcttcctc gctcactgac tcgctgcgct cggtcgttcg  5760
gctgcggcga gcggtatcag ctcactcaaa ggcggtaata cggttatcca cagaatcagg  5820
ggataacgca ggaaagaaca tgtgagcaaa aggccagcaa aaggccagga accgtaaaaa  5880
ggccgcgttg ctggcgtttt tccataggct ccgcccccct gacgagcatc acaaaaatcg  5940
acgctcaagt cagaggtggc gaaacccgac aggactataa agataccagg cgtttccccc  6000
tggaagctcc ctcgtgcgct ctcctgttcc gaccctgccg cttaccggat acctgtccgc  6060
ctttctccct tcgggaagcg tggcgctttc tcatagctca cgctgtaggt atctcagttc  6120
ggtgtaggtc gttcgctcca agctgggctg tgtgcacgaa ccccccgttc agcccgaccg  6180
```

```
ctgcgcctta tccggtaact atcgtcttga gtccaacccg gtaagacacg acttatcgcc  6240
actggcagca gccactggta acaggattag cagagcgagg tatgtaggcg gtgctacaga  6300
gttcttgaag tggtggccta actacggcta cactagaagg acagtatttg gtatctgcgc  6360
tctgctgaag ccagttacct tcggaaaaag agttggtagc tcttgatccg gcaaacaaac  6420
caccgctggt agcggtggtt tttttgtttg caagcagcag attacgcgca gaaaaaaagg  6480
atctcaagaa gatcctttga tcttttctac ggggtctgac gctcagtgga acgaaaactc  6540
acgttaaggg attttggtca tgagattatc aaaaaggatc ttcacctaga tccttttaaa  6600
ttaaaaatga agttttaaat caatctaaag tatatatgag taaacttggt ctgacagtta  6660
ccaatgctta atcagtgagg cacctatctc agcgatctgt ctatttcgtt catccatagt  6720
tgcctgactc cccgtcgtgt agataactac gatacgggag ggcttaccat ctggccccag  6780
tgctgcaatg ataccgcgag acccacgctc accggctcca gatttatcag caataaacca  6840
gccagccgga agggccgagc gcagaagtgg tcctgcaact ttatccgcct ccatccagtc  6900
tattaattgt tgccgggaag ctagagtaag tagttcgcca gttaatagtt tgcgcaacgt  6960
tgttgccatt gctacaggca tcgtggtgtc acgctcgtcg tttggtatgg cttcattcag  7020
ctccggttcc caacgatcaa ggcgagttac atgatccccc atgttgtgca aaaaagcggt  7080
tagctccttc ggtcctccga tcgttgtcag aagtaagttg gccgcagtgt tatcactcat  7140
ggttatggca gcactgcata attctcttac tgtcatgcca tccgtaagat gcttttctgt  7200
gactggtgag tactcaacca agtcattctg agaatagtgt atgcggcgac cgagttgctc  7260
ttgcccggcg tcaatacggg ataataccgc gccacatagc agaactttaa aagtgctcat  7320
cattggaaaa cgttcttcgg ggcgaaaact ctcaaggatc ttaccgctgt tgagatccag  7380
ttcgatgtaa cccactcgtg cacccaactg atcttcagca tcttttactt tcaccagcgt  7440
ttctgggtga gcaaaaacag gaaggcaaaa tgccgcaaaa aagggaataa gggcgacacg  7500
gaaatgttga atactcatac tcttcctttt tcaatattat tgaagcattt atcagggtta  7560
ttgtctcatg agcggataca tatttgaatg tatttag                           7597

SEQ ID NO: 15          moltype = AA  length = 324
FEATURE                Location/Qualifiers
REGION                 1..324
                       note = DmrC-TM-41BB-CD3z protein
source                 1..324
                       mol_type = protein
                       organism = synthetic construct
SEQUENCE: 15
MGSILWHEMW HEGLEEASRL YFGERNVKGM FEVLEPLHAM MERGPQTLKE TSFNQAYGRD  60
LMEAQEWCRK YMKSGNVKDL LQAWDLYYHV FRRISKASAK PTTTPAPRPP TPAPTIASQP  120
LSLRPEACRP AAGGAVHTRG LDFACDIYIW APLAGTCGVL LLSLVITMHK RGRKKLLYIF  180
KQPFMRPVQT TQEEDGCSCR FPEEEEGGCE LRVKFSRSAD APAYQQGQNQ LYNELNLGRR  240
EEYDVLDKRR GRDPEMGGKP RRKNPQEGLY NELQKDKMAE AYSEIGMKGE RRRGKGHDGL  300
YQGLSTATKD TYDALHMQAL PPRG                                         324

SEQ ID NO: 16          moltype = RNA  length = 1032
FEATURE                Location/Qualifiers
misc_feature           1..1032
                       note = SS-DmrC-TM-41BB-CD3z mRNA
source                 1..1032
                       mol_type = other RNA
                       organism = synthetic construct
SEQUENCE: 16
atggctctgc ctgtgacagc tctgctgctg cctctggccc tgctgctcca tgccgccaga  60
cccggatcca tcctctggca tgagatgtgg catgaaggcc tggaagaggc atctcgtttg  120
tactttgggg aaaggaacgt gaaaggcatg tttgaggtgc tggagccctt gcatgctatg  180
atggaacggg gcccccagac tctgaaggaa acatccttta atcaggccta tggtcgagat  240
ttaatggagg cccaagagtg gtgcaggaag tacatgaaat cagggaatgt caaggacctc  300
ctccaagcct gggacctcta ttatcatgtg ttccgacgaa tctcaaaggc tagcgccaag  360
cctaccacca cccctgcccc tagacctcca acacccgccc caacaatcgc cagccagcct  420
ctgtctctga ggcccgaggc ttgtagacca gctgctggcg gagccgtgca caccagagga  480
ctggatttcg cctgcgacat ctacatctgg gcccctctgg ccggcacatg tggcgtgctg  540
ctgctgagcc tcgtgatcac catgcataaa cggggcagaa agaaactcct gtatatattc  600
aaacaaccat ttatgagacc agtacaaact actcaagagg aagatggctg tagctgccga  660
tttccagaag aagaagaagg aggatgtgaa ctgcgggtga agttcagcag aagcgccgac  720
gcccctgcct accagcaggg ccagaatcag ctgtacaacg agctgaacct gggcagaagg  780
gaagagtacg acgtcctgga taagcggaga ggccgggacc ctgagatggg cggcaagcct  840
cggcggaaga acccccagga aggcctgtat aacgaactgc agaaagacaa gatggccgag  900
gcctacagcg agatcggcat gaagggcgag cggaggcggg gcaagggcca cgacggcctg  960
tatcagggcc tgtccaccgc caccaaggat acctacgacg ccctgcacat gcaggccctg  1020
cccccaaggg gc                                                      1032

SEQ ID NO: 17          moltype = DNA  length = 1032
FEATURE                Location/Qualifiers
misc_feature           1..1032
                       note = SS-DmrC-TM-41BB-CD3z DNA
source                 1..1032
                       mol_type = other DNA
                       organism = synthetic construct
SEQUENCE: 17
atggctctgc ctgtgacagc tctgctgctg cctctggccc tgctgctcca tgccgccaga  60
cccggatcca tcctctggca tgagatgtgg catgaaggcc tggaagaggc atctcgtttg  120
tactttgggg aaaggaacgt gaaaggcatg tttgaggtgc tggagccctt gcatgctatg  180
atggaacggg gcccccagac tctgaaggaa acatccttta atcaggccta tggtcgagat  240
```

```
ttaatggagg cccaagagtg gtgcaggaag tacatgaaat cagggaatgt caaggacctc  300
ctccaagcct gggacctcta ttatcatgtg ttccgacgaa tctcaaaggc tagcgccaag  360
cctaccacca cccctgcccc tagacctcca acacccgccc caacaatcgc cagccagcct  420
ctgtctctga ggcccgaggc ttgtagacca gctgctggcg gagccgtgca caccagagga  480
ctggatttcg cctgcgacat ctacatctgg gcccctctgg ccggcacatg tggcgtgctg  540
ctgctgagcc tcgtgatcac catgcataaa cggggcagaa agaaactcct gtatatattc  600
aaacaaccat ttatgagacc agtacaaact actcaagagg aagatggctg tagctgccga  660
tttccagaag aagaagaagg aggatgtgaa ctgcgggtga agttcagcag aagcgccgac  720
gcccctgcct accagcaggg ccagaatcag ctgtacaacg agctgaacct gggcagaagg  780
gaagagtacg acgtcctgga taagcggaga ggccgggacc ctgagatggg cggcaagcct  840
cggcggaaga acccccagga aggcctgtat aacgaactgc agaaagacaa gatggccgag  900
gcctacagcg agatcggcat gaagggcgag cggaggcggg gcaagggcca cgacggcctg  960
tatcagggcc tgtccaccgc caccaaggat acctacgacg ccctgcacat gcaggccctg  1020
cccccaaggg gc                                                     1032
```

```
SEQ ID NO: 18          moltype = DNA  length = 1512
FEATURE                Location/Qualifiers
misc_feature           1..1512
                       note = SS-DmrC-spacer-TM-41BB-CD3z DNA
source                 1..1512
                       mol_type = other DNA
                       organism = synthetic construct
SEQUENCE: 18
atggctctgc ctgtgacagc tctgctgctg cctctggccc tgctgctcca tgccgccaga  60
cccggatcca tcctctggca tgagatgtgg catgaaggcc tggaagaggc atctcgtttg  120
tactttgggg aaaggaacgt gaaaggcatg tttgaggtgc tggagccctt gcatgctatg  180
atggaacggg gcccccagac tctgaaggaa acatccttta atcaggccta tggtcgagat  240
ttaatggagg cccaagagtg gtgcaggaag tacatgaaat cagggaatgt caaggacctc  300
ctccaagcct gggacctcta ttatcatgtg ttccgacgaa tctcaaaggc tagcgagagc  360
aagtacggac cgccctgccc accttgccct gcccccgagt tcctgggcgg acccagcgtg  420
ttcctgttcc cacccaagcc caaggacacc ctgatgatca gccggacccc cgaggtgacc  480
tgcgtggtgg tggacgtgag ccaggaagat cccgaggtcc agttcaattg gtacgtggac  540
ggcgtggaag tgcacaacgc caagaccaag cccagagagg aacagttcaa cagcacctac  600
cgggtggtgt ctgtgctgac cgtgctgcac caggactggc tgaacggcaa agaatacaag  660
tgcaaggtgt ccaacaaggg cctgcccagc agcatcgaaa agaccatcag caaggccaag  720
ggccagcctc gcgagcccca ggtgtacacc ctgcctccct cccaggaaga gatgaccaag  780
aaccaggtgt ccctgacctg cctggtgaag ggcttctacc ccagcgacat cgccgtggag  840
tgggagagca acggccagcc tgagaacaac tacaagacca cccctcccgt gctggacagc  900
gacggcagct tcttcctgta cagccggctg accgtggaca agagccggtg gcaggaaggc  960
aacgtcttta gctgcagcgt gatgcacgag gccctgcaca accactacac ccagaagagc  1020
ctgagcctgt ccctgggcaa gatgcataaa cggggcagaa agaaactcct gtatatattc  1080
aaacaaccat ttatgagacc agtacaaact actcaagagg aagatggctg tagctgccga  1140
tttccagaag aagaagaagg aggatgtgaa ctgcgggtga agttcagcag aagcgccgac  1200
gcccctgcct accagcaggg ccagaatcag ctgtacaacg agctgaacct gggcagaagg  1260
gaagagtacg acgtcctgga taagcggaga ggccgggacc ctgagatggg cggcaagcct  1320
cggcggaaga acccccagga aggcctgtat aacgaactgc agaaagacaa gatggccgag  1380
gcctacagcg agatcggcat gaagggcgag cggaggcggg gcaagggcca cgacggcctg  1440
tatcagggcc tgtccaccgc caccaaggat acctacgacg ccctgcacat gcaggccctg  1500
cccccaaggg gc                                                     1512
```

```
SEQ ID NO: 19          moltype = AA  length = 338
FEATURE                Location/Qualifiers
REGION                 1..338
                       note = DmrB-TM-41BB-CD3z protein
source                 1..338
                       mol_type = protein
                       organism = synthetic construct
SEQUENCE: 19
MGSGVQVETI SPGDGRTFPK RGQTCVVHYT GMLEDGKKVD SSRDRNKPFK FMLGKQEVIR  60
GWEEGVAQMS VGQRAKLTIS PDYAYGATGH PGIIPPHATL VFDVELLKLE ASAKPTTTPA  120
PRPPTPAPTI ASQPLSLRPE ACRPAAGGAV HTRGLDFACD IYIWAPLAGT CGVLLLSLVI  180
TMHKRGRKKL LYIFKQPFMR PVQTTQEEDG CSCRFPEEEE GGCELRVKFS RSADAPAYQQ  240
GQNQLYNELN LGRREEYDVL DKRRGRDPEM GGKPRRKNPQ EGLYNELQKD KMAEAYSEIG  300
MKGERRRGKG HDGLYQGLST ATKDTYDALH MQALPPRG                         338
```

```
SEQ ID NO: 20          moltype = RNA  length = 1074
FEATURE                Location/Qualifiers
misc_feature           1..1074
                       note = SS-DmrB-TM-41BB-CD3z mRNA
source                 1..1074
                       mol_type = other RNA
                       organism = synthetic construct
SEQUENCE: 20
atggctctgc ctgtgacagc tctgctgctg cctctggccc tgctgctcca tgccgccaga  60
cccggatccg gagtgcaggt ggaaaccatc tccccaggag acgggcgcac cttccccaag  120
cgcggccaga cctgcgtggt gcactacacc gggatgcttg aagatggaaa gaaagttgat  180
tcctcccggg acagaaacaa gccctttaag tttatgctag gcaagcagga ggtgatccga  240
ggctgggaag aaggggttgc ccagatgagt gtgggtcaga gagccaaact gactatatct  300
ccagattatg cctatggtgc cactgggcac ccaggcatca tcccaccaca tgccactctc  360
```

```
gtcttcgatg tggagcttct aaaactggaa gctagcgcca agcctaccac cacccctgcc  420
cctagacctc caacacccgc cccaacaatc gccagccagc ctctgtctct gaggcccgag  480
gcttgtagac cagctgctgg cggagccgtg cacaccagag gactggattt cgcctgcgac  540
atctacatct gggcccctct ggccggcaca tgtggcgtgc tgctgctgag cctcgtgatc  600
accatgcata aacggggcag aaagaaactc ctgtatatat tcaaacaacc atttatgaga  660
ccagtacaaa ctactcaaga ggaagatggc tgtagctgcc gatttccaga agaagaagaa  720
ggaggatgtg aactgcgggt gaagttcagc agaagcgccg acgcccctgc ctaccagcag  780
ggccagaatc agctgtacaa cgagctgaac ctgggcagaa gggaagagta cgacgtcctg  840
gataagcgga gaggccggga ccctgagatg ggcggcaagc ctcggcggaa gaacccccag  900
gaaggcctgt ataacgaact gcagaaagac aagatggccg aggcctacag cgagatcggc  960
atgaagggcg agcggaggcg gggcaagggc cacgacggcc tgtatcaggg cctgtccacc  1020
gccaccaagg atacctacga cgccctgcac atgcaggccc tgcccccaag ggc        1074
```

```
SEQ ID NO: 21          moltype = DNA  length = 1074
FEATURE                Location/Qualifiers
misc_feature           1..1074
                       note = SS-DmrB-TM-41BB-CD3z DNA
source                 1..1074
                       mol_type = other DNA
                       organism = synthetic construct
SEQUENCE: 21
atggctctgc ctgtgacagc tctgctgctg cctctggccc tgctgctcca tgccgccaga  60
cccggatccg gagtgcaggt ggaaaccatc tccccaggag acgggcgcac cttccccaag  120
cgcggccaga cctgcgtggt gcactacacc gggatgcttg aagatggaaa gaaagttgat  180
tcctcccggg acagaaacaa gcccttttaag tttatgctag gcaagcagga ggtgatccga  240
ggctgggaag aaggggttgc ccagatgagt gtgggtcaga gagccaaact gactatatct  300
ccagattatg cctatggtgc cactgggcac ccaggcatca tcccaccaca tgccactctc  360
gtcttcgatg tggagcttct aaaactggaa gctagcgcca agcctaccac cacccctgcc  420
cctagacctc caacacccgc cccaacaatc gccagccagc ctctgtctct gaggcccgag  480
gcttgtagac cagctgctgg cggagccgtg cacaccagag gactggattt cgcctgcgac  540
atctacatct gggcccctct ggccggcaca tgtggcgtgc tgctgctgag cctcgtgatc  600
accatgcata aacggggcag aaagaaactc ctgtatatat tcaaacaacc atttatgaga  660
ccagtacaaa ctactcaaga ggaagatggc tgtagctgcc gatttccaga agaagaagaa  720
ggaggatgtg aactgcgggt gaagttcagc agaagcgccg acgcccctgc ctaccagcag  780
ggccagaatc agctgtacaa cgagctgaac ctgggcagaa gggaagagta cgacgtcctg  840
gataagcgga gaggccggga ccctgagatg ggcggcaagc ctcggcggaa gaacccccag  900
gaaggcctgt ataacgaact gcagaaagac aagatggccg aggcctacag cgagatcggc  960
atgaagggcg agcggaggcg gggcaagggc cacgacggcc tgtatcaggg cctgtccacc  1020
gccaccaagg atacctacga cgccctgcac atgcaggccc tgcccccaag ggc        1074
```

```
SEQ ID NO: 22          moltype = DNA  length = 1554
FEATURE                Location/Qualifiers
misc_feature           1..1554
                       note = SS-DmrB-spacer-TM-41BB-CD3z DNA
source                 1..1554
                       mol_type = other DNA
                       organism = synthetic construct
SEQUENCE: 22
atggctctgc ctgtgacagc tctgctgctg cctctggccc tgctgctcca tgccgccaga  60
cccggatccg gagtgcaggt ggaaaccatc tccccaggag acgggcgcac cttccccaag  120
cgcggccaga cctgcgtggt gcactacacc gggatgcttg aagatggaaa gaaagttgat  180
tcctcccggg acagaaacaa gcccttttaag tttatgctag gcaagcagga ggtgatccga  240
ggctgggaag aaggggttgc ccagatgagt gtgggtcaga gagccaaact gactatatct  300
ccagattatg cctatggtgc cactgggcac ccaggcatca tcccaccaca tgccactctc  360
gtcttcgatg tggagcttct aaaactggaa gctagcgaga gcaagtacgg accgccctgc  420
ccaccttgcc ctgcccccga gttcctgggc ggacccagcg tgttcctgtt cccacccaag  480
cccaaggaca ccctgatgat cagccggacc cccgaggtga cctgcgtggt ggtggacgtg  540
agccaggaag atcccgaggt ccagttcaat tggtacgtgg acggcgtgga agtgcacaac  600
gccaagacca agcccagaga ggaacagttc aacagcacct accgggtggt gtctgtgctg  660
accgtgctgc accaggactg gctgaacggc aaagaataca agtgcaaggt gtccaacaag  720
ggcctgccca gcagcatcga aaagaccatc agcaaggcca agggccagcc tcgcgagccc  780
caggtgtaca ccctgcctcc ctcccaggaa gagatgacca agaaccaggt gtccctgacc  840
tgcctggtga agggcttcta ccccagcgac atcgccgtgg agtgggagag caacggccag  900
cctgagaaca actacaagac cacccctccc gtgctggaca gcgacggcag cttcttcctg  960
tacagccggc tgaccgtgga caagagccgg tggcaggaag gcaacgtctt tagctgcagc  1020
gtgatgcacg aggccctgca caaccactac acccagaaga gcctgagcct gtccctgggc  1080
aagatgcata aacggggcag aaagaaactc ctgtatatat tcaaacaacc atttatgaga  1140
ccagtacaaa ctactcaaga ggaagatggc tgtagctgcc gatttccaga agaagaagaa  1200
ggaggatgtg aactgcgggt gaagttcagc agaagcgccg acgcccctgc ctaccagcag  1260
ggccagaatc agctgtacaa cgagctgaac ctgggcagaa gggaagagta cgacgtcctg  1320
gataagcgga gaggccggga ccctgagatg ggcggcaagc ctcggcggaa gaacccccag  1380
gaaggcctgt ataacgaact gcagaaagac aagatggccg aggcctacag cgagatcggc  1440
atgaagggcg agcggaggcg gggcaagggc cacgacggcc tgtatcaggg cctgtccacc  1500
gccaccaagg atacctacga cgccctgcac atgcaggccc tgcccccaag ggc        1554
```

```
SEQ ID NO: 23          moltype = AA  length = 338
FEATURE                Location/Qualifiers
REGION                 1..338
                       note = DmrA-TM-41BB-CD3z protein
```

```
source                  1..338
                        mol_type = protein
                        organism = synthetic construct
SEQUENCE: 23
MGSGVQVETI SPGDGRTFPK RGQTCVVHYT GMLEDGKKFD SSRDRNKPFK FMLGKQEVIR  60
GWEEGVAQMS VGQRAKLTIS PDYAYGATGH PGIIPPHATL VFDVELLKLE ASAKPTTTPA  120
PRPPTPAPTI ASQPLSLRPE ACRPAAGGAV HTRGLDFACD IYIWAPLAGT CGVLLLSLVI  180
TMHKRGRKKL LYIFKQPFMR PVQTTQEEDG CSCRFPEEEE GGCELRVKFS RSADAPAYQQ  240
GQNQLYNELN LGRREEYDVL DKRRGRDPEM GGKPRRKNPQ EGLYNELQKD KMAEAYSEIG  300
MKGERRRGKG HDGLYQGLST ATKDTYDALH MQALPPRG                         338

SEQ ID NO: 24           moltype = RNA  length = 1074
FEATURE                 Location/Qualifiers
misc_feature            1..1074
                        note = DmrA-TM-41BB-CD3z mRNA
source                  1..1074
                        mol_type = other RNA
                        organism = synthetic construct
SEQUENCE: 24
atggctctgc ctgtgacagc tctgctgctg cctctggccc tgctgctcca tgccgccaga  60
cccggatccg gagtgcaggt ggaaaccatc tccccaggag acgggcgcac cttccccaag  120
cgcggccaga cctgcgtggt gcactacacc gggatgcttg aagatggaaa gaaatttgat  180
tcctcccggg acagaaacaa gccctttaag tttatgctag gcaagcagga ggtgatccga  240
ggctgggaag aaggggttgc ccagatgagt gtgggtcaga gagccaaact gactatatct  300
ccagattatg cctatggtgc cactgggcac ccaggcatca tcccaccaca tgccactctc  360
gtcttcgatg tggagcttct aaaactggaa gctagcgcca agcctaccac cacccctgcc  420
cctagacctc caacacccgc cccaacaatc gccagccagc ctctgtctct gaggcccgag  480
gcttgtagac cagctgctgg cggagccgtg cacaccagag gactggattt cgcctgcgac  540
atctacatct gggcccctct ggccggcaca tgtggcgtgc tgctgctgag cctcgtgatc  600
accatgcata aacggggcag aaagaaactc ctgtatatat tcaaacaacc atttatgaga  660
ccagtacaaa ctactcaaga ggaagatggc tgtagctgcc gatttccaga agaagaagaa  720
ggaggatgtg aactgcgggt gaagttcagc agaagcgccg acgcccctgc ctaccagcag  780
ggccagaatc agctgtacaa cgagctgaac ctgggcagaa gggaagagta cgacgtcctg  840
gataagcgga gaggccggga ccctgagatg ggcggcaagc ctcggcggaa gaacccccag  900
gaaggcctgt ataacgaact gcagaaagac aagatggccg aggcctacag cgagatcggc  960
atgaagggcg agcggaggcg gggcaagggc cacgacggcc tgtatcaggg cctgtccacc  1020
gccaccaagg atacctacga cgccctgcac atgcaggccc tgcccccaag gggc        1074

SEQ ID NO: 25           moltype = DNA  length = 1074
FEATURE                 Location/Qualifiers
misc_feature            1..1074
                        note = DmrA-TM-41BB-CD3z DNA
source                  1..1074
                        mol_type = other DNA
                        organism = synthetic construct
SEQUENCE: 25
atggctctgc ctgtgacagc tctgctgctg cctctggccc tgctgctcca tgccgccaga  60
cccggatccg gagtgcaggt ggaaaccatc tccccaggag acgggcgcac cttccccaag  120
cgcggccaga cctgcgtggt gcactacacc gggatgcttg aagatggaaa gaaatttgat  180
tcctcccggg acagaaacaa gccctttaag tttatgctag gcaagcagga ggtgatccga  240
ggctgggaag aaggggttgc ccagatgagt gtgggtcaga gagccaaact gactatatct  300
ccagattatg cctatggtgc cactgggcac ccaggcatca tcccaccaca tgccactctc  360
gtcttcgatg tggagcttct aaaactggaa gctagcgcca agcctaccac cacccctgcc  420
cctagacctc caacacccgc cccaacaatc gccagccagc ctctgtctct gaggcccgag  480
gcttgtagac cagctgctgg cggagccgtg cacaccagag gactggattt cgcctgcgac  540
atctacatct gggcccctct ggccggcaca tgtggcgtgc tgctgctgag cctcgtgatc  600
accatgcata aacggggcag aaagaaactc ctgtatatat tcaaacaacc atttatgaga  660
ccagtacaaa ctactcaaga ggaagatggc tgtagctgcc gatttccaga agaagaagaa  720
ggaggatgtg aactgcgggt gaagttcagc agaagcgccg acgcccctgc ctaccagcag  780
ggccagaatc agctgtacaa cgagctgaac ctgggcagaa gggaagagta cgacgtcctg  840
gataagcgga gaggccggga ccctgagatg ggcggcaagc ctcggcggaa gaacccccag  900
gaaggcctgt ataacgaact gcagaaagac aagatggccg aggcctacag cgagatcggc  960
atgaagggcg agcggaggcg gggcaagggc cacgacggcc tgtatcaggg cctgtccacc  1020
gccaccaagg atacctacga cgccctgcac atgcaggccc tgcccccaag gggc        1074

SEQ ID NO: 26           moltype = DNA  length = 1554
FEATURE                 Location/Qualifiers
misc_feature            1..1554
                        note = DmrA-spacer-TM-41BB-CD3z DNA
source                  1..1554
                        mol_type = other DNA
                        organism = synthetic construct
SEQUENCE: 26
atggctctgc ctgtgacagc tctgctgctg cctctggccc tgctgctcca tgccgccaga  60
cccggatccg gagtgcaggt ggaaaccatc tccccaggag acgggcgcac cttccccaag  120
cgcggccaga cctgcgtggt gcactacacc gggatgcttg aagatggaaa gaaatttgat  180
tcctcccggg acagaaacaa gccctttaag tttatgctag gcaagcagga ggtgatccga  240
ggctgggaag aaggggttgc ccagatgagt gtgggtcaga gagccaaact gactatatct  300
ccagattatg cctatggtgc cactgggcac ccaggcatca tcccaccaca tgccactctc  360
```

```
gtcttcgatg tggagcttct aaaactggaa gctagcgaga gcaagtacgg accgccctgc  420
ccaccttgcc ctgcccccga gttcctgggc ggacccagcg tgttcctgtt cccacccaag  480
cccaaggaca ccctgatgat cagccggacc cccgaggtga cctgcgtggt ggtggacgtg  540
agccaggaag atcccgaggt ccagttcaat tggtacgtgg acggcgtgga agtgcacaac  600
gccaagacca agcccagaga ggaacagttc aacagcacct accgggtggt gtctgtgctg  660
accgtgctgc accaggactg gctgaacggc aaagaataca agtgcaaggt gtccaacaag  720
ggcctgccca gcagcatcga aaagaccatc agcaaggcca agggccagcc tcgcgagccc  780
caggtgtaca ccctgcctcc ctcccaggaa gagatgacca agaaccaggt gtccctgacc  840
tgcctggtga agggcttcta ccccagcgac atcgccgtgg agtgggagag caacggccag  900
cctgagaaca actacaagac cacccctccc gtgctggaca gcgacggcag cttcttcctg  960
tacagccggc tgaccgtgga caagagccgg tggcaggaag gcaacgtctt tagctgcagc  1020
gtgatgcacg aggccctgca caaccactac acccagaaga gcctgagcct gtccctgggc  1080
aagatgcata aacggggcag aaagaaactc ctgtatatat tcaaacaacc atttatgaga  1140
ccagtacaaa ctactcaaga ggaagatggc tgtagctgcc gatttccaga agaagaagaa  1200
ggaggatgtg aactgcgggt gaagttcagc agaagcgccg acgcccctgc ctaccagcag  1260
ggccagaatc agctgtacaa cgagctgaac ctgggcagaa gggaagagta cgacgtcctg  1320
gataagcgga gaggccggga ccctgagatg ggcggcaagc ctcggcggaa gaacccccag  1380
gaaggcctgt ataacgaact gcagaaagac aagatggccg aggcctacag cgagatcggc  1440
atgaagggcg agcggaggcg gggcaagggc cacgacggcc tgtatcaggg cctgtccacc  1500
gccaccaagg atacctacga cgccctgcac atgcaggccc tgcccccaag ggc        1554
```

```
SEQ ID NO: 27           moltype = DNA  length = 7141
FEATURE                 Location/Qualifiers
misc_feature            1..7141
                        note = pCVL_T7_DmrC-TM-41BB-CD3z lentiviral vector
source                  1..7141
                        mol_type = other DNA
                        organism = synthetic construct
SEQUENCE: 27
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tgggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatggct ctgcctgtga  2280
cagctctgct gctgcctctg gccctgctgc tccatgccgc cagacccgga tccatcctct  2340
ggcatgagat gtggcatgaa ggcctggaag aggcatctcg tttgtacttt ggggaaagga  2400
acgtgaaagg catgtttgag gtgctggagc ccttgcatgc tatgatggaa cggggccccc  2460
agactctgaa ggaaacatcc tttaatcagg cctatggtcg agatttaatg gaggcccaag  2520
agtggtgcag gaagtacatg aaatcaggga atgtcaagga cctcctccaa gcctgggacc  2580
tctattatca tgtgttccga cgaatctcaa aggctagcgc caagcctacc accacccctg  2640
cccctagacc tccaacaccc gccccaacaa tcgccagcca gcctctgtct ctgaggcccg  2700
aggcttgtag accagctgct ggcggagccg tgcacaccag aggactggat ttcgcctgcg  2760
acatctacat ctgggcccct ctggccggca catgtggcgt gctgctgctg agcctcgtga  2820
tcaccatgca taaacggggc agaaagaaac tcctgtatat attcaaacaa ccatttatga  2880
gaccagtaca aactactcaa gaggaagatg gctgtagctg ccgatttcca gaagaagaag  2940
aaggaggatg tgaactgcgg gtgaagttca gcagaagcgc cgacgcccct gcctaccagc  3000
```

```
agggccagaa tcagctgtac aacgagctga acctgggcag aagggaagag tacgacgtcc  3060
tggataagcg gagaggccgg gaccctgaga tgggcggcaa gcctcggcgg aagaaccccc  3120
aggaaggcct gtataacgaa ctgcagaaag acaagatggc cgaggcctac agcgagatcg  3180
gcatgaaggg cgagcggagg cggggcaagg gccacgacgg cctgtatcag ggcctgtcca  3240
ccgccaccaa ggatacctac gacgccctgc acatgcaggc cctgccccca aggggcggcc  3300
gctccggtga gggcagagga agtcttctaa catgcggtga cgtggaggag aatccgggcc  3360
cctctagaag cgagctgatt aaggagaaca tgcacatgaa gctgtacatg gagggcaccg  3420
tggacaacca tcacttcaag tgcacatccg agggcgaagg caagccctac gagggcaccc  3480
agaccatgag aatcaaggtg gtcgagggcg gccctctccc cttcgccttc gacatcctgg  3540
ctactagctt cctctacggc agcaagacct tcatcaacca cacccagggc atccccgact  3600
tcttcaagca gtccttccct gagggcttca catgggagag agtcaccaca tacgaagacg  3660
gggcgtgct gaccgctacc caggacacca gcctccagga cggctgcctc atctacaacg  3720
tcaagatcag aggggtgaac ttcacatcca acggccctgt gatgcagaag aaaacactcg  3780
gctgggaggc cttcaccgag acgctgtacc ccgctgacgg cggcctggaa ggcagaaacg  3840
acatggccct gaagctcgtg ggcgggagcc atctgatcgc aaacatcaag accacatata  3900
gatccaagaa acccgctaag aacctcaaga tgcctggcgt ctactatgtg gactacagac  3960
tggaaagaat caaggaggcc aacaacgaga cctacgtcga gcagcacgag gtggcagtgg  4020
ccagatactg cgacctccct agcaaactgg ggcacaagct taattgagtc gaccgagcat  4080
cttaccgcca tttataccca tatttgttct gtttttcttg atttgggtat acatttaaat  4140
gttaatagaa caaaatggtg gggcaatcat ttacattttt agggatatgt aattactagt  4200
tcaggtgtat tgccacaaga caaacatgtt aagaaacttt cccgttattt acgctctgtt  4260
cctgttaatc aacctctgga ttacaaaatt tgtgaaagat tgactgatat tcttaactat  4320
gttgctcctt ttacgctgtg tggatatgct gctttatagc ctctgtatct agctattgct  4380
tcccgtacgg ctttcgtttt ctcctccttg tataaatcct ggttgctgtc tcttttagag  4440
gagttgtggc ccgttgtccg tcaacgtggc gtggtgtgct ctgtgtttgc tgacgcaacc  4500
cccactggct ggggcattgc caccacctgt caactccttt ctgggacttt cgctttcccc  4560
ctcccgatcg ccacggcaga actcatcgcc gcctgccttg cccgctgctg gacaggggct  4620
aggttgctgg gcactgataa ttccgtggtg ttgtcatcga attcggtacc tttttaaaag  4680
aaaagggggg actggaaggg ctaattcact cccaacgaag acaagatatc ataacttcgt  4740
atagcataca ttatacgaag ttataattta tttgtgaaat ttgtgatgct attgctttat  4800
ttgtaaccat atgtttattt gtgaaatttg tgatgctatt gctttatttg taaccattgc  4860
tttttgcttg tactgggtct ctctggttag accagatctg agcctgggag ctctctggct  4920
aactagggaa cccactgctt aagcctcaat aaagcttgcc tcgaccagcc tcgactgtgc  4980
cttctagttg ccagccatct gttgtttgcc cctcccccgt gccttccttg accctggaag  5040
gtgccactcc cactgtcctt tcctaataaa atgaggaaat tgcatcgcat tgtctgagta  5100
ggtgtcattc tattctgggg ggtggggtgg ggcaggacag caagggggag gattgggaag  5160
acaatagcag gcatgctggg gatgcggtgg gctctatggc ctgcagctgc attaatgaat  5220
cggccaacgc gcggggagag gcggtttgcg tattgggcgc tcttccgctt cctcgctcac  5280
tgactcgctg cgctcggtcg ttcggctgcg gcgagcggta tcagctcact caaaggcggt  5340
aatacggtta tccacagaat caggggataa cgcaggaaag aacatgtgag caaaaggcca  5400
gcaaaaggcc aggaaccgta aaaaggccgc gttgctggcg tttttccata ggctccgccc  5460
ccctgacgag catcacaaaa atcgacgctc aagtcagagg tggcgaaacc cgacaggact  5520
ataaagatac caggcgtttc cccctggaag ctccctcgtg cgctctcctg ttccgaccct  5580
gccgcttacc ggatacctgt ccgcctttct cccttcggga agcgtggcgc tttctcatag  5640
ctcacgctgt aggtatctca gttcggtgta ggtcgttcgc tccaagctgg gctgtgtgca  5700
cgaacccccc gttcagcccg accgctgcgc cttatccggt aactatcgtc ttgagtccaa  5760
cccggtaaga cacgacttat cgccactggc agcagccact ggtaacagga ttagcagagc  5820
gaggtatgta ggcggtgcta cagagttctt gaagtggtgg cctaactacg gctacactag  5880
aaggacagta tttggtatct gcgctctgct gaagccagtt accttcggaa aaagagttgg  5940
tagctcttga tccggcaaac aaaccaccgc tggtagcggt ggtttttttg tttgcaagca  6000
gcagattacg cgcagaaaaa aaggatctca agaagatcct ttgatctttt ctacggggtc  6060
tgacgctcag tggaacgaaa actcacgtta agggattttg gtcatgagat tatcaaaaag  6120
gatcttcacc tagatccttt taaattaaaa atgaagtttt aaatcaatct aaagtatata  6180
tgagtaaact tggtctgaca gttaccaatg cttaatcagt gaggcaccta tctcagcgat  6240
ctgtctattt cgttcatcca tagttgcctg actccccgtc gtgtagataa ctacgatacg  6300
ggagggctta ccatctggcc ccagtgctgc aatgataccg cgagacccac gctcaccggc  6360
tccagattta tcagcaataa accagccagc cggaagggcc gagcgcagaa gtggtcctgc  6420
aactttatcc gcctccatcc agtctattaa ttgttgccgg gaagctagag taagtagttc  6480
gccagttaat agtttgcgca acgttgttgc cattgctaca ggcatcgtgg tgtcacgctc  6540
gtcgtttggt atggcttcat tcagctccgg ttcccaacga tcaaggcgag ttacatgatc  6600
ccccatgttg tgcaaaaaag cggttagctc cttcggtcct ccgatcgttg tcagaagtaa  6660
gttggccgca gtgttatcac tcatggttat ggcagcactg cataattctc ttactgtcat  6720
gccatccgta agatgctttt ctgtgactgg tgagtactca accaagtcat tctgagaata  6780
gtgtatgcgg cgaccgagtt gctcttgccc ggcgtcaata cgggataata ccgcgccaca  6840
tagcagaact ttaaaagtgc tcatcattgg aaaacgttct tcggggcgaa aactctcaag  6900
gatcttaccg ctgttgagat ccagttcgat gtaacccact cgtgcaccca actgatcttc  6960
agcatctttt actttcacca gcgtttctgg gtgagcaaaa acaggaaggc aaaatgccgc  7020
aaaaaaggga ataagggcga cacggaaatg ttgaatactc atactcttcc tttttcaata  7080
ttattgaagc atttatcagg gttattgtct catgagcgga tacatatttg aatgtattta  7140
g                                                                  7141
```

```
SEQ ID NO: 28           moltype = DNA  length = 7621
FEATURE                 Location/Qualifiers
misc_feature            1..7621
                        note = pCVL_T7_DmrC-spacer-TM-41BB-CD3z lentiviral vector
source                  1..7621
                        mol_type = other DNA
                        organism = synthetic construct
SEQUENCE: 28
```

```
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tgggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatggct ctgcctgtga  2280
cagctctgct gctgcctctg gccctgctgc tccatgccgc cagacccgga tccatcctct  2340
ggcatgagat gtggcatgaa ggcctggaag aggcatctcg tttgtacttt ggggaaagga  2400
acgtgaaagg catgtttgag gtgctggagc ccttgcatgc tatgatggaa cggggccccc  2460
agactctgaa ggaaacatcc tttaatcagg cctatggtcg agatttaatg gaggcccaag  2520
agtggtgcag gaagtacatg aaatcaggga atgtcaagga cctcctccaa gcctgggacc  2580
tctattatca tgtgttccga cgaatctcaa aggctagcga gagcaagtac ggaccgccct  2640
gcccaccttg ccctgccccc gagttcctgg gcggacccag cgtgttcctg ttcccaccca  2700
agcccaagga caccctgatg atcagccgga cccccgaggt gacctgcgtg gtggtggacg  2760
tgagccagga agatcccgag gtccagttca attggtacgt ggacggcgtg gaagtgcaca  2820
acgccaagac caagcccaga gaggaacagt tcaacagcac ctaccgggtg gtgtctgtgc  2880
tgaccgtgct gcaccaggac tggctgaacg gcaaagaata caagtgcaag gtgtccaaca  2940
agggcctgcc cagcagcatc gaaaagacca tcagcaaggc caagggccag cctcgcgagc  3000
cccaggtgta caccctgcct ccctcccagg aagagatgac caagaaccag gtgtccctga  3060
cctgcctggt gaagggcttc taccccagcg acatcgccgt ggagtgggag agcaacggcc  3120
agcctgagaa caactacaag accacccctc ccgtgctgga cagcgacggc agcttcttcc  3180
tgtacagccg gctgaccgtg gacaagagcc ggtggcagga aggcaacgtc tttagctgca  3240
gcgtgatgca cgaggccctg cacaaccact acacccagaa gagcctgagc ctgtccctgg  3300
gcaagatgca taaacggggc agaaagaaac tcctgtatat attcaaacaa ccatttatga  3360
gaccagtaca aactactcaa gaggaagatg gctgtagctg ccgatttcca gaagaagaag  3420
aaggaggatg tgaactgcgg gtgaagttca gcagaagcgc cgacgcccct gcctaccagc  3480
agggccagaa tcagctgtac aacgagctga acctgggcag aagggaagag tacgacgtcc  3540
tggataagcg gagaggccgg gaccctgaga tgggcggcaa gcctcggcgg aagaaccccc  3600
aggaaggcct gtataacgaa ctgcagaaag acaagatggc cgaggcctac agcgagatcg  3660
gcatgaaggg cgagcggagg cggggcaagg gccacgacgg cctgtatcag ggcctgtcca  3720
ccgccaccaa ggatacctac gacgccctgc acatgcaggc cctgcccccca aggggcggcc  3780
gctccggtga gggcagagga agtcttctaa catgcggtga cgtggaggag aatccgggcc  3840
cctctagaag cgagctgatt aaggagaaca tgcacatgaa gctgtacatg gagggcaccg  3900
tggacaacca tcacttcaag tgcacatccg agggcgaagg caagccctac gagggcaccc  3960
agaccatgag aatcaaggtg gtcgagggcg gccctctccc cttcgccttc gacatcctgg  4020
ctactagctt cctctacggc agcaagacct tcatcaacca cacccagggc atccccgact  4080
tcttcaagca gtccttccct gagggcttca catgggagag agtcaccaca tacgaagacg  4140
gggggcgtgct gaccgctacc caggacacca gcctccagga cggctgcctc atctacaacg  4200
tcaagatcag aggggtgaac ttcacatcca acggccctgt gatgcagaag aaaacactcg  4260
gctgggaggc cttcaccgag acgctgtacc ccgctgacgg cggcctggaa ggcagaaacg  4320
acatggccct gaagctcgtg ggcgggagcc atctgatcgc aaacatcaag accacatata  4380
gatccaagaa acccgctaag aacctcaaga tgcctggcgt ctactatgtg gactacagac  4440
tggaaagaat caaggaggcc aacaacgaga cctacgtcga gcagcacgag gtggcagtgg  4500
ccagatactg cgacctccct agcaaactgg ggcacaagct taattgagtc gaccgagcat  4560
cttaccgcca tttataccca tatttgttct gtttttcttg atttgggtat acatttaaat  4620
gttaatagaa caaaatggtg gggcaatcat ttacattttt agggatatgt aattactagt  4680
tcaggtgtat tgccacaaga caaacatgtt aagaaacttt cccgttattt acgctctgtt  4740
```

-continued

```
cctgttaatc aacctctgga ttacaaaatt tgtgaaagat tgactgatat tcttaactat  4800
gttgctcctt ttacgctgtg tggatatgct gctttatagc ctctgtatct agctattgct  4860
tcccgtacgg ctttcgtttt ctcctccttg tataaatcct ggttgctgtc tcttttagag  4920
gagttgtggc ccgttgtccg tcaacgtggc gtggtgtgct ctgtgtttgc tgacgcaacc  4980
cccactggct ggggcattgc caccacctgt caactccttt ctgggacttt cgctttcccc  5040
ctcccgatcg ccacggcaga actcatcgcc gcctgccttg cccgctgctg gacaggggct  5100
aggttgctgg gcactgataa ttccgtggtg ttgtcatcga attcggtacc tttttaaaag  5160
aaaagggggg actggaaggg ctaattcact cccaacgaag acaagatatc ataacttcgt  5220
atagcataca ttatacgaag ttataattta tttgtgaaat ttgtgatgct attgctttat  5280
ttgtaaccat atgtttattt gtgaaatttg tgatgctatt gctttatttg taaccattgc  5340
tttttgcttg tactgggtct ctctggttag accagatctg agcctgggag ctctctggct  5400
aactagggaa cccactgctt aagcctcaat aaagcttgcc tcgaccagcc tcgactgtgc  5460
cttctagttg ccagccatct gttgtttgcc cctcccccgt gccttccttg accctggaag  5520
gtgccactcc cactgtcctt tcctaataaa atgaggaaat tgcatcgcat tgtctgagta  5580
ggtgtcattc tattctgggg ggtggggtgg ggcaggacag caagggggag gattgggaag  5640
acaatagcag gcatgctggg gatgcggtgg gctctatggc ctgcagctgc attaatgaat  5700
cggccaacgc gcggggagag gcggtttgcg tattgggcgc tcttccgctt cctcgctcac  5760
tgactcgctg cgctcggtcg ttcggctgcg gcgagcggta tcagctcact caaaggcggt  5820
aatacggtta tccacagaat caggggataa cgcaggaaag aacatgtgag caaaaggcca  5880
gcaaaaggcc aggaaccgta aaaaggccgc gttgctggcg tttttccata ggctccgccc  5940
ccctgacgag catcacaaaa atcgacgctc aagtcagagg tggcgaaacc cgacaggact  6000
ataaagatac caggcgtttc cccctggaag ctccctcgtg cgctctcctg ttccgaccct  6060
gccgcttacc ggatacctgt ccgcctttct cccttcggga agcgtggcgc tttctcatag  6120
ctcacgctgt aggtatctca gttcggtgta ggtcgttcgc tccaagctgg gctgtgtgca  6180
cgaacccccc gttcagcccg accgctgcgc cttatccggt aactatcgtc ttgagtccaa  6240
cccggtaaga cacgacttat cgccactggc agcagccact ggtaacagga ttagcagagc  6300
gaggtatgta ggcggtgcta cagagttctt gaagtggtgg cctaactacg gctacactag  6360
aaggacagta tttggtatct gcgctctgct gaagccagtt accttcggaa aaagagttgg  6420
tagctcttga tccggcaaac aaaccaccgc tggtagcggt ggtttttttg tttgcaagca  6480
gcagattacg cgcagaaaaa aaggatctca agaagatcct ttgatctttt ctacggggtc  6540
tgacgctcag tggaacgaaa actcacgtta agggattttg gtcatgagat tatcaaaaag  6600
gatcttcacc tagatccttt taaattaaaa atgaagtttt aaatcaatct aaagtatata  6660
tgagtaaact tggtctgaca gttaccaatg cttaatcagt gaggcaccta tctcagcgat  6720
ctgtctattt cgttcatcca tagttgcctg actccccgtc gtgtagataa ctacgatacg  6780
ggagggctta ccatctggcc ccagtgctgc aatgataccg cgagacccac gctcaccggc  6840
tccagattta tcagcaataa accagccagc cggaagggcc gagcgcagaa gtggtcctgc  6900
aactttatcc gcctccatcc agtctattaa ttgttgccgg gaagctagag taagtagttc  6960
gccagttaat agtttgcgca acgttgttgc cattgctaca ggcatcgtgg tgtcacgctc  7020
gtcgtttggt atggcttcat tcagctccgg ttcccaacga tcaaggcgag ttacatgatc  7080
ccccatgttg tgcaaaaaag cggttagctc cttcggtcct ccgatcgttg tcagaagtaa  7140
gttggccgca gtgttatcac tcatggttat ggcagcactg cataattctc ttactgtcat  7200
gccatccgta agatgctttt ctgtgactgg tgagtactca accaagtcat tctgagaata  7260
gtgtatgcgg cgaccgagtt gctcttgccc ggcgtcaata cgggataata ccgcgccaca  7320
tagcagaact ttaaaagtgc tcatcattgg aaaacgttct tcggggcgaa aactctcaag  7380
gatcttaccg ctgttgagat ccagttcgat gtaacccact cgtgcaccca actgatcttc  7440
agcatctttt actttcacca gcgtttctgg gtgagcaaaa acaggaaggc aaaatgccgc  7500
aaaaaaggga ataagggcga cacggaaatg ttgaatactc atactcttcc tttttcaata  7560
ttattgaagc atttatcagg gttattgtct catgagcgga tacatatttg aatgtattta  7620
g                                                                 7621

SEQ ID NO: 29          moltype = DNA  length = 7183
FEATURE                Location/Qualifiers
misc_feature           1..7183
                       note = pCVL_T7_DmrB-TM-41BB-CD3z lentiviral vector
source                 1..7183
                       mol_type = other DNA
                       organism = synthetic construct
SEQUENCE: 29
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
```

```
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tgggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatggct ctgcctgtga  2280
cagctctgct gctgcctctg gccctgctgc tccatgccgc cagacccgga tccggagtgc  2340
aggtggaaac catctcccca ggagacgggc gcaccttccc caagcgcggc cagacctgcg  2400
tggtgcacta caccgggatg cttgaagatg gaaagaaagt tgattcctcc cgggacagaa  2460
acaagccctt taagtttatg ctaggcaagc aggaggtgat ccgaggctgg gaagaagggg  2520
ttgcccagat gagtgtgggt cagagagcca aactgactat atctccagat tatgcctatg  2580
gtgccactgg gcacccaggc atcatcccac cacatgccac tctcgtcttc gatgtggagc  2640
ttctaaaact ggaagctagc gccaagccta ccaccacccc tgcccctaga cctccaacac  2700
ccgcccccaac aatcgccagc cagcctctgt ctctgaggcc cgaggcttgt agaccagctg  2760
ctggcggagc cgtgcacacc agaggactgg atttcgcctg cgacatctac atctgggccc  2820
ctctggccgg cacatgtggc gtgctgctgc tgagcctcgt gatcaccatg cataaacggg  2880
gcagaaagaa actcctgtat atattcaaac aaccatttat gagaccagta caaactactc  2940
aagaggaaga tggctgtagc tgccgatttc cagaagaaga agaaggagga tgtgaactgc  3000
gggtgaagtt cagcagaagc gccgacgccc ctgcctacca gcagggccag aatcagctgt  3060
acaacgagct gaacctgggc agaagggaag agtacgacgt cctggataag cggagaggcc  3120
gggaccctga gatgggcggc aagcctcggc ggaagaaccc ccaggaaggc ctgtataacg  3180
aactgcagaa agacaagatg gccgaggcct acagcgagat cggcatgaag ggcgagcgga  3240
ggcggggcaa gggccacgac ggcctgtatc agggcctgtc caccgccacc aaggatacct  3300
acgacgccct gcacatgcag gccctgcccc caaggggcgg ccgctccggt gagggcagag  3360
gaagtcttct aacatgcggt gacgtggagg agaatccggg cccctctaga agcgagctga  3420
ttaaggagaa catgcacatg aagctgtaca tggagggcac cgtggacaac catcacttca  3480
agtgcacatc cgagggcgaa ggcaagccct acgagggcac ccagaccatg agaatcaagg  3540
tggtcgaggg cggccctctc cccttcgcct tcgacatcct ggctactagc ttcctctacg  3600
gcagcaagac cttcatcaac cacacccagg gcatccccga cttcttcaag cagtccttcc  3660
ctgagggctt cacatgggag agagtcacca catacgaaga cgggggcgtg ctgaccgcta  3720
cccaggacac cagcctccag gacggctgcc tcatctacaa cgtcaagatc agaggggtga  3780
acttcacatc caacggccct gtgatgcaga agaaaacact cggctgggag gccttcaccg  3840
agacgctgta ccccgctgac ggcggcctgg aaggcagaaa cgacatggcc ctgaagctcg  3900
tgggcgggag ccatctgatc gcaaacatca agaccacata tagatccaag aaacccgcta  3960
agaacctcaa gatgcctggc gtctactatg tggactacag actggaaaga atcaaggagg  4020
ccaacaacga gacctacgtc gagcagcacg aggtggcagt ggccagatac tgcgacctcc  4080
ctagcaaact ggggcacaag cttaattgag tcgaccgagc atcttaccgc catttatacc  4140
catatttgtt ctgtttttct tgatttgggt atacatttaa atgttaatag aacaaaatgg  4200
tggggcaatc atttacattt ttagggatat gtaattacta gttcaggtgt attgccacaa  4260
gacaaacatg ttaagaaact ttcccgttat ttacgctctg ttcctgttaa tcaacctctg  4320
gattacaaaa tttgtgaaag attgactgat attcttaact atgttgctcc ttttacgctg  4380
tgtggatatg ctgctttata gcctctgtat ctagctattg cttcccgtac ggctttcgtt  4440
ttctcctcct tgtataaatc ctggttgctg tctcttttag aggagttgtg gcccgttgtc  4500
cgtcaacgtg gcgtggtgtg ctctgtgttt gctgacgcaa cccccactgg ctggggcatt  4560
gccaccacct gtcaactcct ttctgggact ttcgctttcc ccctcccgat cgccacggca  4620
gaactcatcg ccgcctgcct tgcccgctgc tggacagggg ctaggttgct gggcactgat  4680
aattccgtgg tgttgtcatc gaattcggta cctttttaaa agaaaagggg ggactggaag  4740
ggctaattca ctcccaacga agacaagata tcataacttc gtatagcata cattatacga  4800
agttataatt tatttgtgaa atttgtgatg ctattgcttt atttgtaacc atatgtttat  4860
ttgtgaaatt tgtgatgcta ttgctttatt tgtaaccatt gctttttgct tgtactgggt  4920
ctctctggtt agaccagatc tgagcctggg agctctctgg ctaactaggg aacccactgc  4980
ttaagcctca ataaagcttg cctcgaccag cctcgactgt gccttctagt tgccagccat  5040
ctgttgtttg cccctccccc gtgccttcct tgaccctgga aggtgccact cccactgtcc  5100
tttcctaata aaatgaggaa attgcatcgc attgtctgag taggtgtcat tctattctgg  5160
ggggtggggt ggggcaggac agcaaggggg aggattggga agacaatagc aggcatgctg  5220
gggatgcggt gggctctatg gcctgcagct gcattaatga atcggccaac gcgcggggag  5280
aggcggtttg cgtattgggc gctcttccgc ttcctcgctc actgactcgc tgcgctcggt  5340
cgttcggctg cggcgagcgg tatcagctca ctcaaaggcg gtaatacggt tatccacaga  5400
atcaggggat aacgcaggaa agaacatgtg agcaaaaggc cagcaaaagg ccaggaaccg  5460
taaaaaggcc gcgttgctgg cgtttttcca taggctccgc ccccctgacg agcatcacaa  5520
aaatcgacgc tcaagtcaga ggtggcgaaa cccgacagga ctataaagat accaggcgtt  5580
tccccctgga agctccctcg tgcgctctcc tgttccgacc ctgccgctta ccggatacct  5640
gtccgccttt ctcccttcgg gaagcgtggc gctttctcat agctcacgct gtaggtatct  5700
cagttcggtg taggtcgttc gctccaagct gggctgtgtg cacgaacccc ccgttcagcc  5760
cgaccgctgc gccttatccg gtaactatcg tcttgagtcc aacccggtaa gacacgactt  5820
atcgccactg gcagcagcca ctggtaacag gattagcaga gcgaggtatg taggcggtgc  5880
tacagagttc ttgaagtggt ggcctaacta cggctacact agaaggacag tatttggtat  5940
ctgcgctctg ctgaagccag ttaccttcgg aaaaagagtt ggtagctctt gatccggcaa  6000
```

```
acaaaccacc gctggtagcg gtggtttttt tgtttgcaag cagcagatta cgcgcagaaa  6060
aaaaggatct caagaagatc ctttgatctt ttctacgggg tctgacgctc agtggaacga  6120
aaactcacgt taagggattt tggtcatgag attatcaaaa aggatcttca cctagatcct  6180
tttaaattaa aaatgaagtt ttaaatcaat ctaaagtata tatgagtaaa cttggtctga  6240
cagttaccaa tgcttaatca gtgaggcacc tatctcagcg atctgtctat ttcgttcatc  6300
catagttgcc tgactccccg tcgtgtagat aactacgata cgggagggct taccatctgg  6360
ccccagtgct gcaatgatac cgcgagaccc acgctcaccg gctccagatt tatcagcaat  6420
aaaccagcca gccggaaggg ccgagcgcag aagtggtcct gcaactttat ccgcctccat  6480
ccagtctatt aattgttgcc gggaagctag agtaagtagt tcgccagtta atagtttgcg  6540
caacgttgtt gccattgcta caggcatcgt ggtgtcacgc tcgtcgtttg gtatggcttc  6600
attcagctcc ggttcccaac gatcaaggcg agttacatga tcccccatgt tgtgcaaaaa  6660
agcggttagc tccttcggtc ctccgatcgt tgtcagaagt aagttggccg cagtgttatc  6720
actcatggtt atggcagcac tgcataattc tcttactgtc atgccatccg taagatgctt  6780
ttctgtgact ggtgagtact caaccaagtc attctgagaa tagtgtatgc ggcgaccgag  6840
ttgctcttgc ccggcgtcaa tacgggataa taccgcgcca catagcagaa ctttaaaagt  6900
gctcatcatt ggaaaacgtt cttcggggcg aaaactctca aggatcttac cgctgttgag  6960
atccagttcg atgtaaccca ctcgtgcacc caactgatct tcagcatctt ttactttcac  7020
cagcgtttct gggtgagcaa aaacaggaag gcaaaatgcc gcaaaaaagg gaataagggc  7080
gacacggaaa tgttgaatac tcatactctt cctttttcaa tattattgaa gcatttatca  7140
gggttattgt ctcatgagcg gatacatatt tgaatgtatt tag                   7183
```

```
SEQ ID NO: 30          moltype = DNA  length = 7663
FEATURE                Location/Qualifiers
misc_feature           1..7663
                       note = pCVL_T7_DmrB-spacer-TM-41BB-CD3z lentiviral vector
source                 1..7663
                       mol_type = other DNA
                       organism = synthetic construct
SEQUENCE: 30
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tgggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatggct ctgcctgtga  2280
cagctctgct gctgcctctg gccctgctgc tccatgccgc cagacccgga tccggagtgc  2340
aggtggaaac catctcccca ggagacgggc gcaccttccc caagcgcggc cagacctgcg  2400
tggtgcacta caccgggatg cttgaagatg gaaagaaagt tgattcctcc cgggacagaa  2460
acaagccctt taagtttatg ctaggcaagc aggaggtgat ccgaggctgg gaagaagggg  2520
ttgcccagat gagtgtgggt cagagagcca aactgactat atctccagat tatgcctatg  2580
gtgccactgg gcacccaggc atcatcccac cacatgccac tctcgtcttc gatgtggagc  2640
ttctaaaact ggaagctagc gagagcaagt acggaccgcc ctgcccacct tgccctgccc  2700
ccgagttcct gggcggaccc agcgtgttcc tgttcccacc caagcccaag gacaccctga  2760
tgatcagccg gacccccgag gtgacctgcg tggtggtgga cgtgagccag gaagatcccg  2820
aggtccagtt caattggtac gtggacggcg tggaagtgca caacgccaag accaagccca  2880
gagaggaaca gttcaacagc acctaccggg tggtgtctgt gctgaccgtg ctgcaccagg  2940
actggctgaa cggcaaagaa tacaagtgca aggtgtccaa caagggcctg cccagcagca  3000
```

-continued

```
tcgaaaagac catcagcaag gccaagggcc agcctcgcga gccccaggtg tacaccctgc 3060
ctccctccca ggaagagatg accaagaacc aggtgtccct gacctgcctg gtgaagggct 3120
tctaccccag cgacatcgcc gtggagtggg agagcaacgg ccagcctgag aacaactaca 3180
agaccacccc tcccgtgctg gacagcgacg gcagcttctt cctgtacagc cggctgaccg 3240
tggacaagag ccggtggcag gaaggcaacg tctttagctg cagcgtgatg cacgaggccc 3300
tgcacaacca ctacacccag aagagcctga gcctgtccct gggcaagatg cataaacggg 3360
gcagaaagaa actcctgtat atattcaaac aaccatttat gagaccagta caaactactc 3420
aagaggaaga tggctgtagc tgccgatttc cagaagaaga agaaggagga tgtgaactgc 3480
gggtgaagtt cagcagaagc gccgacgccc ctgcctacca gcagggccag aatcagctgt 3540
acaacgagct gaacctgggc agaagggaag agtacgacgt cctggataag cggagaggcc 3600
gggaccctga gatgggcggc aagcctcggc ggaagaaccc ccaggaaggc ctgtataacg 3660
aactgcagaa agacaagatg gccgaggcct acagcgagat cggcatgaag ggcgagcgga 3720
ggcggggcaa gggccacgac ggcctgtatc agggcctgtc caccgccacc aaggatacct 3780
acgacgccct gcacatgcag gccctgcccc caaggggcgg ccgctccggt gagggcagag 3840
gaagtcttct aacatgcggt gacgtggagg agaatccggg cccctctaga agcgagctga 3900
ttaaggagaa catgcacatg aagctgtaca tggagggcac cgtggacaac catcacttca 3960
agtgcacatc cgagggcgaa ggcaagccct acgagggcac ccagaccatg agaatcaagg 4020
tggtcgaggg cggccctctc cccttcgcct tcgacatcct ggctactagc ttcctctacg 4080
gcagcaagac cttcatcaac cacacccagg gcatccccga cttcttcaag cagtccttcc 4140
ctgagggctt cacatgggag agagtcacca catacgaaga cgggggcgtg ctgaccgcta 4200
cccaggacac cagcctccag gacggctgcc tcatctacaa cgtcaagatc agaggggtga 4260
acttcacatc caacggccct gtgatgcaga agaaaacact cggctgggag gccttcaccg 4320
agacgctgta ccccgctgac ggcggcctgg aaggcagaaa cgacatggcc ctgaagctcg 4380
tgggcgggag ccatctgatc gcaaacatca agaccacata tagatccaag aaacccgcta 4440
agaacctcaa gatgcctggc gtctactatg tggactacag actggaaaga atcaaggagg 4500
ccaacaacga gacctacgtc gagcagcacg aggtggcagt ggccagatac tgcgacctcc 4560
ctagcaaact ggggcacaag cttaattgag tcgaccgagc atcttaccgc catttatacc 4620
catatttgtt ctgtttttct tgatttgggt atacatttaa atgttaatag aacaaaatgg 4680
tggggcaatc atttacattt ttagggatat gtaattacta gttcaggtgt attgccacaa 4740
gacaaacatg ttaagaaact ttcccgttat ttacgctctg ttcctgttaa tcaacctctg 4800
gattacaaaa tttgtgaaag attgactgat attcttaact atgttgctcc ttttacgctg 4860
tgtggatatg ctgctttata gcctctgtat ctagctattg cttcccgtac ggctttcgtt 4920
ttctcctcct tgtataaatc ctggttgctg tctcttttag aggagttgtg gcccgttgtc 4980
cgtcaacgtg gcgtggtgtg ctctgtgttt gctgacgcaa cccccactgg ctggggcatt 5040
gccaccacct gtcaactcct ttctgggact ttcgctttcc ccctccccgat cgccacggca 5100
gaactcatcg ccgcctgcct tgcccgctgc tggacagggg ctaggttgct gggcactgat 5160
aattccgtgg tgttgtcatc gaattcggta cctttttaaa agaaaagggg ggactggaag 5220
ggctaattca ctcccaacga agacaagata tcataacttc gtatagcata cattatacga 5280
agttataatt tatttgtgaa atttgtgatg ctattgcttt atttgtaacc atatgtttat 5340
ttgtgaaatt tgtgatgcta ttgctttatt tgtaaccatt gctttttgct tgtactgggt 5400
ctctctggtt agaccagatc tgagcctggg agctctctgg ctaactaggg aacccactgc 5460
ttaagcctca ataaagcttg cctcgaccag cctcgactgt gccttctagt tgccagccat 5520
ctgttgtttg cccctccccc gtgccttcct tgaccctgga aggtgccact cccactgtcc 5580
tttcctaata aaatgaggaa attgcatcgc attgtctgag taggtgtcat tctattctgg 5640
ggggtggggt ggggcaggac agcaaggggg aggattggga agacaatagc aggcatgctg 5700
gggatgcggt gggctctatg gcctgcagct gcattaatga atcggccaac gcgcggggag 5760
aggcggtttg cgtattgggc gctcttccgc ttcctcgctc actgactcgc tgcgctcggt 5820
cgttcggctg cggcgagcgg tatcagctca ctcaaaggcg gtaatacggt tatccacaga 5880
atcaggggat aacgcaggaa agaacatgtg agcaaaaggc cagcaaaagg ccaggaaccg 5940
taaaaaggcc gcgttgctgg cgtttttcca taggctccgc ccccctgacg agcatcacaa 6000
aaatcgacgc tcaagtcaga ggtggcgaaa cccgacagga ctataaagat accaggcgtt 6060
tccccctgga agctccctcg tgcgctctcc tgttccgacc ctgccgctta ccggatacct 6120
gtccgccttt ctcccttcgg gaagcgtggc gctttctcat agctcacgct gtaggtatct 6180
cagttcggtg taggtcgttc gctccaagct gggctgtgtg cacgaacccc ccgttcagcc 6240
cgaccgctgc gccttatccg gtaactatcg tcttgagtcc aacccggtaa gacacgactt 6300
atcgccactg gcagcagcca ctggtaacag gattagcaga gcgaggtatg taggcggtgc 6360
tacagagttc ttgaagtggt ggcctaacta cggctacact agaaggacag tatttggtat 6420
ctgcgctctg ctgaagccag ttaccttcgg aaaaagagtt ggtagctctt gatccggcaa 6480
acaaaccacc gctggtagcg gtggtttttt tgtttgcaag cagcagatta cgcgcagaaa 6540
aaaaggatct caagaagatc ctttgatctt ttctacgggg tctgacgctc agtggaacga 6600
aaactcacgt taagggattt tggtcatgag attatcaaaa aggatcttca cctagatcct 6660
tttaaattaa aaatgaagtt ttaaatcaat ctaaagtata tatgagtaaa cttggtctga 6720
cagttaccaa tgcttaatca gtgaggcacc tatctcagcg atctgtctat ttcgttcatc 6780
catagttgcc tgactccccg tcgtgtagat aactacgata cgggagggct taccatctgg 6840
ccccagtgct gcaatgatac cgcgagaccc acgctcaccg gctccagatt tatcagcaat 6900
aaaccagcca gccggaaggg ccgagcgcag aagtggtcct gcaactttat ccgcctccat 6960
ccagtctatt aattgttgcc gggaagctag agtaagtagt tcgccagtta atagtttgcg 7020
caacgttgtt gccattgcta caggcatcgt ggtgtcacgc tcgtcgtttg gtatggcttc 7080
attcagctcc ggttcccaac gatcaaggcg agttacatga tcccccatgt tgtgcaaaaa 7140
agcggttagc tccttcggtc ctccgatcgt tgtcagaagt aagttggccg cagtgttatc 7200
actcatggtt atggcagcac tgcataattc tcttactgtc atgccatccg taagatgctt 7260
ttctgtgact ggtgagtact caaccaagtc attctgagaa tagtgtatgc ggcgaccgag 7320
ttgctcttgc ccggcgtcaa tacgggataa taccgcgcca catagcagaa ctttaaaagt 7380
gctcatcatt ggaaaacgtt cttcggggcg aaaactctca aggatcttac cgctgttgag 7440
atccagttcg atgtaaccca ctcgtgcacc caactgatct tcagcatctt ttactttcac 7500
cagcgtttct gggtgagcaa aaacaggaag gcaaaatgcc gcaaaaaagg gaataagggc 7560
gacacggaaa tgttgaatac tcatactctt cctttttcaa tattattgaa gcatttatca 7620
gggttattgt ctcatgagcg gatacatatt tgaatgtatt tag 7663
```

```
SEQ ID NO: 31           moltype = DNA  length = 7183
FEATURE                 Location/Qualifiers
misc_feature            1..7183
                        note = pCVL_T7_DmrA-TM-41BB-CD3z lentiviral vector
source                  1..7183
                        mol_type = other DNA
                        organism = synthetic construct
SEQUENCE: 31
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatggct ctgcctgtga  2280
cagctctgct gctgcctctg gccctgctgc tccatgccgc cagacccgga tccggagtgc  2340
aggtggaaac catctcccca ggagacgggc gcaccttccc caagcgcggc cagacctgcg  2400
tggtgcacta caccgggatg cttgaagatg gaaagaaatt tgattcctcc cgggacagaa  2460
acaagccctt taagtttatg ctaggcaagc aggaggtgat ccgaggctgg gaagaagggg  2520
ttgcccagat gagtgtgggt cagagagcca aactgactat atctccagat tatgcctatg  2580
gtgccactgg gcacccaggc atcatcccac cacatgccac tctcgtcttc gatgtggagc  2640
ttctaaaact ggaagctagc gccaagccta ccaccacccc tgcccctaga cctccaacac  2700
ccgccccaac aatcgccagc cagcctctgt ctctgaggcc cgaggcttgt agaccagctg  2760
ctggcggagc cgtgcacacc agaggactgg atttcgcctg cgacatctac atctgggccc  2820
ctctggccgg cacatgtggc gtgctgctgc tgagcctcgt gatcaccatg cataaacggg  2880
gcagaaagaa actcctgtat atattcaaac aaccatttat gagaccagta caaactactc  2940
aagaggaaga tggctgtagc tgccgatttc cagaagaaga agaaggagga tgtgaactgc  3000
gggtgaagtt cagcagaagc gccgacgccc ctgcctacca gcagggccag aatcagctgt  3060
acaacgagct gaacctgggc agaagggaag agtacgacgt cctggataag cggagaggcc  3120
gggaccctga gatgggcggc aagcctcggc ggaagaaccc ccaggaaggc ctgtataacg  3180
aactgcagaa agacaagatg gccgaggcct acagcgagat cggcatgaag ggcgagcgga  3240
ggcggggcaa gggccacgac ggcctgtatc agggcctgtc caccgccacc aaggatacct  3300
acgacgccct gcacatgcag gccctgcccc caaggggcgg ccgctccggt gagggcagag  3360
gaagtcttct aacatgcggt gacgtggagg agaatccggg cccctctaga agcgagctga  3420
ttaaggagaa catgcacatg aagctgtaca tggagggcac cgtggacaac catcacttca  3480
agtgcacatc cgagggcgaa ggcaagccct acgagggcac ccagaccatg agaatcaagg  3540
tggtcgaggg cggccctctc cccttcgcct tcgacatcct ggctactagc ttcctctacg  3600
gcagcaagac cttcatcaac cacacccagg gcatccccga cttcttcaag cagtccttcc  3660
ctgagggctt cacatgggag agagtcacca catacgaaga cgggggcgtg ctgaccgcta  3720
cccaggacac cagcctccag gacggctgcc tcatctacaa cgtcaagatc agaggggtga  3780
acttcacatc caacggccct gtgatgcaga agaaaacact cggctgggag gccttcaccg  3840
agacgctgta ccccgctgac ggcggcctgg aaggcagaaa cgacatggcc ctgaagctcg  3900
tgggcgggag ccatctgatc gcaaacatca agaccacata tagatccaag aaacccgcta  3960
agaacctcaa gatgcctggc gtctactatg tggactacag actggaaaga atcaaggagg  4020
ccaacaacga gacctacgtc gagcagcacg aggtggcagt ggccagatac tgcgacctcc  4080
ctagcaaact ggggcacaag cttaattgag tcgaccgagc atcttaccgc catttatacc  4140
catatttgtt ctgtttttct tgatttgggt atacatttaa atgttaatag aacaaaatgg  4200
tggggcaatc atttacattt ttagggatat gtaattacta gttcaggtgt attgccacaa  4260
```

```
gacaaacatg ttaagaaact ttcccgttat ttacgctctg ttcctgttaa tcaacctctg  4320
gattacaaaa tttgtgaaag attgactgat attcttaact atgttgctcc ttttacgctg  4380
tgtggatatg ctgctttata gcctctgtat ctagctattg cttcccgtac ggctttcgtt  4440
ttctcctcct tgtataaatc ctggttgctg tctcttttag aggagttgtg gcccgttgtc  4500
cgtcaacgtg gcgtggtgtg ctctgtgttt gctgacgcaa cccccactgg ctggggcatt  4560
gccaccacct gtcaactcct ttctgggact ttcgctttcc ccctcccgat cgccacggca  4620
gaactcatcg ccgcctgcct tgcccgctgc tggacagggg ctaggttgct gggcactgat  4680
aattccgtgg tgttgtcatc gaattcggta ccttttaaa agaaaagggg ggactggaag  4740
ggctaattca ctcccaacga agacaagata tcataacttc gtatagcata cattatacga  4800
agttataatt tatttgtgaa atttgtgatg ctattgcttt atttgtaacc atatgtttat  4860
ttgtgaaatt tgtgatgcta ttgctttatt tgtaaccatt gctttttgct tgtactgggt  4920
ctctctggtt agaccagatc tgagcctggg agctctctgg ctaactaggg aacccactgc  4980
ttaagcctca ataaagcttg cctcgaccag cctcgactgt gccttctagt tgccagccat  5040
ctgttgtttg cccctccccc gtgccttcct tgaccctgga aggtgccact cccactgtcc  5100
tttcctaata aaatgaggaa attgcatcgc attgtctgag taggtgtcat tctattctgg  5160
ggggtggggt ggggcaggac agcaaggggg aggattggga agacaatagc aggcatgctg  5220
gggatgcggt gggctctatg gcctgcagct gcattaatga atcggccaac gcgcggggag  5280
aggcggtttg cgtattgggc gctcttccgc ttcctcgctc actgactcgc tgcgctcggt  5340
cgttcggctg cggcgagcgg tatcagctca ctcaaaggcg gtaatacggt tatccacaga  5400
atcaggggat aacgcaggaa agaacatgtg agcaaaaggc cagcaaaagg ccaggaaccg  5460
taaaaaggcc gcgttgctgg cgtttttcca taggctccgc ccccctgacg agcatcacaa  5520
aaatcgacgc tcaagtcaga ggtggcgaaa cccgacagga ctataaagat accaggcgtt  5580
tccccctgga agctccctcg tgcgctctcc tgttccgacc ctgccgctta ccggatacct  5640
gtccgccttt ctcccttcgg gaagcgtggc gctttctcat agctcacgct gtaggtatct  5700
cagttcggtg taggtcgttc gctccaagct gggctgtgtg cacgaacccc ccgttcagcc  5760
cgaccgctgc gccttatccg gtaactatcg tcttgagtcc aacccggtaa gacacgactt  5820
atcgccactg gcagcagcca ctggtaacag gattagcaga gcgaggtatg taggcggtgc  5880
tacagagttc ttgaagtggt ggcctaacta cggctacact agaaggacag tatttggtat  5940
ctgcgctctg ctgaagccag ttaccttcgg aaaaagagtt ggtagctctt gatccggcaa  6000
acaaaccacc gctggtagcg gtggtttttt tgtttgcaag cagcagatta cgcgcagaaa  6060
aaaaggatct caagaagatc ctttgatctt ttctacgggg tctgacgctc agtggaacga  6120
aaactcacgt taagggattt tggtcatgag attatcaaaa aggatcttca cctagatcct  6180
tttaaattaa aaatgaagtt ttaaatcaat ctaaagtata tatgagtaaa cttggtctga  6240
cagttaccaa tgcttaatca gtgaggcacc tatctcagcg atctgtctat ttcgttcatc  6300
catagttgcc tgactccccg tcgtgtagat aactacgata cgggagggct taccatctgg  6360
ccccagtgct gcaatgatac cgcgagaccc acgctcaccg gctccagatt tatcagcaat  6420
aaaccagcca gccggaaggg ccgagcgcag aagtggtcct gcaactttat ccgcctccat  6480
ccagtctatt aattgttgcc gggaagctag agtaagtagt tcgccagtta atagtttgcg  6540
caacgttgtt gccattgcta caggcatcgt ggtgtcacgc tcgtcgtttg gtatggcttc  6600
attcagctcc ggttcccaac gatcaaggcg agttacatga tcccccatgt tgtgcaaaaa  6660
agcggttagc tccttcggtc ctccgatcgt tgtcagaagt aagttggccg cagtgttatc  6720
actcatggtt atggcagcac tgcataattc tcttactgtc atgccatccg taagatgctt  6780
ttctgtgact ggtgagtact caaccaagtc attctgagaa tagtgtatgc ggcgaccgag  6840
ttgctcttgc ccggcgtcaa tacgggataa taccgcgcca catagcagaa ctttaaaagt  6900
gctcatcatt ggaaaacgtt cttcggggcg aaaactctca aggatcttac cgctgttgag  6960
atccagttcg atgtaaccca ctcgtgcacc caactgatct tcagcatctt ttactttcac  7020
cagcgtttct gggtgagcaa aaacaggaag gcaaaatgcc gcaaaaaagg gaataagggc  7080
gacacggaaa tgttgaatac tcatactctt cctttttcaa tattattgaa gcatttatca  7140
gggttattgt ctcatgagcg gatacatatt tgaatgtatt tag                   7183

SEQ ID NO: 32           moltype = DNA  length = 7663
FEATURE                 Location/Qualifiers
misc_feature            1..7663
                        note = pCVL_T7_DmrA-spacer-TM-41BB-CD3z lentiviral vector
source                  1..7663
                        mol_type = other DNA
                        organism = synthetic construct
SEQUENCE: 32
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
```

```
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tgggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatggct ctgcctgtga  2280
cagctctgct gctgcctctg gccctgctgc tccatgccgc cagacccgga tccggagtgc  2340
aggtggaaac catctcccca ggagacgggc gcaccttccc caagcgcggc cagacctgcg  2400
tggtgcacta caccgggatg cttgaagatg gaaagaaatt tgattcctcc cgggacagaa  2460
acaagccctt taagtttatg ctaggcaagc aggaggtgat ccgaggctgg gaagaagggg  2520
ttgcccagat gagtgtgggt cagagagcca aactgactat atctccagat tatgcctatg  2580
gtgccactgg gcacccaggc atcatcccac cacatgccac tctcgtcttc gatgtggagc  2640
ttctaaaact ggaagctagc gagagcaagt acggaccgcc ctgcccacct tgccctgccc  2700
ccgagttcct gggcggaccc agcgtgttcc tgttcccacc caagcccaag gacaccctga  2760
tgatcagccg gacccccgag gtgacctgcg tggtggtgga cgtgagccag gaagatcccg  2820
aggtccagtt caattggtac gtggacggcg tggaagtgca caacgccaag accaagccca  2880
gagaggaaca gttcaacagc acctaccggg tggtgtctgt gctgaccgtg ctgcaccagg  2940
actggctgaa cggcaaagaa tacaagtgca aggtgtccaa caagggcctg cccagcagca  3000
tcgaaaagac catcagcaag gccaagggcc agcctcgcga gccccaggtg tacaccctgc  3060
ctccctccca ggaagagatg accaagaacc aggtgtccct gacctgcctg gtgaagggct  3120
tctaccccag cgacatcgcc gtggagtggg agagcaacgg ccagcctgag aacaactaca  3180
agaccacccc tcccgtgctg gacagcgacg gcagcttctt cctgtacagc cggctgaccg  3240
tggacaagag ccggtggcag gaaggcaacg tctttagctg cagcgtgatg cacgaggccc  3300
tgcacaacca ctacacccag aagagcctga gcctgtccct gggcaagatg cataaacggg  3360
gcagaaagaa actcctgtat atattcaaac aaccatttat gagaccagta caaactactc  3420
aagaggaaga tggctgtagc tgccgatttc cagaagaaga agaaggagga tgtgaactgc  3480
gggtgaagtt cagcagaagc gccgacgccc ctgcctacca gcagggccag aatcagctgt  3540
acaacgagct gaacctgggc agaagggaag agtacgacgt cctggataag cggagaggcc  3600
gggaccctga gatgggcggc aagcctcggc ggaagaaccc ccaggaaggc ctgtataacg  3660
aactgcagaa agacaagatg gccgaggcct acagcgagat cggcatgaag ggcgagcgga  3720
ggcggggcaa gggccacgac ggcctgtatc agggcctgtc caccgccacc aaggatacct  3780
acgacgccct gcacatgcag gccctgcccc caaggggcgg ccgctccggt gagggcagag  3840
gaagtcttct aacatgcggt gacgtggagg agaatccggg cccctctaga agcgagctga  3900
ttaaggagaa catgcacatg aagctgtaca tggagggcac cgtggacaac catcacttca  3960
agtgcacatc cgagggcgaa ggcaagccct acgagggcac ccagaccatg agaatcaagg  4020
tggtcgaggg cggccctctc cccttcgcct tcgacatcct ggctactagc ttcctctacg  4080
gcagcaagac cttcatcaac cacacccagg gcatccccga cttcttcaag cagtccttcc  4140
ctgagggctt cacatgggag agagtcacca catacgaaga cgggggcgtg ctgaccgcta  4200
cccaggacac cagcctccag gacggctgcc tcatctacaa cgtcaagatc agaggggtga  4260
acttcacatc caacggccct gtgatgcaga agaaaacact cggctgggag gccttcaccg  4320
agacgctgta ccccgctgac ggcggcctgg aaggcagaaa cgacatggcc ctgaagctcg  4380
tgggcgggag ccatctgatc gcaaacatca agaccacata tagatccaag aaacccgcta  4440
agaacctcaa gatgcctggc gtctactatg tggactacag actggaaaga atcaaggagg  4500
ccaacaacga gacctacgtc gagcagcacg aggtggcagt ggccagatac tgcgacctcc  4560
ctagcaaact ggggcacaag cttaattgag tcgaccgagc atcttaccgc catttatacc  4620
catatttgtt ctgtttttct tgatttgggt atacatttaa atgttaatag aacaaaatgg  4680
tggggcaatc atttacattt ttagggatat gtaattacta gttcaggtgt attgccacaa  4740
gacaaacatg ttaagaaact ttcccgttat ttacgctctg ttcctgttaa tcaacctctg  4800
gattacaaaa tttgtgaaag attgactgat attcttaact atgttgctcc ttttacgctg  4860
tgtggatatg ctgctttata gcctctgtat ctagctattg cttcccgtac ggctttcgtt  4920
ttctcctcct tgtataaatc ctggttgctg tctcttttag aggagttgtg gcccgttgtc  4980
cgtcaacgtg gcgtggtgtg ctctgtgttt gctgacgcaa cccccactgg ctggggcatt  5040
gccaccacct gtcaactcct ttctgggact ttcgctttcc ccctcccgat cgccacggca  5100
gaactcatcg ccgcctgcct tgcccgctgc tggacagggg ctaggttgct gggcactgat  5160
aattccgtgg tgttgtcatc gaattcggta ccttttttaaa agaaaagggg ggactggaag  5220
ggctaattca ctcccaacga agacaagata tcataacttc gtatagcata cattatacga  5280
agttataatt tatttgtgaa atttgtgatg ctattgcttt atttgtaacc atatgtttat  5340
ttgtgaaatt tgtgatgcta ttgctttatt tgtaaccatt gcttttgct tgtactgggt  5400
ctctctggtt agaccagatc tgagcctggg agctctctgg ctaactaggg aacccactgc  5460
ttaagcctca ataaagcttg cctcgaccag cctcgactgt gccttctagt tgccagccat  5520
ctgttgtttg cccctccccc gtgccttcct tgaccctgga aggtgccact cccactgtcc  5580
tttcctaata aaatgaggaa attgcatcgc attgtctgag taggtgtcat tctattctgg  5640
ggggtggggt ggggcaggac agcaaggggg aggattggga agacaatagc aggcatgctg  5700
gggatgcggt gggctctatg gcctgcagct gcattaatga atcggccaac gcgcggggag  5760
aggcggtttg cgtattgggc gctcttccgc ttcctcgctc actgactcgc tgcgctcggt  5820
cgttcggctg cggcgagcgg tatcagctca ctcaaaggcg gtaatacggt tatccacaga  5880
atcaggggat aacgcaggaa agaacatgtg agcaaaaggc cagcaaaagg ccaggaaccg  5940
taaaaaggcc gcgttgctgg cgtttttcca taggctccgc ccccctgacg agcatcacaa  6000
```

```
aaatcgacgc tcaagtcaga ggtggcgaaa cccgacagga ctataaagat accaggcgtt  6060
tccccctgga agctccctcg tgcgctctcc tgttccgacc ctgccgctta ccggatacct  6120
gtccgccttt ctcccttcgg gaagcgtggc gctttctcat agctcacgct gtaggtatct  6180
cagttcggtg taggtcgttc gctccaagct gggctgtgtg cacgaacccc ccgttcagcc  6240
cgaccgctgc gccttatccg gtaactatcg tcttgagtcc aacccggtaa gacacgactt  6300
atcgccactg gcagcagcca ctggtaacag gattagcaga gcgaggtatg taggcggtgc  6360
tacagagttc ttgaagtggt ggcctaacta cggctacact agaaggacag tatttggtat  6420
ctgcgctctg ctgaagccag ttaccttcgg aaaaagagtt ggtagctctt gatccggcaa  6480
acaaaccacc gctggtagcg gtggtttttt tgtttgcaag cagcagatta cgcgcagaaa  6540
aaaaggatct caagaagatc ctttgatctt ttctacgggg tctgacgctc agtggaacga  6600
aaactcacgt taagggattt tggtcatgag attatcaaaa aggatcttca cctagatcct  6660
tttaaattaa aaatgaagtt ttaaatcaat ctaaagtata tatgagtaaa cttggtctga  6720
cagttaccaa tgcttaatca gtgaggcacc tatctcagcg atctgtctat ttcgttcatc  6780
catagttgcc tgactccccg tcgtgtagat aactacgata cgggagggct taccatctgg  6840
ccccagtgct gcaatgatac cgcgagaccc acgctcaccg gctccagatt tatcagcaat  6900
aaaccagcca gccggaaggg ccgagcgcag aagtggtcct gcaactttat ccgcctccat  6960
ccagtctatt aattgttgcc gggaagctag agtaagtagt tcgccagtta atagtttgcg  7020
caacgttgtt gccattgcta caggcatcgt ggtgtcacgc tcgtcgtttg gtatggcttc  7080
attcagctcc ggttcccaac gatcaaggcg agttacatga tcccccatgt tgtgcaaaaa  7140
agcggttagc tccttcggtc ctccgatcgt tgtcagaagt aagttggccg cagtgttatc  7200
actcatggtt atggcagcac tgcataattc tcttactgtc atgccatccg taagatgctt  7260
ttctgtgact ggtgagtact caaccaagtc attctgagaa tagtgtatgc ggcgaccgag  7320
ttgctcttgc ccggcgtcaa tacgggataa taccgcgcca catagcagaa ctttaaaagt  7380
gctcatcatt ggaaaacgtt cttcggggcg aaaactctca aggatcttac cgctgttgag  7440
atccagttcg atgtaaccca ctcgtgcacc caactgatct tcagcatctt ttactttcac  7500
cagcgtttct gggtgagcaa aaacaggaag gcaaaatgcc gcaaaaaagg gaataagggc  7560
gacacggaaa tgttgaatac tcatactctt cctttttcaa tattattgaa gcatttatca  7620
gggttattgt ctcatgagcg gatacatatt tgaatgtatt tag                   7663

SEQ ID NO: 33          moltype = DNA  length = 7477
FEATURE                Location/Qualifiers
misc_feature           1..7477
                       note = pCVL_T7_DmrB-DmrC-TM-41BB-CD3z lentiviral vector
source                 1..7477
                       mol_type = other DNA
                       organism = synthetic construct
SEQUENCE: 33
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actataggt ccactgccgc caccatggct ctgcctgtga  2280
cagctctgct gctgcctctg gccctgctgc tccatgccgc cagacccgga tccggagtgc  2340
aggtggaaac catctcccca ggagacgggc gcaccttccc caagcgcggc cagacctgcg  2400
tggtgcacta caccgggatg cttgaagatg gaaagaaagt tgattcctcc cgggacagaa  2460
acaagccctt taagtttatg ctaggcaagc aggaggtgat ccgaggctgg gaagaagggg  2520
```

```
ttgcccagat gagtgtgggt cagagagcca aactgactat atctccagat tatgcctatg  2580
gtgccactgg gcacccaggc atcatcccac cacatgccac tctcgtcttc gatgtggagc  2640
ttctaaaact ggaaggcgga ggtgggagca tcctctggca tgagatgtgg catgaaggcc  2700
tggaagaggc atctcgtttg tactttgggg aaaggaacgt gaaaggcatg tttgaggtgc  2760
tggagccctt gcatgctatg atggaacggg gcccccagac tctgaaggaa acatccttta  2820
atcaggccta tggtcgagat ttaatggagg cccaagagtg gtgcaggaag tacatgaaat  2880
cagggaatgt caaggacctc ctccaagcct gggacctcta ttatcatgtg ttccgacgaa  2940
tctcaaaggc tagcgccaag cctaccacca cccctgcccc tagacctcca acacccgccc  3000
caacaatcgc cagccagcct ctgtctctga ggcccgaggc ttgtagacca gctgctggcg  3060
gagccgtgca caccagagga ctggatttcg cctgcgacat ctacatctgg gcccctctgg  3120
ccggcacatg tggcgtgctg ctgctgagcc tcgtgatcac catgcataaa cggggcagaa  3180
agaaactcct gtatatattc aaacaaccat ttatgagacc agtacaaact actcaagagg  3240
aagatggctg tagctgccga tttccagaag aagaagaagg aggatgtgaa ctgcgggtga  3300
agttcagcag aagcgccgac gcccctgcct accagcaggg ccagaatcag ctgtacaacg  3360
agctgaacct gggcagaagg gaagagtacg acgtcctgga taagcggaga ggccgggacc  3420
ctgagatggg cggcaagcct cggcggaaga acccccagga aggcctgtat aacgaactgc  3480
agaaagacaa gatggccgag gcctacagcg agatcggcat gaagggcgag cggaggcggg  3540
gcaagggcca cgacggcctg tatcagggcc tgtccaccgc caccaaggat acctacgacg  3600
ccctgcacat gcaggccctg cccccaaggg gcggccgctc cggtgagggc agaggaagtc  3660
ttctaacatg cggtgacgtg gaggagaatc cgggcccctc tagaagcgag ctgattaagg  3720
agaacatgca catgaagctg tacatggagg gcaccgtgga caaccatcac ttcaagtgca  3780
catccgaggg cgaaggcaag ccctacgagg gcacccagac catgagaatc aaggtggtcg  3840
agggcggccc tctccccttc gccttcgaca tcctggctac tagcttcctc tacggcagca  3900
agaccttcat caaccacacc cagggcatcc ccgacttctt caagcagtcc ttccctgagg  3960
gcttcacatg ggagagagtc accacatacg aagacggggg cgtgctgacc gctacccagg  4020
acaccagcct ccaggacggc tgcctcatct acaacgtcaa gatcagaggg gtgaacttca  4080
catccaacgg ccctgtgatg cagaagaaaa cactcggctg ggaggccttc accgagacgc  4140
tgtaccccgc tgacggcggc ctggaaggca gaaacgacat ggccctgaag ctcgtgggcg  4200
ggagccatct gatcgcaaac atcaagacca catatagatc caagaaaccc gctaagaacc  4260
tcaagatgcc tggcgtctac tatgtggact acagactgga aagaatcaag gaggccaaca  4320
acgagaccta cgtcgagcag cacgaggtgg cagtggccag atactgcgac ctccctagca  4380
aactggggca caagcttaat tgagtcgacc gagcatctta ccgccattta tacccatatt  4440
tgttctgttt ttcttgattt gggtatacat ttaaatgtta atagaacaaa atggtggggc  4500
aatcatttac atttttaggg atatgtaatt actagttcag gtgtattgcc acaagacaaa  4560
catgttaaga aactttcccg ttatttacgc tctgttcctg ttaatcaacc tctggattac  4620
aaaatttgtg aaagattgac tgatattctt aactatgttg ctccttttac gctgtgtgga  4680
tatgctgctt tatagcctct gtatctagct attgcttccc gtacggcttt cgttttctcc  4740
tccttgtata aatcctggtt gctgtctctt ttagaggagt tgtggcccgt tgtccgtcaa  4800
cgtggcgtgg tgtgctctgt gtttgctgac gcaaccccca ctggctgggg cattgccacc  4860
acctgtcaac tcctttctgg gactttcgct ttccccctcc cgatcgccac ggcagaactc  4920
atcgccgcct gccttgcccg ctgctggaca ggggctaggt tgctgggcac tgataattcc  4980
gtggtgttgt catcgaattc ggtacctttt taaaagaaaa ggggggactg gaagggctaa  5040
ttcactccca acgaagacaa gatatcataa cttcgtatag catacattat acgaagttat  5100
aatttatttg tgaaatttgt gatgctattg ctttatttgt aaccatatgt ttatttgtga  5160
aatttgtgat gctattgctt tatttgtaac cattgctttt tgcttgtact gggtctctct  5220
ggttagacca gatctgagcc tgggagctct ctggctaact agggaaccca ctgcttaagc  5280
ctcaataaag cttgcctcga ccagcctcga ctgtgccttc tagttgccag ccatctgttg  5340
tttgcccctc ccccgtgcct tccttgaccc tggaaggtgc cactcccact gtcctttcct  5400
aataaaatga ggaaattgca tcgcattgtc tgagtaggtg tcattctatt ctggggggtg  5460
gggtggggca ggacagcaag ggggaggatt gggaagacaa tagcaggcat gctggggatg  5520
cggtgggctc tatggcctgc agctgcatta atgaatcggc caacgcgcgg ggagaggcgg  5580
tttgcgtatt gggcgctctt ccgcttcctc gctcactgac tcgctgcgct cggtcgttcg  5640
gctgcggcga gcggtatcag ctcactcaaa ggcggtaata cggttatcca cagaatcagg  5700
ggataacgca ggaaagaaca tgtgagcaaa aggccagcaa aaggccagga accgtaaaaa  5760
ggccgcgttg ctggcgtttt tccataggct ccgcccccct gacgagcatc acaaaaatcg  5820
acgctcaagt cagaggtggc gaaacccgac aggactataa agataccagg cgtttccccc  5880
tggaagctcc ctcgtgcgct ctcctgttcc gaccctgccg cttaccggat acctgtccgc  5940
ctttctccct tcgggaagcg tggcgctttc tcatagctca cgctgtaggt atctcagttc  6000
ggtgtaggtc gttcgctcca agctgggctg tgtgcacgaa ccccccgttc agcccgaccg  6060
ctgcgcctta tccggtaact atcgtcttga gtccaacccg gtaagacacg acttatcgcc  6120
actggcagca gccactggta acaggattag cagagcgagg tatgtaggcg gtgctacaga  6180
gttcttgaag tggtggccta actacggcta cactagaagg acagtatttg gtatctgcgc  6240
tctgctgaag ccagttacct tcggaaaaag agttggtagc tcttgatccg gcaaacaaac  6300
caccgctggt agcggtggtt tttttgtttg caagcagcag attacgcgca gaaaaaaagg  6360
atctcaagaa gatcctttga tcttttctac ggggtctgac gctcagtgga acgaaaactc  6420
acgttaaggg attttggtca tgagattatc aaaaaggatc ttcacctaga tccttttaaa  6480
ttaaaaatga agttttaaat caatctaaag tatatatgag taaacttggt ctgacagtta  6540
ccaatgctta atcagtgagg cacctatctc agcgatctgt ctatttcgtt catccatagt  6600
tgcctgactc cccgtcgtgt agataactac gatacgggag ggcttaccat ctggccccag  6660
tgctgcaatg ataccgcgag acccacgctc accggctcca gatttatcag caataaacca  6720
gccagccgga agggccgagc gcagaagtgg tcctgcaact ttatccgcct ccatccagtc  6780
tattaattgt tgccgggaag ctagagtaag tagttcgcca gttaatagtt tgcgcaacgt  6840
tgttgccatt gctacaggca tcgtggtgtc acgctcgtcg tttggtatgg cttcattcag  6900
ctccggttcc caacgatcaa ggcgagttac atgatccccc atgttgtgca aaaaagcggt  6960
tagctccttc ggtcctccga tcgttgtcag aagtaagttg gccgcagtgt tatcactcat  7020
ggttatggca gcactgcata attctcttac tgtcatgcca tccgtaagat gcttttctgt  7080
gactggtgag tactcaacca agtcattctg agaatagtgt atgcggcgac cgagttgctc  7140
ttgcccggcg tcaatacggg ataataccgc gccacatagc agaactttaa aagtgctcat  7200
cattggaaaa cgttcttcgg ggcgaaaact ctcaaggatc ttaccgctgt tgagatccag  7260
```

```
ttcgatgtaa cccactcgtg cacccaactg atcttcagca tcttttactt tcaccagcgt  7320
ttctgggtga gcaaaaacag gaaggcaaaa tgccgcaaaa aagggaataa gggcgacacg  7380
gaaatgttga atactcatac tcttcctttt tcaatattat tgaagcattt atcagggtta  7440
ttgtctcatg agcggataca tatttgaatg tatttag                           7477

SEQ ID NO: 34          moltype = DNA  length = 7519
FEATURE                Location/Qualifiers
misc_feature           1..7519
                       note = pCVL_T7_DmrB-DmrA-TM-41BB-CD3z lentiviral vector
source                 1..7519
                       mol_type = other DNA
                       organism = synthetic construct
SEQUENCE: 34
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgagggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gccttttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatggct ctgcctgtga  2280
cagctctgct gctgcctctg gccctgctgc tccatgccgc cagacccgga tccggagtgc  2340
aggtggaaac catctcccca ggagacgggc gcaccttccc caagcgcggc cagacctgcg  2400
tggtgcacta caccgggatg cttgaagatg gaaagaaagt tgattcctcc cgggacagaa  2460
acaagccctt taagtttatg ctaggcaagc aggaggtgat ccgaggctgg gaagaagggg  2520
ttgcccagat gagtgtgggt cagagagcca aactgactat atctccagat tatgcctatg  2580
gtgccactgg gcacccaggc atcatcccac cacatgccac tctcgtcttc gatgtggagc  2640
ttctaaaact ggaaggcgga ggtgggagcg gagtgcaggt ggaaaccatc tccccaggag  2700
acgggcgcac cttccccaag cgcggccaga cctgcgtggt gcactacacc gggatgcttg  2760
aagatggaaa gaaatttgat tcctcccggg acagaaacaa gccctttaag tttatgctag  2820
gcaagcagga ggtgatccga ggctgggaag aaggggttgc ccagatgagt gtgggtcaga  2880
gagccaaact gactatatct ccagattatg cctatggtgc cactgggcac ccaggcatca  2940
tcccaccaca tgccactctc gtcttcgatg tggagcttct aaaactggaa gctagcgcca  3000
agcctaccac caccccctgcc cctagacctc caacacccgc cccaacaatc gccagccagc  3060
ctctgtctct gaggcccgag gcttgtagac cagctgctgg cggagccgtg cacaccagag  3120
gactggattt cgcctgcgac atctacatct gggcccctct ggccggcaca tgtggcgtgc  3180
tgctgctgag cctcgtgatc accatgcata aacggggcag aaagaaactc ctgtatatat  3240
tcaaacaacc atttatgaga ccagtacaaa ctactcaaga ggaagatggc tgtagctgcc  3300
gatttccaga agaagaagaa ggaggatgtg aactgcgggt gaagttcagc agaagcgccg  3360
acgcccctgc ctaccagcag ggccagaatc agctgtacaa cgagctgaac ctgggcagaa  3420
gggaagagta cgacgtcctg gataagcgga gaggccggga ccctgagatg ggcggcaagc  3480
ctcggcggaa gaaccccccag gaaggcctgt ataacgaact gcagaaagac aagatggccg  3540
aggcctacag cgagatcggc atgaagggcg agcggaggcg gggcaagggc cacgacggcc  3600
tgtatcaggg cctgtccacc gccaccaagg atacctacga cgccctgcac atgcaggccc  3660
tgcccccaag ggcggccgc tccggtgagg gcagaggaag tcttctaaca tgcggtgacg  3720
tggaggagaa tcccgggcccc tctagaagcg agctgattaa ggagaacatg cacatgaagc  3780
tgtacatgga gggcaccgtg gacaaccatc acttcaagtg cacatccgag ggcgaaggca  3840
agccctacga gggcacccag accatgagaa tcaaggtggt cgagggcggc cctctcccct  3900
tcgccttcga catcctggct actagcttcc tctacggcag caagaccttc atcaaccaca  3960
```

```
cccagggcat ccccgacttc ttcaagcagt ccttccctga gggcttcaca tgggagagag  4020
tcaccacata cgaagacggg ggcgtgctga ccgctaccca ggacaccagc ctccaggacg  4080
gctgcctcat ctacaacgtc aagatcagag gggtgaactt cacatccaac ggccctgtga  4140
tgcagaagaa aacactcggc tgggaggcct tcaccgagac gctgtacccc gctgacggcg  4200
gcctggaagg cagaaacgac atggccctga agctcgtggg cgggagccat ctgatcgcaa  4260
acatcaagac cacatataga tccaagaaac ccgctaagaa cctcaagatg cctggcgtct  4320
actatgtgga ctacagactg gaaagaatca aggaggccaa caacgagacc tacgtcgagc  4380
agcacgaggt ggcagtggcc agatactgcg acctccctag caaactgggg cacaagctta  4440
attgagtcga ccgagcatct taccgccatt tatacccata tttgttctgt ttttcttgat  4500
ttgggtatac atttaaatgt taatagaaca aaatggtggg gcaatcattt acatttttag  4560
ggatatgtaa ttactagttc aggtgtattg ccacaagaca aacatgttaa gaaactttcc  4620
cgttatttac gctctgttcc tgttaatcaa cctctggatt acaaaatttg tgaaagattg  4680
actgatattc ttaactatgt tgctcctttt acgctgtgtg gatatgctgc tttatagcct  4740
ctgtatctag ctattgcttc ccgtacggct ttcgttttct cctccttgta taaatcctgg  4800
ttgctgtctc ttttagagga gttgtggccc gttgtccgtc aacgtggcgt ggtgtgctct  4860
gtgtttgctg acgcaacccc cactggctgg ggcattgcca ccacctgtca actcctttct  4920
gggactttcg ctttccccct cccgatcgcc acggcagaac tcatcgccgc ctgccttgcc  4980
cgctgctgga caggggctag gttgctgggc actgataatt ccgtggtgtt gtcatcgaat  5040
tcggtacctt tttaaaagaa aaggggggac tggaagggct aattcactcc caacgaagac  5100
aagatatcat aacttcgtat agcatacatt atacgaagtt ataatttatt tgtgaaattt  5160
gtgatgctat tgctttattt gtaaccatat gtttatttgt gaaatttgtg atgctattgc  5220
tttatttgta accattgctt tttgcttgta ctgggtctct ctggttagac cagatctgag  5280
cctgggagct ctctggctaa ctagggaacc cactgcttaa gcctcaataa agcttgcctc  5340
gaccagcctc gactgtgcct tctagttgcc agccatctgt tgtttgcccc tcccccgtgc  5400
cttccttgac cctggaaggt gccactccca ctgtcctttc ctaataaaat gaggaaattg  5460
catcgcattg tctgagtagg tgtcattcta ttctgggggg tggggtgggg caggacagca  5520
agggggagga ttgggaagac aatagcaggc atgctgggga tgcggtgggc tctatggcct  5580
gcagctgcat taatgaatcg gccaacgcgc ggggagaggc ggtttgcgta ttgggcgctc  5640
ttccgcttcc tcgctcactg actcgctgcg ctcggtcgtt cggctgcggc gagcggtatc  5700
agctcactca aaggcggtaa tacggttatc cacagaatca ggggataacg caggaaagaa  5760
catgtgagca aaaggccagc aaaaggccag gaaccgtaaa aaggccgcgt tgctggcgtt  5820
tttccatagg ctccgccccc ctgacgagca tcacaaaaat cgacgctcaa gtcagaggtg  5880
gcgaaacccg acaggactat aaagatacca ggcgtttccc cctggaagct ccctcgtgcg  5940
ctctcctgtt ccgaccctgc cgcttaccgg atacctgtcc gcctttctcc cttcgggaag  6000
cgtggcgctt tctcatagct cacgctgtag gtatctcagt tcggtgtagg tcgttcgctc  6060
caagctgggc tgtgtgcacg aaccccccgt tcagcccgac cgctgcgcct tatccggtaa  6120
ctatcgtctt gagtccaacc cggtaagaca cgacttatcg ccactggcag cagccactgg  6180
taacaggatt agcagagcga ggtatgtagg cggtgctaca gagttcttga agtggtggcc  6240
taactacggc tacactagaa ggacagtatt tggtatctgc gctctgctga agccagttac  6300
cttcggaaaa agagttggta gctcttgatc cggcaaacaa accaccgctg gtagcggtgg  6360
tttttttgtt tgcaagcagc agattacgcg cagaaaaaaa ggatctcaag aagatccttt  6420
gatcttttct acggggtctg acgctcagtg gaacgaaaac tcacgttaag ggattttggt  6480
catgagatta tcaaaaagga tcttcaccta gatcctttta aattaaaaat gaagttttaa  6540
atcaatctaa agtatatatg agtaaacttg gtctgacagt taccaatgct taatcagtga  6600
ggcacctatc tcagcgatct gtctatttcg ttcatccata gttgcctgac tccccgtcgt  6660
gtagataact acgatacggg agggcttacc atctggcccc agtgctgcaa tgataccgcg  6720
agacccacgc tcaccggctc cagatttatc agcaataaac cagccagccg gaagggccga  6780
gcgcagaagt ggtcctgcaa ctttatccgc ctccatccag tctattaatt gttgccggga  6840
agctagagta agtagttcgc cagttaatag tttgcgcaac gttgttgcca ttgctacagg  6900
catcgtggtg tcacgctcgt cgtttggtat ggcttcattc agctccggtt cccaacgatc  6960
aaggcgagtt acatgatccc ccatgttgtg caaaaaagcg gttagctcct tcggtcctcc  7020
gatcgttgtc agaagtaagt tggccgcagt gttatcactc atggttatgg cagcactgca  7080
taattctctt actgtcatgc catccgtaag atgcttttct gtgactggtg agtactcaac  7140
caagtcattc tgagaatagt gtatgcggcg accgagttgc tcttgcccgg cgtcaatacg  7200
ggataatacc gcgccacata gcagaacttt aaaagtgctc atcattggaa aacgttcttc  7260
ggggcgaaaa ctctcaagga tcttaccgct gttgagatcc agttcgatgt aacccactcg  7320
tgcacccaac tgatcttcag catcttttac tttcaccagc gtttctgggt gagcaaaaac  7380
aggaaggcaa aatgccgcaa aaaagggaat aagggcgaca cggaaatgtt gaatactcat  7440
actcttcctt tttcaatatt attgaagcat ttatcagggt tattgtctca tgagcggata  7500
catatttgaa tgtatttag                                               7519
```

```
SEQ ID NO: 35          moltype = DNA  length = 7672
FEATURE                Location/Qualifiers
misc_feature           1..7672
                       note = pCVL_sEF1a_CD19-Puro lentiviral vector
source                 1..7672
                       mol_type = other DNA
                       organism = synthetic construct
SEQUENCE: 35
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
```

-continued

```
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggagggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggg ccgccaccat gccacctcct cgcctcctct tcttcctcct cttcctcacc  2280
cccatggaag tcaggcccga ggaacctcta gtggtgaagg tggaagaggg agataacgct  2340
gtgctgcagt gcctcaaggg gacctcagat ggccccactc agcagctgac ctggtctcgg  2400
gagtccccgc ttaaaccctt cttaaaactc agcctgggat tacctgggtt aggcatccac  2460
atgaggcccc tggccatctg gcttttcatc ttcaacgtct ctcaacagat gggaggcttc  2520
tacctgtgcc agccggggcc tccctctgag aaggcctggc agcctggctg gacagtcaat  2580
gtggagggca gcggggagct gttccggtgg aatgtttcgg acctaggtgg cctgggctgt  2640
ggcctgaaga acaggtcctc agagggcccc agctcccctt ccgggaagct catgagcccc  2700
aagctgtatg tgtgggccaa agaccgccct gagatctggg agggagagcc tccgtgtctc  2760
ccaccgaggg acagcctgaa ccagagcctc agccaggacc tcaccatggc ccctggctcc  2820
acactctggc tgtcctgtgg ggtacccccct gactctgtgt ccaggggccc cctctcctgg  2880
acccatgtgc accccaaggg gcctaagtca ttgctgagcc tagagctgaa ggacgatcgc  2940
ccggccagag atatgtgggt aatggagacg ggtctgttgt tgccccgggc cacagctcaa  3000
gacgctggaa agtattattg tcaccgtggc aacctgacca tgtcattcca cctggagatc  3060
actgctcggc cagtactatg gcactggctg ctgaggactg gtggctggaa ggtctcagct  3120
gtgactttgg cttatctgat cttctgcctg tgttcccttg tgggcattct tcatcttcaa  3180
agagccctgg tcctgaggag gaagaggaag cgtatgactg accccaccag gagatttttc  3240
aaagtgacgc ctcccccagg aagcgggccc cagaaccagt acgggaacgt gctgtctctc  3300
cccacaccca cctcaggcct cggacgcgcc cagcgttggg ccgcaggcct gggaggcact  3360
gccccgtctt atggaaaccc gagcagcgac gtccaggcgg atggagcctt ggggtcccgg  3420
agcccgccgg gagtgggccc agaagaagag gaaggggagg gctacgagga acctgacagt  3480
gaggaggact ccgagttcta tgagaacgac tccaaccttg ggcaggacca gctctcccag  3540
gatggcagcg gctacgagaa ccctgaggat gagcccctgg gtcctgagga cgaggactcc  3600
ttctccaacg ctgagagcta tgaaaatgaa gatgaggagc tcacacaacc cgtcgccagg  3660
acaatggact tcctgagccc tcatgggtca gcatgggatc cgagccggga agcaacctcc  3720
ctggcagggt cccagtccta tgaggatatg agaggaatcc tgtatgcagc ccctcagctc  3780
cgctccattc ggggccagcc tggacccaat catgaggaag atgcagactc ttatgagaac  3840
atggataatc ccgatgggcc agacccagcc tggggaggag ggggccgcat gggcacctgg  3900
agcactcgcg gcggccgctc cggtgagggc agaggaagtc ttctaacatg cggtgacgtg  3960
gaggagaatc cgggccccctc tagaaccgag tacaagccca cggtgcgcct cgccacccgc  4020
gacgacgtcc cccgggccgt acgcaccctc gccgccgcgt tcgccgacta ccccgccacg  4080
cgccacaccg tcgatcccga ccgccacatc gagcgggtca ccgagctgca agaactcttc  4140
ctcacgcgcg tcgggctcga catcggcaag gtgtgggtcg cggacgacgg cgccgcggtg  4200
gcggtctgga ccacgccgga gagcgtcgaa gcgggggcgg tgttcgccga gatcggcccg  4260
cgcatggccg agttgagcgg ttcccggctg gccgcgcagc aacagatgga aggcctcctg  4320
gcgccgcacc ggcccaagga gcccgcgtgg ttcctggcca ccgtcggcgt ctcgcccgac  4380
caccagggca agggtctggg cagcgccgtc gtgctccccg gagtggaggc ggccgagcgc  4440
gccggggtgc ccgccttcct ggagacctcc gcgccccgca acctccccct ctacgagcgg  4500
ctcggcttca ccgtcaccgc cgacgtcgag gtgcccgaag gaccgcgcac ctggtgcatg  4560
acccgcaagc ccggtgccct cgagtgatga gagtcatcgt cgaccgagca tcttaccgcc  4620
atttataccc atatttgttc tgtttttctt gatttgggta tacatttaaa tgttaataga  4680
acaaaatggt ggggcaatca tttacatttt tagggatatg taattactag ttcaggtgta  4740
ttgccacaag acaaacatgt taagaaactt tcccgttatt tacgctctgt tcctgttaat  4800
caacctctgg attacaaaat ttgtgaaaga ttgactgata ttcttaacta tgttgctcct  4860
tttacgctgt gtggatatgc tgctttatag cctctgtatc tagctattgc ttcccgtacg  4920
gctttcgttt tctcctcctt gtataaatcc tggttgctgt ctcttttaga ggagttgtgg  4980
cccgttgtcc gtcaacgtgg cgtggtgtgc tctgtgtttg ctgacgcaac ccccactggc  5040
tggggcattg ccaccacctg tcaactcctt tctgggactt tcgctttccc cctcccgatc  5100
gccacggcag aactcatcgc cgcctgcctt gcccgctgct ggacaggggc taggttgctg  5160
ggcactgata attccgtggt gttgtcatcg aattcggtac ctttttaaaa gaaaaggggg  5220
gactggaagg gctaattcac tcccaacgaa gacaagatat cataacttcg tatagcatac  5280
attatacgaa gttataattt atttgtgaaa tttgtgatgc tattgcttta tttgtaacca  5340
```

```
tatgtttatt tgtgaaattt gtgatgctat tgctttattt gtaaccattg ctttttgctt  5400
gtactgggtc tctctggtta gaccagatct gagcctggga gctctctggc taactaggga  5460
acccactgct taagcctcaa taaagcttgc ctcgaccagc ctcgactgtg ccttctagtt  5520
gccagccatc tgttgtttgc ccctcccccg tgccttcctt gaccctggaa ggtgccactc  5580
ccactgtcct ttcctaataa aatgaggaaa ttgcatcgca ttgtctgagt aggtgtcatt  5640
ctattctggg gggtggggtg gggcaggaca gcaaggggga ggattgggaa gacaatagca  5700
ggcatgctgg ggatgcggtg ggctctatgg cctgcagctg cattaatgaa tcggccaacg  5760
cgcggggaga ggcggtttgc gtattgggcg ctcttccgct tcctcgctca ctgactcgct  5820
gcgctcggtc gttcggctgc ggcgagcggt atcagctcac tcaaaggcgg taatacggtt  5880
atccacagaa tcaggggata acgcaggaaa gaacatgtga gcaaaaggcc agcaaaaggc  5940
caggaaccgt aaaaaggccg cgttgctggc gtttttccat aggctccgcc cccctgacga  6000
gcatcacaaa aatcgacgct caagtcagag gtggcgaaac ccgacaggac tataaagata  6060
ccaggcgttt ccccctggaa gctccctcgt gcgctctcct gttccgaccc tgccgcttac  6120
cggatacctg tccgcctttc tcccttcggg aagcgtggcg ctttctcata gctcacgctg  6180
taggtatctc agttcggtgt aggtcgttcg ctccaagctg ggctgtgtgc acgaaccccc  6240
cgttcagccc gaccgctgcg ccttatccgg taactatcgt cttgagtcca acccggtaag  6300
acacgactta tcgccactgg cagcagccac tggtaacagg attagcagag cgaggtatgt  6360
aggcggtgct acagagttct tgaagtggtg gcctaactac ggctacacta gaaggacagt  6420
atttggtatc tgcgctctgc tgaagccagt taccttcgga aaaagagttg gtagctcttg  6480
atccggcaaa caaaccaccg ctggtagcgg tggttttttt gtttgcaagc agcagattac  6540
gcgcagaaaa aaaggatctc aagaagatcc tttgatcttt tctacggggt ctgacgctca  6600
gtggaacgaa aactcacgtt aagggatttt ggtcatgaga ttatcaaaaa ggatcttcac  6660
ctagatcctt ttaaattaaa aatgaagttt taaatcaatc taaagtatat atgagtaaac  6720
ttggtctgac agttaccaat gcttaatcag tgaggcacct atctcagcga tctgtctatt  6780
tcgttcatcc atagttgcct gactccccgt cgtgtagata actacgatac gggagggctt  6840
accatctggc cccagtgctg caatgatacc gcgagaccca cgctcaccgg ctccagattt  6900
atcagcaata aaccagccag ccggaagggc cgagcgcaga agtggtcctg caactttatc  6960
cgcctccatc cagtctatta attgttgccg ggaagctaga gtaagtagtt cgccagttaa  7020
tagtttgcgc aacgttgttg ccattgctac aggcatcgtg gtgtcacgct cgtcgtttgg  7080
tatggcttca ttcagctccg gttcccaacg atcaaggcga gttacatgat cccccatgtt  7140
gtgcaaaaaa gcggttagct ccttcggtcc tccgatcgtt gtcagaagta agttggccgc  7200
agtgttatca ctcatggtta tggcagcact gcataattct cttactgtca tgccatccgt  7260
aagatgcttt tctgtgactg gtgagtactc aaccaagtca ttctgagaat agtgtatgcg  7320
gcgaccgagt tgctcttgcc cggcgtcaat acgggataat accgcgccac atagcagaac  7380
tttaaaagtg ctcatcattg gaaaacgttc ttcggggcga aaactctcaa ggatcttacc  7440
gctgttgaga tccagttcga tgtaacccac tcgtgcaccc aactgatctt cagcatcttt  7500
tactttcacc agcgtttctg ggtgagcaaa aacaggaagg caaaatgccg caaaaaaggg  7560
aataagggcg acacggaaat gttgaatact catactcttc ctttttcaat attattgaag  7620
catttatcag ggttattgtc tcatgagcgg atacatattt gaatgtattt ag          7672

SEQ ID NO: 36          moltype = DNA  length = 6892
FEATURE                Location/Qualifiers
misc_feature           1..6892
                       note = pCVL_sEF1a_CD20-Puro lentiviral vector
source                 1..6892
                       mol_type = other DNA
                       organism = synthetic construct
SEQUENCE: 36
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
```

```
tttaaaagaa aagggggggat tgggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggg ccgccaccat gacaacaccc agaaattcag taaatgggac tttcccggca  2280
gagccaatga aaggccctat tgctatgcaa tctggtccaa aaccactctt caggaggatg  2340
tcttcactgg tgggccccac gcaaagcttc ttcatgaggg aatctaagac tttgggggct  2400
gtccagatta tgaatgggct cttccacatt gccctgggag gtcttctgat gatcccagca  2460
gggatctatg cacccatctg tgtgactgtg tggtaccctc tctggggagg cattatgtat  2520
attatttccg gatcactcct ggcagcaacg gagaaaaact ccaggaagtg tttggtcaaa  2580
ggaaaaatga taatgaattc attgagcctc tttgctgcca tttctggaat gattctttca  2640
atcatggaca tacttaatat taaaatttcc catttttttaa aaatggagag tctgaatttt  2700
attagagctc acacaccata tattaacata tacaactgtg aaccagctaa tccctctgag  2760
aaaaactccc catctaccca atactgttac agcatacaat ctctgttctt gggcattttg  2820
tcagtgatgc tgatctttgc cttcttccag gaacttgtaa tagctggcat cgttgagaat  2880
gaatggaaaa gaacgtgctc cagacccaaa tctaacatag ttctcctgtc agcagaagaa  2940
aaaaaagaac agactattga aataaaagaa gaagtggttg ggctaactga aacatcttcc  3000
caaccaaaga atgaagaaga cattgaaatt attccaatcc aagaagagga agaagaagaa  3060
acagagacga actttccaga acctccccaa gatcaggaat cctcaccaat agaaaatgac  3120
agctctcctg gcggccgctc cggtgagggc agaggaagtc ttctaacatg cggtgacgtg  3180
gaggagaatc cgggcccctc tagaaccgag tacaagccca cggtgcgcct cgccacccgc  3240
gacgacgtcc cccgggccgt acgcaccctc gccgccgcgt tcgccgacta ccccgccacg  3300
cgccacaccg tcgatcccga ccgccacatc gagcgggtca ccgagctgca agaactcttc  3360
ctcacgcgcg tcgggctcga catcggcaag gtgtgggtcg cggacgacgg cgccgcggtg  3420
gcggtctgga ccacgccgga gagcgtcgaa gcgggggcgg tgttcgccga gatcggcccg  3480
cgcatggccg agttgagcgg ttcccggctg gccgcgcagc aacagatgga aggcctcctg  3540
gcgccgcacc ggcccaagga gcccgcgtgg ttcctggcca ccgtcggcgt ctcgcccgac  3600
caccagggca agggtctggg cagcgccgtc gtgctccccg gagtggaggc ggccgagcgc  3660
gccggggtgc ccgccttcct ggagacctcc gcgccccgca acctcccctt ctacgagcgg  3720
ctcggcttca ccgtcaccgc cgacgtcgag gtgcccgaag gaccgcgcac ctggtgcatg  3780
acccgcaagc ccggtgccct cgagtgatga gagtcatcgt cgaccgagca tcttaccgcc  3840
atttataccc atatttgttc tgtttttctt gatttgggta tacatttaaa tgttaataga  3900
acaaaatggt ggggcaatca tttacatttt tagggatatg taattactag ttcaggtgta  3960
ttgccacaag acaaacatgt taagaaactt tcccgttatt tacgctctgt tcctgttaat  4020
caacctctgg attacaaaat ttgtgaaaga ttgactgata ttcttaacta tgttgctcct  4080
tttacgctgt gtggatatgc tgctttatag cctctgtatc tagctattgc ttcccgtacg  4140
gctttcgttt tctcctcctt gtataaatcc tggttgctgt ctcttttaga ggagttgtgg  4200
cccgttgtcc gtcaacgtgg cgtggtgtgc tctgtgtttg ctgacgcaac ccccactggc  4260
tggggcattg ccaccacctg tcaactcctt tctgggactt tcgctttccc cctcccgatc  4320
gccacggcag aactcatcgc cgcctgcctt gcccgctgct ggacaggggc taggttgctg  4380
ggcactgata attccgtggt gttgtcatcg aattcggtac ctttttaaaa gaaaaggggg  4440
gactggaagg gctaattcac tcccaacgaa gacaagatat cataacttcg tatagcatac  4500
attatacgaa gttataattt atttgtgaaa tttgtgatgc tattgcttta tttgtaacca  4560
tatgtttatt tgtgaaattt gtgatgctat tgctttattt gtaaccattg ctttttgctt  4620
gtactgggtc tctctggtta gaccagatct gagcctggga gctctctggc taactaggga  4680
acccactgct taagcctcaa taaagcttgc ctcgaccagc ctcgactgtg ccttctagtt  4740
gccagccatc tgttgtttgc ccctcccccg tgccttcctt gaccctggaa ggtgccactc  4800
ccactgtcct ttcctaataa aatgaggaaa ttgcatcgca ttgtctgagt aggtgtcatt  4860
ctattctggg gggtggggtg gggcaggaca gcaaggggga ggattgggaa gacaatagca  4920
ggcatgctgg ggatgcggtg ggctctatgg cctgcagctg cattaatgaa tcggccaacg  4980
cgcggggaga ggcggtttgc gtattgggcg ctcttccgct tcctcgctca ctgactcgct  5040
gcgctcggtc gttcggctgc ggcgagcggt atcagctcac tcaaaggcgg taatacggtt  5100
atccacagaa tcaggggata acgcaggaaa gaacatgtga gcaaaaggcc agcaaaaggc  5160
caggaaccgt aaaaaggccg cgttgctggc gtttttccat aggctccgcc cccctgacga  5220
gcatcacaaa aatcgacgct caagtcagag gtggcgaaac ccgacaggac tataaagata  5280
ccaggcgttt ccccctggaa gctccctcgt gcgctctcct gttccgaccc tgccgcttac  5340
cggatacctg tccgcctttc tcccttcggg aagcgtggcg ctttctcata gctcacgctg  5400
taggtatctc agttcggtgt aggtcgttcg ctccaagctg ggctgtgtgc acgaaccccc  5460
cgttcagccc gaccgctgcg ccttatccgg taactatcgt cttgagtcca acccggtaag  5520
acacgactta tcgccactgg cagcagccac tggtaacagg attagcagag cgaggtatgt  5580
aggcggtgct acagagttct tgaagtggtg gcctaactac ggctacacta gaaggacagt  5640
atttggtatc tgcgctctgc tgaagccagt taccttcgga aaaagagttg gtagctcttg  5700
atccggcaaa caaaccaccg ctggtagcgg tggttttttt gtttgcaagc agcagattac  5760
gcgcagaaaa aaaggatctc aagaagatcc tttgatcttt tctacggggt ctgacgctca  5820
gtggaacgaa aactcacgtt aagggatttt ggtcatgaga ttatcaaaaa ggatcttcac  5880
ctagatcctt ttaaattaaa aatgaagttt taaatcaatc taaagtatat atgagtaaac  5940
ttggtctgac agttaccaat gcttaatcag tgaggcacct atctcagcga tctgtctatt  6000
tcgttcatcc atagttgcct gactccccgt cgtgtagata actacgatac gggagggctt  6060
accatctggc cccagtgctg caatgatacc gcgagaccca cgctcaccgg ctccagattt  6120
atcagcaata aaccagccag ccggaagggc cgagcgcaga agtggtcctg caactttatc  6180
cgcctccatc cagtctatta attgttgccg ggaagctaga gtaagtagtt cgccagttaa  6240
tagtttgcgc aacgttgttg ccattgctac aggcatcgtg gtgtcacgct cgtcgtttgg  6300
tatggcttca ttcagctccg gttcccaacg atcaaggcga gttacatgat cccccatgtt  6360
gtgcaaaaaa gcggttagct ccttcggtcc tccgatcgtt gtcagaagta agttggccgc  6420
agtgttatca ctcatggtta tggcagcact gcataattct cttactgtca tgccatccgt  6480
aagatgcttt tctgtgactg gtgagtactc aaccaagtca ttctgagaat agtgtatgcg  6540
gcgaccgagt tgctcttgcc cggcgtcaat acgggataat accgcgccac atagcagaac  6600
```

```
tttaaaagtg ctcatcattg gaaaacgttc ttcggggcga aaactctcaa ggatcttacc  6660
gctgttgaga tccagttcga tgtaacccac tcgtgcaccc aactgatctt cagcatcttt  6720
tactttcacc agcgtttctg ggtgagcaaa aacaggaagg caaaatgccg caaaaaaggg  6780
aataagggcg acacggaaat gttgaatact catactcttc ctttttcaat attattgaag  6840
catttatcag ggttattgtc tcatgagcgg atacatattt gaatgtattt ag          6892

SEQ ID NO: 37          moltype = AA  length = 570
FEATURE                Location/Qualifiers
REGION                 1..570
                       note = SS-2xDmrB-DmrC-TM-41BB-CD3z protein
source                 1..570
                       mol_type = protein
                       organism = synthetic construct
SEQUENCE: 37
MALPVTALLL PLALLLHAAR PGSGGVQVET ISPGDGRTFP KRGQTCVVHY TGMLEDGKKV  60
DSSRDRNKPF KFMLGKQEVI RGWEEGVAQM SVGQRAKLTI SPDYAYGATG HPGIIPPHAT  120
LVFDVEFLKL ESGTSGTSGV QVETISPGDG RTFPKRGQTC VVHYTGMLED GKKVDSSRDR  180
NKPFKFMLGK QEVIRGWEEG VAQMSVGQRA KLTISPDYAY GATGHPGIIP PHATLVFDVE  240
LLKLEGSRSI LWHEMWHEGL EEASRLYFGE RNVKGMFEVL EPLHAMMERG PQTLKETSFN  300
QAYGRDLMEA QEWCRKYMKS GNVKDLLQAW DLYYHVFRRI SKASAKPTTT PAPRPPTPAP  360
TIASQPLSLR PEACRPAAGG AVHTRGLDFA CDIYIWAPLA GTCGVLLLSL VITMHKRGRK  420
KLLYIFKQPF MRPVQTTQEE DGCSCRFPEE EEGGCELRVK FSRSADAPAY QQGQNQLYNE  480
LNLGRREEYD VLDKRRGRDP EMGGKPRRKN PQEGLYNELQ KDKMAEAYSE IGMKGERRRG  540
KGHDGLYQGL STATKDTYDA LHMQALPPRG                                   570

SEQ ID NO: 38          moltype = RNA  length = 1710
FEATURE                Location/Qualifiers
misc_feature           1..1710
                       note = SS-2xDmrB-DmrC-TM-41BB-CD3z mRNA
source                 1..1710
                       mol_type = other RNA
                       organism = synthetic construct
SEQUENCE: 38
atggctctgc ctgtgacagc tctgctgctg cctctggccc tgctgctcca tgccgccaga  60
cccggatccg gcggtgtcca agtcgaaact atatcgcctg gcgatggcag aacgtttccc  120
aaacgtggcc agacctgtgt cgtacactat accggcatgc tagaggatgg gaaaaaggtt  180
gattccagtc gcgatcggaa caaaccgttt aaattcatgt tggggaagca agaggttatc  240
aggggatggg aagagggtgt cgcgcaaatg tcggttgggc aacgtgcgaa actcacaatt  300
tccccggatt acgcatacgg agctaccgga caccctggga ttatcccacc gcatgcgacg  360
ctagtgtttg acgtagagtt cttgaagctc gaatcaggta caagcggcac ttctggcgta  420
caggttgaga caattagtcc cggagacgga cgtacattcc caaagagagg gcaaacttgc  480
gtagtccatt acactggaat gttggaagac ggcaagaaag tggacagttc aagagaccgc  540
aataagcctt tcaagtttat gctcggaaaa caggaagtca tacgcggttg ggaggaaggc  600
gtggctcaga tgagcgtcgg acagagggca aagttgacca tcagtcccga ctatgcgtat  660
ggcgcgacag gccatcccgg aatcatacct ccccacgcaa ccttggtatt cgatgtcgaa  720
ctgctcaaat tagagggtag tagatccatc ctctggcatg agatgtggca tgaaggcctg  780
gaagaggcat ctcgtttgta ctttggggaa aggaacgtga aaggcatgtt tgaggtgctg  840
gagcccttgc atgctatgat ggaacggggc ccccagactc tgaaggaaac atcctttaat  900
caggcctatg gtcgagattt aatggaggcc caagagtggt gcaggaagta catgaaatca  960
gggaatgtca aggacctcct ccaagcctgg gacctctatt atcatgtgtt ccgacgaatc  1020
tcaaaggcta gcgccaagcc taccaccacc cctgccccta gacctccaac acccgcccca  1080
acaatcgcca gccagcctct gtctctgagg cccgaggctt gtagaccagc tgctggcgga  1140
gccgtacaca ccagaggact ggatttcgcc tgcgacatct acatctgggc ccctctggcc  1200
ggcacatgtg gcgtgctgct gctgagcctc gtgatcacca tgcataaacg gggcagaaag  1260
aaactcctgt atatattcaa acaaccattt atgagaccag tacaaactac tcaagaggaa  1320
gatggctgta gctgccgatt tccagaagaa gaagaaggag gatgtgaact gcgggtgaag  1380
ttcagcagaa gcgccgacgc ccctgcctac cagcagggcc agaatcagct gtacaacgag  1440
ctgaacctgg gcagaaggga agagtacgac gtcctggata agcggagagg ccgggaccct  1500
gagatgggcg gcaagcctcg gcggaagaac ccccaggaag gcctgtataa cgaactgcag  1560
aaagacaaga tggccgaggc ctacagcgag atcggcatga agggcgagcg gaggcggggc  1620
aagggccacg acggcctgta tcagggcctg tccaccgcca ccaaggatac ctacgacgcc  1680
ctgcacatgc aggccctgcc cccaaggggc                                   1710

SEQ ID NO: 39          moltype = DNA  length = 1710
FEATURE                Location/Qualifiers
misc_feature           1..1710
                       note = SS-2xDmrB-DmrC-TM-41BB-CD3z DNA
source                 1..1710
                       mol_type = other DNA
                       organism = synthetic construct
SEQUENCE: 39
atggctctgc ctgtgacagc tctgctgctg cctctggccc tgctgctcca tgccgccaga  60
cccggatccg gcggtgtcca agtcgaaact atatcgcctg gcgatggcag aacgtttccc  120
aaacgtggcc agacctgtgt cgtacactat accggcatgc tagaggatgg gaaaaaggtt  180
gattccagtc gcgatcggaa caaaccgttt aaattcatgt tggggaagca agaggttatc  240
aggggatggg aagagggtgt cgcgcaaatg tcggttgggc aacgtgcgaa actcacaatt  300
tccccggatt acgcatacgg agctaccgga caccctggga ttatcccacc gcatgcgacg  360
ctagtgtttg acgtagagtt cttgaagctc gaatcaggta caagcggcac ttctggcgta  420
caggttgaga caattagtcc cggagacgga cgtacattcc caaagagagg gcaaacttgc  480
```

```
gtagtccatt acactggaat gttggaagac ggcaagaaag tggacagttc aagagaccgc  540
aataagcctt tcaagtttat gctcggaaaa caggaagtca tacgcggttg ggaggaaggc  600
gtggctcaga tgagcgtcgg acagagggca aagttgacca tcagtcccga ctatgcgtat  660
ggcgcgacag gccatcccgg aatcatacct ccccacgcaa ccttggtatt cgatgtcgaa  720
ctgctcaaat tagagggtag tagatccatc ctctggcatg agatgtggca tgaaggcctg  780
gaagaggcat ctcgtttgta ctttggggaa aggaacgtga aaggcatgtt tgaggtgctg  840
gagcccttgc atgctatgat ggaacggggc ccccagactc tgaaggaaac atcctttaat  900
caggcctatg gtcgagattt aatggaggcc caagagtggt gcaggaagta catgaaatca  960
gggaatgtca aggacctcct ccaagcctgg gacctctatt atcatgtgtt ccgacgaatc  1020
tcaaaggcta gcgccaagcc taccaccacc cctgccccta gacctccaac acccgcccca  1080
acaatcgcca gccagcctct gtctctgagg cccgaggctt gtagaccagc tgctggcgga  1140
gccgtacaca ccagaggact ggatttcgcc tgcgacatct acatctgggc ccctctggcc  1200
ggcacatgtg gcgtgctgct gctgagcctc gtgatcacca tgcataaacg gggcagaaag  1260
aaactcctgt atatattcaa acaaccattt atgagaccag tacaaactac tcaagaggaa  1320
gatggctgta gctgccgatt tccagaagaa gaagaaggag gatgtgaact gcgggtgaag  1380
ttcagcagaa gcgccgacgc ccctgcctac cagcagggcc agaatcagct gtacaacgag  1440
ctgaacctgg gcagaaggga agagtacgac gtcctggata agcggagagg ccgggaccct  1500
gagatgggcg gcaagcctcg gcggaagaac ccccaggaag gcctgtataa cgaactgcag  1560
aaagacaaga tggccgaggc ctacagcgag atcggcatga agggcgagcg gaggcggggc  1620
aagggccacg acggcctgta tcagggcctg tccaccgcca ccaaggatac ctacgacgcc  1680
ctgcacatgc aggccctgcc cccaagggc                                   1710

SEQ ID NO: 40          moltype = DNA  length = 7819
FEATURE                Location/Qualifiers
misc_feature           1..7819
                       note = pCVL_sEF1a_T7_2xDmrB-DmrC-TM-41BB-CD3z lentiviral
                        vector
source                 1..7819
                       mol_type = other DNA
                       organism = synthetic construct
SEQUENCE: 40
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actataggct ccactgccgc caccatggct ctgcctgtga  2280
cagctctgct gctgcctctg gccctgctgc tccatgccgc cagacccgga tccggcggtg  2340
tccaagtcga aactatatcg cctggcgatg gcagaacgtt tcccaaacgt ggccagacct  2400
gtgtcgtaca ctataccggc atgctagagg atgggaaaaa ggttgattcc agtcgcgatc  2460
ggaacaaacc gtttaaattc atgttgggga agcaagaggt tatcagggga tgggaagagg  2520
gtgtcgcgca aatgtcggtt gggcaacgtg cgaaactcac aatttccccg gattacgcat  2580
acggagctac cggacaccct gggattatcc caccgcatgc gacgctagtg tttgacgtag  2640
agttcttgaa gctcgaatca ggtacaagcg gcacttctgg cgtacaggtt gagacaatta  2700
gtcccggaga cggacgtaca ttcccaaaga gagggcaaac ttgcgtagtc cattacactg  2760
gaatgttgga agacggcaag aaagtggaca gttcaagaga ccgcaataag cctttcaagt  2820
ttatgctcgg aaaacaggaa gtcatacgcg gttgggagga aggcgtggct cagatgagcg  2880
```

-continued

```
tcggacagag ggcaaagttg accatcagtc ccgactatgc gtatggcgcg acaggccatc  2940
ccggaatcat acctccccac gcaaccttgg tattcgatgt cgaactgctc aaattagagg  3000
gtagtagatc catcctctgg catgagatgt ggcatgaagg cctggaagag gcatctcgtt  3060
tgtactttgg ggaaaggaac gtgaaaggca tgtttgaggt gctggagccc ttgcatgcta  3120
tgatggaacg gggcccccag actctgaagg aaacatcctt taatcaggcc tatggtcgag  3180
atttaatgga ggcccaagag tggtgcagga agtacatgaa atcagggaat gtcaaggacc  3240
tcctccaagc ctgggacctc tattatcatg tgttccgacg aatctcaaag gctagcgcca  3300
agcctaccac caccccctgcc cctagacctc caacacccgc cccaacaatc gccagccagc  3360
ctctgtctct gaggcccgag gcttgtagac cagctgctgg cggagccgta cacaccagag  3420
gactggattt cgcctgcgac atctacatct gggcccctct ggccggcaca tgtggcgtgc  3480
tgctgctgag cctcgtgatc accatgcata aacggggcag aaagaaactc ctgtatatat  3540
tcaaacaacc atttatgaga ccagtacaaa ctactcaaga ggaagatggc tgtagctgcc  3600
gatttccaga agaagaagaa ggaggatgtg aactgcgggt gaagttcagc agaagcgccg  3660
acgcccctgc ctaccagcag ggccagaatc agctgtacaa cgagctgaac ctgggcagaa  3720
gggaagagta cgacgtcctg gataagcgga gaggccggga ccctgagatg ggcggcaagc  3780
ctcggcggaa gaacccccag gaaggcctgt ataacgaact gcagaaagac aagatggccg  3840
aggcctacag cgagatcggc atgaagggcg agcggaggcg gggcaagggc cacgacggcc  3900
tgtatcaggg cctgtccacc gccaccaagg atacctacga cgccctgcac atgcaggccc  3960
tgcccccaag gggcggccgc tccggtgagg gcagaggaag tcttctaaca tgcggtgacg  4020
tggaggagaa tccgggcccc tctagaagcg agctgattaa ggagaacatg cacatgaagc  4080
tgtacatgga gggcaccgtg gacaaccatc acttcaagtg cacatccgag ggcgaaggca  4140
agccctacga gggcacccag accatgagaa tcaaggtggt cgagggcggc cctctcccct  4200
tcgccttcga catcctggct actagcttcc tctacggcag caagaccttc atcaaccaca  4260
cccagggcat ccccgacttc ttcaagcagt ccttccctga gggcttcaca tgggagagag  4320
tcaccacata cgaagacggg ggcgtgctga ccgctaccca ggacaccagc ctccaggacg  4380
gctgcctcat ctacaacgtc aagatcagag gggtgaactt cacatccaac ggccctgtga  4440
tgcagaagaa aacactcggc tgggaggcct tcaccgagac gctgtacccc gctgacggcg  4500
gcctggaagg cagaaacgac atggccctga agctcgtggg cgggagccat ctgatcgcaa  4560
acatcaagac cacatataga tccaagaaac ccgctaagaa cctcaagatg cctggcgtct  4620
actatgtgga ctacagactg gaaagaatca aggaggccaa caacgagacc tacgtcgagc  4680
agcacgaggt ggcagtggcc agatactgcg acctccctag caaactgggg cacaagctta  4740
attgagtcga ccgagcatct taccgccatt tatacccata tttgttctgt ttttcttgat  4800
ttgggtatac atttaaatgt taatagaaca aaatggtggg gcaatcattt acatttttag  4860
ggatatgtaa ttactagttc aggtgtattg ccacaagaca aacatgttaa gaaactttcc  4920
cgttatttac gctctgttcc tgttaatcaa cctctggatt acaaaatttg tgaaagattg  4980
actgatattc ttaactatgt tgctcctttt acgctgtgtg gatatgctgc tttatagcct  5040
ctgtatctag ctattgcttc ccgtacggct ttcgttttct cctccttgta taaatcctgg  5100
ttgctgtctc ttttagagga gttgtggccc gttgtccgtc aacgtggcgt ggtgtgctct  5160
gtgtttgctg acgcaacccc cactggctgg ggcattgcca ccacctgtca actcctttct  5220
gggactttcg ctttccccct cccgatcgcc acggcagaac tcatcgccgc ctgccttgcc  5280
cgctgctgga caggggctag gttgctgggc actgataatt ccgtggtgtt gtcatcgaat  5340
tcggtacctt tttaaaagaa aaggggggac tggaagggct aattcactcc caacgaagac  5400
aagatatcat aacttcgtat agcatacatt atacgaagtt ataatttatt tgtgaaattt  5460
gtgatgctat tgctttattt gtaaccatat gtttatttgt gaaatttgtg atgctattgc  5520
tttatttgta accattgctt tttgcttgta ctgggtctct ctggttagac cagatctgag  5580
cctgggagct ctctggctaa ctagggaacc cactgcttaa gcctcaataa agcttgcctc  5640
gaccagcctc gactgtgcct tctagttgcc agccatctgt tgtttgcccc tcccccgtgc  5700
cttccttgac cctggaaggt gccactccca ctgtcctttc ctaataaaat gaggaaattg  5760
catcgcattg tctgagtagg tgtcattcta ttctgggggg tggggtgggg caggacagca  5820
agggggagga ttgggaagac aatagcaggc atgctgggga tgcggtgggc tctatggcct  5880
gcagctgcat taatgaatcg gccaacgcgc ggggagaggc ggtttgcgta ttgggcgctc  5940
ttccgcttcc tcgctcactg actcgctgcg ctcggtcgtt cggctgcggc gagcggtatc  6000
agctcactca aaggcggtaa tacggttatc cacagaatca ggggataacg caggaaagaa  6060
catgtgagca aaaggccagc aaaaggccag gaaccgtaaa aaggccgcgt tgctggcgtt  6120
tttccatagg ctccgccccc ctgacgagca tcacaaaaat cgacgctcaa gtcagaggtg  6180
gcgaaacccg acaggactat aaagatacca ggcgtttccc cctggaagct ccctcgtgcg  6240
ctctcctgtt ccgaccctgc cgcttaccgg atacctgtcc gcctttctcc cttcgggaag  6300
cgtggcgctt tctcatagct cacgctgtag gtatctcagt tcggtgtagg tcgttcgctc  6360
caagctgggc tgtgtgcacg aaccccccgt tcagcccgac cgctgcgcct tatccggtaa  6420
ctatcgtctt gagtccaacc cggtaagaca cgacttatcg ccactggcag cagccactgg  6480
taacaggatt agcagagcga ggtatgtagg cggtgctaca gagttcttga agtggtggcc  6540
taactacggc tacactagaa ggacagtatt tggtatctgc gctctgctga agccagttac  6600
cttcggaaaa agagttggta gctcttgatc cggcaaacaa accaccgctg gtagcggtgg  6660
tttttttgtt tgcaagcagc agattacgcg cagaaaaaaa ggatctcaag aagatccttt  6720
gatcttttct acggggtctg acgctcagtg gaacgaaaac tcacgttaag ggattttggt  6780
catgagatta tcaaaaagga tcttcaccta gatcctttta aattaaaaat gaagttttaa  6840
atcaatctaa agtatatatg agtaaacttg gtctgacagt taccaatgct taatcagtga  6900
ggcacctatc tcagcgatct gtctatttcg ttcatccata gttgcctgac tccccgtcgt  6960
gtagataact acgatacggg agggcttacc atctggcccc agtgctgcaa tgataccgcg  7020
agacccacgc tcaccggctc cagatttatc agcaataaac cagccagccg gaagggccga  7080
gcgcagaagt ggtcctgcaa ctttatccgc ctccatccag tctattaatt gttgccggga  7140
agctagagta agtagttcgc cagttaatag tttgcgcaac gttgttgcca ttgctacagg  7200
catcgtggtg tcacgctcgt cgtttggtat ggcttcattc agctccggtt cccaacgatc  7260
aaggcgagtt acatgatccc ccatgttgtg caaaaaagcg gttagctcct tcggtcctcc  7320
gatcgttgtc agaagtaagt tggccgcagt gttatcactc atggttatgg cagcactgca  7380
taattctctt actgtcatgc catccgtaag atgcttttct gtgactggtg agtactcaac  7440
caagtcattc tgagaatagt gtatgcggcg accgagttgc tcttgcccgg cgtcaatacg  7500
ggataatacc gcgccacata gcagaacttt aaaagtgctc atcattggaa aacgttcttc  7560
ggggcgaaaa ctctcaagga tcttaccgct gttgagatcc agttcgatgt aacccactcg  7620
```

```
tgcacccaac tgatcttcag catcttttac tttcaccagc gtttctgggt gagcaaaaac  7680
aggaaggcaa aatgccgcaa aaaagggaat aagggcgaca cggaaatgtt gaatactcat  7740
actcttcctt tttcaatatt attgaagcat ttatcagggt tattgtctca tgagcggata  7800
catatttgaa tgtatttag                                                 7819

SEQ ID NO: 41          moltype = AA  length = 741
FEATURE                Location/Qualifiers
REGION                 1..741
                       note = SS-scFvCD19-DmrA-fuP2A-DmrC-TM-41BB-CD3z protein
source                 1..741
                       mol_type = protein
                       organism = synthetic construct
SEQUENCE: 41
METDTLLLWV LLLWVPGSTG DYKDEGSDIQ MTQTTSSLSA SLGDRVTISC RASQDISKYL  60
NWYQQKPDGT VKLLIYHTSR LHSGVPSRFS GSGSGTDYSL TISNLEQEDI ATYFCQQGNT  120
LPYTFGGGTK LEITGSTSGS GKPGSGEGST KGEVKLQESG PGLVAPSQSL SVTCTVSGVS  180
LPDYGVSWIR QPPRKGLEWL GVIWGSETTY YNSALKSRLT IIKDNSKSQV FLKMNSLQTD  240
DTAIYYCAKH YYYGGSYAMD YWGQGTSVTV SSASGSGGVQ VETISPGDGR TFPKRGQTCV  300
VHYTGMLEDG KKFDSSRDRN KPFKFMLGKQ EVIRGWEEGV AQMSVGQRAK LTISPDYAYG  360
ATGHPGIIPP HATLVFDVEL LKLEGGRARY KRSVSGSGAT NFSLLKQAGD VEENPGPSRS  420
ILWHEMWHEG LEEASRLYFG ERNVKGMFEV LEPLHAMMER GPQTLKETSF NQAYGRDLME  480
AQEWCRKYMK SGNVKDLLQA WDLYYHVFRR ISKASAKPTT TPAPRPPTPA PTIASQPLSL  540
RPEACRPAAG GAVHTRGLDF ACDIYIWAPL AGTCGVLLLS LVITMHKRGR KKLLYIFKQP  600
FMRPVQTTQE EDGCSCRFPE EEEGGCELRV KFSRSADAPA YQQGQNQLYN ELNLGRREEY  660
DVLDKRRGRD PEMGGKPRRK NPQEGLYNEL QKDKMAEAYS EIGMKGERRR GKGHDGLYQG  720
LSTATKDTYD ALHMQALPPR G                                              741

SEQ ID NO: 42          moltype = DNA  length = 2223
FEATURE                Location/Qualifiers
misc_feature           1..2223
                       note = SS-scFvCD19-DmrA-fuP2A-DmrC-TM-41BB-CD3z DNA
source                 1..2223
                       mol_type = other DNA
                       organism = synthetic construct
SEQUENCE: 42
atggagacag acacactcct gctatgggta ctgctgctct gggttccagg ttccactggt  60
gactacaagg acgagggatc cgatatccag atgacccaga ccaccagcag cctgagcgcc  120
agcctgggcg atagagtgac catcagctgc agagccagcc aggacatcag caagtacctg  180
aactggtatc agcagaaacc cgacggcacc gtgaagctgc tgatctacca caccagcaga  240
ctgcacagcg gcgtgcccag cagattttct ggcagcggct ccggcaccga ctacagcctg  300
accatctcca acctggaaca ggaagatatc gctacctact tctgtcagca aggcaacacc  360
ctgccctaca ccttcggcgg aggcaccaag ctggaaatca ccggcagcac aagcggcagc  420
ggcaagcctg gatctggcga gggaagcacc aagggcgaag tgaaactgca ggaaagcggc  480
cctggactgg tggccccaag ccagtctctg agcgtgacct gtaccgtgtc cggcgtgtcc  540
ctgcctgact atggcgtgtc ctggatcaga cagccaccca gaaagggcct ggaatggctg  600
ggagtgatct ggggcagcga gacaacctac tacaacagcg ccctgaagtc ccggctgacc  660
atcatcaagg acaactccaa gagccaggtg ttcctgaaga tgaacagcct gcagaccgac  720
gacaccgcca tctactactg cgccaagcac tactactacg gcggcagcta cgccatggac  780
tactggggcc agggcacaag cgtgaccgtg tccagcgcta gcggctcagg aggagtgcag  840
gttgaaacca tctccccagg agacgggcgc accttcccga agcgcggaca gacatgcgtg  900
gtgcactaca ccgggatgct tgaagatgga aagaaattcg attcatcgcg ggacagaaac  960
aagcccttta agtttatgct gggcaagcag gaggtcatcc gaggctggga agaaggggtt  1020
gcccagatga gtgtcggcca gagagccaaa ctgactatat cacctgacta cgcctatggg  1080
gccactgggc accctggcat aattccgcca cacgccactc tcgtcttcga tgtggagctt  1140
ctaaaactgg aaggcggccg cgctcgttac aagcgaagtg tctcaggatc tggcgccacg  1200
aacttctctc tgttaaagca agcaggagat gttgaagaaa accccgggcc ttcaagatcc  1260
atcctctggc atgagatgtg gcatgaaggc ctggaagagg catctcgttt gtactttggg  1320
gaaaggaacg tgaaaggcat gtttgaggtg ctggagccct tgcatgctat gatggaacgg  1380
ggcccccaga ctctgaagga aacatccttt aatcaggcct atggtcgaga tttaatggag  1440
gcccaagagt ggtgcaggaa gtacatgaaa tcagggaatg tcaaggacct cctccaagcc  1500
tgggacctct attatcatgt gttccgacga atctcaaagg ctagcgccaa gcctaccacc  1560
acccctgccc ctagacctcc aacacccgcc ccaacaatcg ccagccagcc tctgtctctg  1620
aggcccgagg cttgtagacc agctgctggc ggagccgtac acaccagagg actggatttc  1680
gcctgcgaca tctacatctg ggcccctctg gccggcacat gtggcgtgct gctgctgagc  1740
ctcgtgatca ccatgcataa acggggcaga aagaaactcc tgtatatatt caaacaacca  1800
tttatgagac cagtacaaac tactcaagag gaagatggct gtagctgccg atttccagaa  1860
gaagaagaag gaggatgtga actgcgggtg aagttcagca gaagcgccga cgcccctgcc  1920
taccagcagg gccagaatca gctgtacaac gagctgaacc tgggcagaag ggaagagtac  1980
gacgtcctgg ataagcggag aggccgggac cctgagatgg gcggcaagcc tcggcggaag  2040
aacccccagg aaggcctgta taacgaactg cagaaagaca agatggccga ggcctacagc  2100
gagatcggca tgaagggcga gcggaggcgg ggcaagggcc acgacggcct gtatcagggc  2160
ctgtccaccg ccaccaagga tacctacgac gccctgcaca tgcaggccct gcccccaagg  2220
ggc                                                                  2223

SEQ ID NO: 43          moltype = DNA  length = 8306
FEATURE                Location/Qualifiers
misc_feature           1..8306
                       note = SS-scFvCD19-DmrA-fuP2A-DmrC-TM-41BB-CD3z lentiviral
                        vector
```

```
source                 1..8306
                       mol_type = other DNA
                       organism = synthetic construct
SEQUENCE: 43
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggg ccgccaccat ggagacagac acactcctgc tatgggtact gctgctctgg  2280
gttccaggtt ccactggtga ctacaaggac gagggatccg atatccagat gacccagacc  2340
accagcagcc tgagcgccag cctgggcgat agagtgacca tcagctgcag agccagccag  2400
gacatcagca agtacctgaa ctggtatcag cagaaacccg acggcaccgt gaagctgctg  2460
atctaccaca ccagcagact gcacagcggc gtgcccagca gatttctcgg cagcggctcc  2520
ggcaccgact acagcctgac catctccaac ctggaacagg aagatatcgc tacctacttc  2580
tgtcagcaag gcaacaccct gccctacacc ttcggcggag gcaccaagct ggaaatcacc  2640
ggcagcacaa gcggcagcgg caagcctgga tctggcgagg gaagcaccaa gggcgaagtg  2700
aaactgcagg aaagcggccc tggactggtg gccccaagcc agtctctgag cgtgacctgt  2760
accgtgtccg gcgtgtccct gcctgactat ggcgtgtcct ggatcagaca gccacccaga  2820
aagggcctgg aatggctggg agtgatctgg ggcagcgaga caacctacta caacagcgcc  2880
ctgaagtccc ggctgaccat catcaaggac aactccaaga gccaggtgtt cctgaagatg  2940
aacagcctgc agaccgacga caccgccatc tactactgcg ccaagcacta ctactacggc  3000
ggcagctacg ccatggacta ctggggccag ggcacaagcg tgaccgtgtc cagcgctagc  3060
ggctcaggag gagtgcaggt tgaaaccatc tccccaggag acgggcgcac cttccccgaag  3120
cgcggacaga catgcgtggt gcactacacc gggatgcttg aagatggaaa gaaattcgat  3180
tcatcgcggg acagaaacaa gccctttaag tttatgctgg gcaagcagga ggtcatccga  3240
ggctgggaag aaggggttgc ccagatgagt gtcggccaga gagccaaact gactatatca  3300
cctgactacg cctatggggc cactgggcac cctggcataa ttccgccaca cgccactctc  3360
gtcttcgatg tggagcttct aaaactggaa ggcggccgcg ctcgttacaa gcgaagtgtc  3420
tcaggatctg gcgccacgaa cttctctctg ttaaagcaag caggagatgt tgaagaaaac  3480
cccgggcctt caagatccat cctctggcat gagatgtggc atgaaggcct ggaagaggca  3540
tctcgtttgt actttgggga aaggaacgtg aaaggcatgt ttgaggtgct ggagcccttg  3600
catgctatga tggaacgggg cccccagact ctgaaggaaa catcctttaa tcaggcctat  3660
ggtcgagatt taatggaggc ccaagagtgg tgcaggaagt acatgaaatc agggaatgtc  3720
aaggacctcc tccaagcctg ggacctctat tatcatgtgt tccgacgaat ctcaaaggct  3780
agcgccaagc ctaccaccac ccctgcccct agacctccaa cacccgcccc aacaatcgcc  3840
agccagcctc tgtctctgag gcccgaggct tgtagaccag ctgctggcgg agccgtacac  3900
accagaggac tggatttcgc ctgcgacatc tacatctggg cccctctggc cggcacatgt  3960
ggcgtgctgc tgctgagcct cgtgatcacc atgcataaac ggggcagaaa gaaactcctg  4020
tatatattca aacaaccatt tatgagacca gtacaaacta ctcaagagga agatggctgt  4080
agctgccgat ttccagaaga agaagaagga ggatgtgaac tgcgggtgaa gttcagcaga  4140
agcgccgacg cccctgccta ccagcagggc cagaatcagc tgtacaacga gctgaacctg  4200
ggcagaaggg aagagtacga cgtcctggat aagcggagag gccgggaccc tgagatgggc  4260
ggcaagcctc ggcggaagaa cccccaggaa ggcctgtata acgaactgca gaaagacaag  4320
atggccgagg cctacagcga gatcggcatg aagggcgagc ggaggcgggg caagggccac  4380
gacggcctgt atcagggcct gtccaccgcc accaaggata cctacgacgc cctgcacatg  4440
caggccctgc cccaaggggg cggccgctcc ggtgagggca gaggaagtct tctaacatgc  4500
```

```
ggtgacgtgg aggagaatcc gggcccctct agaagcgagc tgattaagga gaacatgcac  4560
atgaagctgt acatggaggg caccgtggac aaccatcact tcaagtgcac atccgagggc  4620
gaaggcaagc cctacgaggg cacccagacc atgagaatca aggtggtcga gggcggccct  4680
ctccccttcg ccttcgacat cctggctact agcttcctct acggcagcaa gaccttcatc  4740
aaccacaccc agggcatccc cgacttcttc aagcagtcct tccctgaggg cttcacatgg  4800
gagagagtca ccacatacga agacgggggc gtgctgaccg ctacccagga caccagcctc  4860
caggacggct gcctcatcta caacgtcaag atcagagggg tgaacttcac atccaacggc  4920
cctgtgatgc agaagaaaac actcggctgg gaggccttca ccgagacgct gtaccccgct  4980
gacggcggcc tggaaggcag aaacgacatg gccctgaagc tcgtgggcgg gagccatctg  5040
atcgcaaaca tcaagaccac atatagatcc aagaaacccg ctaagaacct caagatgcct  5100
ggcgtctact atgtggacta cagactggaa agaatcaagg aggccaacaa cgagacctac  5160
gtcgagcagc acgaggtggc agtggccaga tactgcgacc tccctagcaa actggggcac  5220
aagcttaatt gagtcgaccg agcatcttac cgccatttat acccatattt gttctgtttt  5280
tcttgatttg ggtatacatt taaatgttaa tagaacaaaa tggtggggca atcatttaca  5340
tttttaggga tatgtaatta ctagttcagg tgtattgcca caagacaaac atgttaagaa  5400
actttcccgt tatttacgct ctgttcctgt taatcaacct ctggattaca aaatttgtga  5460
aagattgact gatattctta actatgttgc tccttttacg ctgtgtggat atgctgcttt  5520
atagcctctg tatctagcta ttgcttcccg tacggctttc gttttctcct ccttgtataa  5580
atcctggttg ctgtctcttt tagaggagtt gtggcccgtt gtccgtcaac gtggcgtggt  5640
gtgctctgtg tttgctgacg caacccccac tggctggggc attgccacca cctgtcaact  5700
cctttctggg actttcgctt tccccctccc gatcgccacg gcagaactca tcgccgcctg  5760
ccttgcccgc tgctggacag gggctaggtt gctgggcact gataattccg tggtgttgtc  5820
atcgaattcg gtaccttttt aaaagaaaag gggggactgg aagggctaat tcactcccaa  5880
cgaagacaag atatcataac ttcgtatagc atacattata cgaagttata atttatttgt  5940
gaaatttgtg atgctattgc tttatttgta accatatgtt tatttgtgaa atttgtgatg  6000
ctattgcttt atttgtaacc attgctttt gcttgtactg ggtctctctg gttagaccag  6060
atctgagcct gggagctctc tggctaacta gggaacccac tgcttaagcc tcaataaagc  6120
ttgcctcgac cagcctcgac tgtgccttct agttgccagc catctgttgt ttgcccctcc  6180
cccgtgcctt ccttgaccct ggaaggtgcc actcccactg tcctttccta ataaaatgag  6240
gaaattgcat cgcattgtct gagtaggtgt cattctattc tggggggtgg ggtggggcag  6300
gacagcaagg gggaggattg ggaagacaat agcaggcatg ctggggatgc ggtgggctct  6360
atggcctgca gctgcattaa tgaatcggcc aacgcgcggg gagaggcggt ttgcgtattg  6420
ggcgctcttc cgcttcctcg ctcactgact cgctgcgctc ggtcgttcgg ctgcggcgag  6480
cggtatcagc tcactcaaag gcggtaatac ggttatccac agaatcaggg gataacgcag  6540
gaaagaacat gtgagcaaaa ggccagcaaa aggccaggaa ccgtaaaaag gccgcgttgc  6600
tggcgttttt ccataggctc cgcccccctg acgagcatca caaaaatcga cgctcaagtc  6660
agaggtggcg aaacccgaca ggactataaa gataccaggc gtttccccct ggaagctccc  6720
tcgtgcgctc tcctgttccg accctgccgc ttaccggata cctgtccgcc tttctccctt  6780
cgggaagcgt ggcgctttct catagctcac gctgtaggta tctcagttcg gtgtaggtcg  6840
ttcgctccaa gctgggctgt gtgcacgaac cccccgttca gcccgaccgc tgcgccttat  6900
ccggtaacta tcgtcttgag tccaacccgg taagacacga cttatcgcca ctggcagcag  6960
ccactggtaa caggattagc agagcgaggt atgtaggcgg tgctacagag ttcttgaagt  7020
ggtggcctaa ctacggctac actagaagga cagtatttgg tatctgcgct ctgctgaagc  7080
cagttacctt cggaaaaaga gttggtagct cttgatccgg caaacaaacc accgctggta  7140
gcggtggttt ttttgtttgc aagcagcaga ttacgcgcag aaaaaaagga tctcaagaag  7200
atcctttgat cttttctacg gggtctgacg ctcagtggaa cgaaaactca cgttaaggga  7260
ttttggtcat gagattatca aaaaggatct tcacctagat ccttttaaat taaaaatgaa  7320
gttttaaatc aatctaaagt atatatgagt aaacttggtc tgacagttac caatgcttaa  7380
tcagtgaggc acctatctca gcgatctgtc tatttcgttc atccatagtt gcctgactcc  7440
ccgtcgtgta gataactacg atacgggagg gcttaccatc tggccccagt gctgcaatga  7500
taccgcgaga cccacgctca ccggctccag atttatcagc aataaaccag ccagccggaa  7560
gggccgagcg cagaagtggt cctgcaactt tatccgcctc catccagtct attaattgtt  7620
gccgggaagc tagagtaagt agttcgccag ttaatagttt gcgcaacgtt gttgccattg  7680
ctacaggcat cgtggtgtca cgctcgtcgt ttggtatggc ttcattcagc tccggttccc  7740
aacgatcaag gcgagttaca tgatccccca tgttgtgcaa aaaagcggtt agctccttcg  7800
gtcctccgat cgttgtcaga agtaagttgg ccgcagtgtt atcactcatg gttatggcag  7860
cactgcataa ttctcttact gtcatgccat ccgtaagatg cttttctgtg actggtgagt  7920
actcaaccaa gtcattctga gaatagtgta tgcggcgacc gagttgctct tgcccggcgt  7980
caatacggga taataccgcg ccacatagca gaactttaaa agtgctcatc attggaaaac  8040
gttcttcggg gcgaaaactc tcaaggatct taccgctgtt gagatccagt tcgatgtaac  8100
ccactcgtgc acccaactga tcttcagcat cttttacttt caccagcgtt tctgggtgag  8160
caaaaacagg aaggcaaaat gccgcaaaaa agggaataag ggcgacacgg aaatgttgaa  8220
tactcatact cttccttttt caatattatt gaagcattta tcagggttat tgtctcatga  8280
gcggatacat atttgaatgt atttag                                      8306
```

```
SEQ ID NO: 44          moltype = AA  length = 741
FEATURE                Location/Qualifiers
REGION                 1..741
                       note = SS-scFvCD19-DmrA-fuP2A-FRB-TM-41BB-CD3z protein
source                 1..741
                       mol_type = protein
                       organism = synthetic construct
SEQUENCE: 44
METDTLLLWV LLLWVPGSTG DYKDEGSDIQ MTQTTSSLSA SLGDRVTISC RASQDISKYL  60
NWYQQKPDGT VKLLIYHTSR LHSGVPSRFS GSGSGTDYSL TISNLEQEDI ATYFCQQGNT  120
LPYTFGGGTK LEITGSTSGS GKPGSGEGST KGEVKLQESG PGLVAPSQSL SVTCTVSGVS  180
LPDYGVSWIR QPPRKGLEWL GVIWGSETTY YNSALKSRLT IIKDNSKSQV FLKMNSLQTD  240
DTAIYYCAKH YYYGGSYAMD YWGQGTSVTV SSASGSGGVQ VETISPGDGR TFPKRGQTCV  300
VHYTGMLEDG KKFDSSRDRN KPFKFMLGKQ EVIRGWEEGV AQMSVGQRAK LTISPDYAYG  360
```

```
ATGHPGIIPP HATLVFDVEL LKLEGGRARY KRSVSGSGAT NFSLLKQAGD VEENPGPSRS  420
ILWHEMWHEG LEEASRLYFG ERNVKGMFEV LEPLHAMMER GPQTLKETSF NQAYGRDLME  480
AQEWCRKYMK SGNVKDLTQA WDLYYHVFRR ISKASAKPTT TPAPRPPTPA PTIASQPLSL  540
RPEACRPAAG GAVHTRGLDF ACDIYIWAPL AGTCGVLLLS LVITMHKRGR KKLLYIFKQP  600
FMRPVQTTQE EDGCSCRFPE EEEGGCELRV KFSRSADAPA YQQGQNQLYN ELNLGRREEY  660
DVLDKRRGRD PEMGGKPRRK NPQEGLYNEL QKDKMAEAYS EIGMKGERRR GKGHDGLYQG  720
LSTATKDTYD ALHMQALPPR G                                            741

SEQ ID NO: 45          moltype = DNA  length = 2223
FEATURE                Location/Qualifiers
misc_feature           1..2223
                       note = SS-scFvCD19-DmrA-fuP2A-FRB-TM-41BB-CD3z DNA
source                 1..2223
                       mol_type = other DNA
                       organism = synthetic construct
SEQUENCE: 45
atggagacag acacactcct gctatgggta ctgctgctct gggttccagg ttccactggt  60
gactacaagg acgagggatc cgatatccag atgacccaga ccaccagcag cctgagcgcc  120
agcctgggcg atagagtgac catcagctgc agagccagcc aggacatcag caagtacctg  180
aactggtatc agcagaaacc cgacggcacc gtgaagctgc tgatctacca caccagcaga  240
ctgcacagcg gcgtgcccag cagattttct ggcagcggct ccggcaccga ctacagcctg  300
accatctcca acctggaaca ggaagatatc gctacctact tctgtcagca aggcaacacc  360
ctgccctaca ccttcggcgg aggcaccaag ctggaaatca ccggcagcac aagcggcagc  420
ggcaagcctg gatctggcga gggaagcacc aagggcgaag tgaaactgca ggaaagcggc  480
cctggactgg tggccccaag ccagtctctg agcgtgacct gtaccgtgtc cggcgtgtcc  540
ctgcctgact atggcgtgtc ctggatcaga cagccaccca gaaagggcct ggaatggctg  600
ggagtgatct ggggcagcga gacaacctac tacaacagcg ccctgaagtc ccggctgacc  660
atcatcaagg acaactccaa gagccaggtg ttcctgaaga tgaacagcct gcagaccgac  720
gacaccgcca tctactactg cgccaagcac tactactacg gcggcagcta cgccatggac  780
tactggggcc agggcacaag cgtgaccgtg tccagcgcta gcggctcagg aggagtgcag  840
gttgaaacca tctccccagg agacgggcgc accttcccga agcgcggaca gacatgcgtg  900
gtgcactaca ccgggatgct tgaagatgga aagaaattcg attcatcgcg ggacagaaac  960
aagcccttta agtttatgct gggcaagcag gaggtcatcc gaggctggga agaaggggtt  1020
gcccagatga gtgtcggcca gagagccaaa ctgactatat cacctgacta cgcctatggg  1080
gccactgggc accctggcat aattccgcca cacgccactc tcgtcttcga tgtggagctt  1140
ctaaaactgg aaggcggccg cgctcgttac aagcgaagtg tctcaggatc tggcgccacg  1200
aacttctctc tgttaaagca agcaggagat gttgaagaaa accccgggcc ttcaagatcc  1260
atcctctggc atgagatgtg gcatgaaggc ctggaagagg catctcgttt gtactttggg  1320
gaaaggaacg tgaaaggcat gtttgaggtg ctggagccct tgcatgctat gatggaacgg  1380
ggcccccaga ctctgaagga aacatccttt aatcaggcct atggtcgaga tttaatggag  1440
gcccaagagt ggtgcaggaa gtacatgaaa tcagggaatg tcaaggacct cacccaagcc  1500
tgggacctct attatcatgt gttccgacga atctcaaagg ctagcgccaa gcctaccacc  1560
acccctgccc ctagacctcc aacacccgcc ccaacaatcg ccagccagcc tctgtctctg  1620
aggcccgagg cttgtagacc agctgctggc ggagccgtac acaccagagg actggatttc  1680
gcctgcgaca tctacatctg ggcccctctg gccggcacat gtggcgtgct gctgctgagc  1740
ctcgtgatca ccatgcataa acggggcaga aagaaactcc tgtatatatt caaacaacca  1800
tttatgagac cagtacaaac tactcaagag gaagatggct gtagctgccg atttccagaa  1860
gaagaagaag gaggatgtga actgcgggtg aagttcagca gaagcgccga cgcccctgcc  1920
taccagcagg gccagaatca gctgtacaac gagctgaacc tgggcagaag ggaagagtac  1980
gacgtcctgg ataagcggag aggccgggac cctgagatgg gcggcaagcc tcggcggaag  2040
aacccccagg aaggcctgta taacgaactg cagaaagaca agatggccga ggcctacagc  2100
gagatcggca tgaagggcga gcggaggcgg ggcaagggcc acgacggcct gtatcagggc  2160
ctgtccaccg ccaccaagga tacctacgac gccctgcaca tgcaggccct gcccccaagg  2220
ggc                                                                2223

SEQ ID NO: 46          moltype = DNA  length = 8306
FEATURE                Location/Qualifiers
misc_feature           1..8306
                       note = SS-scFvCD19-DmrA-fuP2A-FRB-TM-41BB-CD3z lentiviral
                        vector
source                 1..8306
                       mol_type = other DNA
                       organism = synthetic construct
SEQUENCE: 46
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
```

-continued

```
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tgggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggg ccgccaccat ggagacagac acactcctgc tatgggtact gctgctctgg  2280
gttccaggtt ccactggtga ctacaaggac gagggatccg atatccagat gacccagacc  2340
accagcagcc tgagcgccag cctgggcgat agagtgacca tcagctgcag agccagccag  2400
gacatcagca agtacctgaa ctggtatcag cagaaacccg acggcaccgt gaagctgctg  2460
atctaccaca ccagcagact gcacagcggc gtgcccagca gattttctgg cagcggctcc  2520
ggcaccgact acagcctgac catctccaac ctggaacagg aagatatcgc tacctacttc  2580
tgtcagcaag gcaacaccct gccctacacc ttcggcggag gcaccaagct ggaaatcacc  2640
ggcagcacaa gcggcagcgg caagcctgga tctggcgagg gaagcaccaa gggcgaagtg  2700
aaactgcagg aaagcggccc tggactggtg gccccaagcc agtctctgag cgtgacctgt  2760
accgtgtccg gcgtgtccct gcctgactat ggcgtgtcct ggatcagaca gccacccaga  2820
aagggcctgg aatggctggg agtgatctgg ggcagcgaga caacctacta caacagcgcc  2880
ctgaagtccc ggctgaccat catcaaggac aactccaaga gccaggtgtt cctgaagatg  2940
aacagcctgc agaccgacga caccgccatc tactactgcg ccaagcacta ctactacggc  3000
ggcagctacg ccatggacta ctggggccag ggcacaagcg tgaccgtgtc cagcgctagc  3060
ggctcaggag gagtgcaggt tgaaaccatc tccccaggag acgggcgcac cttcccgaag  3120
cgcggacaga catgcgtggt gcactacacc gggatgcttg aagatggaaa gaaattcgat  3180
tcatcgcggg acagaaacaa gccctttaag tttatgctgg gcaagcagga ggtcatccga  3240
ggctgggaag aaggggttgc ccagatgagt gtcggccaga gagccaaact gactatatca  3300
cctgactacg cctatggggc cactgggcac cctggcataa ttccgccaca cgccactctc  3360
gtcttcgatg tggagcttct aaaactggaa ggcggccgcg ctcgttacaa gcgaagtgtc  3420
tcaggatctg gcgccacgaa cttctctctg ttaaagcaag caggagatgt tgaagaaaac  3480
cccgggcctt caagatccat cctctggcat gagatgtggc atgaaggcct ggaagaggca  3540
tctcgtttgt actttgggga aaggaacgtg aaaggcatgt ttgaggtgct ggagcccttg  3600
catgctatga tggaacgggg cccccagact ctgaaggaaa catcctttaa tcaggcctat  3660
ggtcgagatt taatggaggc ccaagagtgg tgcaggaagt acatgaaatc agggaatgtc  3720
aaggacctca cccaagcctg ggacctctat tatcatgtgt tccgacgaat ctcaaaggct  3780
agcgccaagc ctaccaccac ccctgcccct agacctccaa cacccgcccc aacaatcgcc  3840
agccagcctc tgtctctgag gcccgaggct tgtagaccag ctgctggcgg agccgtacac  3900
accagaggac tggatttcgc ctgcgacatc tacatctggg cccctctggc cggcacatgt  3960
ggcgtgctgc tgctgagcct cgtgatcacc atgcataaac ggggcagaaa gaaactcctg  4020
tatatattca aacaaccatt tatgagacca gtacaaacta ctcaagagga agatggctgt  4080
agctgccgat ttccagaaga agaagaagga ggatgtgaac tgcgggtgaa gttcagcaga  4140
agcgccgacg cccctgccta ccagcagggc cagaatcagc tgtacaacga gctgaacctg  4200
ggcagaaggg aagagtacga cgtcctggat aagcggagag gccgggaccc tgagatgggc  4260
ggcaagcctc ggcggaagaa cccccaggaa ggcctgtata acgaactgca gaaagacaag  4320
atggccgagg cctacagcga gatcggcatg aagggcgagc ggaggcgggg caagggccac  4380
gacggcctgt atcagggcct gtccaccgcc accaaggata cctacgacgc cctgcacatg  4440
caggccctgc ccccaagggg cggccgctcc ggtgagggca gaggaagtct tctaacatgc  4500
ggtgacgtgg aggagaatcc gggcccctct agaagcgagc tgattaagga gaacatgcac  4560
atgaagctgt acatggaggg caccgtggac aaccatcact tcaagtgcac atccgagggc  4620
gaaggcaagc cctacgaggg cacccagacc atgagaatca aggtggtcga gggcggccct  4680
ctccccttcg ccttcgacat cctggctact agcttcctct acggcagcaa gaccttcatc  4740
aaccacaccc agggcatccc cgacttcttc aagcagtcct tccctgaggg cttcacatgg  4800
gagagagtca ccacatacga agacgggggc gtgctgaccg ctacccagga caccagcctc  4860
caggacggct gcctcatcta caacgtcaag atcagagggg tgaacttcac atccaacggc  4920
cctgtgatgc agaagaaaac actcggctgg gaggccttca ccgagacgct gtaccccgct  4980
gacggcggcc tggaaggcag aaacgacatg gccctgaagc tcgtgggcgg gagccatctg  5040
atcgcaaaca tcaagaccac atatagatcc aagaaacccg ctaagaacct caagatgcct  5100
ggcgtctact atgtggacta cagactggaa agaatcaagg aggccaacaa cgagacctac  5160
gtcgagcagc acgaggtggc agtggccaga tactgcgacc tccctagcaa actggggcac  5220
aagcttaatt gagtcgaccg agcatcttac cgccatttat acccatattt gttctgtttt  5280
tcttgatttg ggtatacatt taaatgttaa tagaacaaaa tggtggggca atcatttaca  5340
tttttaggga tatgtaatta ctagttcagg tgtattgcca caagacaaac atgttaagaa  5400
actttcccgt tatttacgct ctgttcctgt taatcaacct ctggattaca aaatttgtga  5460
aagattgact gatattctta actatgttgc tccttttacg ctgtgtggat atgctgcttt  5520
atagcctctg tatctagcta ttgcttcccg tacggctttc gttttctcct ccttgtataa  5580
atcctggttg ctgtctcttt tagaggagtt gtggcccgtt gtccgtcaac gtggcgtggt  5640
```

-continued

```
gtgctctgtg tttgctgacg caaccccac tggctggggc attgccacca cctgtcaact  5700
cctttctggg actttcgctt tccccctccc gatcgccacg gcagaactca tcgccgcctg  5760
ccttgcccgc tgctggacag gggctaggtt gctgggcact gataattccg tggtgttgtc  5820
atcgaattcg gtaccttttt aaaagaaaag gggggactgg aagggctaat tcactcccaa  5880
cgaagacaag atatcataac ttcgtatagc atacattata cgaagttata atttatttgt  5940
gaaatttgtg atgctattgc tttatttgta accatatgtt tatttgtgaa atttgtgatg  6000
ctattgcttt atttgtaacc attgcttttt gcttgtactg ggtctctctg gttagaccag  6060
atctgagcct gggagctctc tggctaacta gggaacccac tgcttaagcc tcaataaagc  6120
ttgcctcgac cagcctcgac tgtgccttct agttgccagc catctgttgt ttgcccctcc  6180
cccgtgcctt ccttgaccct ggaaggtgcc actcccactg tcctttccta ataaaatgag  6240
gaaattgcat cgcattgtct gagtaggtgt cattctattc tggggggtgg ggtggggcag  6300
gacagcaagg gggaggattg ggaagacaat agcaggcatg ctggggatgc ggtgggctct  6360
atggcctgca gctgcattaa tgaatcggcc aacgcgcggg gagaggcggt ttgcgtattg  6420
ggcgctcttc cgcttcctcg ctcactgact cgctgcgctc ggtcgttcgg ctgcggcgag  6480
cggtatcagc tcactcaaag gcggtaatac ggttatccac agaatcaggg gataacgcag  6540
gaaagaacat gtgagcaaaa ggccagcaaa aggccaggaa ccgtaaaaag gccgcgttgc  6600
tggcgttttt ccataggctc cgcccccctg acgagcatca caaaaatcga cgctcaagtc  6660
agaggtggcg aaacccgaca ggactataaa gataccaggc gtttccccct ggaagctccc  6720
tcgtgcgctc tcctgttccg accctgccgc ttaccggata cctgtccgcc tttctccctt  6780
cgggaagcgt ggcgctttct catagctcac gctgtaggta tctcagttcg gtgtaggtcg  6840
ttcgctccaa gctgggctgt gtgcacgaac cccccgttca gcccgaccgc tgcgccttat  6900
ccggtaacta tcgtcttgag tccaacccgg taagacacga cttatcgcca ctggcagcag  6960
ccactggtaa caggattagc agagcgaggt atgtaggcgg tgctacagag ttcttgaagt  7020
ggtggcctaa ctacggctac actagaagga cagtatttgg tatctgcgct ctgctgaagc  7080
cagttacctt cggaaaaaga gttggtagct cttgatccgg caaacaaacc accgctggta  7140
gcggtggttt ttttgtttgc aagcagcaga ttacgcgcag aaaaaaagga tctcaagaag  7200
atcctttgat cttttctacg gggtctgacg ctcagtggaa cgaaaactca cgttaaggga  7260
ttttggtcat gagattatca aaaaggatct tcacctagat ccttttaaat taaaaatgaa  7320
gttttaaatc aatctaaagt atatatgagt aaacttggtc tgacagttac caatgcttaa  7380
tcagtgaggc acctatctca gcgatctgtc tatttcgttc atccatagtt gcctgactcc  7440
ccgtcgtgta gataactacg atacgggagg gcttaccatc tggccccagt gctgcaatga  7500
taccgcgaga cccacgctca ccggctccag atttatcagc aataaaccag ccagccggaa  7560
gggccgagcg cagaagtggt cctgcaactt tatccgcctc catccagtct attaattgtt  7620
gccgggaagc tagagtaagt agttcgccag ttaatagttt gcgcaacgtt gttgccattg  7680
ctacaggcat cgtggtgtca cgctcgtcgt ttggtatggc ttcattcagc tccggttccc  7740
aacgatcaag gcgagttaca tgatccccca tgttgtgcaa aaaagcggtt agctccttcg  7800
gtcctccgat cgttgtcaga agtaagttgg ccgcagtgtt atcactcatg gttatggcag  7860
cactgcataa ttctcttact gtcatgccat ccgtaagatg cttttctgtg actggtgagt  7920
actcaaccaa gtcattctga gaatagtgta tgcggcgacc gagttgctct tgcccggcgt  7980
caatacggga taataccgcg ccacatagca gaactttaaa agtgctcatc attggaaaac  8040
gttcttcggg gcgaaaactc tcaaggatct taccgctgtt gagatccagt tcgatgtaac  8100
ccactcgtgc acccaactga tcttcagcat cttttacttt caccagcgtt tctgggtgag  8160
caaaaacagg aaggcaaaat gccgcaaaaa agggaataag ggcgacacgg aaatgttgaa  8220
tactcatact cttccttttt caatattatt gaagcattta tcagggttat tgtctcatga  8280
gcggatacat atttgaatgt atttag                                      8306

SEQ ID NO: 47          moltype = AA  length = 967
FEATURE                Location/Qualifiers
REGION                 1..967
                       note = SS-scFvCD19-DmrA-fuP2A-2xDmrB-DmrC-TM-41BB-CD3z
                        protein
source                 1..967
                       mol_type = protein
                       organism = synthetic construct
SEQUENCE: 47
METDTLLLWV LLLWVPGSTG DYKDEGSDIQ MTQTTSSLSA SLGDRVTISC RASQDISKYL  60
NWYQQKPDGT VKLLIYHTSR LHSGVPSRFS GSGSGTDYSL TISNLEQEDI ATYFCQQGNT  120
LPYTFGGGTK LEITGSTSGS GKPGSGEGST KGEVKLQESG PGLVAPSQSL SVTCTVSGVS  180
LPDYGVSWIR QPPRKGLEWL GVIWGSETTY YNSALKSRLT IIKDNSKSQV FLKMNSLQTD  240
DTAIYYCAKH YYYGGSYAMD YWGQGTSVTV SSASGSGGVQ VETISPGDGR TFPKRGQTCV  300
VHYTGMLEDG KKFDSSRDRN KPFKFMLGKQ EVIRGWEEGV AQMSVGQRAK LTISPDYAYG  360
ATGHPGIIPP HATLVFDVEL LKLEGGRARY KRSVSGSGAT NFSLLKQAGD VEENPGPSRS  420
GGVQVETISP GDGRTFPKRG QTCVVHYTGM LEDGKKVDSS RDRNKPFKFM LGKQEVIRGW  480
EEGVAQMSVG QRAKLTISPD YAYGATGHPG IIPPHATLVF DVEFLKLESG TSGTSGVQVE  540
TISPGDGRTF PKRGQTCVVH YTGMLEDGKK VDSSRDRNKP FKFMLGKQEV IRGWEEGVAQ  600
MSVGQRAKLT ISPDYAYGAT GHPGIIPPHA TLVFDVELLK LEGSRSILWH EMWHEGLEEA  660
SRLYFGERNV KGMFEVLEPL HAMMERGPQT LKETSFNQAY GRDLMEAQEW CRKYMKSGNV  720
KDLLQAWDLY YHVFRRISKA SAKPTTTPAP RPPTPAPTIA SQPLSLRPEA CRPAAGGAVH  780
TRGLDFACDI YIWAPLAGTC GVLLLSLVIT MHKRGRKKLL YIFKQPFMRP VQTTQEEDGC  840
SCRFPEEEEG GCELRVKFSR SADAPAYQQG QNQLYNELNL GRREEYDVLD KRRGRDPEMG  900
GKPRRKNPQE GLYNELQKDK MAEAYSEIGM KGERRRGKGH DGLYQGLSTA TKDTYDALHM  960
QALPPRG                                                           967

SEQ ID NO: 48          moltype = DNA  length = 2901
FEATURE                Location/Qualifiers
misc_feature           1..2901
                       note = SS-scFvCD19-DmrA-fuP2A-2xDmrB-DmrC-TM-41BB-CD3z DNA
source                 1..2901
                       mol_type = other DNA
```

```
                         organism = synthetic construct
SEQUENCE: 48
atggagacag acacactcct gctatgggta ctgctgctct gggttccagg ttccactggt  60
gactacaagg acgagggatc cgatatccag atgacccaga ccaccagcag cctgagcgcc  120
agcctgggcg atagagtgac catcagctgc agagccagcc aggacatcag caagtacctg  180
aactggtatc agcagaaacc cgacggcacc gtgaagctgc tgatctacca caccagcaga  240
ctgcacagcg gcgtgcccag cagattttct ggcagcggct ccggcaccga ctacagcctg  300
accatctcca acctggaaca ggaagatatc gctacctact tctgtcagca aggcaacacc  360
ctgccctaca ccttcggcgg aggcaccaag ctggaaatca ccggcagcac aagcggcagc  420
ggcaagcctg gatctggcga gggaagcacc aagggcgaag tgaaactgca ggaaagcggc  480
cctggactgg tggccccaag ccagtctctg agcgtgacct gtaccgtgtc cggcgtgtcc  540
ctgcctgact atggcgtgtc ctggatcaga cagccaccca gaaagggcct ggaatggctg  600
ggagtgatct ggggcagcga gacaacctac tacaacagcg ccctgaagtc ccggctgacc  660
atcatcaagg acaactccaa gagccaggtg ttcctgaaga tgaacagcct gcagaccgac  720
gacaccgcca tctactactg cgccaagcac tactactacg gcggcagcta cgccatggac  780
tactggggcc agggcacaag cgtgaccgtg tccagcgcta gcggctcagg aggagtgcag  840
gttgaaacca tctccccagg agacgggcgc accttcccga agcgcggaca gacatgcgtg  900
gtgcactaca ccgggatgct tgaagatgga aagaaattcg attcatcgcg ggacagaaac  960
aagcccttta agtttatgct gggcaagcag gaggtcatcc gaggctggga agaaggggtt  1020
gcccagatga gtgtcggcca gagagccaaa ctgactatat cacctgacta cgcctatggg  1080
gccactgggc accctggcat aattccgcca cacgccactc tcgtcttcga tgtggagctt  1140
ctaaaactgg aaggcggccg cgctcgttac aagcgaagtg tctcaggatc tggcgccacg  1200
aacttctctc tgttaaagca agcaggagat gttgaagaaa accccgggcc ttcaagatcc  1260
ggcggtgtcc aagtcgaaac tatatcgcct ggcgatggca gaacgtttcc caaacgtggc  1320
cagacctgtg tcgtacacta taccggcatg ctagaggatg ggaaaaaggt tgattccagt  1380
cgcgatcgga acaaaccgtt taaattcatg ttggggaagc aagaggttat caggggatgg  1440
gaagagggtg tcgcgcaaat gtcggttggg caacgtgcga aactcacaat ttccccggat  1500
tacgcatacg gagctaccgg acaccctggg attatcccac cgcatgcgac gctagtgttt  1560
gacgtagagt tcttgaagct cgaatcaggt acaagcggca cttctggcgt acaggttgag  1620
acaattagtc ccggagacgg acgtacattc ccaaagagag ggcaaacttg cgtagtccat  1680
tacactggaa tgttggaaga cggcaagaaa gtggacagtt caagagaccg caataagcct  1740
ttcaagttta tgctcggaaa acaggaagtc atacgcggtt gggaggaagg cgtggctcag  1800
atgagcgtcg gacagagggc aaagttgacc atcagtcccg actatgcgta tggcgcgaca  1860
ggccatcccg gaatcatacc tccccacgca accttggtat tcgatgtcga actgctcaaa  1920
ttagagggta gtagatccat cctctggcat gagatgtggc atgaaggcct ggaagaggca  1980
tctcgtttgt actttgggga aaggaacgtg aaaggcatgt ttgaggtgct ggagcccttg  2040
catgctatga tggaacgggg cccccagact ctgaaggaaa catcctttaa tcaggcctat  2100
ggtcgagatt taatggaggc ccaagagtgg tgcaggaagt acatgaaatc agggaatgtc  2160
aaggacctcc tccaagcctg ggacctctat tatcatgtgt tccgacgaat ctcaaaggct  2220
agcgccaagc ctaccaccac ccctgcccct agacctccaa cacccgcccc aacaatcgcc  2280
agccagcctc tgtctctgag gcccgaggct tgtagaccag ctgctggcgg agccgtacac  2340
accagaggac tggatttcgc ctgcgacatc tacatctggg cccctctggc cggcacatgt  2400
ggcgtgctgc tgctgagcct cgtgatcacc atgcataaac ggggcagaaa gaaactcctg  2460
tatatattca aacaaccatt tatgagacca gtacaaacta ctcaagagga agatggctgt  2520
agctgccgat ttccagaaga agaagaagga ggatgtgaac tgcgggtgaa gttcagcaga  2580
agcgccgacg cccctgccta ccagcagggc cagaatcagc tgtacaacga gctgaacctg  2640
ggcagaaggg aagagtacga cgtcctggat aagcggagag gccgggaccc tgagatgggc  2700
ggcaagcctc ggcggaagaa cccccaggaa ggcctgtata acgaactgca gaaagacaag  2760
atggccgagg cctacagcga gatcggcatg aagggcgagc ggaggcgggg caagggccac  2820
gacggcctgt atcagggcct gtccaccgcc accaaggata cctacgacgc cctgcacatg  2880
caggccctgc cccaaggggg c                                            2901

SEQ ID NO: 49            moltype = DNA  length = 8984
FEATURE                  Location/Qualifiers
misc_feature             1..8984
                         note = SS-scFvCD19-DmrA-fuP2A-2xDmrB-DmrC-TM-41BB-CD3z
                          lentiviral vector
source                   1..8984
                         mol_type = other DNA
                         organism = synthetic construct
SEQUENCE: 49
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
```

```
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tgggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggg ccgccaccat ggagacagac acactcctgc tatgggtact gctgctctgg  2280
gttccaggtt ccactggtga ctacaaggac gagggatccg atatccagat gacccagacc  2340
accagcagcc tgagcgccag cctgggcgat agagtgacca tcagctgcag agccagccag  2400
gacatcagca agtacctgaa ctggtatcag cagaaacccg acggcaccgt gaagctgctg  2460
atctaccaca ccagcagact gcacagcggc gtgcccagca gattttctgg cagcggctcc  2520
ggcaccgact acagcctgac catctccaac ctggaacagg aagatatcgc tacctacttc  2580
tgtcagcaag gcaacaccct gccctacacc ttcggcggag gcaccaagct ggaaatcacc  2640
ggcagcacaa gcggcagcgg caagcctgga tctggcgagg gaagcaccaa gggcgaagtg  2700
aaactgcagg aaagcggccc tggactggtg gccccaagcc agtctctgag cgtgacctgt  2760
accgtgtccg gcgtgtccct gcctgactat ggcgtgtcct ggatcagaca gccacccaga  2820
aagggcctgg aatggctggg agtgatctgg ggcagcgaga caacctacta caacagcgcc  2880
ctgaagtccc ggctgaccat catcaaggac aactccaaga gccaggtgtt cctgaagatg  2940
aacagcctgc agaccgacga caccgccatc tactactgcg ccaagcacta ctactacggc  3000
ggcagctacg ccatggacta ctggggccag ggcacaagcg tgaccgtgtc cagcgctagc  3060
ggctcaggag gagtgcaggt tgaaaccatc tccccaggag acgggcgcac cttcccgaag  3120
cgcggacaga catgcgtggt gcactacacc gggatgcttg aagatggaaa gaaattcgat  3180
tcatcgcggg acagaaacaa gccctttaag tttatgctgg gcaagcagga ggtcatccga  3240
ggctgggaag aaggggttgc ccagatgagt gtcggccaga gagccaaact gactatatca  3300
cctgactacg cctatggggc cactgggcac cctggcataa ttccgccaca cgccactctc  3360
gtcttcgatg tggagcttct aaaactggaa ggcggccgcg ctcgttacaa gcgaagtgtc  3420
tcaggatctg gcgccacgaa cttctctctg ttaaagcaag caggagatgt tgaagaaaac  3480
cccgggcctt caagatccgg cggtgtccaa gtcgaaacta tatcgcctgg cgatggcaga  3540
acgtttccca aacgtggcca gacctgtgtc gtacactata ccggcatgct agaggatggg  3600
aaaaaggttg attccagtcg cgatcggaac aaaccgttta aattcatgtt ggggaagcaa  3660
gaggttatca ggggatggga agagggtgtc gcgcaaatgt cggttgggca acgtgcgaaa  3720
ctcacaattt ccccggatta cgcatacgga gctaccggac accctgggat tatcccaccg  3780
catgcgacgc tagtgtttga cgtagagttc ttgaagctcg aatcaggtac aagcggcact  3840
tctggcgtac aggttgagac aattagtccc ggagacggac gtacattccc aaagagaggg  3900
caaacttgcg tagtccatta cactggaatg ttggaagacg gcaagaaagt ggacagttca  3960
agagaccgca ataagccttt caagtttatg ctcggaaaac aggaagtcat acgcggttgg  4020
gaggaaggcg tggctcagat gagcgtcgga cagagggcaa agttgaccat cagtcccgac  4080
tatgcgtatg gcgcgacagg ccatcccgga atcatacctc cccacgcaac cttggtattc  4140
gatgtcgaac tgctcaaatt agagggtagt agatccatcc tctggcatga gatgtggcat  4200
gaaggcctgg aagaggcatc tcgtttgtac tttggggaaa ggaacgtgaa aggcatgttt  4260
gaggtgctgg agcccttgca tgctatgatg gaacggggcc cccagactct gaaggaaaca  4320
tcctttaatc aggcctatgg tcgagattta atggaggccc aagagtggtg caggaagtac  4380
atgaaatcag ggaatgtcaa ggacctcctc caagcctggg acctctatta tcatgtgttc  4440
cgacgaatct caaaggctag cgccaagcct accaccaccc ctgcccctag acctccaaca  4500
cccgccccaa caatcgccag ccagcctctg tctctgaggc ccgaggcttg tagaccagct  4560
gctggcggag ccgtacacac cagaggactg gatttcgcct gcgacatcta catctgggcc  4620
cctctggccg gcacatgtgg cgtgctgctg ctgagcctcg tgatcaccat gcataaacgg  4680
ggcagaaaga aactcctgta tatattcaaa caaccattta tgagaccagt acaaactact  4740
caagaggaag atggctgtag ctgccgattt ccagaagaag aagaaggagg atgtgaactg  4800
cgggtgaagt tcagcagaag cgccgacgcc cctgcctacc agcagggcca gaatcagctg  4860
tacaacgagc tgaacctggg cagaagggaa gagtacgacg tcctggataa gcggagaggc  4920
cgggaccctg agatgggcgg caagcctcgg cggaagaacc cccaggaagg cctgtataac  4980
gaactgcaga aagacaagat ggccgaggcc tacagcgaga tcggcatgaa gggcgagcgg  5040
aggcggggca agggccacga cggcctgtat cagggcctgt ccaccgccac caaggatacc  5100
tacgacgccc tgcacatgca ggccctgccc ccaaggggcg gccgctccgg tgagggcaga  5160
ggaagtcttc taacatgcgg tgacgtggag gagaatccgg gcccctctag aagcgagctg  5220
attaaggaga acatgcacat gaagctgtac atggagggca ccgtggacaa ccatcacttc  5280
aagtgcacat ccgagggcga aggcaagccc tacgagggca cccagaccat gagaatcaag  5340
gtggtcgagg gcggccctct ccccttcgcc ttcgacatcc tggctactag cttcctctac  5400
ggcagcaaga ccttcatcaa ccacacccag ggcatccccg acttcttcaa gcagtccttc  5460
cctgagggct tcacatggga gagagtcacc acatacgaag acgggggcgt gctgaccgct  5520
acccaggaca ccagcctcca ggacggctgc ctcatctaca acgtcaagat cagaggggtg  5580
aacttcacat ccaacggccc tgtgatgcag aagaaaacac tcggctggga ggccttcacc  5640
gagacgctgt accccgctga cggcggcctg gaaggcagaa acgacatggc cctgaagctc  5700
gtgggcggga gccatctgat cgcaaacatc aagaccacat atagatccaa gaaacccgct  5760
aagaacctca agatgcctgg cgtctactat gtggactaca gactggaaag aatcaaggag  5820
```

```
gccaacaacg agacctacgt cgagcagcac gaggtggcag tggccagata ctgcgacctc  5880
cctagcaaac tggggcacaa gcttaattga gtcgaccgag catcttaccg ccatttatac  5940
ccatatttgt tctgtttttc ttgatttggg tatacattta aatgttaata gaacaaaatg  6000
gtggggcaat catttacatt tttagggata tgtaattact agttcaggtg tattgccaca  6060
agacaaacat gttaagaaac tttcccgtta tttacgctct gttcctgtta atcaacctct  6120
ggattacaaa atttgtgaaa gattgactga tattcttaac tatgttgctc cttttacgct  6180
gtgtggatat gctgctttat agcctctgta tctagctatt gcttcccgta cggctttcgt  6240
tttctcctcc ttgtataaat cctggttgct gtctctttta gaggagttgt ggcccgttgt  6300
ccgtcaacgt ggcgtggtgt gctctgtgtt tgctgacgca acccccactg gctggggcat  6360
tgccaccacc tgtcaactcc tttctgggac tttcgctttc cccctcccga tcgccacggc  6420
agaactcatc gccgcctgcc ttgcccgctg ctggacaggg gctaggttgc tgggcactga  6480
taattccgtg gtgttgtcat cgaattcggt accttttttaa aagaaaaggg gggactggaa  6540
gggctaattc actcccaacg aagacaagat atcataactt cgtatagcat acattatacg  6600
aagttataat ttatttgtga aatttgtgat gctattgctt tatttgtaac catatgttta  6660
tttgtgaaat ttgtgatgct attgctttat ttgtaaccat tgctttttgc ttgtactggg  6720
tctctctggt tagaccagat ctgagcctgg gagctctctg gctaactagg gaacccactg  6780
cttaagcctc aataaagctt gcctcgacca gcctcgactg tgccttctag ttgccagcca  6840
tctgttgttt gcccctcccc cgtgccttcc ttgaccctgg aaggtgccac tcccactgtc  6900
ctttcctaat aaaatgagga aattgcatcg cattgtctga gtaggtgtca ttctattctg  6960
gggggtgggg tggggcagga cagcaagggg gaggattggg aagacaatag caggcatgct  7020
ggggatgcgg tgggctctat ggcctgcagc tgcattaatg aatcggccaa cgcgcgggga  7080
gaggcggttt gcgtattggg cgctcttccg cttcctcgct cactgactcg ctgcgctcgg  7140
tcgttcggct gcggcgagcg gtatcagctc actcaaaggc ggtaatacgg ttatccacag  7200
aatcagggga taacgcagga aagaacatgt gagcaaaagg ccagcaaaag gccaggaacc  7260
gtaaaaaggc cgcgttgctg gcgtttttcc ataggctccg cccccctgac gagcatcaca  7320
aaaatcgacg ctcaagtcag aggtggcgaa acccgacagg actataaaga taccaggcgt  7380
ttccccctgg aagctccctc gtgcgctctc ctgttccgac cctgccgctt accggatacc  7440
tgtccgcctt tctcccttcg ggaagcgtgg cgctttctca tagctcacgc tgtaggtatc  7500
tcagttcggt gtaggtcgtt cgctccaagc tgggctgtgt gcacgaaccc cccgttcagc  7560
ccgaccgctg cgccttatcc ggtaactatc gtcttgagtc caacccggta agacacgact  7620
tatcgccact ggcagcagcc actggtaaca ggattagcag agcgaggtat gtaggcggtg  7680
ctacagagtt cttgaagtgg tggcctaact acggctacac tagaaggaca gtatttggta  7740
tctgcgctct gctgaagcca gttaccttcg gaaaaagagt tggtagctct tgatccggca  7800
aacaaaccac cgctggtagc ggtggttttt ttgtttgcaa gcagcagatt acgcgcagaa  7860
aaaaaggatc tcaagaagat cctttgatct tttctacggg gtctgacgct cagtggaacg  7920
aaaactcacg ttaagggatt ttggtcatga gattatcaaa aaggatcttc acctagatcc  7980
ttttaaatta aaaatgaagt tttaaatcaa tctaaagtat atatgagtaa acttggtctg  8040
acagttacca atgcttaatc agtgaggcac ctatctcagc gatctgtcta tttcgttcat  8100
ccatagttgc ctgactcccc gtcgtgtaga taactacgat acgggagggc ttaccatctg  8160
gccccagtgc tgcaatgata ccgcgagacc cacgctcacc ggctccagat ttatcagcaa  8220
taaaccagcc agccggaagg gccgagcgca gaagtggtcc tgcaacttta tccgcctcca  8280
tccagtctat taattgttgc cgggaagcta gagtaagtag ttcgccagtt aatagtttgc  8340
gcaacgttgt tgccattgct acaggcatcg tggtgtcacg ctcgtcgttt ggtatggctt  8400
cattcagctc cggttcccaa cgatcaaggc gagttacatg atcccccatg ttgtgcaaaa  8460
aagcggttag ctccttcggt cctccgatcg ttgtcagaag taagttggcc gcagtgttat  8520
cactcatggt tatggcagca ctgcataatt ctcttactgt catgccatcc gtaagatgct  8580
tttctgtgac tggtgagtac tcaaccaagt cattctgaga atagtgtatg cggcgaccga  8640
gttgctcttg cccggcgtca atacgggata ataccgcgcc acatagcaga actttaaaag  8700
tgctcatcat tggaaaacgt tcttcggggc gaaaactctc aaggatctta ccgctgttga  8760
gatccagttc gatgtaaccc actcgtgcac ccaactgatc ttcagcatct tttactttca  8820
ccagcgtttc tgggtgagca aaaacaggaa ggcaaaatgc cgcaaaaaag ggaataaggg  8880
cgacacggaa atgttgaata ctcatactct tcctttttca atattattga agcatttatc  8940
agggttattg tctcatgagc ggatacatat ttgaatgtat ttag                  8984
```

```
SEQ ID NO: 50          moltype = AA  length = 406
FEATURE                Location/Qualifiers
REGION                 1..406
                       note = SS-CD19scFv-DmrA-CD4TM protein
source                 1..406
                       mol_type = protein
                       organism = synthetic construct
SEQUENCE: 50
MPLGLLWLGL ALLGALHAQA GSDIQMTQTT SSLSASLGDR VTISCRASQD ISKYLNWYQQ  60
KPDGTVKLLI YHTSRLHSGV PSRFSGSGSG TDYSLTISNL EQEDIATYFC QQGNTLPYTF  120
GGGTKLEITG STSGSGKPGS GEGSTKGEVK LQESGPGLVA PSQSLSVTCT VSGVSLPDYG  180
VSWIRQPPRK GLEWLGVIWG SETTYYNSAL KSRLTIIKDN SKSQVFLKMN SLQTDDTAIY  240
YCAKHYYYGG SYAMDYWGQG TSVTVSSASG GGGSGVQVET ISPGDGRTFP KRGQTCVVHY  300
TGMLEDGKKF DSSRDRNKPF KFMLGKQEVI RGWEEGVAQM SVGQRAKLTI SPDYAYGATG  360
HPGIIPPHAT LVFDVELLKL EGGRMALIVL GGVAGLLLFI GLGIFF                 406
```

```
SEQ ID NO: 51          moltype = DNA  length = 1218
FEATURE                Location/Qualifiers
misc_feature           1..1218
                       note = SS-CD19scFv-DmrA-CD4TM DNA
source                 1..1218
                       mol_type = other DNA
                       organism = synthetic construct
SEQUENCE: 51
atgcccctgg gcctgctgtg gctgggcctg gccctgctgg gcgccctgca cgcccaggcc  60
```

```
ggatccgata tccagatgac ccagaccacc agcagcctga gcgccagcct gggcgataga  120
gtgaccatca gctgcagagc cagccaggac atcagcaagt acctgaactg gtatcagcag  180
aaacccgacg gcaccgtgaa gctgctgatc taccacacca gcagactgca cagcggcgtg  240
cccagcagat tttctggcag cggctccggc accgactaca gcctgaccat ctccaacctg  300
gaacaggaag atatcgctac ctacttctgt cagcaaggca acaccctgcc ctacaccttc  360
ggcggaggca ccaagctgga aatcaccggc agcacaagcg gcagcggcaa gcctggatct  420
ggcgagggaa gcaccaaggg cgaagtgaaa ctgcaggaaa gcggccctgg actggtggcc  480
ccaagccagt ctctgagcgt gacctgtacc gtgtccggcg tgtccctgcc tgactatggc  540
gtgtcctgga tcagacagcc acccagaaag ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tactgcgcca agcactacta ctacggcggc agctacgcca tggactactg gggccagggc  780
acaagcgtga ccgtgtccag cgctagcggc ggaggtggga gcggagtgca ggtggaaacc  840
atctccccag gagacgggcg caccttcccc aagcgcggcc agacctgcgt ggtgcactac  900
accgggatgc ttgaagatgg aaagaaattt gattcctccc gggacagaaa caagcccttt  960
aagtttatgc taggcaagca ggaggtgatc cgaggctggg aagaaggggt tgcccagatg  1020
agtgtgggtc agagagccaa actgactata tctccagatt atgcctatgg tgccactggg  1080
cacccaggca tcatcccacc acatgccact ctcgtcttcg atgtggagct tctaaaactg  1140
gaaggcggcc gcatggccct gattgtgctg gggggcgtcg ccggcctcct gcttttcatt  1200
gggctaggca tcttcttc                                                1218
```

```
SEQ ID NO: 52          moltype = DNA  length = 7336
FEATURE                Location/Qualifiers
misc_feature           1..7336
                       note = pCVL_sEF1a-T7-hScnSS-CD19scFv-DmrA-CD4TM lentiviral
                        vector
source                 1..7336
                       mol_type = other DNA
                       organism = synthetic construct
SEQUENCE: 52
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tgggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatgccc ctgggcctgc  2280
tgtggctggg cctggccctg ctgggcgccc tgcacgccca ggccggatcc gatatccaga  2340
tgacccagac caccagcagc ctgagcgcca gcctgggcga tagagtgacc atcagctgca  2400
gagccagcca ggacatcagc aagtacctga actggtatca gcagaaaccc gacggcaccg  2460
tgaagctgct gatctaccac accagcagac tgcacagcgg cgtgcccagc agattttctg  2520
gcagcggctc cggcaccgac tacagcctga ccatctccaa cctggaacag gaagatatcg  2580
ctacctactt ctgtcagcaa ggcaacaccc tgccctacac cttcggcgga ggcaccaagc  2640
tggaaatcac cggcagcaca agcggcagcg gcaagcctgg atctggcgag ggaagcacca  2700
agggcgaagt gaaactgcag gaaagcggcc ctggactggt ggccccaagc cagtctctga  2760
gcgtgacctg taccgtgtcc ggcgtgtccc tgcctgacta tggcgtgtcc tggatcagac  2820
agccacccag aaagggcctg gaatggctgg gagtgatctg gggcagcgag acaacctact  2880
acaacagcgc cctgaagtcc cggctgacca tcatcaagga caactccaag agccaggtgt  2940
```

```
tcctgaagat gaacagcctg cagaccgacg acaccgccat ctactactgc gccaagcact 3000
actactacgg cggcagctac gccatggact actggggcca gggcacaagc gtgaccgtgt 3060
ccagcgctag cggcggaggt gggagcggag tgcaggtgga aaccatctcc ccaggagacg 3120
ggcgcacctt ccccaagcgc ggccagacct gcgtggtgca ctacaccggg atgcttgaag 3180
atggaaagaa atttgattcc tcccgggaca gaaacaagcc ctttaagttt atgctaggca 3240
agcaggaggt gatccgaggc tgggaagaag gggttgccca gatgagtgtg ggtcagagag 3300
ccaaactgac tatatctcca gattatgcct atggtgccac tgggcaccca ggcatcatcc 3360
caccacatgc cactctcgtc ttcgatgtgg agcttctaaa actggaaggc ggccgcatgg 3420
ccctgattgt gctgggggc gtcgccggcc tcctgctttt cattgggcta ggcatcttct 3480
tcatgcattc cggtgagggc agaggaagtc ttctaacatg cggtgacgtg gaggagaatc 3540
cgggcccctc tagagtgagc aagggcgagg aggataacat ggccatcatc aaggagttca 3600
tgcgcttcaa ggtgcacatg gagggctccg tgaacggcca cgagttcgag atcgagggcg 3660
agggcgaggg ccgcccctac gagggcaccc agaccgccaa gctgaaggtg accaagggtg 3720
gcccccctgcc cttcgcctgg gacatcctgt cccctcagtt catgtacggc tccaaggcct 3780
acgtgaagca ccccgccgac atccccgact acttgaagct gtccttcccc gagggcttca 3840
agtgggagcg cgtgatgaac ttcgaggacg gcggcgtggt gaccgtgacc caggactcct 3900
ctctgcagga cggcgagttc atctacaagg tgaagctgcg cggcaccaac ttcccctccg 3960
acggccccgt aatgcagaag aagactatgg gctgggaggc ctcctccgag cggatgtacc 4020
ccgaggacgg cgccctgaag ggcgagatca agcagaggct gaagctgaag gacggcggcc 4080
actacgacgc tgaggtcaag accacctaca aggccaagaa gcccgtgcag ctgcccggcg 4140
cctacaacgt caacatcaag ttggacatca cctcccacaa cgaggactac accatcgtgg 4200
aacagtacga acgcgccgag ggccgccact ccaccggcgg catggacgag ctgtacaagt 4260
aagtcgaccg agcatcttac cgccatttat acccatattt gttctgtttt tcttgatttg 4320
ggtatacatt taaatgttaa tagaacaaaa tggtggggca atcatttaca tttttaggga 4380
tatgtaatta ctagttcagg tgtattgcca caagacaaac atgttaagaa actttcccgt 4440
tatttacgct ctgttcctgt taatcaacct ctggattaca aaatttgtga aagattgact 4500
gatattctta actatgttgc tccttttacg ctgtgtggat atgctgcttt atagcctctg 4560
tatctagcta ttgcttcccg tacggctttc gttttctcct ccttgtataa atcctggttg 4620
ctgtctcttt tagaggagtt gtggcccgtt gtccgtcaac gtggcgtggt gtgctctgtg 4680
tttgctgacg caacccccac tggctggggc attgccacca cctgtcaact cctttctggg 4740
actttcgctt tccccctccc gatcgccacg gcagaactca tcgccgcctg ccttgcccgc 4800
tgctggacag gggctaggtt gctgggcact gataattccg tggtgttgtc atcgaattcg 4860
gtaccttttt aaaagaaaag gggggactgg aagggctaat tcactcccaa cgaagacaag 4920
atatcataac ttcgtatagc atacattata cgaagttata atttatttgt gaaatttgtg 4980
atgctattgc tttatttgta accatatgtt tatttgtgaa atttgtgatg ctattgcttt 5040
atttgtaacc attgcttttt gcttgtactg ggtctctctg gttagaccag atctgagcct 5100
gggagctctc tggctaacta gggaacccac tgcttaagcc tcaataaagc ttgcctcgac 5160
cagcctcgac tgtgccttct agttgccagc catctgttgt ttgcccctcc cccgtgcctt 5220
ccttgaccct ggaaggtgcc actcccactg tcctttccta ataaaatgag gaaattgcat 5280
cgcattgtct gagtaggtgt cattctattc tggggggtgg ggtggggcag gacagcaagg 5340
gggaggattg ggaagacaat agcaggcatg ctggggatgc ggtgggctct atggcctgca 5400
gctgcattaa tgaatcggcc aacgcgcggg gagaggcggt ttgcgtattg ggcgctcttc 5460
cgcttcctcg ctcactgact cgctgcgctc ggtcgttcgg ctgcggcgag cggtatcagc 5520
tcactcaaag gcggtaatac ggttatccac agaatcaggg gataacgcag gaaagaacat 5580
gtgagcaaaa ggccagcaaa aggccaggaa ccgtaaaaag gccgcgttgc tggcgttttt 5640
ccataggctc cgcccccctg acgagcatca caaaaatcga cgctcaagtc agaggtggcg 5700
aaacccgaca ggactataaa gataccaggc gtttccccct ggaagctccc tcgtgcgctc 5760
tcctgttccg accctgccgc ttaccggata cctgtccgcc tttctccctt cgggaagcgt 5820
ggcgctttct catagctcac gctgtaggta tctcagttcg gtgtaggtcg ttcgctccaa 5880
gctgggctgt gtgcacgaac cccccgttca gcccgaccgc tgcgccttat ccggtaacta 5940
tcgtcttgag tccaacccgg taagacacga cttatcgcca ctggcagcag ccactggtaa 6000
caggattagc agagcgaggt atgtaggcgg tgctacagag ttcttgaagt ggtggcctaa 6060
ctacggctac actagaagga cagtatttgg tatctgcgct ctgctgaagc cagttacctt 6120
cggaaaaaga gttggtagct cttgatccgg caaacaaacc accgctggta gcggtggttt 6180
ttttgtttgc aagcagcaga ttacgcgcag aaaaaaagga tctcaagaag atcctttgat 6240
cttttctacg gggtctgacg ctcagtggaa cgaaaactca cgttaaggga ttttggtcat 6300
gagattatca aaaaggatct tcacctagat ccttttaaat taaaaatgaa gttttaaatc 6360
aatctaaagt atatatgagt aaacttggtc tgacagttac caatgcttaa tcagtgaggc 6420
acctatctca gcgatctgtc tatttcgttc atccatagtt gcctgactcc ccgtcgtgta 6480
gataactacg atacgggagg gcttaccatc tggccccagt gctgcaatga taccgcgaga 6540
cccacgctca ccggctccag atttatcagc aataaaccag ccagccggaa gggccgagcg 6600
cagaagtggt cctgcaactt tatccgcctc catccagtct attaattgtt gccgggaagc 6660
tagagtaagt agttcgccag ttaatagttt gcgcaacgtt gttgccattg ctacaggcat 6720
cgtggtgtca cgctcgtcgt ttggtatggc ttcattcagc tccggttccc aacgatcaag 6780
gcgagttaca tgatccccca tgttgtgcaa aaaagcggtt agctccttcg gtcctccgat 6840
cgttgtcaga agtaagttgg ccgcagtgtt atcactcatg gttatggcag cactgcataa 6900
ttctcttact gtcatgccat ccgtaagatg cttttctgtg actggtgagt actcaaccaa 6960
gtcattctga gaatagtgta tgcggcgacc gagttgctct tgcccggcgt caatacggga 7020
taataccgcg ccacatagca gaactttaaa agtgctcatc attggaaaac gttcttcggg 7080
gcgaaaactc tcaaggatct taccgctgtt gagatccagt tcgatgtaac ccactcgtgc 7140
acccaactga tcttcagcat cttttacttt caccagcgtt tctgggtgag caaaaacagg 7200
aaggcaaaat gccgcaaaaa agggaataag ggcgacacgg aaatgttgaa tactcatact 7260
cttccttttt caatattatt gaagcattta tcagggttat tgtctcatga gcggatacat 7320
atttgaatgt atttag 7336
```

```
SEQ ID NO: 53          moltype = AA  length = 453
FEATURE                Location/Qualifiers
REGION                 1..453
                       note = SS-CD19scFv-DmrA-CD8hingeTM protein
```

```
source                  1..453
                        mol_type = protein
                        organism = synthetic construct
SEQUENCE: 53
MPLGLLWLGL ALLGALHAQA GSDIQMTQTT SSLSASLGDR VTISCRASQD ISKYLNWYQQ  60
KPDGTVKLLI YHTSRLHSGV PSRFSGSGSG TDYSLTISNL EQEDIATYFC QQGNTLPYTF  120
GGGTKLEITG STSGSGKPGS GEGSTKGEVK LQESGPGLVA PSQSLSVTCT VSGVSLPDYG  180
VSWIRQPPRK GLEWLGVIWG SETTYYNSAL KSRLTIIKDN SKSQVFLKMN SLQTDDTAIY  240
YCAKHYYYGG SYAMDYWGQG TSVTVSSASG GGGSGVQVET ISPGDGRTFP KRGQTCVVHY  300
TGMLEDGKKF DSSRDRNKPF KFMLGKQEVI RGWEEGVAQM SVGQRAKLTI SPDYAYGATG  360
HPGIIPPHAT LVFDVELLKL EGGRAKPTTT PAPRPPTPAP TIASQPLSLR PEACRPAAGG  420
AVHTRGLDFA CDIYIWAPLA GTCGVLLLSL VIT                              453

SEQ ID NO: 54           moltype = DNA  length = 1359
FEATURE                 Location/Qualifiers
misc_feature            1..1359
                        note = SS-CD19scFv-DmrA-CD8hingeTM DNA
source                  1..1359
                        mol_type = other DNA
                        organism = synthetic construct
SEQUENCE: 54
atgcccctgg gcctgctgtg gctgggcctg gccctgctgg gcgccctgca cgcccaggcc  60
ggatccgata tccagatgac ccagaccacc agcagcctga gcgccagcct gggcgataga  120
gtgaccatca gctgcagagc cagccaggac atcagcaagt acctgaactg gtatcagcag  180
aaacccgacg gcaccgtgaa gctgctgatc taccacacca gcagactgca cagcggcgtg  240
cccagcagat tttctggcag cggctccggc accgactaca gcctgaccat ctccaacctg  300
gaacaggaag atatcgctac ctacttctgt cagcaaggca acaccctgcc ctacaccttc  360
ggcggaggca ccaagctgga aatcaccggc agcacaagcg gcagcggcaa gcctggatct  420
ggcgagggaa gcaccaaggg cgaagtgaaa ctgcaggaaa gcggccctgg actggtggcc  480
ccaagccagt ctctgagcgt gacctgtacc gtgtccggcg tgtccctgcc tgactatggc  540
gtgtcctgga tcagacagcc acccagaaag ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tactgcgcca agcactacta ctacggcggc agctacgcca tggactactg gggccagggc  780
acaagcgtga ccgtgtccag cgctagcggc ggaggtggga gcggagtgca ggtggaaacc  840
atctccccag gagacgggcg caccttcccc aagcgcggcc agacctgcgt ggtgcactac  900
accgggatgc ttgaagatgg aaagaaattt gattcctccc gggacagaaa caagcccttt  960
aagtttatgc taggcaagca ggaggtgatc cgaggctggg aagaaggggt tgcccagatg  1020
agtgtgggtc agagagccaa actgactata tctccagatt atgcctatgg tgccactggg  1080
cacccaggca tcatcccacc acatgccact ctcgtcttcg atgtggagct tctaaaactg  1140
gaaggcggcc gcgccaagcc taccaccacc cctgccccta gacctccaac acccgcccca  1200
acaatcgcca gccagcctct gtctctgagg cccgaggctt gtagaccagc tgctggcgga  1260
gccgtgcaca ccagaggact ggatttcgcc tgcgacatct acatctgggc ccctctggcc  1320
ggcacatgtg gcgtgctgct gctgagcctc gtgatcacc                        1359

SEQ ID NO: 55           moltype = DNA  length = 7477
FEATURE                 Location/Qualifiers
misc_feature            1..7477
                        note = pCVL_sEF1a-T7-hScnSS-CD19scFv-DmrA-CD8hingeTM
                         lentiviral vector
source                  1..7477
                        mol_type = other DNA
                        organism = synthetic construct
SEQUENCE: 55
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
```

```
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatgccc ctgggcctgc  2280
tgtggctggg cctggccctg ctgggcgccc tgcacgccca ggccggatcc gatatccaga  2340
tgacccagac caccagcagc ctgagcgcca gcctgggcga tagagtgacc atcagctgca  2400
gagccagcca ggacatcagc aagtacctga actggtatca gcagaaaccc gacggcaccg  2460
tgaagctgct gatctaccac accagcagac tgcacagcgg cgtgcccagc agattttctg  2520
gcagcggctc cggcaccgac tacagcctga ccatctccaa cctggaacag gaagatatcg  2580
ctacctactt ctgtcagcaa ggcaacaccc tgccctacac cttcggcgga ggcaccaagc  2640
tggaaatcac cggcagcaca agcggcagcg gcaagcctgg atctggcgag ggaagcacca  2700
agggcgaagt gaaactgcag gaaagcggcc ctggactggt ggccccaagc cagtctctga  2760
gcgtgacctg taccgtgtcc ggcgtgtccc tgcctgacta tggcgtgtcc tggatcagac  2820
agccacccag aaagggcctg gaatggctgg gagtgatctg gggcagcgag acaacctact  2880
acaacagcgc cctgaagtcc cggctgacca tcatcaagga caactccaag agccaggtgt  2940
tcctgaagat gaacagcctg cagaccgacg acaccgccat ctactactgc gccaagcact  3000
actactacgg cggcagctac gccatggact actggggcca gggcacaagc gtgaccgtgt  3060
ccagcgctag cggcggaggt gggagcggag tgcaggtgga aaccatctcc ccaggagacg  3120
ggcgcacctt ccccaagcgc ggccagacct gcgtggtgca ctacaccggg atgcttgaag  3180
atggaaagaa atttgattcc tcccgggaca gaaacaagcc ctttaagttt atgctaggca  3240
agcaggaggt gatccgaggc tgggaagaag gggttgccca gatgagtgtg ggtcagagag  3300
ccaaactgac tatatctcca gattatgcct atggtgccac tgggcaccca ggcatcatcc  3360
caccacatgc cactctcgtc ttcgatgtgg agcttctaaa actggaaggc ggccgcgcca  3420
agcctaccac caccctgcc cctagacctc caacacccgc cccaacaatc gccagccagc  3480
ctctgtctct gaggcccgag gcttgtagac cagctgctgg cggagccgtg cacaccagag  3540
gactggattt cgcctgcgac atctacatct gggcccctct ggccggcaca tgtggcgtgc  3600
tgctgctgag cctcgtgatc accatgcatt ccggtgaggg cagaggaagt cttctaacat  3660
gcggtgacgt ggaggagaat ccgggcccct ctagagtgag caagggcgag gaggataaca  3720
tggccatcat caaggagttc atgcgcttca aggtgcacat ggagggctcc gtgaacggcc  3780
acgagttcga gatcgagggc gagggcgagg gccgccccta cgagggcacc cagaccgcca  3840
agctgaaggt gaccaagggt ggccccctgc ccttcgcctg ggacatcctg tcccctcagt  3900
tcatgtacgg ctccaaggcc tacgtgaagc accccgccga catccccgac tacttgaagc  3960
tgtccttccc cgagggcttc aagtgggagc gcgtgatgaa cttcgaggac ggcggcgtgg  4020
tgaccgtgac ccaggactcc tctctgcagg acggcgagtt catctacaag gtgaagctgc  4080
gcggcaccaa cttcccctcc gacggccccg taatgcagaa gaagactatg ggctgggagg  4140
cctcctccga gcggatgtac cccgaggacg gcgccctgaa gggcgagatc aagcagaggc  4200
tgaagctgaa ggacggcggc cactacgacg ctgaggtcaa gaccacctac aaggccaaga  4260
agcccgtgca gctgcccggc gcctacaacg tcaacatcaa gttggacatc acctcccaca  4320
acgaggacta caccatcgtg gaacagtacg aacgcgccga gggccgccac tccaccggcg  4380
gcatggacga gctgtacaag taagtcgacc gagcatctta ccgccattta tacccatatt  4440
tgttctgttt ttcttgattt gggtatacat ttaaatgtta atagaacaaa atggtggggc  4500
aatcatttac atttttaggg atatgtaatt actagttcag gtgtattgcc acaagacaaa  4560
catgttaaga aactttcccg ttatttacgc tctgttcctg ttaatcaacc tctggattac  4620
aaaatttgtg aaagattgac tgatattctt aactatgttg ctccttttac gctgtgtgga  4680
tatgctgctt tatagcctct gtatctagct attgcttccc gtacggcttt cgttttctcc  4740
tccttgtata aatcctggtt gctgtctctt ttagaggagt tgtggcccgt tgtccgtcaa  4800
cgtggcgtgg tgtgctctgt gtttgctgac gcaaccccca ctggctgggg cattgccacc  4860
acctgtcaac tcctttctgg gactttcgct ttccccctcc cgatcgccac ggcagaactc  4920
atcgccgcct gccttgcccg ctgctggaca ggggctaggt tgctgggcac tgataattcc  4980
gtggtgttgt catcgaattc ggtacctttt taaaagaaaa ggggggactg gaagggctaa  5040
ttcactccca acgaagacaa gatatcataa cttcgtatag catacattat acgaagttat  5100
aatttatttg tgaaatttgt gatgctattg ctttatttgt aaccatatgt ttatttgtga  5160
aatttgtgat gctattgctt tatttgtaac cattgctttt tgcttgtact gggtctctct  5220
ggttagacca gatctgagcc tgggagctct ctggctaact agggaaccca ctgcttaagc  5280
ctcaataaag cttgcctcga ccagcctcga ctgtgccttc tagttgccag ccatctgttg  5340
tttgcccctc ccccgtgcct tccttgaccc tggaaggtgc cactcccact gtcctttcct  5400
aataaaatga ggaaattgca tcgcattgtc tgagtaggtg tcattctatt ctggggggtg  5460
gggtggggca ggacagcaag ggggaggatt gggaagacaa tagcaggcat gctggggatg  5520
cggtgggctc tatggcctgc agctgcatta atgaatcggc caacgcgcgg ggagaggcgg  5580
tttgcgtatt gggcgctctt ccgcttcctc gctcactgac tcgctgcgct cggtcgttcg  5640
gctgcggcga gcggtatcag ctcactcaaa ggcggtaata cggttatcca cagaatcagg  5700
ggataacgca ggaaagaaca tgtgagcaaa aggccagcaa aaggccagga accgtaaaaa  5760
ggccgcgttg ctggcgtttt tccataggct ccgcccccct gacgagcatc acaaaaatcg  5820
acgctcaagt cagaggtggc gaaacccgac aggactataa agataccagg cgtttccccc  5880
tggaagctcc ctcgtgcgct ctcctgttcc gaccctgccg cttaccggat acctgtccgc  5940
ctttctccct tcgggaagcg tggcgctttc tcatagctca cgctgtaggt atctcagttc  6000
ggtgtaggtc gttcgctcca agctgggctg tgtgcacgaa ccccccgttc agcccgaccg  6060
ctgcgcctta tccggtaact atcgtcttga gtccaacccg gtaagacacg acttatcgcc  6120
actggcagca gccactggta acaggattag cagagcgagg tatgtaggcg gtgctacaga  6180
gttcttgaag tggtggccta actacggcta cactagaagg acagtatttg gtatctgcgc  6240
```

```
tctgctgaag ccagttacct tcggaaaaag agttggtagc tcttgatccg gcaaacaaac  6300
caccgctggt agcggtggtt tttttgtttg caagcagcag attacgcgca gaaaaaaagg  6360
atctcaagaa gatcctttga tcttttctac ggggtctgac gctcagtgga acgaaaactc  6420
acgttaaggg attttggtca tgagattatc aaaaaggatc ttcacctaga tccttttaaa  6480
ttaaaaatga agttttaaat caatctaaag tatatatgag taaacttggt ctgacagtta  6540
ccaatgctta atcagtgagg cacctatctc agcgatctgt ctatttcgtt catccatagt  6600
tgcctgactc cccgtcgtgt agataactac gatacgggag ggcttaccat ctggccccag  6660
tgctgcaatg ataccgcgag acccacgctc accggctcca gatttatcag caataaacca  6720
gccagccgga agggccgagc gcagaagtgg tcctgcaact ttatccgcct ccatccagtc  6780
tattaattgt tgccgggaag ctagagtaag tagttcgcca gttaatagtt tgcgcaacgt  6840
tgttgccatt gctacaggca tcgtggtgtc acgctcgtcg tttggtatgg cttcattcag  6900
ctccggttcc caacgatcaa ggcgagttac atgatccccc atgttgtgca aaaaagcggt  6960
tagctccttc ggtcctccga tcgttgtcag aagtaagttg gccgcagtgt tatcactcat  7020
ggttatggca gcactgcata attctcttac tgtcatgcca tccgtaagat gcttttctgt  7080
gactggtgag tactcaacca agtcattctg agaatagtgt atgcggcgac cgagttgctc  7140
ttgcccggcg tcaatacggg ataataccgc gccacatagc agaactttaa aagtgctcat  7200
cattggaaaa cgttcttcgg ggcgaaaact ctcaaggatc ttaccgctgt tgagatccag  7260
ttcgatgtaa cccactcgtg cacccaactg atcttcagca tcttttactt tcaccagcgt  7320
ttctgggtga gcaaaaacag gaaggcaaaa tgccgcaaaa aagggaataa gggcgacacg  7380
gaaatgttga atactcatac tcttcctttt tcaatattat tgaagcattt atcagggtta  7440
ttgtctcatg agcggataca tatttgaatg tatttag                         7477
```

```
SEQ ID NO: 56          moltype = AA  length = 635
FEATURE                Location/Qualifiers
REGION                 1..635
                       note = SS-CD19scFv-DmrA-Spacer-CD4TM protein
source                 1..635
                       mol_type = protein
                       organism = synthetic construct
SEQUENCE: 56
MPLGLLWLGL ALLGALHAQA GSDIQMTQTT SSLSASLGDR VTISCRASQD ISKYLNWYQQ  60
KPDGTVKLLI YHTSRLHSGV PSRFSGSGSG TDYSLTISNL EQEDIATYFC QQGNTLPYTF  120
GGGTKLEITG STSGSGKPGS GEGSTKGEVK LQESGPGLVA PSQSLSVTCT VSGVSLPDYG  180
VSWIRQPPRK GLEWLGVIWG SETTYYNSAL KSRLTIIKDN SKSQVFLKMN SLQTDDTAIY  240
YCAKHYYYGG SYAMDYWGQG TSVTVSSASG GGGSGVQVET ISPGDGRTFP KRGQTCVVHY  300
TGMLEDGKKF DSSRDRNKPF KFMLGKQEVI RGWEEGVAQM SVGQRAKLTI SPDYAYGATG  360
HPGIIPPHAT LVFDVELLKL EGGRESKYGP PCPPCPAPEF LGGPSVFLFP PKPKDTLMIS  420
RTPEVTCVVV DVSQEDPEVQ FNWYVDGVEV HNAKTKPREE QFNSTYRVVS VLTVLHQDWL  480
NGKEYKCKVS NKGLPSSIEK TISKAKGQPR EPQVYTLPPS QEEMTKNQVS LTCLVKGFYP  540
SDIAVEWESN GQPENNYKTT PPVLDSDGSF FLYSRLTVDK SRWQEGNVFS CSVMHEALHN  600
HYTQKSLSLS LGKMALIVLG GVAGLLLFIG LGIFF                            635
```

```
SEQ ID NO: 57          moltype = DNA  length = 1905
FEATURE                Location/Qualifiers
misc_feature           1..1905
                       note = SS-CD19scFv-DmrA-Spacer-CD4TM DNA
source                 1..1905
                       mol_type = other DNA
                       organism = synthetic construct
SEQUENCE: 57
atgcccctgg gcctgctgtg gctgggcctg gccctgctgg gcgccctgca cgcccaggcc  60
ggatccgata tccagatgac ccagaccacc agcagcctga gcgccagcct gggcgataga  120
gtgaccatca gctgcagagc cagccaggac atcagcaagt acctgaactg gtatcagcag  180
aaacccgacg gcaccgtgaa gctgctgatc taccacacca gcagactgca cagcggcgtg  240
cccagcagat tttctggcag cggctccggc accgactaca gcctgaccat ctccaacctg  300
gaacaggaag atatcgctac ctacttctgt cagcaaggca acaccctgcc ctacaccttc  360
ggcggaggca ccaagctgga aatcaccggc agcacaagcg gcagcggcaa gcctggatct  420
ggcgagggaa gcaccaaggg cgaagtgaaa ctgcaggaaa gcggccctgg actggtggcc  480
ccaagccagt ctctgagcgt gacctgtacc gtgtccggcg tgtccctgcc tgactatggc  540
gtgtcctgga tcagacagcc acccagaaag ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tactgcgcca agcactacta ctacggcggc agctacgcca tggactactg gggccagggc  780
acaagcgtga ccgtgtccag cgctagcggc ggaggtggga gcggagtgca ggtggaaacc  840
atctccccag gagacgggcg caccttcccc aagcgcggcc agacctgcgt ggtgcactac  900
accgggatgc ttgaagatgg aaagaaattt gattcctccc gggacagaaa caagcccttt  960
aagtttatgc taggcaagca ggaggtgatc cgaggctggg aagaaggggt tgcccagatg  1020
agtgtgggtc agagagccaa actgactata tctccagatt atgcctatgg tgccactggg  1080
cacccaggca tcatcccacc acatgccact ctcgtcttcg atgtggagct tctaaaactg  1140
gaaggcggcc gcgagagcaa gtacggaccg ccctgcccac cttgccctgc ccccgagttc  1200
ctgggcggac ccagcgtgtt cctgttccca cccaagccca aggacaccct gatgatcagc  1260
cggacccccg aggtgacctg cgtggtggtg gacgtgagcc aggaagatcc cgaggtccag  1320
ttcaattggt acgtggacgg cgtggaagtg cacaacgcca agaccaagcc cagagaggaa  1380
cagttcaaca gcacctaccg ggtggtgtct gtgctgaccg tgctgcacca ggactggctg  1440
aacggcaaag aatacaagtg caaggtgtcc aacaagggcc tgcccagcag catcgaaaag  1500
accatcagca aggccaaggg ccagcctcgc gagccccagg tgtacaccct gcctccctcc  1560
caggaagaga tgaccaagaa ccaggtgtcc ctgacctgcc tggtgaaggg cttctacccc  1620
agcgacatcg ccgtggagtg ggagagcaac ggccagcctg agaacaacta caagaccacc  1680
cctcccgtgc tggacagcga cggcagcttc ttcctgtaca gccggctgac cgtggacaag  1740
```

```
agccggtggc aggaaggcaa cgtctttagc tgcagcgtga tgcacgaggc cctgcacaac  1800
cactacaccc agaagagcct gagcctgtcc ctgggcaaga tggccctgat tgtgctgggg  1860
ggcgtcgccg gcctcctgct tttcattggg ctaggcatct tcttc                  1905

SEQ ID NO: 58           moltype = DNA  length = 8023
FEATURE                 Location/Qualifiers
misc_feature            1..8023
                        note = pCVL_sEF1a-T7-hScnSS-CD19scFv-DmrA-Spacer-CD4TM
                         lentiviral vector
source                  1..8023
                        mol_type = other DNA
                        organism = synthetic construct
SEQUENCE: 58
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatgccc ctgggcctgc  2280
tgtggctggg cctggccctg ctgggcgccc tgcacgccca ggccggatcc gatatccaga  2340
tgacccagac caccagcagc ctgagcgcca gcctgggcga tagagtgacc atcagctgca  2400
gagccagcca ggacatcagc aagtacctga actggtatca gcagaaaccc gacggcaccg  2460
tgaagctgct gatctaccac accagcagac tgcacagcgg cgtgcccagc agattttctg  2520
gcagcggctc cggcaccgac tacagcctga ccatctccaa cctggaacag gaagatatcg  2580
ctacctactt ctgtcagcaa ggcaacaccc tgccctacac cttcggcgga ggcaccaagc  2640
tggaaatcac cggcagcaca agcggcagcg gcaagcctgg atctggcgag ggaagcacca  2700
agggcgaagt gaaactgcag gaaagcggcc ctggactggt ggccccaagc cagtctctga  2760
gcgtgacctg taccgtgtcc ggcgtgtccc tgcctgacta tggcgtgtcc tggatcagac  2820
agccacccag aaagggcctg gaatggctgg gagtgatctg gggcagcgag acaacctact  2880
acaacagcgc cctgaagtcc cggctgacca tcatcaagga caactccaag agccaggtgt  2940
tcctgaagat gaacagcctg cagaccgacg acaccgccat ctactactgc gccaagcact  3000
actactacgg cggcagctac gccatggact actggggcca gggcacaagc gtgaccgtgt  3060
ccagcgctag cggcggaggt gggagcggag tgcaggtgga aaccatctcc ccaggagacg  3120
ggcgcacctt ccccaagcgc ggccagacct gcgtggtgca ctacaccggg atgcttgaag  3180
atggaaagaa atttgattcc tcccgggaca gaaacaagcc ctttaagttt atgctaggca  3240
agcaggaggt gatccgaggc tgggaagaag gggttgccca gatgagtgtg ggtcagagag  3300
ccaaactgac tatatctcca gattatgcct atggtgccac tgggcaccca ggcatcatcc  3360
caccacatgc cactctcgtc ttcgatgtgg agcttctaaa actggaaggc ggccgcgaga  3420
gcaagtacgg accgccctgc ccaccttgcc ctgcccccga gttcctgggc ggacccagcg  3480
tgttcctgtt cccacccaag cccaaggaca ccctgatgat cagccggacc cccgaggtga  3540
cctgcgtggt ggtggacgtg agccaggaag atcccgaggt ccagttcaat tggtacgtgg  3600
acggcgtgga agtgcacaac gccaagacca agcccagaga ggaacagttc aacagcacct  3660
accgggtggt gtctgtgctg accgtgctgc accaggactg gctgaacggc aaagaataca  3720
agtgcaaggt gtccaacaag ggcctgccca gcagcatcga aaagaccatc agcaaggcca  3780
agggccagcc tcgcgagccc caggtgtaca ccctgcctcc ctcccaggaa gagatgacca  3840
agaaccaggt gtccctgacc tgcctggtga agggcttcta ccccagcgac atcgccgtgg  3900
agtgggagag caacggccag cctgagaaca actacaagac cacccctccc gtgctggaca  3960
```

```
gcgacggcag cttcttcctg tacagccggc tgaccgtgga caagagccgg tggcaggaag  4020
gcaacgtctt tagctgcagc gtgatgcacg aggccctgca caaccactac acccagaaga  4080
gcctgagcct gtccctgggc aagatggccc tgattgtgct ggggggcgtc gccggcctcc  4140
tgcttttcat tgggctaggc atcttcttca tgcattccgg tgagggcaga ggaagtcttc  4200
taacatgcgg tgacgtggag gagaatccgg gcccctctag agtgagcaag ggcgaggagg  4260
ataacatggc catcatcaag gagttcatgc gcttcaaggt gcacatggag ggctccgtga  4320
acggccacga gttcgagatc gagggcgagg gcgagggccg cccctacgag ggcacccaga  4380
ccgccaagct gaaggtgacc aagggtggcc ccctgccctt cgcctgggac atcctgtccc  4440
ctcagttcat gtacggctcc aaggcctacg tgaagcaccc cgccgacatc cccgactact  4500
tgaagctgtc cttccccgag ggcttcaagt gggagcgcgt gatgaacttc gaggacggcg  4560
gcgtggtgac cgtgacccag gactcctctc tgcaggacgg cgagttcatc tacaaggtga  4620
agctgcgcgg caccaacttc ccctccgacg gccccgtaat gcagaagaag actatgggct  4680
gggaggcctc ctccgagcgg atgtaccccg aggacggcgc cctgaagggc gagatcaagc  4740
agaggctgaa gctgaaggac ggcggccact acgacgctga ggtcaagacc acctacaagg  4800
ccaagaagcc cgtgcagctg cccggcgcct acaacgtcaa catcaagttg gacatcacct  4860
cccacaacga ggactacacc atcgtggaac agtacgaacg cgccgagggc cgccactcca  4920
ccggcggcat ggacgagctg tacaagtaag tcgaccgagc atcttaccgc catttatacc  4980
catatttgtt ctgtttttct tgatttgggt atacatttaa atgttaatag aacaaaatgg  5040
tggggcaatc atttacattt ttagggatat gtaattacta gttcaggtgt attgccacaa  5100
gacaaacatg ttaagaaact ttcccgttat ttacgctctg ttcctgttaa tcaacctctg  5160
gattacaaaa tttgtgaaag attgactgat attcttaact atgttgctcc ttttacgctg  5220
tgtggatatg ctgctttata gcctctgtat ctagctattg cttcccgtac ggctttcgtt  5280
ttctcctcct tgtataaatc ctggttgctg tctcttttag aggagttgtg gcccgttgtc  5340
cgtcaacgtg gcgtggtgtg ctctgtgttt gctgacgcaa cccccactgg ctggggcatt  5400
gccaccacct gtcaactcct ttctgggact ttcgctttcc ccctcccgat cgccacggca  5460
gaactcatcg ccgcctgcct tgcccgctgc tggacagggg ctaggttgct gggcactgat  5520
aattccgtgg tgttgtcatc gaattcggta cctttttaaa agaaaagggg ggactggaag  5580
ggctaattca ctcccaacga agacaagata tcataacttc gtatagcata cattatacga  5640
agttataatt tatttgtgaa atttgtgatg ctattgcttt atttgtaacc atatgtttat  5700
ttgtgaaatt tgtgatgcta ttgctttatt tgtaaccatt gctttttgct tgtactgggt  5760
ctctctggtt agaccagatc tgagcctggg agctctctgg ctaactaggg aacccactgc  5820
ttaagcctca ataaagcttg cctcgaccag cctcgactgt gccttctagt tgccagccat  5880
ctgttgtttg cccctccccc gtgccttcct tgaccctgga aggtgccact cccactgtcc  5940
tttcctaata aaatgaggaa attgcatcgc attgtctgag taggtgtcat tctattctgg  6000
ggggtggggt ggggcaggac agcaaggggg aggattggga agacaatagc aggcatgctg  6060
gggatgcggt gggctctatg gcctgcagct gcattaatga atcggccaac gcgcggggag  6120
aggcggtttg cgtattgggc gctcttccgc ttcctcgctc actgactcgc tgcgctcggt  6180
cgttcggctg cggcgagcgg tatcagctca ctcaaaggcg gtaatacggt tatccacaga  6240
atcaggggat aacgcaggaa agaacatgtg agcaaaaggc cagcaaaagg ccaggaaccg  6300
taaaaaggcc gcgttgctgg cgtttttcca taggctccgc ccccctgacg agcatcacaa  6360
aaatcgacgc tcaagtcaga ggtggcgaaa cccgacagga ctataaagat accaggcgtt  6420
tccccctgga agctccctcg tgcgctctcc tgttccgacc ctgccgctta ccggatacct  6480
gtccgccttt ctcccttcgg gaagcgtggc gctttctcat agctcacgct gtaggtatct  6540
cagttcggtg taggtcgttc gctccaagct gggctgtgtg cacgaacccc ccgttcagcc  6600
cgaccgctgc gccttatccg gtaactatcg tcttgagtcc aacccggtaa gacacgactt  6660
atcgccactg gcagcagcca ctggtaacag gattagcaga gcgaggtatg taggcggtgc  6720
tacagagttc ttgaagtggt ggcctaacta cggctacact agaaggacag tatttggtat  6780
ctgcgctctg ctgaagccag ttaccttcgg aaaaagagtt ggtagctctt gatccggcaa  6840
acaaaccacc gctggtagcg gtggtttttt tgtttgcaag cagcagatta cgcgcagaaa  6900
aaaaggatct caagaagatc ctttgatctt ttctacgggg tctgacgctc agtggaacga  6960
aaactcacgt taagggattt tggtcatgag attatcaaaa aggatcttca cctagatcct  7020
tttaaattaa aaatgaagtt ttaaatcaat ctaaagtata tatgagtaaa cttggtctga  7080
cagttaccaa tgcttaatca gtgaggcacc tatctcagcg atctgtctat ttcgttcatc  7140
catagttgcc tgactccccg tcgtgtagat aactacgata cgggagggct taccatctgg  7200
ccccagtgct gcaatgatac cgcgagaccc acgctcaccg gctccagatt tatcagcaat  7260
aaaccagcca gccggaaggg ccgagcgcag aagtggtcct gcaactttat ccgcctccat  7320
ccagtctatt aattgttgcc gggaagctag agtaagtagt tcgccagtta atagtttgcg  7380
caacgttgtt gccattgcta caggcatcgt ggtgtcacgc tcgtcgtttg gtatggcttc  7440
attcagctcc ggttcccaac gatcaaggcg agttacatga tcccccatgt tgtgcaaaaa  7500
agcggttagc tccttcggtc ctccgatcgt tgtcagaagt aagttggccg cagtgttatc  7560
actcatggtt atggcagcac tgcataattc tcttactgtc atgccatccg taagatgctt  7620
ttctgtgact ggtgagtact caaccaagtc attctgagaa tagtgtatgc ggcgaccgag  7680
ttgctcttgc ccggcgtcaa tacgggataa taccgcgcca catagcagaa ctttaaaagt  7740
gctcatcatt ggaaaacgtt cttcggggcg aaaactctca aggatcttac cgctgttgag  7800
atccagttcg atgtaaccca ctcgtgcacc caactgatct tcagcatctt ttactttcac  7860
cagcgtttct gggtgagcaa aaacaggaag gcaaaatgcc gcaaaaaagg gaataagggc  7920
gacacggaaa tgttgaatac tcatactctt cctttttcaa tattattgaa gcatttatca  7980
gggttattgt ctcatgagcg gatacatatt tgaatgtatt tag                   8023
```

```
SEQ ID NO: 59           moltype = AA  length = 417
FEATURE                 Location/Qualifiers
REGION                  1..417
                        note = SS-CD19scFv-DmrA-CD52 GPI anchor protein
source                  1..417
                        mol_type = protein
                        organism = synthetic construct
SEQUENCE: 59
MPLGLLWLGL ALLGALHAQA GSDIQMTQTT SSLSASLGDR VTISCRASQD ISKYLNWYQQ  60
KPDGTVKLLI YHTSRLHSGV PSRFSGSGSG TDYSLTISNL EQEDIATYFC QQGNTLPYTF  120
```

-continued

```
GGGTKLEITG STSGSGKPGS GEGSTKGEVK LQESGPGLVA PSQSLSVTCT VSGVSLPDYG  180
VSWIRQPPRK GLEWLGVIWG SETTYYNSAL KSRLTIIKDN SKSQVFLKMN SLQTDDTAIY  240
YCAKHYYYGG SYAMDYWGQG TSVTVSSASG GGGSGVQVET ISPGDGRTFP KRGQTCVVHY  300
TGMLEDGKKF DSSRDRNKPF KFMLGKQEVI RGWEEGVAQM SVGQRAKLTI SPDYAYGATG  360
HPGIIPPHAT LVFDVELLKL EGGRTSQTSS PSASSNISGG IFLFFVANAI IHLFCFS     417

SEQ ID NO: 60          moltype = DNA  length = 1251
FEATURE                Location/Qualifiers
misc_feature           1..1251
                       note = SS-CD19scFv-DmrA-CD52 GPI anchor DNA
source                 1..1251
                       mol_type = other DNA
                       organism = synthetic construct
SEQUENCE: 60
atgcccctgg gcctgctgtg gctgggcctg gccctgctgg gcgccctgca cgcccaggcc  60
ggatccgata tccagatgac ccagaccacc agcagcctga gcgccagcct gggcgataga  120
gtgaccatca gctgcagagc cagccaggac atcagcaagt acctgaactg gtatcagcag  180
aaacccgacg gcaccgtgaa gctgctgatc taccacacca gcagactgca cagcggcgtg  240
cccagcagat tttctggcag cggctccggc accgactaca gcctgaccat ctccaacctg  300
gaacaggaag atatcgctac ctacttctgt cagcaaggca acaccctgcc ctacaccttc  360
ggcggaggca ccaagctgga aatcaccggc agcacaagcg gcagcggcaa gcctggatct  420
ggcgagggaa gcaccaaggg cgaagtgaaa ctgcaggaaa gcggccctgg actggtggcc  480
ccaagccagt ctctgagcgt gacctgtacc gtgtccggcg tgtccctgcc tgactatggc  540
gtgtcctgga tcagacagcc acccagaaag ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tactgcgcca agcactacta ctacggcggc agctacgcca tggactactg gggccagggc  780
acaagcgtga ccgtgtccag cgctagcggc ggaggtggga gcggagtgca ggtggaaacc  840
atctccccag gagacgggcg caccttcccc aagcgcggcc agacctgcgt ggtgcactac  900
accgggatgc ttgaagatgg aaagaaattt gattcctccc gggacagaaa caagcccttt  960
aagtttatgc taggcaagca ggaggtgatc cgaggctggg aagaaggggt tgcccagatg  1020
agtgtgggtc agagagccaa actgactata tctccagatt atgcctatgg tgccactggg  1080
cacccaggca tcatcccacc acatgccact ctcgtcttcg atgtggagct tctaaaactg  1140
gaaggcggcc gcaccagcca aaccagcagc ccctcagcat ccagcaacat aagcggaggc  1200
attttccttt tcttcgtggc caatgccata atccacctct tctgcttcag t           1251

SEQ ID NO: 61          moltype = DNA  length = 7369
FEATURE                Location/Qualifiers
misc_feature           1..7369
                       note = pCVL_sEF1a-T7-hScnSS-CD19scFv-DmrA-CD52 GPI anchor
                        lentiviral vector
source                 1..7369
                       mol_type = other DNA
                       organism = synthetic construct
SEQUENCE: 61
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tgggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
```

```
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatgccc ctgggcctgc  2280
tgtggctggg cctggccctg ctgggcgccc tgcacgccca ggccggatcc gatatccaga  2340
tgacccagac caccagcagc ctgagcgcca gcctgggcga tagagtgacc atcagctgca  2400
gagccagcca ggacatcagc aagtacctga actggtatca gcagaaaccc gacggcaccg  2460
tgaagctgct gatctaccac accagcagac tgcacagcgg cgtgcccagc agatttctg  2520
gcagcggctc cggcaccgac tacagcctga ccatctccaa cctggaacag gaagatatcg  2580
ctacctactt ctgtcagcaa ggcaacaccc tgccctacac cttcggcgga ggcaccaagc  2640
tggaaatcac cggcagcaca agcggcagcg gcaagcctgg atctggcgag ggaagcacca  2700
agggcgaagt gaaactgcag gaaagcggcc ctggactggt ggccccaagc cagtctctga  2760
gcgtgacctg taccgtgtcc ggcgtgtccc tgcctgacta tggcgtgtcc tggatcagac  2820
agccacccag aaagggcctg gaatggctgg gagtgatctg gggcagcgag acaacctact  2880
acaacagcgc cctgaagtcc cggctgacca tcatcaagga caactccaag agccaggtgt  2940
tcctgaagat gaacagcctg cagaccgacg acaccgccat ctactactgc gccaagcact  3000
actactacgg cggcagctac gccatggact actggggcca gggcacaagc gtgaccgtgt  3060
ccagcgctag cggcggaggt gggagcggag tgcaggtgga aaccatctcc ccaggagacg  3120
ggcgcacctt ccccaagcgc ggccagacct gcgtggtgca ctacaccggg atgcttgaag  3180
atggaaagaa atttgattcc tcccgggaca gaaacaagcc ctttaagttt atgctaggca  3240
agcaggaggt gatccgaggc tgggaagaag gggttgccca gatgagtgtg ggtcagagag  3300
ccaaactgac tatatctcca gattatgcct atggtgccac tgggcaccca ggcatcatcc  3360
caccacatgc cactctcgtc ttcgatgtgg agcttctaaa actggaaggc ggccgcacca  3420
gccaaaccag cagcccctca gcatccagca acataagcgg aggcattttc cttttcttcg  3480
tggccaatgc cataatccac ctcttctgct tcagtatgca ttccggtgag ggcagaggaa  3540
gtcttctaac atgcggtgac gtggaggaga atccgggccc ctctagagtg agcaagggcg  3600
aggaggataa catggccatc atcaaggagt tcatgcgctt caaggtgcac atggagggct  3660
ccgtgaacgg ccacgagttc gagatcgagg gcgagggcga gggccgcccc tacgagggca  3720
cccagaccgc caagctgaag gtgaccaagg gtggccccct gcccttcgcc tgggacatcc  3780
tgtcccctca gttcatgtac ggctccaagg cctacgtgaa gcaccccgcc gacatccccg  3840
actacttgaa gctgtccttc cccgagggct tcaagtggga gcgcgtgatg aacttcgagg  3900
acggcggcgt ggtgaccgtg acccaggact cctctctgca ggacggcgag ttcatctaca  3960
aggtgaagct gcgcggcacc aacttcccct ccgacggccc cgtaatgcag aagaagacta  4020
tgggctggga ggcctcctcc gagcggatgt accccgagga cggcgccctg aagggcgaga  4080
tcaagcagag gctgaagctg aaggacggcg gccactacga cgctgaggtc aagaccacct  4140
acaaggccaa gaagcccgtg cagctgcccg gcgcctacaa cgtcaacatc aagttggaca  4200
tcacctccca caacgaggac tacaccatcg tggaacagta cgaacgcgcc gagggccgcc  4260
actccaccgg cggcatggac gagctgtaca agtaagtcga ccgagcatct taccgccatt  4320
tatacccata tttgttctgt ttttcttgat ttgggtatac atttaaatgt taatagaaca  4380
aaatggtggg gcaatcattt acatttttag ggatatgtaa ttactagttc aggtgtattg  4440
ccacaagaca aacatgttaa gaaactttcc cgttatttac gctctgttcc tgttaatcaa  4500
cctctggatt acaaaatttg tgaaagattg actgatattc ttaactatgt tgctcctttt  4560
acgctgtgtg gatatgctgc tttatagcct ctgtatctag ctattgcttc ccgtacggct  4620
ttcgttttct cctccttgta taaatcctgg ttgctgtctc ttttagagga gttgtggccc  4680
gttgtccgtc aacgtggcgt ggtgtgctct gtgtttgctg acgcaacccc cactggctgg  4740
ggcattgcca ccacctgtca actcctttct gggactttcg ctttccccct cccgatcgcc  4800
acggcagaac tcatcgccgc ctgccttgcc cgctgctgga caggggctag gttgctgggc  4860
actgataatt ccgtggtgtt gtcatcgaat tcggtacctt tttaaaagaa aaggggggac  4920
tggaagggct aattcactcc caacgaagac aagatatcat aacttcgtat agcatacatt  4980
atacgaagtt ataatttatt tgtgaaattt gtgatgctat tgctttattt gtaaccatat  5040
gtttatttgt gaaatttgtg atgctattgc tttatttgta accattgctt tttgcttgta  5100
ctgggtctct ctggttagac cagatctgag cctgggagct ctctggctaa ctagggaacc  5160
cactgcttaa gcctcaataa agcttgcctc gaccagcctc gactgtgcct tctagttgcc  5220
agccatctgt tgtttgcccc tcccccgtgc cttccttgac cctggaaggt gccactccca  5280
ctgtcctttc ctaataaaat gaggaaattg catcgcattg tctgagtagg tgtcattcta  5340
ttctgggggg tggggtgggg caggacagca agggggagga ttgggaagac aatagcaggc  5400
atgctgggga tgcggtgggc tctatggcct gcagctgcat taatgaatcg gccaacgcgc  5460
ggggagaggc ggtttgcgta ttgggcgctc ttccgcttcc tcgctcactg actcgctgcg  5520
ctcggtcgtt cggctgcggc gagcggtatc agctcactca aaggcggtaa tacggttatc  5580
cacagaatca ggggataacg caggaaagaa catgtgagca aaaggccagc aaaaggccag  5640
gaaccgtaaa aaggccgcgt tgctggcgtt tttccatagg ctccgccccc ctgacgagca  5700
tcacaaaaat cgacgctcaa gtcagaggtg gcgaaacccg acaggactat aaagatacca  5760
ggcgtttccc cctggaagct ccctcgtgcg ctctcctgtt ccgaccctgc cgcttaccgg  5820
atacctgtcc gcctttctcc cttcgggaag cgtggcgctt tctcatagct cacgctgtag  5880
gtatctcagt tcggtgtagg tcgttcgctc caagctgggc tgtgtgcacg aaccccccgt  5940
tcagcccgac cgctgcgcct tatccggtaa ctatcgtctt gagtccaacc cggtaagaca  6000
cgacttatcg ccactggcag cagccactgg taacaggatt agcagagcga ggtatgtagg  6060
cggtgctaca gagttcttga agtggtggcc taactacggc tacactagaa ggacagtatt  6120
tggtatctgc gctctgctga agccagttac cttcggaaaa agagttggta gctcttgatc  6180
cggcaaacaa accaccgctg gtagcggtgg tttttttgtt tgcaagcagc agattacgcg  6240
cagaaaaaaa ggatctcaag aagatccttt gatcttttct acggggtctg acgctcagtg  6300
gaacgaaaac tcacgttaag ggattttggt catgagatta tcaaaaagga tcttcaccta  6360
gatcctttta aattaaaaat gaagttttaa atcaatctaa agtatatatg agtaaacttg  6420
gtctgacagt taccaatgct taatcagtga ggcacctatc tcagcgatct gtctatttcg  6480
ttcatccata gttgcctgac tccccgtcgt gtagataact acgatacggg agggcttacc  6540
atctggcccc agtgctgcaa tgataccgcg agacccacgc tcaccggctc cagatttatc  6600
agcaataaac cagccagccg gaagggccga gcgcagaagt ggtcctgcaa ctttatccgc  6660
ctccatccag tctattaatt gttgccggga agctagagta agtagttcgc cagttaatag  6720
tttgcgcaac gttgttgcca ttgctacagg catcgtggtg tcacgctcgt cgtttggtat  6780
```

```
ggcttcattc agctccggtt cccaacgatc aaggcgagtt acatgatccc ccatgttgtg  6840
caaaaaagcg gttagctcct tcggtcctcc gatcgttgtc agaagtaagt tggccgcagt  6900
gttatcactc atggttatgg cagcactgca taattctctt actgtcatgc catccgtaag  6960
atgcttttct gtgactggtg agtactcaac caagtcattc tgagaatagt gtatgcggcg  7020
accgagttgc tcttgcccgg cgtcaatacg ggataatacc gcgccacata gcagaacttt  7080
aaaagtgctc atcattggaa aacgttcttc ggggcgaaaa ctctcaagga tcttaccgct  7140
gttgagatcc agttcgatgt aacccactcg tgcacccaac tgatcttcag catcttttac  7200
tttcaccagc gtttctgggt gagcaaaaac aggaaggcaa aatgccgcaa aaaagggaat  7260
aagggcgaca cggaaatgtt gaatactcat actcttcctt tttcaatatt attgaagcat  7320
ttatcagggt tattgtctca tgagcggata catatttgaa tgtatttag             7369

SEQ ID NO: 62           moltype = DNA  length = 7141
FEATURE                 Location/Qualifiers
misc_feature            1..7141
                        note = pCVL_T7_FRB-TM-41BB-CD3z lentiviral vector
source                  1..7141
                        mol_type = other DNA
                        organism = synthetic construct
SEQUENCE: 62
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatggct ctgcctgtga  2280
cagctctgct gctgcctctg gccctgctgc tccatgccgc cagacccgga tccatcctct  2340
ggcatgagat gtggcatgaa ggcctggaag aggcatctcg tttgtacttt ggggaaagga  2400
acgtgaaagg catgtttgag gtgctggagc ccttgcatgc tatgatggaa cggggccccc  2460
agactctgaa ggaaacatcc tttaatcagg cctatggtcg agatttaatg gaggcccaag  2520
agtggtgcag gaagtacatg aaatcaggga atgtcaagga cctcacccaa gcctgggacc  2580
tctattatca tgtgttccga cgaatctcaa aggctagcgc caagcctacc accacccctg  2640
cccctagacc tccaacaccc gccccaacaa tcgccagcca gcctctgtct ctgaggcccg  2700
aggcttgtag accagctgct ggcggagccg tgcacaccag aggactggat ttcgcctgcg  2760
acatctacat ctgggcccct ctggccggca catgtggcgt gctgctgctg agcctcgtga  2820
tcaccatgca taaacggggc agaaagaaac tcctgtatat attcaaacaa ccatttatga  2880
gaccagtaca aactactcaa gaggaagatg gctgtagctg ccgatttcca gaagaagaag  2940
aaggaggatg tgaactgcgg gtgaagttca gcagaagcgc cgacgcccct gcctaccagc  3000
agggccagaa tcagctgtac aacgagctga acctgggcag aagggaagag tacgacgtcc  3060
tggataagcg gagaggccgg gaccctgaga tgggcggcaa gcctcggcgg aagaaccccc  3120
aggaaggcct gtataacgaa ctgcagaaag acaagatggc cgaggcctac agcgagatcg  3180
gcatgaaggg cgagcggagg cggggcaagg gccacgacgg cctgtatcag ggcctgtcca  3240
ccgccaccaa ggatacctac gacgccctgc acatgcaggc cctgccccca aggggcggcc  3300
gctccggtga gggcagagga agtcttctaa catgcggtga cgtggaggag aatccgggcc  3360
cctctagaag cgagctgatt aaggagaaca tgcacatgaa gctgtacatg gagggcaccg  3420
tggacaacca tcacttcaag tgcacatccg agggcgaagg caagccctac gagggcaccc  3480
agaccatgag aatcaaggtg gtcgagggcg gccctctccc cttcgccttc gacatcctgg  3540
ctactagctt cctctacggc agcaagacct tcatcaacca cacccagggc atccccgact  3600
```

```
tcttcaagca gtccttccct gagggcttca catgggagag agtcaccaca tacgaagacg  3660
ggggcgtgct gaccgctacc caggacacca gcctccagga cggctgcctc atctacaacg  3720
tcaagatcag aggggtgaac ttcacatcca acggccctgt gatgcagaag aaaacactcg  3780
gctgggaggc cttcaccgag acgctgtacc ccgctgacgg cggcctggaa ggcagaaacg  3840
acatggccct gaagctcgtg ggcgggagcc atctgatcgc aaacatcaag accacatata  3900
gatccaagaa acccgctaag aacctcaaga tgcctggcgt ctactatgtg gactacagac  3960
tggaaagaat caaggaggcc aacaacgaga cctacgtcga gcagcacgag gtggcagtgg  4020
ccagatactg cgacctccct agcaaactgg ggcacaagct taattgagtc gaccgagcat  4080
cttaccgcca tttataccca tatttgttct gtttttcttg atttgggtat acatttaaat  4140
gttaatagaa caaaatggtg gggcaatcat ttacattttt agggatatgt aattactagt  4200
tcaggtgtat tgccacaaga caaacatgtt aagaaacttt cccgttattt acgctctgtt  4260
cctgttaatc aacctctgga ttacaaaatt tgtgaaagat tgactgatat tcttaactat  4320
gttgctcctt ttacgctgtg tggatatgct gctttatagc ctctgtatct agctattgct  4380
tcccgtacgg ctttcgtttt ctcctccttg tataaatcct ggttgctgtc tcttttagag  4440
gagttgtggc ccgttgtccg tcaacgtggc gtggtgtgct ctgtgtttgc tgacgcaacc  4500
cccactggct ggggcattgc caccacctgt caactccttt ctgggacttt cgctttcccc  4560
ctcccgatcg ccacggcaga actcatcgcc gcctgccttg cccgctgctg gacaggggct  4620
aggttgctgg gcactgataa ttccgtggtg ttgtcatcga attcggtacc tttttaaaag  4680
aaaagggggg actggaaggg ctaattcact cccaacgaag acaagatatc ataacttcgt  4740
atagcataca ttatacgaag ttataattta tttgtgaaat ttgtgatgct attgctttat  4800
ttgtaaccat atgtttattt gtgaaatttg tgatgctatt gctttatttg taaccattgc  4860
tttttgcttg tactgggtct ctctggttag accagatctg agcctgggag ctctctggct  4920
aactagggaa cccactgctt aagcctcaat aaagcttgcc tcgaccagcc tcgactgtgc  4980
cttctagttg ccagccatct gttgtttgcc cctcccccgt gccttccttg accctggaag  5040
gtgccactcc cactgtcctt tcctaataaa atgaggaaat tgcatcgcat tgtctgagta  5100
ggtgtcattc tattctgggg ggtggggtgg ggcaggacag caagggggag gattgggaag  5160
acaatagcag gcatgctggg gatgcggtgg gctctatggc ctgcagctgc attaatgaat  5220
cggccaacgc gcggggagag gcggtttgcg tattgggcgc tcttccgctt cctcgctcac  5280
tgactcgctg cgctcggtcg ttcggctgcg gcgagcggta tcagctcact caaaggcggt  5340
aatacggtta tccacagaat caggggataa cgcaggaaag aacatgtgag caaaaggcca  5400
gcaaaaggcc aggaaccgta aaaaggccgc gttgctggcg tttttccata ggctccgccc  5460
ccctgacgag catcacaaaa atcgacgctc aagtcagagg tggcgaaacc cgacaggact  5520
ataaagatac caggcgtttc cccctggaag ctccctcgtg cgctctcctg ttccgaccct  5580
gccgcttacc ggatacctgt ccgcctttct cccttcggga agcgtggcgc tttctcatag  5640
ctcacgctgt aggtatctca gttcggtgta ggtcgttcgc tccaagctgg gctgtgtgca  5700
cgaacccccc gttcagcccg accgctgcgc cttatccggt aactatcgtc ttgagtccaa  5760
cccggtaaga cacgacttat cgccactggc agcagccact ggtaacagga ttagcagagc  5820
gaggtatgta ggcggtgcta cagagttctt gaagtggtgg cctaactacg gctacactag  5880
aaggacagta tttggtatct gcgctctgct gaagccagtt accttcggaa aaagagttgg  5940
tagctcttga tccggcaaac aaaccaccgc tggtagcggt ggtttttttg tttgcaagca  6000
gcagattacg cgcagaaaaa aaggatctca agaagatcct ttgatctttt ctacggggtc  6060
tgacgctcag tggaacgaaa actcacgtta agggattttg gtcatgagat tatcaaaaag  6120
gatcttcacc tagatccttt taaattaaaa atgaagtttt aaatcaatct aaagtatata  6180
tgagtaaact tggtctgaca gttaccaatg cttaatcagt gaggcaccta tctcagcgat  6240
ctgtctattt cgttcatcca tagttgcctg actccccgtc gtgtagataa ctacgatacg  6300
ggagggctta ccatctggcc ccagtgctgc aatgataccg cgagacccac gctcaccggc  6360
tccagattta tcagcaataa accagccagc cggaagggcc gagcgcagaa gtggtcctgc  6420
aactttatcc gcctccatcc agtctattaa ttgttgccgg gaagctagag taagtagttc  6480
gccagttaat agtttgcgca acgttgttgc cattgctaca ggcatcgtgg tgtcacgctc  6540
gtcgtttggt atggcttcat tcagctccgg ttcccaacga tcaaggcgag ttacatgatc  6600
ccccatgttg tgcaaaaaag cggttagctc cttcggtcct ccgatcgttg tcagaagtaa  6660
gttggccgca gtgttatcac tcatggttat ggcagcactg cataattctc ttactgtcat  6720
gccatccgta agatgctttt ctgtgactgg tgagtactca accaagtcat tctgagaata  6780
gtgtatgcgg cgaccgagtt gctcttgccc ggcgtcaata cgggataata ccgcgccaca  6840
tagcagaact ttaaaagtgc tcatcattgg aaaacgttct tcggggcgaa aactctcaag  6900
gatcttaccg ctgttgagat ccagttcgat gtaacccact cgtgcaccca actgatcttc  6960
agcatctttt actttcacca gcgtttctgg gtgagcaaaa acaggaaggc aaaatgccgc  7020
aaaaaaggga ataagggcga cacggaaatg ttgaatactc atactcttcc tttttcaata  7080
ttattgaagc atttatcagg gttattgtct catgagcgga tacatatttg aatgtattta  7140
g                                                                  7141

SEQ ID NO: 63           moltype = DNA  length = 7264
FEATURE                 Location/Qualifiers
misc_feature            1..7264
                        note = pCVL_T7_scFvCD19-DmrA-mCherry lentiviral vector
source                  1..7264
                        mol_type = other DNA
                        organism = synthetic construct
SEQUENCE: 63
aaaaataaac aaataggggt tccgcgcaca tttccccgaa aagtgccacc tgacgtcaat  60
gtagtcttat gcaatactct tgtagtcttg caacatggta acgatgagtt agcaacatgc  120
cttacaagga gagaaaaagc accgtgcatg ccgattggtg gaagtaaggt ggtacgatcg  180
tgccttatta ggaaggcaac agacgggtct gacatggatt ggacgaacca ctgaattgcc  240
gcattgcaga gatattgtat ttaagtgcct agctcgatac ataaacgggt ctctctggtt  300
agaccagatc tgagcctggg agctctctgg ctaactaggg aacccactgc ttaagcctca  360
ataaagcttg ccttgagtgc ttcaagtagt gtgtgcccgt ctgttgtgtg actctggtaa  420
ctagagatcc ctcagaccct tttagtcagt gtggaaaatc tctagcagtg gcgcccgaac  480
agggacttga aagcgaaagg gaaaccagag gagctctctc gacgcaggac tcggcttgct  540
gaagcgcgca cggcaagagg cgaggggcgg cgactggtga gtacgccaaa aattttgact  600
```

```
agcggaggct agaaggagag agatgggtgc gagagcgtca gtattaagcg ggggagaatt  660
agatcgcgat gggaaaaaat tcggttaagg ccagggggaa agaaaaaata taaattaaaa  720
catatagtat gggcaagcag ggagctagaa cgattcgcag ttaatcctgg cctgttagaa  780
acatcagaag gctgtagaca aatactggga cagctacaac catcccttca gacaggatca  840
gaagaactta gatcattata taatacagta gcaaccctct attgtgtgca tcaaaggata  900
gagataaaag acaccaagga agctttagac aagatagagg aagagcaaaa caaaagtaag  960
accaccgcac agcaagcggc cctgatcttc agacctggag gaggagatat gagggacaat  1020
tggagaagtg aattatataa atataaagta gtaaaaattg aaccattagg agtagcaccc  1080
accaaggcaa agagaagagt ggtgcagaga gaaaaaagag cagtgggaat aggagctttg  1140
ttccttgggt tcttgggagc agcaggaagc actatgggcg cagcgtcaat gacgctgacg  1200
gtacaggcca gacaattatt gtctggtata gtgcagcagc agaacaattt gctgagggct  1260
attgaggcgc aacagcatct gttgcaactc acagtctggg gcatcaagca gctccaggca  1320
agaatcctgg ctgtggaaag atacctaaag gatcaacagc tcctggggat ttggggttgc  1380
tctggaaaac tcatttgcac cactgctgtg ccttggaatg ctagttggag taatgaatct  1440
ctggaacaga tttggaatca cacgacctgg atggagtggg acagagaaat taacaattac  1500
acaagcttaa tacactcctt aattgaagaa tcgcaaaacc agcaagaaaa gaatgaacaa  1560
gaattattgg aattagataa atgggcaagt ttgtggaatt ggtttaacat aacaaattgg  1620
ctgtggtata taaaattatt cataatgata gtaggaggct tggtaggttt aagaatagtt  1680
tttgctgtac tttctatagt gaatagagtt aggcagggat attcaccatt atcgtttcag  1740
acccacctcc caaccccgag gggacccgac aggcccgaag gaatagaaga agaaggtgga  1800
gagagagaca gagacagatc cattcgatta gtgaacggat ctcgacggta tcggttaact  1860
tttaaaagaa aaggggggat tggggggtac agtgcagggg aaagaatagt agacataata  1920
gcaacagaca tacaaactaa agaattacaa aaacaaatta caaaaattca aaattttatc  1980
gattacgcgt aggctccggt gcccgtcagt gggcagagcg cacatcgccc acagtccccg  2040
agaagttggg gggaggggtc ggcaattgaa ccggtgccta gagaaggtgg cgcggggtaa  2100
actgggaaag tgatgtcgtg tactggctcc gcctttttcc cgagggtggg ggagaaccgt  2160
atataagtgc agtagtcgcc gtgaacgttc tttttcgcaa cgggtttgcc gccagaacac  2220
acctgcaggt aatacgactc actatagggt ccactgccgc caccatgccc ctgggcctgc  2280
tgtggctggg cctggccctg ctgggcgccc tgcacgccca ggccggatcc gatatccaga  2340
tgacccagac caccagcagc ctgagcgcca gcctgggcga tagagtgacc atcagctgca  2400
gagccagcca ggacatcagc aagtacctga actggtatca gcagaaaccc gacggcaccg  2460
tgaagctgct gatctaccac accagcagac tgcacagcgg cgtgcccagc agattttctg  2520
gcagcggctc cggcaccgac tacagcctga ccatctccaa cctggaacag gaagatatcg  2580
ctacctactt ctgtcagcaa ggcaacaccc tgccctacac cttcggcgga ggcaccaagc  2640
tggaaatcac cggcagcaca agcggcagcg gcaagcctgg atctggcgag ggaagcacca  2700
agggcgaagt gaaactgcag gaaagcggcc ctggactggt ggccccaagc cagtctctga  2760
gcgtgacctg taccgtgtcc ggcgtgtccc tgcctgacta tggcgtgtcc tggatcagac  2820
agccacccag aaagggcctg gaatggctgg gagtgatctg gggcagcgag acaacctact  2880
acaacagcgc cctgaagtcc cggctgacca tcatcaagga caactccaag agccaggtgt  2940
tcctgaagat gaacagcctg cagaccgacg acaccgccat ctactactgc gccaagcact  3000
actactacgg cggcagctac gccatggact actggggcca gggcacaagc gtgaccgtgt  3060
ccagcgctag cggcggaggt gggagcggag tgcaggtgga aaccatctcc ccaggagacg  3120
ggcgcacctt ccccaagcgc ggccagacct gcgtggtgca ctacaccggg atgcttgaag  3180
atggaaagaa atttgattcc tcccgggaca gaaacaagcc ctttaagttt atgctaggca  3240
agcaggaggt gatccgaggc tgggaagaag gggttgccca gatgagtgtg ggtcagagag  3300
ccaaactgac tatatctcca gattatgcct atggtgccac tgggcaccca ggcatcatcc  3360
caccacatgc cactctcgtc ttcgatgtgg agcttctaaa actggaaggc ggccgctccg  3420
gtgagggcag aggaagtctt ctaacatgcg gtgacgtgga ggagaatccg ggcccctcta  3480
gagtgagcaa gggcgaggag gataacatgg ccatcatcaa ggagttcatg cgcttcaagg  3540
tgcacatgga gggctccgtg aacggccacg agttcgagat cgagggcgag ggcgagggcc  3600
gcccctacga gggcacccag accgccaagc tgaaggtgac caagggtggc cccctgccct  3660
tcgcctggga catcctgtcc cctcagttca tgtacggctc caaggcctac gtgaagcacc  3720
ccgccgacat ccccgactac ttgaagctgt ccttccccga gggcttcaag tgggagcgcg  3780
tgatgaactt cgaggacggc ggcgtggtga ccgtgaccca ggactcctct ctgcaggacg  3840
gcgagttcat ctacaaggtg aagctgcgcg gcaccaactt cccctccgac ggccccgtaa  3900
tgcagaagaa gactatgggc tgggaggcct cctccgagcg gatgtacccc gaggacggcg  3960
ccctgaaggg cgagatcaag cagaggctga agctgaagga cggcggccac tacgacgctg  4020
aggtcaagac cacctacaag gccaagaagc ccgtgcagct gcccggcgcc tacaacgtca  4080
acatcaagtt ggacatcacc tcccacaacg aggactacac catcgtggaa cagtacgaac  4140
gcgccgaggg ccgccactcc accggcggca tggacgagct gtacaagtaa gtcgaccgag  4200
catcttaccg ccatttatac ccatatttgt tctgtttttc ttgatttggg tatacattta  4260
aatgttaata gaacaaaatg gtggggcaat catttacatt tttagggata tgtaattact  4320
agttcaggtg tattgccaca agacaaacat gttaagaaac tttcccgtta tttacgctct  4380
gttcctgtta atcaacctct ggattacaaa atttgtgaaa gattgactga tattcttaac  4440
tatgttgctc cttttacgct gtgtggatat gctgctttat agcctctgta tctagctatt  4500
gcttcccgta cggctttcgt tttctcctcc ttgtataaat cctggttgct gtctctttta  4560
gaggagttgt ggcccgttgt ccgtcaacgt ggcgtggtgt gctctgtgtt tgctgacgca  4620
acccccactg gctggggcat tgccaccacc tgtcaactcc tttctgggac tttcgctttc  4680
cccctcccga tcgccacggc agaactcatc gccgcctgcc ttgcccgctg ctggacaggg  4740
gctaggttgc tgggcactga taattccgtg gtgttgtcat cgaattcggt acctttttaa  4800
aagaaaaggg gggactggaa gggctaattc actcccaacg aagacaagat atcataactt  4860
cgtatagcat acattatacg aagttataat ttatttgtga aatttgtgat gctattgctt  4920
tatttgtaac catatgttta tttgtgaaat ttgtgatgct attgctttat ttgtaaccat  4980
tgctttttgc ttgtactggg tctctctggt tagaccagat ctgagcctgg gagctctctg  5040
gctaactagg gaacccactg cttaagcctc aataaagctt gcctcgacca gcctcgactg  5100
tgccttctag ttgccagcca tctgttgttt gcccctcccc cgtgccttcc ttgaccctgg  5160
aaggtgccac tcccactgtc ctttcctaat aaaatgagga aattgcatcg cattgtctga  5220
gtaggtgtca ttctattctg gggggtgggg tggggcagga cagcaagggg gaggattggg  5280
aagacaatag caggcatgct ggggatgcgg tgggctctat ggcctgcagc tgcattaatg  5340
```

```
aatcggccaa cgcgcgggga gaggcggttt gcgtattggg cgctcttccg cttcctcgct  5400
cactgactcg ctgcgctcgg tcgttcggct gcggcgagcg gtatcagctc actcaaaggc  5460
ggtaatacgg ttatccacag aatcagggga taacgcagga aagaacatgt gagcaaaagg  5520
ccagcaaaag gccaggaacc gtaaaaaggc cgcgttgctg gcgtttttcc ataggctccg  5580
cccccctgac gagcatcaca aaaatcgacg ctcaagtcag aggtggcgaa acccgacagg  5640
actataaaga taccaggcgt ttccccctgg aagctccctc gtgcgctctc ctgttccgac  5700
cctgccgctt accggatacc tgtccgcctt tctcccttcg ggaagcgtgg cgctttctca  5760
tagctcacgc tgtaggtatc tcagttcggt gtaggtcgtt cgctccaagc tgggctgtgt  5820
gcacgaaccc cccgttcagc ccgaccgctg cgccttatcc ggtaactatc gtcttgagtc  5880
caacccggta agacacgact tatcgccact ggcagcagcc actggtaaca ggattagcag  5940
agcgaggtat gtaggcggtg ctacagagtt cttgaagtgg tggcctaact acggctacac  6000
tagaaggaca gtatttggta tctgcgctct gctgaagcca gttaccttcg gaaaaagagt  6060
tggtagctct tgatccggca aacaaaccac cgctggtagc ggtggttttt ttgtttgcaa  6120
gcagcagatt acgcgcagaa aaaaaggatc tcaagaagat cctttgatct tttctacggg  6180
gtctgacgct cagtggaacg aaaactcacg ttaagggatt ttggtcatga gattatcaaa  6240
aaggatcttc acctagatcc ttttaaatta aaaatgaagt tttaaatcaa tctaaagtat  6300
atatgagtaa acttggtctg acagttacca atgcttaatc agtgaggcac ctatctcagc  6360
gatctgtcta tttcgttcat ccatagttgc ctgactcccc gtcgtgtaga taactacgat  6420
acgggagggc ttaccatctg gccccagtgc tgcaatgata ccgcgagacc cacgctcacc  6480
ggctccagat ttatcagcaa taaaccagcc agccggaagg gccgagcgca gaagtggtcc  6540
tgcaacttta tccgcctcca tccagtctat taattgttgc cgggaagcta gagtaagtag  6600
ttcgccagtt aatagtttgc gcaacgttgt tgccattgct acaggcatcg tggtgtcacg  6660
ctcgtcgttt ggtatggctt cattcagctc cggttcccaa cgatcaaggc gagttacatg  6720
atcccccatg ttgtgcaaaa aagcggttag ctccttcggt cctccgatcg ttgtcagaag  6780
taagttggcc gcagtgttat cactcatggt tatggcagca ctgcataatt ctcttactgt  6840
catgccatcc gtaagatgct tttctgtgac tggtgagtac tcaaccaagt cattctgaga  6900
atagtgtatg cggcgaccga gttgctcttg cccggcgtca atacgggata ataccgcgcc  6960
acatagcaga actttaaaag tgctcatcat tggaaaacgt tcttcggggc gaaaactctc  7020
aaggatctta ccgctgttga gatccagttc gatgtaaccc actcgtgcac ccaactgatc  7080
ttcagcatct tttactttca ccagcgtttc tgggtgagca aaaacaggaa ggcaaaatgc  7140
cgcaaaaaag ggaataaggg cgacacggaa atgttgaata ctcatactct tcctttttca  7200
atattattga agcatttatc agggttattg tctcatgagc ggatacatat ttgaatgtat  7260
ttag                                                                7264

SEQ ID NO: 64          moltype = AA  length = 740
FEATURE                Location/Qualifiers
REGION                 1..740
                       note =
                        CD8ss-DmrC-CD8TM-41BB-CD3z-P2A-IgKss-CD19scFv-DmrA-CD4TM
                        protein
source                 1..740
                       mol_type = protein
                       organism = synthetic construct
SEQUENCE: 64
MALPVTALLL PLALLLHAAR PGSILWHEMW HEGLEEASRL YFGERNVKGM FEVLEPLHAM  60
MERGPQTLKE TSFNQAYGRD LMEAQEWCRK YMKSGNVKDL LQAWDLYYHV FRRISKASAG  120
TGSDIYIWAP LAGTCGVLLL SLVITMHKRG RKKLLYIFKQ PFMRPVQTTQ EEDGCSCRFP  180
EEEEGGCELR VKFSRSADAP AYQQGQNQLY NELNLGRREE YDVLDKRRGR DPEMGGKPRR  240
KNPQEGLYNE LQKDKMAEAY SEIGMKGERR RGKGHDGLYQ GLSTATKDTY DALHMQALPP  300
RSGSGATNFS LLKQAGDVEE NPGPSMETDT LLLWVLLLWV PGSTGSDIQM TQTTSSLSAS  360
LGDRVTISCR ASQDISKYLN WYQQKPDGTV KLLIYHTSRL HSGVPSRFSG SGSGTDYSLT  420
ISNLEQEDIA TYFCQQGNTL PYTFGGGTKL EITGSTSGSG KPGSGEGSTK GEVKLQESGP  480
GLVAPSQSLS VTCTVSGVSL PDYGVSWIRQ PPRKGLEWLG VIWGSETTYY NSALKSRLTI  540
IKDNSKSQVF LKMNSLQTDD TAIYYCAKHY YYGGSYAMDY WGQGTSVTVS SASGGGGSGV  600
QVETISPGDG RTFPKRGQTC VVHYTGMLED GKKFDSSRDR NKPFKFMLGK QEVIRGWEEG  660
VAQMSVGQRA KLTISPDYAY GATGHPGIIP PHATLVFDVE LLKLEGGRMA LIVLGGVAGL  720
LLFIGLGIFF CVRCRHRRRQ                                               740

SEQ ID NO: 65          moltype = DNA  length = 2223
FEATURE                Location/Qualifiers
misc_feature           1..2223
                       note =
                        CD8ss-DmrC-CD8TM-41BB-CD3z-P2A-IgKss-CD19scFv-DmrA-CD4TM
                        DNA
source                 1..2223
                       mol_type = other DNA
                       organism = synthetic construct
SEQUENCE: 65
atggctctgc ctgtgacagc tctgctgctg cctctggccc tgctgctcca tgccgccaga  60
cccggatcca tcctctggca tgagatgtgg catgaaggcc tggaagaggc atctcgtttg  120
tactttgggg aaaggaacgt gaaaggcatg tttgaggtgc tggagccctt gcatgctatg  180
atggaacggg gcccccagac tctgaaggaa acatccttta atcaggccta tggtcgagat  240
ttaatggagg cccaagagtg gtgcaggaag tacatgaaat cagggaatgt caaggacctc  300
ctccaagcct gggacctcta ttatcatgtg ttccgacgaa tctcaaaggc tagcgccggc  360
actggttccg acatctacat ctgggcccct ctggccggca catgtggcgt gctgctgctg  420
agcctcgtga tcaccatgca taaacggggc agaaagaaac tcctgtatat attcaaacaa  480
ccatttatga gaccagtaca aactactcaa gaggaagatg gctgtagctg ccgatttcca  540
gaagaagaag aaggaggatg tgaactgcgg gtgaagttca gcagaagcgc cgacgcccct  600
gcctaccagc agggccagaa tcagctgtac aacgagctga acctgggcag aagggaagag  660
```

```
tacgacgtcc tggataagcg gagaggccgg gaccctgaga tgggcggcaa gcctcggcgg  720
aagaaccccc aggaaggcct gtataacgaa ctgcagaaag acaagatggc cgaggcctac  780
agcgagatcg gcatgaaggg cgagcggagg cggggcaagg gccacgacgg cctgtatcag  840
ggcctgtcca ccgccaccaa ggatacctac gacgccctgc acatgcaggc cctgccccca  900
aggtcaggat ctggcgccac gaacttctct ctgttaaagc aagcaggaga tgttgaagaa  960
aaccccgggc cttcaatgga gacagacaca ctcctgctat gggtactgct gctctgggtt  1020
ccaggttcca ctggttccga tatccagatg acccagacca ccagcagcct gagcgccagc  1080
ctgggcgata gagtgaccat cagctgcaga gccagccagg acatcagcaa gtacctgaac  1140
tggtatcagc agaaacccga cggcaccgtg aagctgctga tctaccacac cagcagactg  1200
cacagcggcg tgcccagcag atttctggc agcggctccg gcaccgacta cagcctgacc  1260
atctccaacc tggaacagga agatatcgct acctacttct gtcagcaagg caacaccctg  1320
ccctacacct tcggcggagg caccaagctg gaaatcaccg gcagcacaag cggcagcggc  1380
aagcctggat ctggcgaggg aagcaccaag ggcgaagtga aactgcagga aagcggccct  1440
ggactggtgg ccccaagcca gtctctgagc gtgacctgta ccgtgtccgg cgtgtccctg  1500
cctgactatg gcgtgtcctg gatcagacag ccacccagaa agggcctgga atggctggga  1560
gtgatctggg gcagcgagac aacctactac aacagcgccc tgaagtcccg gctgaccatc  1620
atcaaggaca actccaagag ccaggtgttc ctgaagatga acagcctgca gaccgacgac  1680
accgccatct actactgcgc caagcactac tactacggcg gcagctacgc catggactac  1740
tggggccagg gcacaagcgt gaccgtgtcc agcgctagcg gcggaggtgg gagcggagtg  1800
caggtggaaa ccatctcccc aggagacggg cgcaccttcc ccaagcgcgg ccagacctgc  1860
gtggtgcact acaccgggat gcttgaagat ggaaagaaat ttgattcctc ccgggacaga  1920
aacaagccct ttaagtttat gctaggcaag caggaggtga tccgaggctg ggaagaaggg  1980
gttgcccaga tgagtgtggg tcagagagcc aaactgacta tatctccaga ttatgcctat  2040
ggtgccactg ggcacccagg catcatccca ccacatgcca ctctcgtctt cgatgtggag  2100
cttctaaaac tggaaggcgg ccgcatggcc ctgattgtgc tggggggcgt cgccggcctc  2160
ctgcttttca ttgggctagg catcttcttc tgtgtcaggt gccggcaccg aaggcgccaa  2220
taa                                                                2223
```

```
SEQ ID NO: 66          moltype = DNA  length = 7651
FEATURE                Location/Qualifiers
misc_feature           1..7651
                       note =
                        pCVL_MND-CD8ss-DmrC-CD8TM-41BB-CD3z-P2A-IgKss-CD19scFv-DmrA
                        -CD4TM lentiviral vector
source                 1..7651
                       mol_type = other DNA
                       organism = synthetic construct
SEQUENCE: 66
aatgtagtct tatgcaatac tcttgtagtc ttgcaacatg gtaacgatga gttagcaaca  60
tgccttacaa ggagagaaaa agcaccgtgc atgccgattg gtggaagtaa ggtggtacga  120
tcgtgcctta ttaggaaggc aacagacggg tctgacatgg attggacgaa ccactgaatt  180
gccgcattgc agagatattg tatttaagtg cctagctcga tacataaacg ggtctctctg  240
gttagaccag atctgagcct gggagctctc tggctaacta gggaacccac tgcttaagcc  300
tcaataaagc ttgccttgag tgcttcaagt agtgtgtgcc cgtctgttgt gtgactctgg  360
taactagaga tccctcagac ccttttagtc agtgtggaaa atctctagca gtggcgcccg  420
aacagggact tgaaagcgaa agggaaacca gaggagctct ctcgacgcag gactcggctt  480
gctgaagcgc gcacggcaag aggcgagggg cggcgactgg tgagtacgcc aaaaattttg  540
actagcggag gctagaagga gagagatggg tgcgagagcg tcagtattaa gcgggggaga  600
attagatcgc gatgggaaaa aattcggtta aggccagggg gaaagaaaaa atataaatta  660
aaacatatag tatgggcaag cagggagcta gaacgattcg cagttaatcc tggcctgtta  720
gaaacatcag aaggctgtag acaaatactg ggacagctac aaccatccct tcagacagga  780
tcagaagaac ttagatcatt atataataca gtagcaaccc tctattgtgt gcatcaaagg  840
atagagataa aagacaccaa ggaagcttta gacaagatag aggaagagca aaacaaaagt  900
aagaccaccg cacagcaagc ggccctgatc ttcagacctg gaggaggaga tatgagggac  960
aattggagaa gtgaattata taaatataaa gtagtaaaaa ttgaaccatt aggagtagca  1020
cccaccaagg caaagagaag agtggtgcag agagaaaaaa gagcagtggg aataggagct  1080
ttgttccttg ggttcttggg agcagcagga agcactatgg gcgcagcgtc aatgacgctg  1140
acggtacagg ccagacaatt attgtctggt atagtgcagc agcagaacaa tttgctgagg  1200
gctattgagg cgcaacagca tctgttgcaa ctcacagtct ggggcatcaa gcagctccag  1260
gcaagaatcc tggctgtgga aagataccta aaggatcaac agctcctggg gatttggggt  1320
tgctctggaa aactcatttg caccactgct gtgccttgga atgctagttg gagtaatgaa  1380
tctctggaac agatttggaa tcacacgacc tggatggagt gggacagaga aattaacaat  1440
tacacaagct taatacactc cttaattgaa gaatcgcaaa accagcaaga aaagaatgaa  1500
caagaattat tggaattaga taaatgggca agtttgtgga attggtttaa cataacaaat  1560
tggctgtggt atataaaatt attcataatg atagtaggag gcttggtagg tttaagaata  1620
gtttttgctg tactttctat agtgaataga gttaggcagg gatattcacc attatcgttt  1680
cagacccacc tcccaacccc gaggggaccc gacaggcccg aaggaataga agaagaaggt  1740
ggagagagag acagagacag atccattcga ttagtgaacg gatctcgacg gtatcggtta  1800
acttttaaaa gaaaaggggg gattgggggg tacagtgcag gggaaagaat agtagacata  1860
atagcaacag acatacaaac taaagaatta caaaaacaaa ttacaaaaat tcaaaatttt  1920
atcgattacg cgtgtacaga gagacagcag aatatgggcc aaacaggata tctgtggtaa  1980
gcagttcctg ccccggctca gggccaagaa cagttggaac agcagaatat gggccaaaca  2040
ggatatctgt ggtaagcagt tcctgccccg gctcagggcc aagaacagat ggtccccaga  2100
tgcggtcccg ccctcagcag tttctagaga accatcagat gtttccaggg tgccccaagg  2160
acctgaaatg accctgtgcc ttatttgaac taaccaatca gttcgcttct cgcttctgtt  2220
cgcgcgcttc tgctccccga gctctatata agcagagctc gtttagtgaa ccgtcagatc  2280
cctgcagggc cgccaccatg gctctgcctg tgacagctct gctgctgcct ctggccctgc  2340
tgctccatgc cgccagaccc ggatccatcc tctggcatga gatgtggcat gaaggcctgg  2400
aagaggcatc tcgtttgtac tttggggaaa ggaacgtgaa aggcatgttt gaggtgctgg  2460
```

-continued

```
agcccttgca tgctatgatg gaacggggcc cccagactct gaaggaaaca tcctttaatc  2520
aggcctatgg tcgagattta atggaggccc aagagtggtg caggaagtac atgaaatcag  2580
ggaatgtcaa ggacctcctc caagcctggg acctctatta tcatgtgttc cgacgaatct  2640
caaaggctag cgccggcact ggttccgaca tctacatctg ggcccctctg gccggcacat  2700
gtggcgtgct gctgctgagc ctcgtgatca ccatgcataa acggggcaga aagaaactcc  2760
tgtatatatt caaacaacca tttatgagac cagtacaaac tactcaagag gaagatggct  2820
gtagctgccg atttccagaa gaagaagaag gaggatgtga actgcgggtg aagttcagca  2880
gaagcgccga cgcccctgcc taccagcagg gccagaatca gctgtacaac gagctgaacc  2940
tgggcagaag ggaagagtac gacgtcctgg ataagcggag aggccgggac cctgagatgg  3000
gcggcaagcc tcggcggaag aacccccagg aaggcctgta taacgaactg cagaaagaca  3060
agatggccga ggcctacagc gagatcggca tgaagggcga gcggaggcgg ggcaagggcc  3120
acgacggcct gtatcagggc ctgtccaccg ccaccaagga tacctacgac gccctgcaca  3180
tgcaggccct gcccccaagg tcaggatctg gcgccacgaa cttctctctg ttaaagcaag  3240
caggagatgt tgaagaaaac cccgggcctt caatggagac agacacactc ctgctatggg  3300
tactgctgct ctgggttcca ggttccactg gttccgatat ccagatgacc cagaccacca  3360
gcagcctgag cgccagcctg ggcgatagag tgaccatcag ctgcagagcc agccaggaca  3420
tcagcaagta cctgaactgg tatcagcaga aacccgacgg caccgtgaag ctgctgatct  3480
accacaccag cagactgcac agcggcgtgc ccagcagatt ttctggcagc ggctccggca  3540
ccgactacag cctgaccatc tccaacctgg aacaggaaga tatcgctacc tacttctgtc  3600
agcaaggcaa caccctgccc tacaccttcg gcggaggcac caagctggaa atcaccggca  3660
gcacaagcgg cagcggcaag cctggatctg gcgagggaag caccaagggc gaagtgaaac  3720
tgcaggaaag cggccctgga ctggtggccc caagccagtc tctgagcgtg acctgtaccg  3780
tgtccggcgt gtccctgcct gactatggcg tgtcctggat cagacagcca cccagaaagg  3840
gcctggaatg gctgggagtg atctggggca gcgagacaac ctactacaac agcgccctga  3900
agtcccggct gaccatcatc aaggacaact ccaagagcca ggtgttcctg aagatgaaca  3960
gcctgcagac cgacgacacc gccatctact actgcgccaa gcactactac tacggcggca  4020
gctacgccat ggactactgg ggccagggca caagcgtgac cgtgtccagc gctagcggcg  4080
gaggtgggag cggagtgcag gtggaaacca tctccccagg agacgggcgc accttcccca  4140
agcgcggcca gacctgcgtg gtgcactaca ccgggatgct tgaagatgga aagaaatttg  4200
attcctcccg ggacagaaac aagcccttta agtttatgct aggcaagcag gaggtgatcc  4260
gaggctggga agaaggggtt gcccagatga gtgtgggtca gagagccaaa ctgactatat  4320
ctccagatta tgcctatggt gccactgggc acccaggcat catcccacca catgccactc  4380
tcgtcttcga tgtggagctt ctaaaactgg aaggcggccg catggccctg attgtgctgg  4440
ggggcgtcgc cggcctcctg cttttcattg ggctaggcat cttcttctgt gtcaggtgcc  4500
ggcaccgaag gcgccaataa gtcgaccgag catcttaccg ccatttatac ccatatttgt  4560
tctgtttttc ttgatttggg tatacattta aatgttaata gaacaaaatg gtggggcaat  4620
catttacatt tttagggata tgtaattact agttcaggtg tattgccaca agacaaacat  4680
gttaagaaac tttcccgtta tttacgctct gttcctgtta atcaacctct ggattacaaa  4740
atttgtgaaa gattgactga tattcttaac tatgttgctc cttttacgct gtgtggatat  4800
gctgctttat agcctctgta tctagctatt gcttcccgta cggctttcgt tttctcctcc  4860
ttgtataaat cctggttgct gtctctttta gaggagttgt ggcccgttgt ccgtcaacgt  4920
ggcgtggtgt gctctgtgtt tgctgacgca acccccactg gctggggcat tgccaccacc  4980
tgtcaactcc tttctgggac tttcgctttc cccctcccga tcgccacggc agaactcatc  5040
gccgcctgcc ttgcccgctg ctggacaggg gctaggttgc tgggcactga taattccgtg  5100
gtgttgtcat cgaattcggt acctttttaa aagaaaaggg gggactggaa gggctaattc  5160
actcccaacg aagacaagat atcataactt cgtatagcat acattatacg aagttataat  5220
ttatttgtga aatttgtgat gctattgctt tatttgtaac catatgttta tttgtgaaat  5280
ttgtgatgct attgctttat ttgtaaccat tgctttttgc ttgtactggg tctctctggt  5340
tagaccagat ctgagcctgg gagctctctg gctaactagg gaacccactg cttaagcctc  5400
aataaagctt gcctcgacca gcctcgactg tgccttctag ttgccagcca tctgttgttt  5460
gcccctcccc cgtgccttcc ttgaccctgg aaggtgccac tcccactgtc ctttcctaat  5520
aaaatgagga aattgcatcg cattgtctga gtaggtgtca ttctattctg gggggtgggg  5580
tggggcagga cagcaagggg gaggattggg aagacaatag caggcatgct ggggatgcgg  5640
tgggctctat ggcctgcagc tgcattaatg aatcggccaa cgcgcgggga gaggcggttt  5700
gcgtattggg cgctcttccg cttcctcgct cactgactcg ctgcgctcgg tcgttcggct  5760
gcggcgagcg gtatcagctc actcaaaggc ggtaatacgg ttatccacag aatcagggga  5820
taacgcagga aagaacatgt gagcaaaagg ccagcaaaag gccaggaacc gtaaaaaggc  5880
cgcgttgctg gcgtttttcc ataggctccg cccccctgac gagcatcaca aaaatcgacg  5940
ctcaagtcag aggtggcgaa acccgacagg actataaaga taccaggcgt ttccccctgg  6000
aagctccctc gtgcgctctc ctgttccgac cctgccgctt accggatacc tgtccgcctt  6060
tctcccttcg ggaagcgtgg cgctttctca tagctcacgc tgtaggtatc tcagttcggt  6120
gtaggtcgtt cgctccaagc tgggctgtgt gcacgaaccc cccgttcagc ccgaccgctg  6180
cgccttatcc ggtaactatc gtcttgagtc caacccggta agacacgact tatcgccact  6240
ggcagcagcc actggtaaca ggattagcag agcgaggtat gtaggcggtg ctacagagtt  6300
cttgaagtgg tggcctaact acggctacac tagaaggaca gtatttggta tctgcgctct  6360
gctgaagcca gttaccttcg gaaaaagagt tggtagctct tgatccggca aacaaaccac  6420
cgctggtagc ggtggttttt ttgtttgcaa gcagcagatt acgcgcagaa aaaaaggatc  6480
tcaagaagat cctttgatct tttctacggg gtctgacgct cagtggaacg aaaactcacg  6540
ttaagggatt ttggtcatga gattatcaaa aaggatcttc acctagatcc ttttaaatta  6600
aaaatgaagt tttaaatcaa tctaaagtat atatgagtaa acttggtctg acagttacca  6660
atgcttaatc agtgaggcac ctatctcagc gatctgtcta tttcgttcat ccatagttgc  6720
ctgactcccc gtcgtgtaga taactacgat acgggagggc ttaccatctg gccccagtgc  6780
tgcaatgata ccgcgagacc cacgctcacc ggctccagat ttatcagcaa taaaccagcc  6840
agccggaagg gccgagcgca gaagtggtcc tgcaacttta tccgcctcca tccagtctat  6900
taattgttgc cgggaagcta gagtaagtag ttcgccagtt aatagtttgc gcaacgttgt  6960
tgccattgct acaggcatcg tggtgtcacg ctcgtcgttt ggtatggctt cattcagctc  7020
cggttcccaa cgatcaaggc gagttacatg atcccccatg ttgtgcaaaa aagcggttag  7080
ctccttcggt cctccgatcg ttgtcagaag taagttggcc gcagtgttat cactcatggt  7140
tatggcagca ctgcataatt ctcttactgt catgccatcc gtaagatgct tttctgtgac  7200
```

```
tggtgagtac tcaaccaagt cattctgaga atagtgtatg cggcgaccga gttgctcttg  7260
cccggcgtca atacgggata ataccgcgcc acatagcaga actttaaaag tgctcatcat  7320
tggaaaacgt tcttcggggc gaaaactctc aaggatctta ccgctgttga gatccagttc  7380
gatgtaaccc actcgtgcac ccaactgatc ttcagcatct tttactttca ccagcgtttc  7440
tgggtgagca aaaacaggaa ggcaaaatgc cgcaaaaaag ggaataaggg cgacacggaa  7500
atgttgaata ctcatactct tcctttttca atattattga agcatttatc agggttattg  7560
tctcatgagc ggatacatat ttgaatgtat ttagaaaaat aaacaaatag gggttccgcg  7620
cacatttccc cgaaaagtgc cacctgacgt c                                7651

SEQ ID NO: 67          moltype = AA  length = 739
FEATURE                Location/Qualifiers
REGION                 1..739
                       note =
                        CD8ss-DmrC-CD8TM-41BB-CD3z-P2A-IgKss-CD19scFv-DmrA-CD4TM
                        codon optimized protein
source                 1..739
                       mol_type = protein
                       organism = synthetic construct
SEQUENCE: 67
MALPVTALLL PLALLLHAAR PGSILWHEMW HEGLEEASRL YFGERNVKGM FEVLEPLHAM  60
MERGPQTLKE TSFNQAYGRD LMEAQEWCRK YMKSGNVKDL LQAWDLYYHV FRRISKASAG  120
TGSDIYIWAP LAGTCGVLLL SLVITMHKRG RKKLLYIFKQ PFMRPVQTTQ EEDGCSCRFP  180
EEEEGGCELR VKFSRSADAP AYQQGQNQLY NELNLGRREE YDVLDKRRGR DPEMGGKPRR  240
KNPQEGLYNE LQKDKMAEAY SEIGMKGERR RGKGHDGLYQ GLSTATKDTY DALHMQALPP  300
RSGSGATNFS LLKQAGDVEE NPGPSMETDT LLLWVLLLWV PGSTGDIQMT QTTSSLSASL  360
GDRVTISCRA SQDISKYLNW YQQKPDGTVK LLIYHTSRLH SGVPSRFSGS GSGTDYSLTI  420
SNLEQEDIAT YFCQQGNTLP YTFGGGTKLE ITGSTSGSGK PGSGEGSTKG EVKLQESGPG  480
LVAPSQSLSV TCTVSGVSLP DYGVSWIRQP PRKGLEWLGV IWGSETTYYN SALKSRLTII  540
KDNSKSQVFL KMNSLQTDDT AIYYCAKHYY YGGSYAMDYW GQGTSVTVSS PRGGGGSGVQ  600
VETISPGDGR TFPKRGQTCV VHYTGMLEDG KKFDSSRDRN KPFKFMLGKQ EVIRGWEEGV  660
AQMSVGQRAK LTISPDYAYG ATGHPGIIPP HATLVFDVEL LKLEGGRMAL IVLGGVAGLL  720
LFIGLGIFFC VRCRHRRRQ                                              739

SEQ ID NO: 68          moltype = DNA  length = 2220
FEATURE                Location/Qualifiers
misc_feature           1..2220
                       note =
                        CD8ss-DmrC-CD8TM-41BB-CD3z-P2A-IgKss-CD19scFv-DmrA-CD4TM
                        codon optimized DNA
source                 1..2220
                       mol_type = other DNA
                       organism = synthetic construct
SEQUENCE: 68
atggccctcc ctgtgaccgc cctgctgctc cccctcgccc tgttgctcca tgctgcccga  60
cctggatcca tcctttggca cgagatgtgg cacgagggac tcgaagaagc gtcccggctg  120
tacttcggag agcggaacgt gaaggggatg ttcgaagtgc tggaacccct gcacgccatg  180
atggagcggg gtcctcagac ccttaaagaa acaagcttca accaggcgta cgggcgcgac  240
ctgatggaag cccaggagtg gtgccgcaag tacatgaagt ccggaaacgt gaaggatctg  300
ctgcaagcct gggatctgta ctaccacgtg ttcagaagga tctcaaaggc tagcgccggc  360
actggttcgg atatctacat ttgggcaccg ctcgccggca cttgtggagt gctgttgctg  420
tccctcgtga tcaccatgca taagagggga cggaagaagc tgctgtacat tttcaagcag  480
ccattcatgc ggcctgtgca aaccacccag gaggaggacg ggtgcagctg ccggttccct  540
gaggaagagg agggcggatg cgaactgcgc gtgaagttca gccggagcgc agatgctccc  600
gcataccaac agggacagaa ccagctgtat aacgagctga acctgggcag aagggaagag  660
tacgacgtcc tcgacaagcg gcggggacgc gacccagaaa tgggaggaaa gccccgccgg  720
aagaacccgc aggaaggcct gtacaacgag ttgcagaaag acaagatggc tgaagcttac  780
tcggagattg gcatgaaggg ggagagaaga agagggaagg gccacgacgg cctttaccaa  840
ggactgagca ctgccaccaa ggacacctac gatgcgctgc acatgcaggc cctgcccccg  900
cggtccggtt cgggcgcgac taacttcagc ctgctgaagc aggccggaga tgtggaggaa  960
aaccctggac cgtccatgga gactgatacc ctgcttctgt gggtcctgct cctctgggtg  1020
ccgggctcca ccggtgacat ccagatgacc cagaccacct catccctgag cgcctctctg  1080
ggtgatcgcg tgactatctc ctgccgggcg tcgcaggata tctccaagta cctgaactgg  1140
taccagcaaa aaccggacgg gaccgtgaaa ctgctgatct accatacttc ccgccttcat  1200
tccggagtgc cctcccggtt ttccggctcg ggttcaggga ctgattattc gctgaccatt  1260
tccaacctgg agcaggagga cattgcgacc tacttctgcc aacaaggaaa caccctgccc  1320
tacactttcg gtggtggaac caagctcgag atcaccggat caacctcggg cagcgggaag  1380
ccgggcagcg gagagggatc gacgaaagga gaagtcaagc tgcaggaatc cggcccggga  1440
ctggtggccc cgagccagtc gctctccgtc acttgcaccg tgtcgggagt gtccttgccc  1500
gactacggag tgtcatggat tcggcagcca cctcgcaagg gcctggaatg gctcggcgtg  1560
atttggggct cagaaaccac atactacaac agcgccctga agtctcggct caccatcatc  1620
aaggacaatt ccaagtccca agtgttcctg aagatgaata gcttgcagac tgacgacacc  1680
gcgatctact actgtgccaa gcactactac tacggcggtt cctacgccat ggactactgg  1740
ggacaaggaa cttccgtgac tgtctcctcc cctagggggg gtggtggttc gggggtccag  1800
gtggaaacca tttcccccgg cgacgggcgc accttcccga agcgcggaca gacctgtgtg  1860
gtgcactata ccggaatgct cgaagatgga aagaagtttg acagctccag ggaccgcaac  1920
aagcctttca agtttatgct tggaaagcag gaagtcatcc ggggctggga agagggagtc  1980
gcccagatga gcgtcggcca gcgggccaag ctgacgatct cccctgacta tgcctacggc  2040
gctaccggcc atcccggaat cattccgccg cacgcaaccc tcgtgttcga cgtggaattg  2100
ctcaagctgg aaggcggccg catggcgctg atagtgctcg gcggagtggc cggactgctg  2160
```

```
ctgttcatcg gcctgggcat cttcttctgc gtgagatgcc gccatagaag gcggcaatga  2220

SEQ ID NO: 69          moltype = DNA  length = 7648
FEATURE                Location/Qualifiers
misc_feature           1..7648
                       note =
                        pCVL-MND-CD8ss-DmrC-CD8TM-41BB-Zeta-P2A-IgKss-CD19scFv-DmrA
                        -CD4TM codon optimized lentiviral vector
source                 1..7648
                       mol_type = other DNA
                       organism = synthetic construct
SEQUENCE: 69
taacttttaa aagaaaaggg gggattgggg ggtacagtgc aggggaaaga atagtagaca  60
taatagcaac agacatacaa actaaagaat tacaaaaaca aattacaaaa attcaaaatt  120
ttatcgatta cgcgtgtaca gagagacagc agaatatggg ccaaacagga tatctgtggt  180
aagcagttcc tgccccggct cagggccaag aacagttgga acagcagaat atgggccaaa  240
caggatatct gtggtaagca gttcctgccc cggctcaggg ccaagaacag atggtcccca  300
gatgcggtcc cgccctcagc agtttctaga gaaccatcag atgtttccag ggtgccccaa  360
ggacctgaaa tgaccctgtg ccttatttga actaaccaat cagttcgctt ctcgcttctg  420
ttcgcgcgct tctgctcccc gagctctata taagcagagc tcgtttagtg aaccgtcaga  480
tccctgcagg gccgccacca tggccctccc tgtgaccgcc ctgctgctcc ccctcgccct  540
gttgctccat gctgcccgac ctggatccat cctttggcac gagatgtggc acgagggact  600
cgaagaagcg tcccggctgt acttcggaga gcggaacgtg aaggggatgt tcgaagtgct  660
ggaaccccctg cacgccatga tggagcgggg tcctcagacc cttaaagaaa caagcttcaa  720
ccaggcgtac gggcgcgacc tgatggaagc ccaggagtgg tgccgcaagt acatgaagtc  780
cggaaacgtg aaggatctgc tgcaagcctg ggatctgtac taccacgtgt tcagaaggat  840
ctcaaaggct agcgccggca ctggttcgga tatctacatt tgggcaccgc tcgccggcac  900
ttgtggagtg ctgttgctgt ccctcgtgat caccatgcat aagaggggac ggaagaagct  960
gctgtacatt ttcaagcagc cattcatgcg gcctgtgcaa accacccagg aggaggacgg  1020
gtgcagctgc cggttccctg aggaagagga gggcggatgc gaactgcgcg tgaagttcag  1080
ccggagcgca gatgctcccg cataccaaca gggacagaac cagctgtata acgagctgaa  1140
cctgggcaga agggaagagt acgacgtcct cgacaagcgg cggggacgcg acccagaaat  1200
gggaggaaag ccccgccgga agaacccgca ggaaggcctg tacaacgagt tgcagaaaga  1260
caagatggct gaagcttact cggagattgg catgaagggg gagagaagaa gagggaaggg  1320
ccacgacggc ctttaccaag gactgagcac tgccaccaag gacacctacg atgcgctgca  1380
catgcaggcc ctgccccccgc ggtccggttc gggcgcgact aacttcagcc tgctgaagca  1440
ggccggagat gtggaggaaa accctggacc gtccatggag actgataccc tgcttctgtg  1500
ggtcctgctc ctctgggtgc cgggctccac cggtgacatc cagatgaccc agaccacctc  1560
atccctgagc gcctctctgg gtgatcgcgt gactatctcc tgccgggcgt cgcaggatat  1620
ctccaagtac ctgaactggt accagcaaaa accggacggg accgtgaaac tgctgatcta  1680
ccatacttcc cgccttcatt ccggagtgcc ctcccggttt tccggctcgg gttcagggac  1740
tgattattcg ctgaccattt ccaacctgga gcaggaggac attgcgacct acttctgcca  1800
acaaggaaac accctgccct acactttcgg tggtggaacc aagctcgaga tcaccggatc  1860
aacctcgggc agcgggaagc cgggcagcgg agagggatcg acgaaaggag aagtcaagct  1920
gcaggaatcc ggcccgggac tggtggcccc gagccagtcg ctctccgtca cttgcaccgt  1980
gtcgggagtg tccttgcccg actacggagt gtcatggatt cggcagccac ctcgcaaggg  2040
cctggaatgg ctcggcgtga tttggggctc agaaaccaca tactacaaca gcgccctgaa  2100
gtctcggctc accatcatca aggacaattc caagtcccaa gtgttcctga agatgaatag  2160
cttgcagact gacgacaccg cgatctacta ctgtgccaag cactactact acggcggttc  2220
ctacgccatg gactactggg gacaaggaac ttccgtgact gtctcctccc ctaggggggg  2280
tggtggttcg gggtccaggg tggaaaccat ttcccccggc gacgggcgca ccttcccgaa  2340
gcgcggacag acctgtgtgg tgcactatac cggaatgctc gaagatggaa agaagtttga  2400
cagctccagg gaccgcaaca agcctttcaa gtttatgctt ggaaagcagg aagtcatccg  2460
gggctgggaa gagggagtcg cccagatgag cgtcggccag cgggccaagc tgacgatctc  2520
ccctgactat gcctacggcg ctaccggcca tcccggaatc attccgccgc acgcaaccct  2580
cgtgttcgac gtggaattgc tcaagctgga aggcggccgc atggcgctga tagtgctcgg  2640
cggagtggcc ggactgctgc tgttcatcgg cctgggcatc ttcttctgcg tgagatgccg  2700
ccatagaagg cggcaatgag tcgaccgagc atcttaccgc catttatacc catatttgtt  2760
ctgtttttct tgatttgggt atacatttaa atgttaatag aacaaaatgg tggggcaatc  2820
atttacattt ttagggatat gtaattacta gttcaggtgt attgccacaa gacaaacatg  2880
ttaagaaact ttcccgttat ttacgctctg ttcctgttaa tcaacctctg gattacaaaa  2940
tttgtgaaag attgactgat attcttaact atgttgctcc ttttacgctg tgtggatatg  3000
ctgctttata gcctctgtat ctagctattg cttcccgtac ggctttcgtt ttctcctcct  3060
tgtataaatc ctggttgctg tctcttttag aggagttgtg gcccgttgtc cgtcaacgtg  3120
gcgtggtgtg ctctgtgttt gctgacgcaa cccccactgg ctggggcatt gccaccacct  3180
gtcaactcct ttctgggact ttcgctttcc ccctccccgat cgccacggca gaactcatcg  3240
ccgcctgcct tgcccgctgc tggacagggg ctaggttgct gggcactgat aattccgtgg  3300
tgttgtcatc gaattcggta cctttttaaa agaaaagggg ggactggaag ggctaattca  3360
ctcccaacga agacaagata tcataacttc gtatagcata cattatacga agttataatt  3420
tatttgtgaa atttgtgatg ctattgcttt atttgtaacc atatgtttat ttgtgaaatt  3480
tgtgatgcta ttgctttatt tgtaaccatt gctttttgct tgtactgggt ctctctggtt  3540
agaccagatc tgagcctggg agctctctgg ctaactaggg aacccactgc ttaagcctca  3600
ataaagcttg cctcgaccag cctcgactgt gccttctagt tgccagccat ctgttgtttg  3660
cccctccccc gtgccttcct tgaccctgga aggtgccact cccactgtcc tttcctaata  3720
aaatgaggaa attgcatcgc attgtctgag taggtgtcat tctattctgg ggggtggggt  3780
ggggcaggac agcaaggggg aggattggga agacaatagc aggcatgctg gggatgcggt  3840
gggctctatg gcctgcagct gcattaatga atcggccaac gcgcggggag aggcggtttg  3900
cgtattgggc gctcttccgc ttcctcgctc actgactcgc tgcgctcggt cgttcggctg  3960
cggcgagcgg tatcagctca ctcaaaggcg gtaatacggt tatccacaga atcaggggat  4020
```

```
aacgcaggaa agaacatgtg agcaaaaggc cagcaaaagg ccaggaaccg taaaaaggcc  4080
gcgttgctgg cgtttttcca taggctccgc ccccctgacg agcatcacaa aaatcgacgc  4140
tcaagtcaga ggtggcgaaa cccgacagga ctataaagat accaggcgtt tccccctgga  4200
agctccctcg tgcgctctcc tgttccgacc ctgccgctta ccggatacct gtccgccttt  4260
ctcccttcgg gaagcgtggc gctttctcat agctcacgct gtaggtatct cagttcggtg  4320
taggtcgttc gctccaagct gggctgtgtg cacgaacccc ccgttcagcc cgaccgctgc  4380
gccttatccg gtaactatcg tcttgagtcc aacccggtaa gacacgactt atcgccactg  4440
gcagcagcca ctggtaacag gattagcaga gcgaggtatg taggcggtgc tacagagttc  4500
ttgaagtggt ggcctaacta cggctacact agaaggacag tatttggtat ctgcgctctg  4560
ctgaagccag ttaccttcgg aaaaagagtt ggtagctctt gatccggcaa acaaaccacc  4620
gctggtagcg gtggtttttt tgtttgcaag cagcagatta cgcgcagaaa aaaaggatct  4680
caagaagatc ctttgatctt ttctacgggg tctgacgctc agtggaacga aaactcacgt  4740
taagggattt tggtcatgag attatcaaaa aggatcttca cctagatcct tttaaattaa  4800
aaatgaagtt ttaaatcaat ctaaagtata tatgagtaaa cttggtctga cagttaccaa  4860
tgcttaatca gtgaggcacc tatctcagcg atctgtctat ttcgttcatc catagttgcc  4920
tgactccccg tcgtgtagat aactacgata cgggagggct taccatctgg ccccagtgct  4980
gcaatgatac cgcgagaccc acgctcaccg gctccagatt tatcagcaat aaaccagcca  5040
gccggaaggg ccgagcgcag aagtggtcct gcaactttat ccgcctccat ccagtctatt  5100
aattgttgcc gggaagctag agtaagtagt tcgccagtta atagtttgcg caacgttgtt  5160
gccattgcta caggcatcgt ggtgtcacgc tcgtcgtttg gtatggcttc attcagctcc  5220
ggttcccaac gatcaaggcg agttacatga tcccccatgt tgtgcaaaaa agcggttagc  5280
tccttcggtc ctccgatcgt tgtcagaagt aagttggccg cagtgttatc actcatggtt  5340
atggcagcac tgcataattc tcttactgtc atgccatccg taagatgctt ttctgtgact  5400
ggtgagtact caaccaagtc attctgagaa tagtgtatgc ggcgaccgag ttgctcttgc  5460
ccggcgtcaa tacgggataa taccgcgcca catagcagaa ctttaaaagt gctcatcatt  5520
ggaaaacgtt cttcggggcg aaaactctca aggatcttac cgctgttgag atccagttcg  5580
atgtaaccca ctcgtgcacc caactgatct tcagcatctt ttactttcac cagcgtttct  5640
gggtgagcaa aaacaggaag gcaaaatgcc gcaaaaaagg gaataagggc gacacggaaa  5700
tgttgaatac tcatactctt cctttttcaa tattattgaa gcatttatca gggttattgt  5760
ctcatgagcg gatacatatt tgaatgtatt tagaaaaata aacaaatagg ggttccgcgc  5820
acatttcccc gaaaagtgcc acctgacgtc aatgtagtct tatgcaatac tcttgtagtc  5880
ttgcaacatg gtaacgatga gttagcaaca tgccttacaa ggagagaaaa agcaccgtgc  5940
atgccgattg gtggaagtaa ggtggtacga tcgtgcctta ttaggaaggc aacagacggg  6000
tctgacatgg attggacgaa ccactgaatt gccgcattgc agagatattg tatttaagtg  6060
cctagctcga tacataaacg ggtctctctg gttagaccag atctgagcct gggagctctc  6120
tggctaacta gggaacccac tgcttaagcc tcaataaagc ttgccttgag tgcttcaagt  6180
agtgtgtgcc cgtctgttgt gtgactctgg taactagaga tccctcagac ccttttagtc  6240
agtgtggaaa atctctagca gtggcgcccg aacagggact tgaaagcgaa agggaaacca  6300
gaggagctct ctcgacgcag gactcggctt gctgaagcgc gcacggcaag aggcgagggg  6360
cggcgactgg tgagtacgcc aaaaattttg actagcggag gctagaagga gagagatggg  6420
tgcgagagcg tcagtattaa gcgggggaga attagatcgc gatgggaaaa aattcggtta  6480
aggccagggg gaaagaaaaa atataaatta aaacatatag tatgggcaag cagggagcta  6540
gaacgattcg cagttaatcc tggcctgtta gaaacatcag aaggctgtag acaaatactg  6600
ggacagctac aaccatccct tcagacagga tcagaagaac ttagatcatt atataataca  6660
gtagcaaccc tctattgtgt gcatcaaagg atagagataa aagacaccaa ggaagcttta  6720
gacaagatag aggaagagca aaacaaaagt aagaccaccg cacagcaagc ggccctgatc  6780
ttcagacctg gaggaggaga tatgagggac aattggagaa gtgaattata taaatataaa  6840
gtagtaaaaa ttgaaccatt aggagtagca cccaccaagg caaagagaag agtggtgcag  6900
agagaaaaaa gagcagtggg aataggagct ttgttccttg ggttcttggg agcagcagga  6960
agcactatgg gcgcagcgtc aatgacgctg acggtacagg ccagacaatt attgtctggt  7020
atagtgcagc agcagaacaa tttgctgagg gctattgagg cgcaacagca tctgttgcaa  7080
ctcacagtct ggggcatcaa gcagctccag gcaagaatcc tggctgtgga aagataccta  7140
aaggatcaac agctcctggg gatttggggt tgctctggaa aactcatttg caccactgct  7200
gtgccttgga atgctagttg gagtaatgaa tctctggaac agatttggaa tcacacgacc  7260
tggatggagt gggacagaga aattaacaat tacacaagct taatacactc cttaattgaa  7320
gaatcgcaaa accagcaaga aaagaatgaa caagaattat tggaattaga taaatgggca  7380
agtttgtgga attggtttaa cataacaaat tggctgtggt atataaaatt attcataatg  7440
atagtaggag gcttggtagg tttaagaata gtttttgctg tactttctat agtgaataga  7500
gttaggcagg gatattcacc attatcgttt cagacccacc tcccaacccc gaggggaccc  7560
gacaggcccg aaggaataga agaagaaggt ggagagagag acagagacag atccattcga  7620
ttagtgaacg gatctcgacg gtatcggt                                    7648
```

```
SEQ ID NO: 70          moltype = AA  length = 762
FEATURE                Location/Qualifiers
REGION                 1..762
                       note = SS-DmrC-CD8TM-41BB-CD3z-P2A-SS-CD123scFv-DmrA-CD4TM
                        protein
source                 1..762
                       mol_type = protein
                       organism = synthetic construct
SEQUENCE: 70
MRPTWAWWLF LVLLLALWAP ARGGSILWHE MWHEGLEEAS RLYFGERNVK GMFEVLEPLH  60
AMMERGPQTL KETSFNQAYG RDLMEAQEWC RKYMKSGNVK DLLQAWDLYY HVFRRISKAS  120
AGTGSDIYIW APLAGTCGVL LLSLVITMHK RGRKKLLYIF KQPFMRPVQT TQEEDGCSCR  180
FPEEEEGGCE LRVKFSRSAD APAYQQGQNQ LYNELNLGRR EEYDVLDKRR GRDPEMGGKP  240
RRKNPQEGLY NELQKDKMAE AYSEIGMKGE RRRGKGHDGL YQGLSTATKD TYDALHMQAL  300
PPRGGRSGSG ATNFSLLKQA GDVEENPGPS LWWRLWWLLL LLLLLWPMVW APRADYKDIV  360
MTQSHKFMST SVGDRVNITC KASQNVDSAV AWYQQKPGQS PKALIYSASY RYSGVPDRFT  420
GRGSGTDFTL TISSVQAEDL AVYYCQQYYS TPWTFGGGTK LEIKRGGGGS GGGGSGGGGS  480
```

-continued

```
GGGGSEVKLV ESGGGLVQPG GSLSLSCAAS GFTFTDYYMS WVRQPPGKAL EWLALIRSKA  540
DGYTTEYSAS VKGRFTLSRD DSQSILYLQM NALRPEDSAT YYCARDAAYY SYYSPEGAMD  600
YWGQGTSVTV SSSASGGGGS GVQVETISPG DGRTFPKRGQ TCVVHYTGML EDGKKFDSSR  660
DRNKPFKFML GKQEVIRGWE EGVAQMSVGQ RAKLTISPDY AYGATGHPGI IPPHATLVFD  720
VELLKLEGGR MALIVLGGVA GLLLFIGLGI FFCVRCRHRR RQ                    762

SEQ ID NO: 71           moltype = DNA  length = 2289
FEATURE                 Location/Qualifiers
misc_feature            1..2289
                        note = SS-DmrC-CD8TM-41BB-CD3z-P2A-SS-CD123scFv-DmrA-CD4TM
                         DNA
source                  1..2289
                        mol_type = other DNA
                        organism = synthetic construct
SEQUENCE: 71
atgcgcccca cctgggcctg gtggctgttc ctggtgctgc tgctggccct gtgggcaccc  60
gctcgcggcg gatccatcct ctggcatgag atgtggcatg aaggcctgga agaggcatct  120
cgtttgtact ttggggaaag gaacgtgaaa ggcatgtttg aggtgctgga gcccttgcat  180
gctatgatgg aacggggccc ccagactctg aaggaaacat cctttaatca ggcctatggt  240
cgagatttaa tggaggccca agagtggtgc aggaagtaca tgaaatcagg gaatgtcaag  300
gacctcctcc aagcctggga cctctattat catgtgttcc gacgaatctc aaaggctagc  360
gccggcactg gttccgacat ctacatctgg gcccctctgg ccggcacatg tggcgtgctg  420
ctgctgagcc tcgtgatcac catgcataaa cggggcagaa agaaactcct gtatatattc  480
aaacaaccat ttatgagacc agtacaaact actcaagagg aagatggctg tagctgccga  540
tttccagaag aagaagaagg aggatgtgaa ctgcgggtga agttcagcag aagcgccgac  600
gcccctgcct accagcaggg ccagaatcag ctgtacaacg agctgaacct gggcagaagg  660
gaagagtacg acgtcctgga taagcggaga ggccgggacc ctgagatggg cggcaagcct  720
cggcggaaga acccccagga aggcctgtat aacgaactgc agaaagacaa gatggccgag  780
gcctacagcg agatcggcat gaagggcgag cggaggcggg gcaagggcca cgacggcctg  840
tatcagggcc tgtccaccgc caccaaggat acctacgacg ccctgcacat gcaggccctg  900
cccccaaggg gcggccgctc aggatctggc gccacgaact tctctctgtt aaagcaagca  960
ggagatgttg aagaaaaccc cgggccttca ctgtggtggc gcctgtggtg gctgctcctg  1020
cttctgttgc tcctgtggcc catggtgtgg gcccctaggg cggactacaa agatattgtg  1080
atgacccagt ctcacaaatt catgtccaca tcagtaggag acagggtcaa catcacctgc  1140
aaggccagtc agaatgtgga tagtgctgta gcctggtatc aacagaaacc agggcaatct  1200
cctaaagcac tgatttactc ggcatcctac cggtacagtg gagtccctga tcgcttcaca  1260
ggcaggggat ctgggacaga tttcactctc accatcagca gtgtgcaggc tgaagacctg  1320
gcagtttatt actgtcagca atattatagc actccgtgga cgttcggtgg aggcaccaag  1380
ctggaaatca aacgtggtgg tggtggttct ggtggtggtg gttctggcgg cggcggctcc  1440
ggtggtggtg gatccgaggt gaagctggtg gagtctggag gaggcttggt acagcctggg  1500
ggttctctga gtctctcctg tgcagcttct ggattcacct tcactgatta ctacatgagc  1560
tgggtccgcc agcctccagg gaaggcactt gagtggttgg ctttgattag aagcaaagct  1620
gatggttaca caacagaata cagtgcatct gtgaagggtc ggttcaccct ctccagagat  1680
gattcccaaa gcatcctcta tcttcaaatg aatgccctga gacctgaaga cagtgccact  1740
tattactgtg caagagatgc ggcctactat agttactata gtcccgaggg ggctatggac  1800
tactggggtc aaggaacctc agtcaccgtc tcctcgagcg ctagcggcgg aggtgggagc  1860
ggagtgcagg tggaaaccat ctccccagga gacgggcgca ccttccccaa gcgcggccag  1920
acctgcgtgg tgcactacac cgggatgctt gaagatggaa agaaatttga ttcctcccgg  1980
gacagaaaca agccctttaa gtttatgcta ggcaagcagg aggtgatccg aggctgggaa  2040
gaaggggttg cccagatgag tgtgggtcag agagccaaac tgactatatc tccagattat  2100
gcctatggtg ccactgggca cccaggcatc atcccaccac atgccactct cgtcttcgat  2160
gtggagcttc taaaactgga aggcggccgc atggccctga ttgtgctggg gggcgtcgcc  2220
ggcctcctgc ttttcattgg gctaggcatc ttcttctgtg tcaggtgccg gcaccgaagg  2280
cgccaataa                                                          2289

SEQ ID NO: 72           moltype = DNA  length = 7717
FEATURE                 Location/Qualifiers
misc_feature            1..7717
                        note =
                         pCVL_MND-SS34-DmrC-CD8TM-41BB-CD3z-P2A-SS38-CD123scFv-DmrA-
                         CD4TM lentiviral vector
source                  1..7717
                        mol_type = other DNA
                        organism = synthetic construct
SEQUENCE: 72
gtacagagag acagcagaat atgggccaaa caggatatct gtggtaagca gttcctgccc  60
cggctcaggg ccaagaacag ttggaacagc agaatatggg ccaaacagga tatctgtggt  120
aagcagttcc tgccccggct cagggccaag aacagatggt ccccagatgc ggtcccgccc  180
tcagcagttt ctagagaacc atcagatgtt tccagggtgc cccaaggacc tgaaatgacc  240
ctgtgcctta tttgaactaa ccaatcagtt cgcttctcgc ttctgttcgc gcgcttctgc  300
tccccgagct ctatataagc agagctcgtt tagtgaaccg tcagatccct gcagggccgc  360
caccatgcgc cccacctggg cctggtggct gttcctggtg ctgctgctgg ccctgtgggc  420
acccgctcgc ggcggatcca tcctctggca tgagatgtgg catgaaggcc tggaagaggc  480
atctcgtttg tactttgggg aaaggaacgt gaaaggcatg tttgaggtgc tggagccctt  540
gcatgctatg atggaacggg gcccccagac tctgaaggaa acatccttta atcaggccta  600
tggtcgagat ttaatggagg cccaagagtg gtgcaggaag tacatgaaat cagggaatgt  660
caaggacctc ctccaagcct gggacctcta ttatcatgtg ttccgacgaa tctcaaaggc  720
tagcgccggc actggttccg acatctacat ctgggcccct ctggccggca catgtggcgt  780
gctgctgctg agcctcgtga tcaccatgca taaacggggc agaaagaaac tcctgtatat  840
```

-continued

```
attcaaacaa ccatttatga gaccagtaca aactactcaa gaggaagatg gctgtagctg  900
ccgatttcca gaagaagaag aaggaggatg tgaactgcgg gtgaagttca gcagaagcgc  960
cgacgcccct gcctaccagc agggccagaa tcagctgtac aacgagctga acctgggcag  1020
aagggaagag tacgacgtcc tggataagcg gagaggccgg gaccctgaga tgggcggcaa  1080
gcctcggcgg aagaaccccc aggaaggcct gtataacgaa ctgcagaaag acaagatggc  1140
cgaggcctac agcgagatcg gcatgaaggg cgagcggagg cggggcaagg gccacgacgg  1200
cctgtatcag ggcctgtcca ccgccaccaa ggatacctac gacgccctgc acatgcaggc  1260
cctgccccca aggggcggcc gctcaggatc tggcgccacg aacttctctc tgttaaagca  1320
agcaggagat gttgaagaaa accccgggcc ttcactgtgg tggcgcctgt ggtggctgct  1380
cctgcttctg ttgctcctgt ggcccatggt gtgggcccct agggcggact acaaagatat  1440
tgtgatgacc cagtctcaca aattcatgtc cacatcagta ggagacaggg tcaacatcac  1500
ctgcaaggcc agtcagaatg tggatagtgc tgtagcctgg tatcaacaga aaccagggca  1560
atctcctaaa gcactgattt actcggcatc ctaccggtac agtggagtcc ctgatcgctt  1620
cacaggcagg ggatctggga cagatttcac tctcaccatc agcagtgtgc aggctgaaga  1680
cctggcagtt tattactgtc agcaatatta tagcactccg tggacgttcg gtggaggcac  1740
caagctggaa atcaaacgtg gtggtggtgg ttctggtggt ggtggttctg gcggcggcgg  1800
ctccggtggt ggtggatccg aggtgaagct ggtggagtct ggaggaggct tggtacagcc  1860
tgggggttct ctgagtctct cctgtgcagc ttctggattc accttcactg attactacat  1920
gagctgggtc cgccagcctc cagggaaggc acttgagtgg ttggctttga ttagaagcaa  1980
agctgatggt tacacaacag aatacagtgc atctgtgaag ggtcggttca ccctctccag  2040
agatgattcc caaagcatcc tctatcttca aatgaatgcc ctgagacctg aagacagtgc  2100
cacttattac tgtgcaagag atgcggccta ctatagttac tatagtcccg agggggctat  2160
ggactactgg ggtcaaggaa cctcagtcac cgtctcctcg agcgctagcg gcggaggtgg  2220
gagcggagtg caggtggaaa ccatctcccc aggagacggg cgcaccttcc ccaagcgcgg  2280
ccagacctgc gtggtgcact acaccgggat gcttgaagat ggaaagaaat ttgattcctc  2340
ccgggacaga aacaagccct ttaagtttat gctaggcaag caggaggtga tccgaggctg  2400
ggaagaaggg gttgcccaga tgagtgtggg tcagagagcc aaactgacta tatctccaga  2460
ttatgcctat ggtgccactg ggcacccagg catcatccca ccacatgcca ctctcgtctt  2520
cgatgtggag cttctaaaac tggaaggcgg ccgcatggcc ctgattgtgc tgggggggcgt  2580
cgccggcctc ctgcttttca ttgggctagg catcttcttc tgtgtcaggt gccggcaccg  2640
aaggcgccaa taagtcgacc gagcatctta ccgccattta tacccatatt tgttctgttt  2700
ttcttgattt gggtatacat ttaaatgtta atagaacaaa atggtggggc aatcatttac  2760
atttttaggg atatgtaatt actagttcag gtgtattgcc acaagacaaa catgttaaga  2820
aactttcccg ttatttacgc tctgttcctg ttaatcaacc tctggattac aaaatttgtg  2880
aaagattgac tgatattctt aactatgttg ctccttttac gctgtgtgga tatgctgctt  2940
tatagcctct gtatctagct attgcttccc gtacggcttt cgttttctcc tccttgtata  3000
aatcctggtt gctgtctctt ttagaggagt tgtggcccgt tgtccgtcaa cgtggcgtgg  3060
tgtgctctgt gtttgctgac gcaaccccca ctggctgggg cattgccacc acctgtcaac  3120
tcctttctgg gactttcgct ttccccctcc cgatcgccac ggcagaactc atcgccgcct  3180
gccttgcccg ctgctggaca ggggctaggt tgctgggcac tgataattcc gtggtgttgt  3240
catcgaattc ggtacctttt taaaagaaaa ggggggactg gaagggctaa ttcactccca  3300
acgaagacaa gatatcataa cttcgtatag catacattat acgaagttat aatttatttg  3360
tgaaatttgt gatgctattg ctttatttgt aaccatatgt ttatttgtga aatttgtgat  3420
gctattgctt tatttgtaac cattgctttt tgcttgtact gggtctctct ggttagacca  3480
gatctgagcc tgggagctct ctggctaact agggaaccca ctgcttaagc ctcaataaag  3540
cttgcctcga ccagcctcga ctgtgccttc tagttgccag ccatctgttg tttgcccctc  3600
ccccgtgcct tccttgaccc tggaaggtgc cactcccact gtcctttcct aataaaatga  3660
ggaaattgca tcgcattgtc tgagtaggtg tcattctatt ctggggggtg gggtggggca  3720
ggacagcaag ggggaggatt gggaagacaa tagcaggcat gctggggatg cggtgggctc  3780
tatggcctgc agctgcatta atgaatcggc caacgcgcgg ggagaggcgg tttgcgtatt  3840
gggcgctctt ccgcttcctc gctcactgac tcgctgcgct cggtcgttcg gctgcggcga  3900
gcggtatcag ctcactcaaa ggcggtaata cggttatcca cagaatcagg ggataacgca  3960
ggaaagaaca tgtgagcaaa aggccagcaa aaggccagga accgtaaaaa ggccgcgttg  4020
ctggcgtttt tccataggct ccgcccccct gacgagcatc acaaaaatcg acgctcaagt  4080
cagaggtggc gaaacccgac aggactataa agataccagg cgtttccccc tggaagctcc  4140
ctcgtgcgct ctcctgttcc gaccctgccg cttaccggat acctgtccgc ctttctccct  4200
tcgggaagcg tggcgctttc tcatagctca cgctgtaggt atctcagttc ggtgtaggtc  4260
gttcgctcca agctgggctg tgtgcacgaa ccccccgttc agcccgaccg ctgcgcctta  4320
tccggtaact atcgtcttga gtccaacccg gtaagacacg acttatcgcc actggcagca  4380
gccactggta acaggattag cagagcgagg tatgtaggcg gtgctacaga gttcttgaag  4440
tggtggccta actacggcta cactagaagg acagtatttg gtatctgcgc tctgctgaag  4500
ccagttacct tcggaaaaag agttggtagc tcttgatccg gcaaacaaac caccgctggt  4560
agcggtggtt tttttgtttg caagcagcag attacgcgca gaaaaaaagg atctcaagaa  4620
gatcctttga tcttttctac ggggtctgac gctcagtgga acgaaaactc acgttaaggg  4680
attttggtca tgagattatc aaaaaggatc ttcacctaga tccttttaaa ttaaaaatga  4740
agttttaaat caatctaaag tatatatgag taaacttggt ctgacagtta ccaatgctta  4800
atcagtgagg cacctatctc agcgatctgt ctatttcgtt catccatagt tgcctgactc  4860
cccgtcgtgt agataactac gatacgggag ggcttaccat ctggccccag tgctgcaatg  4920
ataccgcgag acccacgctc accggctcca gatttatcag caataaacca gccagccgga  4980
agggccgagc gcagaagtgg tcctgcaact ttatccgcct ccatccagtc tattaattgt  5040
tgccgggaag ctagagtaag tagttcgcca gttaatagtt tgcgcaacgt tgttgccatt  5100
gctacaggca tcgtggtgtc acgctcgtcg tttggtatgg cttcattcag ctccggttcc  5160
caacgatcaa ggcgagttac atgatccccc atgttgtgca aaaaagcggt tagctccttc  5220
ggtcctccga tcgttgtcag aagtaagttg gccgcagtgt tatcactcat ggttatggca  5280
gcactgcata attctcttac tgtcatgcca tccgtaagat gcttttctgt gactggtgag  5340
tactcaacca agtcattctg agaatagtgt atgcggcgac cgagttgctc ttgcccggcg  5400
tcaatacggg ataataccgc gccacatagc agaactttaa aagtgctcat cattggaaaa  5460
cgttcttcgg ggcgaaaact ctcaaggatc ttaccgctgt tgagatccag ttcgatgtaa  5520
cccactcgtg cacccaactg atcttcagca tcttttactt tcaccagcgt ttctgggtga  5580
```

```
gcaaaaacag gaaggcaaaa tgccgcaaaa aagggaataa gggcgacacg gaaatgttga  5640
atactcatac tcttcctttt tcaatattat tgaagcattt atcagggtta ttgtctcatg  5700
agcggataca tatttgaatg tatttagaaa aataaacaaa taggggttcc gcgcacattt  5760
ccccgaaaag tgccacctga cgtcaatgta gtcttatgca atactcttgt agtcttgcaa  5820
catggtaacg atgagttagc aacatgcctt acaaggagag aaaaagcacc gtgcatgccg  5880
attggtggaa gtaaggtggt acgatcgtgc cttattagga aggcaacaga cgggtctgac  5940
atggattgga cgaaccactg aattgccgca ttgcagagat attgtattta agtgcctagc  6000
tcgatacata aacgggtctc tctggttaga ccagatctga gcctgggagc tctctggcta  6060
actagggaac ccactgctta agcctcaata aagcttgcct tgagtgcttc aagtagtgtg  6120
tgcccgtctg ttgtgtgact ctggtaacta gagatccctc agaccctttt agtcagtgtg  6180
gaaaatctct agcagtggcg cccgaacagg gacttgaaag cgaaagggaa accagaggag  6240
ctctctcgac gcaggactcg gcttgctgaa gcgcgcacgg caagaggcga ggggcggcga  6300
ctggtgagta cgccaaaaat tttgactagc ggaggctaga aggagagaga tgggtgcgag  6360
agcgtcagta ttaagcgggg gagaattaga tcgcgatggg aaaaaattcg gttaaggcca  6420
gggggaaaga aaaaatataa attaaaacat atagtatggg caagcaggga gctagaacga  6480
ttcgcagtta atcctggcct gttagaaaca tcagaaggct gtagacaaat actgggacag  6540
ctacaaccat cccttcagac aggatcagaa gaacttagat cattatataa tacagtagca  6600
accctctatt gtgtgcatca aaggatagag ataaaagaca ccaaggaagc tttagacaag  6660
atagaggaag agcaaaacaa aagtaagacc accgcacagc aagcggccct gatcttcaga  6720
cctggaggag gagatatgag ggacaattgg agaagtgaat tatataaata taaagtagta  6780
aaaattgaac cattaggagt agcacccacc aaggcaaaga gaagagtggt gcagagagaa  6840
aaaagagcag tgggaatagg agctttgttc cttgggttct tgggagcagc aggaagcact  6900
atgggcgcag cgtcaatgac gctgacggta caggccagac aattattgtc tggtatagtg  6960
cagcagcaga acaatttgct gagggctatt gaggcgcaac agcatctgtt gcaactcaca  7020
gtctggggca tcaagcagct ccaggcaaga atcctggctg tggaaagata cctaaaggat  7080
caacagctcc tggggatttg gggttgctct ggaaaactca tttgcaccac tgctgtgcct  7140
tggaatgcta gttggagtaa tgaatctctg gaacagattt ggaatcacac gacctggatg  7200
gagtgggaca gagaaattaa caattacaca agcttaatac actccttaat tgaagaatcg  7260
caaaaccagc aagaaaagaa tgaacaagaa ttattggaat tagataaatg ggcaagtttg  7320
tggaattggt ttaacataac aaattggctg tggtatataa aattattcat aatgatagta  7380
ggaggcttgg taggtttaag aatagttttt gctgtacttt ctatagtgaa tagagttagg  7440
cagggatatt caccattatc gtttcagacc cacctcccaa ccccgagggg acccgacagg  7500
cccgaaggaa tagaagaaga aggtggagag agagacagag acagatccat tcgattagtg  7560
aacggatctc gacggtatcg gttaactttt aaaagaaaag gggggattgg ggggtacagt  7620
gcaggggaaa gaatagtaga cataatagca acagacatac aaactaaaga attacaaaaa  7680
caaattacaa aaattcaaaa ttttatcgat tacgcgt                           7717
```

```
SEQ ID NO: 73           moltype = DNA  length = 8230
FEATURE                 Location/Qualifiers
misc_feature            1..8230
                        note =
                         pBB_REV-CMV-IgKss-CD19scFv-DmrA-CD4TM_FOR-MND-CD8ss-DmrC-CD
                         8TM-41 BB-CD3z lentiviral vector
source                  1..8230
                        mol_type = other DNA
                        organism = synthetic construct
SEQUENCE: 73
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatcatat gccagcctat ggtgacattg attattgact agttattaat agtaatcaat  240
tacggggtca ttagttcata gcccatatat ggagttccgc gttacataac ttacggtaaa  300
tggcccgcct ggctgaccgc ccaacgaccc ccgcccattg acgtcaataa tgacgtatgt  360
tcccatagta acgccaatag ggactttcca ttgacgtcaa tgggtggagt atttacggta  420
aactgcccac ttggcagtac atcaagtgta tcatatgcca agtacgcccc ctattgacgt  480
caatgacggt aaatggcccg cctggcatta tgcccagtac atgaccttat gggactttcc  540
tacttggcag tacatctacg tattagtcat cgctattacc atggtgatgc ggttttggca  600
gtacatcaat gggcgtggat agcggtttga ctcacgggga tttccaagtc tccaccccat  660
tgacgtcaat gggagtttgt tttggcacca aaatcaacgg gactttccaa aatgtcgtaa  720
caactccgcc ccattgacgc aaatgggcgg taggcgtgta cggtgggagg tctatataag  780
cagagctcgt ttagtgaacc gggtctctct ggttagacca gatctgagcc tgggagctct  840
ctggctaact agggaaccca ctgcttaagc ctcaataaag cttgccttga gtgctcaaag  900
tagtgtgtgc ccgtctgttg tgtgactctg gtaactagag atccctcaga cccttttagt  960
cagtgtggaa aatctctagc agtggcgccc gaacagggac ttgaaagcga aagtaaagcc  1020
agaggagatc tctcgacgca ggactcggct tgctgaagcg cgcacggcaa gaggcgaggg  1080
gcggcgactg gtgagtacgc caaaaatttt gactagcgga ggctagaagg agagagtagg  1140
gtgcgagagc gtcggtatta agcgggggag aattagataa atgggaaaaa attcggttaa  1200
ggccaggggg aaagaaacaa tataaactaa aacatatagt tagggcaagc agggagctag  1260
aacgattcgc agttaatcct ggccttttag agacatcaga aggctgtaga caaatactgg  1320
gacagctaca accatccctt cagacaggat cagaagaact tagatcatta tataatacaa  1380
tagcagtcct ctattgtgtg catcaaagga tagatgtaaa agacaccaag gaagccttag  1440
ataagataga ggaagagcaa aacaaaagta agaaaaaggc acagcaagca gcagctgaca  1500
caggaaacaa cagccaggtc agccaaaatt accctatagt gcagaacctc caggggcaaa  1560
tggtacatca ggccatatca cctagaactt taaattaaga cagcagtaca aatggcagta  1620
ttcatccaca attttaaaag aaaagggggg attggggggt acagtgcagg ggaaagaata  1680
gtagacataa tagcaacaga catacaaact aaagaattac aaaaacaaat tacaaaaatt  1740
caaaattttc gggtttatta cagggacagc agagatccag tttggaaagg accagcaaag  1800
ctcctctgga aaggtgaagg ggcagtagta atacaagata atagtgacat aaaagtagtg  1860
ccaagaagaa aagcaaagat catcagggat tatggaaaac agatggcagg tgatgattgt  1920
```

-continued

```
gtggcaagta gacaggatga ggattaacac atggaaaaga ttagtaaaac accatagctc  1980
tagagcgatc ccgatcttca gacctggagg aggagatatg agggacaatt ggagaagtga  2040
attatataaa tataaagtag taaaaattga accattagga gtagcaccca ccaaggcaaa  2100
gagaagagtg gtgcagagag aaaaaagagc agtgggaata ggagctttgt tccttgggtt  2160
cttgggagca gcaggaagca ctatgggcgc agcgtcaatg acgctgacgg tacaggccag  2220
acaattattg tctggtatag tgcagcagca gaacaatttg ctgagggcta ttgaggcgca  2280
acagcatctg ttgcaactca cagtctgggg catcaagcag ctccaggcaa gaatcctggc  2340
tgtggaaaga tacctaaagg atcaacagct cctggggatt tggggttgct ctggaaaact  2400
catttgcacc actgctgtgc cttggaatgc tagttggagt aataaatctc tggaacagat  2460
ttggaatcac acgacctgga tggagtggga cagagaaatt aacaattaca caagcttggt  2520
aggtttaaga atagtttttg ctgtactttc tatagtgaat agagttaggc agggatattc  2580
accattatcg tttcagaccc acctcccaac cccgagggga cccgacaggc ccgaaggaat  2640
agaagaagaa ggtggagaga gagacagaga cagatccatt cgattagtga acggatcctc  2700
acacaaaaaa ccaacacaca gatgtctagt agctctgatc ttttattcta gcggccgcgt  2760
accgaagcta tcattgccgc cttctatggc ggcatctcac gcagaagaag atgcccaggc  2820
cgatgaacag cagcagtccg gccactccgc cgagcactat cagcgccatg cggccgcctt  2880
ccagcttgag caattccacg tcgaacacga gggttgcgtg cggcggaatg attccgggat  2940
ggccggtagc gccgtaggca tagtcagggg agatcgtcag cttggcccgc tggccgacgc  3000
tcatctgggc gactccctct tcccagcccc ggatgacttc ctgctttcca agcataaact  3060
tgaaaggctt gttgcggtcc ctggagctgt caaacttctt tccatcttcg agcattccgg  3120
tatagtgcac cacacaggtc tgtccgcgct tcgggaaggt gcgcccgtcg ccgggggaaa  3180
tggtttccac ctggaccccc gaaccaccac ccccccctagg ggaggagaca gtcacggaag  3240
ttccttgtcc ccagtagtcc atggcgtagg aaccgccgta gtagtagtgc ttggcacagt  3300
agtagatcgc ggtgtcgtca gtctgcaagc tattcatctt caggaacact tgggacttgg  3360
aattgtcctt gatgatggtg agccgagact tcagggcgct gttgtagtat gtggtttctg  3420
agccccaaat cacgccgagc cattccaggc ccttgcgagg tggctgccga atccatgaca  3480
ctccgtagtc gggcaaggac actcccgaca cggtgcaagt gacggagagc gactggctcg  3540
gggccaccag tcccgggccg gattcctgca gcttgacttc tcctttcgtc gatccctctc  3600
cgctgcccgg cttcccgctg cccgaggttg atccggtgat ctcgagcttg gttccaccac  3660
cgaaagtgta gggcagggtg tttccttgtt ggcagaagta ggtcgcaatg tcctcctgct  3720
ccaggttgga aatggtcagc gaataatcag tccctgaacc cgagccggaa aaccgggagg  3780
gcactccgga atgaaggcgg gaagtatggt agatcagcag tttcacggtc ccgtccggtt  3840
tttgctggta ccagttcagg tacttggaga tatcctgcga cgcccggcag gagatagtca  3900
cgcgatcacc cagagaggcg ctcagggatg aggtggtctg ggtcatctgg atgtcaccgg  3960
tggagcccgg cacccagagg agcaggaccc acagaagcag ggtatcagtc tccatggtgg  4020
cacgcgcctt gctagctaga caaaagtgtt gtggaattgc tccaggcgat ctgacggttc  4080
actaaacgag ctctgctttt ataggcgccc accgtacacg cctaagcgtc gacggaatga  4140
aagaccccac ctgtaggttt ggcaagctag gatcaaggtt aggaacagag agacagcaga  4200
atatgggcca aacaggatat ctgtggtaag cagttcctgc cccggctcag ggccaagaac  4260
agttggaaca gcagaatatg ggccaaacag gatatctgtg gtaagcagtt cctgccccgg  4320
ctcagggcca agaacagatg gtccccagat gcggtcccgc cctcagcagt ttctagagaa  4380
ccatcagatg tttccagggt gccccaagga cctgaaatga ccctgtgcct tatttgaact  4440
aaccaatcag ttcgcttctc gcttctgttc gcgcgcttct gctccccgag ctcaataaaa  4500
gagcccacaa cccctcactc ggcgcgattc acctgacgcg taccatggcc ctccctgtga  4560
ccgccctgct gctccccctc gccctgttgc tccatgctgc ccgacctgga tccatccttt  4620
ggcacgagat gtggcacgag ggactcgaag aagcgtcccg gctgtacttc ggagagcgga  4680
acgtgaaggg gatgttcgaa gtgctggaac ccctgcacgc catgatggag cggggtcctc  4740
agacccttaa agaaacaagc ttcaaccagg cgtacgggcg cgacctgatg gaagcccagg  4800
agtggtgccg caagtacatg aagtccggaa acgtgaagga tctgctgcaa gcctgggatc  4860
tgtactacca cgtgttcaga aggatctcaa aggctagcgc cggcactggt tcggatatct  4920
acatttgggc accgctcgcc ggcacttgtg gagtgctgtt gctgtccctc gtgatcacca  4980
tgcataagag gggacggaag aagctgctgt acattttcaa gcagccattc atgcggcctg  5040
tgcaaaccac ccaggaggag gacgggtgca gctgccggtt ccctgaggaa gaggagggcg  5100
gatgcgaact gcgcgtgaag ttcagccgga gcgcagatgc tcccgcatac caacagggac  5160
agaaccagct gtataacgag ctgaacctgg gcagaaggga agagtacgac gtcctcgaca  5220
agcggcgggg acgcgaccca gaaatgggag gaaagccccg ccggaagaac ccgcaggaag  5280
gcctgtacaa cgagttgcag aaagacaaga tggctgaagc ttactcggag attggcatga  5340
agggggagag aagaagaggg aagggccacg acggccttta ccaaggactg agcactgcca  5400
ccaaggacac ctacgatgcg ctgcacatgc aggccctgcc cccgcggtga agcggccaac  5460
tcgacgttat tcccttcgaa ggaaacctgc aggtaccttt aagaccaatg acttacaagg  5520
cagctgtaga tcttagccac tttttaaaag aaaagggggg actggaaggg ctaattcact  5580
cccaaagaag acaagatctg ctttttgcct gtactgggtc tctctggtta gaccagatct  5640
gagcctggga gctctctggc taactaggga acccactgct taagcctcaa taaagcttgc  5700
cttgagtgct tcaatgtgtg tgttggtttt ttgtgtgtcg aaattctagc gattctagct  5760
tggcgtaatc atggtcatag ctgtttcctg tgtgaaattg ttatccgctc acaattccac  5820
acaacatacg agccggaagc ataaagtgta aagcctgggg tgcctaatga gtgagctaac  5880
tcacattaat tgcgttgcgc tcactgcccg ctttccagtc gggaaacctg tcgtgccagc  5940
tgcattaatg aatcggccaa cgcgcgggga gaggcggttt gcgtattggg cgctcttccg  6000
cttcctcgct cactgactcg ctgcgctcgg tcgttcggct gcggcgagcg gtatcagctc  6060
actcaaaggc ggtaatacgg ttatccacag aatcagggga taacgcagga aagaacatgt  6120
gagcaaaagg ccagcaaaag gccaggaacc gtaaaaaggc cgcgttgctg gcgtttttcc  6180
ataggctccg cccccctgac gagcatcaca aaaatcgacg ctcaagtcag aggtggcgaa  6240
acccgacagg actataaaga taccaggcgt ttccccctgg aagctccctc gtgcgctctc  6300
ctgttccgac cctgccgctt accggatacc tgtccgcctt tctcccttcg ggaagcgtgg  6360
cgctttctca tagctcacgc tgtaggtatc tcagttcggt gtaggtcgtt cgctccaagc  6420
tgggctgtgt gcacgaaccc cccgttcagc ccgaccgctg cgccttatcc ggtaactatc  6480
gtcttgagtc caacccggta agacacgact tatcgccact ggcagcagcc actggtaaca  6540
ggattagcag agcgaggtat gtaggcggtg ctacagagtt cttgaagtgg tggcctaact  6600
acggctacac tagaagaaca gtatttggta tctgcgctct gctgaagcca gttaccttcg  6660
```

```
gaaaaagagt tggtagctct tgatccggca aacaaaccac cgctggtagc ggtggttttt  6720
ttgtttgcaa gcagcagatt acgcgcagaa aaaaaggatc tcaagaagat cctttgatct  6780
tttctacggg gtctgacgct cagtggaacg aaaactcacg ttaagggatt ttggtcatga  6840
gattatcaaa aaggatcttc acctagatcc ttttaaatta aaaatgaagt tttaaatcaa  6900
tctaaagtat atatgagtaa acttggtctg acagttacca atgcttaatc agtgaggcac  6960
ctatctcagc gatctgtcta tttcgttcat ccatagttgc ctgactcccc gtcgtgtaga  7020
taactacgat acgggagggc ttaccatctg gccccagtgc tgcaatgata ccgcgagacc  7080
cacgctcacc ggctccagat ttatcagcaa taaaccagcc agccggaagg gccgagcgca  7140
gaagtggtcc tgcaacttta tccgcctcca tccagtctat taattgttgc cgggaagcta  7200
gagtaagtag ttcgccagtt aatagtttgc gcaacgttgt tgccattgct acaggcatcg  7260
tggtgtcacg ctcgtcgttt ggtatggctt cattcagctc cggttcccaa cgatcaaggc  7320
gagttacatg atcccccatg ttgtgcaaaa aagcggttag ctccttcggt cctccgatcg  7380
ttgtcagaag taagttggcc gcagtgttat cactcatggt tatggcagca ctgcataatt  7440
ctcttactgt catgccatcc gtaagatgct tttctgtgac tggtgagtac tcaaccaagt  7500
cattctgaga atagtgtatg cggcgaccga gttgctcttg cccggcgtca atacgggata  7560
ataccgcgcc acatagcaga actttaaaag tgctcatcat tggaaaacgt tcttcggggc  7620
gaaaactctc aaggatctta ccgctgttga gatccagttc gatgtaaccc actcgtgcac  7680
ccaactgatc ttcagcatct tttactttca ccagcgtttc tgggtgagca aaaacaggaa  7740
ggcaaaatgc cgcaaaaaag ggaataaggg cgacacggaa atgttgaata ctcatactct  7800
tcctttttca atattattga agcatttatc agggttattg tctcatgagc ggatacatat  7860
ttgaatgtat ttagaaaaat aaacaaatag gggttccgcg cacatttccc cgaaaagtgc  7920
cacctgggac tagctttttg caaaagccta ggcctccaaa aaagcctcct cactacttct  7980
ggaatagctc agaggccgag gcggcctcgg cctctgcata aataaaaaaa attagtcagc  8040
catggggcgg agaatgggcg gaactgggcg gagttagggg cgggatgggc ggagttaggg  8100
gcgggactat ggttgctgac taattgagat gagcttgcat gccgacattg attattgact  8160
agtccctaag aaaccattct tatcatgaca ttaacctata aaaataggcg tatcacgagg  8220
ccctttcgtc                                                         8230

SEQ ID NO: 74          moltype = DNA  length = 7135
FEATURE                Location/Qualifiers
misc_feature           1..7135
                       note = pCVL_sEF1a-CD123target-T2A-Puro lentiviral vector
source                 1..7135
                       mol_type = other DNA
                       organism = synthetic construct
SEQUENCE: 74
aggctccggt gcccgtcagt gggcagagcg cacatcgccc acagtccccg agaagttggg  60
gggaggggtc ggcaattgaa ccggtgccta gagaaggtgg cgcggggtaa actgggaaag  120
tgatgtcgtg tactggctcc gcctttttcc cgagggtggg ggagaaccgt atataagtgc  180
agtagtcgcc gtgaacgttc tttttcgcaa cgggtttgcc gccagaacac acctgcaggg  240
ccgccaccat ggtcctcctt tggctcacgc tgctcctgat cgccctgccc tgtctcctgc  300
aaacgaagga agatccaaac ccaccaatca cgaacctaag gatgaaagca aaggctcagc  360
agttgacctg ggaccttaac agaaatgtga ccgatatcga gtgtgttaaa gacgccgact  420
attctatgcc ggcagtgaac aatagctatt gccagtttgg agcaatttcc ttatgtgaag  480
tgaccaacta caccgtccga gtggccaacc caccattctc cacgtggatc ctcttccctg  540
agaacagtgg gaagccttgg gcaggtgcgg agaatctgac ctgctggatt catgacgtgg  600
atttcttgag ctgcagctgg gcggtaggcc cgggggcccc cgcggacgtc cagtacgacc  660
tgtacttgaa cgttgccaac aggcgtcaac agtacgagtg tcttcactac aaaacggatg  720
ctcagggaac acgtatcggg tgtcgtttcg atgacatctc tcgactctcc agcggttctc  780
aaagttccca catcctggtg cggggcagga gcgcagcctt cggtatcccc tgcacagata  840
agtttgtcgt cttttcacag attgagatat taactccacc caacatgact gcaaagtgta  900
ataagacaca ttcctttatg cactggaaaa tgagaagtca tttcaatcgc aaatttcgct  960
atgagcttca gatacaaaag agaatgcagc ctgtaatcac agaacaggtc agagacagaa  1020
cctccttcca gctactcaat cctggaacgt acacagtaca aataagagcc cgggaaagag  1080
tgtatgaatt cttgagcgcc tggagcaccc cccagcgctt cgagtgcgac caggaggagg  1140
gcgcaaacac acgtgcctgg cggacgtcgc tgctgatcgc gctggggacg ctgctggccc  1200
tggtctgtgt cttcgtgatc tgcagaaggt atctggtgat gcagagactc tttccccgca  1260
tccctcacat gaaagacccc atcggtgaca gcttccaaaa cgacaagctg gtggtctggg  1320
aggcgggcaa agccggcctg gaggagtgtc tggtgactga agtacaggtc gtgcagaaaa  1380
ctggcggccg ctccggtgag ggcagaggaa gtcttctaac atgcggtgac gtggaggaga  1440
atccgggccc ctctagaacc gagtacaagc ccacggtgcg cctcgccacc cgcgacgacg  1500
tcccccgggc cgtacgcacc ctcgccgccg cgttcgccga ctaccccgcc acgcgccaca  1560
ccgtcgatcc ggaccgccac atcgagcggg tcaccgagct gcaagaactc ttcctcacgc  1620
gcgtcgggct cgacatcggc aaggtgtggg tcgcggacga cggcgccgcg gtggcggtct  1680
ggaccacgcc ggagagcgtc gaagcggggg cggtgttcgc cgagatcggc ccgcgcatgg  1740
ccgagttgag cggttcccgg ctggccgcgc agcaacagat ggaaggcctc ctggcgccgc  1800
accggcccaa ggagcccgcg tggttcctgg ccaccgtcgg cgtctcgccc gaccaccagg  1860
gcaagggtct gggcagcgcc gtcgtgctcc ccggagtgga ggcggccgag cgcgccgggg  1920
tgcccgcctt cctggagacc tccgcgcccc gcaacctccc cttctacgag cggctcggct  1980
tcaccgtcac cgccgacgtc gaggtgcccg aaggaccgcg cacctggtgc atgacccgca  2040
agcccggtgc cctcgagtga tgagagtcat cgtcgaccga gcatcttacc gccatttata  2100
cccatatttg ttctgttttt cttgatttgg gtatacattt aaatgttaat agaacaaaat  2160
ggtggggcaa tcatttacat ttttagggat atgtaattac tagttcaggt gtattgccac  2220
aagacaaaca tgttaagaaa ctttcccgtt atttacgctc tgttcctgtt aatcaacctc  2280
tggattacaa aatttgtgaa agattgactg atattcttaa ctatgttgct ccttttacgc  2340
tgtgtggata tgctgcttta tagcctctgt atctagctat tgcttcccgt acggctttcg  2400
ttttctcctc cttgtataaa tcctggttgc tgtctctttt agaggagttg tggcccgttg  2460
tccgtcaacg tggcgtggtg tgctctgtgt ttgctgacgc aacccccact ggctggggca  2520
ttgccaccac ctgtcaactc ctttctggga ctttcgcttt ccccctcccg atcgccacgg  2580
```

```
cagaactcat cgccgcctgc cttgcccgct gctggacagg ggctaggttg ctgggcactg  2640
ataattccgt ggtgttgtca tcgaattcgg tacctttttta aaagaaaagg ggggactgga  2700
agggctaatt cactcccaac gaagacaaga tatcataact tcgtatagca tacattatac  2760
gaagttataa tttatttgtg aaatttgtga tgctattgct ttatttgtaa ccatatgttt  2820
atttgtgaaa tttgtgatgc tattgcttta tttgtaacca ttgcttttttg cttgtactgg  2880
gtctctctgg ttagaccaga tctgagcctg ggagctctct ggctaactag ggaacccact  2940
gcttaagcct caataaagct tgcctcgacc agcctcgact gtgccttcta gttgccagcc  3000
atctgttgtt tgcccctccc ccgtgccttc cttgaccctg gaaggtgcca ctcccactgt  3060
cctttcctaa taaaatgagg aaattgcatc gcattgtctg agtaggtgtc attctattct  3120
ggggggtggg gtggggcagg acagcaaggg ggaggattgg gaagacaata gcaggcatgc  3180
tggggatgcg gtgggctcta tggcctgcag ctgcattaat gaatcggcca acgcgcgggg  3240
agaggcggtt tgcgtattgg gcgctcttcc gcttcctcgc tcactgactc gctgcgctcg  3300
gtcgttcggc tgcggcgagc ggtatcagct cactcaaagg cggtaatacg gttatccaca  3360
gaatcagggg ataacgcagg aaagaacatg tgagcaaaag gccagcaaaa ggccaggaac  3420
cgtaaaaagg ccgcgttgct ggcgtttttc cataggctcc gcccccctga cgagcatcac  3480
aaaaatcgac gctcaagtca gaggtggcga aacccgacag gactataaag ataccaggcg  3540
tttccccctg gaagctccct cgtgcgctct cctgttccga ccctgccgct taccggatac  3600
ctgtccgcct ttctcccttc gggaagcgtg gcgctttctc atagctcacg ctgtaggtat  3660
ctcagttcgg tgtaggtcgt tcgctccaag ctgggctgtg tgcacgaacc ccccgttcag  3720
cccgaccgct gcgccttatc cggtaactat cgtcttgagt ccaacccggt aagacacgac  3780
ttatcgccac tggcagcagc cactggtaac aggattagca gagcgaggta tgtaggcggt  3840
gctacagagt tcttgaagtg gtggcctaac tacggctaca ctagaaggac agtatttggt  3900
atctgcgctc tgctgaagcc agttaccttc ggaaaaagag ttggtagctc ttgatccggc  3960
aaacaaacca ccgctggtag cggtggtttt tttgtttgca agcagcagat tacgcgcaga  4020
aaaaaaggat ctcaagaaga tcctttgatc ttttctacgg ggtctgacgc tcagtggaac  4080
gaaaactcac gttaagggat tttggtcatg agattatcaa aaaggatctt cacctagatc  4140
cttttaaatt aaaaatgaag ttttaaatca atctaaagta tatatgagta aacttggtct  4200
gacagttacc aatgcttaat cagtgaggca cctatctcag cgatctgtct atttcgttca  4260
tccatagttg cctgactccc cgtcgtgtag ataactacga tacgggaggg cttaccatct  4320
ggccccagtg ctgcaatgat accgcgagac ccacgctcac cggctccaga tttatcagca  4380
ataaaccagc cagccggaag ggccgagcgc agaagtggtc ctgcaacttt atccgcctcc  4440
atccagtcta ttaattgttg ccgggaagct agagtaagta gttcgccagt taatagtttg  4500
cgcaacgttg ttgccattgc tacaggcatc gtggtgtcac gctcgtcgtt tggtatggct  4560
tcattcagct ccggttccca acgatcaagg cgagttacat gatcccccat gttgtgcaaa  4620
aaagcggtta gctccttcgg tcctccgatc gttgtcagaa gtaagttggc cgcagtgtta  4680
tcactcatgg ttatggcagc actgcataat tctcttactg tcatgccatc cgtaagatgc  4740
ttttctgtga ctggtgagta ctcaaccaag tcattctgag aatagtgtat gcggcgaccg  4800
agttgctctt gcccggcgtc aatacgggat aataccgcgc cacatagcag aactttaaaa  4860
gtgctcatca ttggaaaacg ttcttcgggg cgaaaactct caaggatctt accgctgttg  4920
agatccagtt cgatgtaacc cactcgtgca cccaactgat cttcagcatc ttttactttc  4980
accagcgttt ctgggtgagc aaaaacagga aggcaaaatg ccgcaaaaaa gggaataagg  5040
gcgacacgga aatgttgaat actcatactc ttcctttttc aatattattg aagcatttat  5100
cagggttatt gtctcatgag cggatacata tttgaatgta tttagaaaaa taaacaaata  5160
ggggttccgc gcacatttcc ccgaaaagtg ccacctgacg tcaatgtagt cttatgcaat  5220
actcttgtag tcttgcaaca tggtaacgat gagttagcaa catgccttac aaggagagaa  5280
aaagcaccgt gcatgccgat tggtggaagt aaggtggtac gatcgtgcct tattaggaag  5340
gcaacagacg ggtctgacat ggattggacg aaccactgaa ttgccgcatt gcagagatat  5400
tgtatttaag tgcctagctc gatacataaa cgggtctctc tggttagacc agatctgagc  5460
ctgggagctc tctggctaac tagggaaccc actgcttaag cctcaataaa gcttgccttg  5520
agtgcttcaa gtagtgtgtg cccgtctgtt gtgtgactct ggtaactaga gatccctcag  5580
acccttttag tcagtgtgga aaatctctag cagtggcgcc cgaacaggga cttgaaagcg  5640
aaagggaaac cagaggagct ctctcgacgc aggactcggc ttgctgaagc gcgcacggca  5700
agaggcgagg ggcggcgact ggtgagtacg ccaaaaattt tgactagcgg aggctagaag  5760
gagagagatg ggtgcgagag cgtcagtatt aagcggggga gaattagatc gcgatgggaa  5820
aaaattcggt taaggccagg gggaaagaaa aaatataaat taaaacatat agtatgggca  5880
agcagggagc tagaacgatt cgcagttaat cctggcctgt tagaaacatc agaaggctgt  5940
agacaaatac tgggacagct acaaccatcc cttcagacag gatcagaaga acttagatca  6000
ttatataata cagtagcaac cctctattgt gtgcatcaaa ggatagagat aaaagacacc  6060
aaggaagctt tagacaagat agaggaagag caaaacaaaa gtaagaccac cgcacagcaa  6120
gcggccctga tcttcagacc tggaggagga gatatgaggg acaattggag aagtgaatta  6180
tataaatata aagtagtaaa aattgaacca ttaggagtag cacccaccaa ggcaaagaga  6240
agagtggtgc agagagaaaa aagagcagtg ggaataggag ctttgttcct tgggttcttg  6300
ggagcagcag gaagcactat gggcgcagcg tcaatgacgc tgacggtaca ggccagacaa  6360
ttattgtctg gtatagtgca gcagcagaac aatttgctga gggctattga ggcgcaacag  6420
catctgttgc aactcacagt ctggggcatc aagcagctcc aggcaagaat cctggctgtg  6480
gaaagatacc taaaggatca acagctcctg gggatttggg gttgctctgg aaaactcatt  6540
tgcaccactg ctgtgccttg gaatgctagt tggagtaatg aatctctgga acagatttgg  6600
aatcacacga cctggatgga gtgggacaga gaaattaaca attacacaag cttaatacac  6660
tccttaattg aagaatcgca aaaccagcaa gaaaagaatg aacaagaatt attggaatta  6720
gataaatggg caagtttgtg gaattggttt aacataacaa attggctgtg gtatataaaa  6780
ttattcataa tgatagtagg aggcttggta ggtttaagaa tagtttttgc tgtactttct  6840
atagtgaata gagttaggca gggatattca ccattatcgt ttcagaccca cctcccaacc  6900
ccgaggggac ccgacaggcc cgaaggaata gaagaagaag gtggagagag agacagagac  6960
agatccattc gattagtgaa cggatctcga cggtatcggt taacttttaa aagaaaaggg  7020
gggattgggg ggtacagtgc aggggaaaga atagtagaca taatagcaac agacatacaa  7080
actaaagaat tacaaaaaca aattacaaaa attcaaaatt ttatcgatta cgcgt        7135
```

SEQ ID NO: 75 moltype = DNA length = 7735
FEATURE Location/Qualifiers

```
misc_feature          1..7735
                      note = pCVL_MND-CD8ss-DmrC-CD3scFv-P2A-IgKss-CD19scFv-DmrA
                       lentiviral vector
source                1..7735
                      mol_type = other DNA
                      organism = synthetic construct
SEQUENCE: 75
taacttttaa aagaaaaggg gggattgggg ggtacagtgc aggggaaaga atagtagaca  60
taatagcaac agacatacaa actaaagaat tacaaaaaca aattacaaaa attcaaaatt  120
ttatcgatta cgcgtgtaca gagagacagc agaatatggg ccaaacagga tatctgtggt  180
aagcagttcc tgccccggct cagggccaag aacagttgga acagcagaat atgggccaaa  240
caggatatct gtggtaagca gttcctgccc cggctcaggg ccaagaacag atggtcccca  300
gatgcggtcc cgccctcagc agtttctaga gaaccatcag atgtttccag ggtgccccaa  360
ggacctgaaa tgaccctgtg ccttatttga actaaccaat cagttcgctt ctcgcttctg  420
ttcgcgcgct tctgctcccc gagctctata taagcagagc tcgtttagtg aaccgtcaga  480
tccctgcagg gccgccacca tggccctccc tgtgaccgcc ctgctgctcc ccctcgccct  540
gttgctccat gctgcccgac ctggatccat cctttggcac gagatgtggc acgagggact  600
cgaagaagcg tcccggctgt acttcggaga gcggaacgtg aaggggatgt tcgaagtgct  660
ggaacccctg cacgccatga tggagcgggg tcctcagacc cttaaagaaa caagcttcaa  720
ccaggcgtac gggcgcgacc tgatggaagc ccaggagtgg tgccgcaagt acatgaagtc  780
cggaaacgtg aaggatctgc tgcaagcctg ggatctgtac taccacgtgt tcagaaggat  840
ctcaaaggct agccaggtgc aactggtgca gagcggcggt ggcgttgtgc agccgggccg  900
cagcctgcgc ctgtcttgca aagcgagcgg ctataccttt acgcgctata ccatgcactg  960
ggtgcgccag gcgccgggca aaggtctgga atggattggc tatattaacc cgtctcgcgg  1020
ctataccaac tataatcaga aagtgaaaga tcgctttacc attagccgcg ataactctaa  1080
aaacaccgcg tttctgcaga tggatagcct gcgcccggaa gataccggcg tgtatttttg  1140
cgcgcgctac tatgatgacc attatagcct ggattattgg ggccagggca ccccggtgac  1200
cgttagctcg ggcagcacaa gcggcagcgg caagcctgga tctggcgagg gaagcaccaa  1260
gggcgatatc cagatgaccc agagcccgag ctctctgagc gcgagcgtgg gcgatcgcgt  1320
gaccattacg tgcagcgcgt ctagctctgt gagctatatg aactggtacc agcaaacccc  1380
aggcaaagcg ccgaaacgct ggatttatga taccagcaaa ctggcgagcg gcgtgccgag  1440
ccgctttagc ggctctggta gcggcaccga ttatacgttt accattagct ctctgcagcc  1500
ggaagatatt gcgacctatt actgccagca atggagctct aacccgttta cctttggcca  1560
gggtaccaaa ctgcagatta cccgctccgg ttcgggcgcg actaacttca gcctgctgaa  1620
gcaggccgga gatgtggagg aaaaccctgg accgtccatg gagactgata ccctgcttct  1680
gtgggtcctg ctcctctggg tgccgggctc caccggtgac atccagatga cccagaccac  1740
ctcatccctg agcgcctctc tgggtgatcg cgtgactatc tcctgccggg cgtcgcagga  1800
tatctccaag tacctgaact ggtaccagca aaaaccggac gggaccgtga aactgctgat  1860
ctaccatact tcccgccttc attccggagt gccctcccgg ttttccggct cgggttcagg  1920
gactgattat tcgctgacca tttccaacct ggagcaggag gacattgcga cctacttctg  1980
ccaacaagga aacaccctgc cctacacttt cggtggtgga accaagctcg agatcaccgg  2040
atcaacctcg ggcagcggga agccgggcag cggagaggga tcgacgaaag gagaagtcaa  2100
gctgcaggaa tccggcccgg gactggtggc cccgagccag tcgctctccg tcacttgcac  2160
cgtgtcggga gtgtccttgc ccgactacgg agtgtcatgg attcggcagc cacctcgcaa  2220
gggcctggaa tggctcggcg tgatttgggg ctcagaaacc acatactaca acagcgccct  2280
gaagtctcgg ctcaccatca tcaaggacaa ttccaagtcc caagtgttcc tgaagatgaa  2340
tagcttgcag actgacgaca ccgcgatcta ctactgtgcc aagcactact actacggcgg  2400
ttcctacgcc atggactact ggggacaagg aacttccgtg actgtctcct cccctagggg  2460
gggtggtggt tcgggggtcc aggtggaaac catttccccc ggcgacgggc gcaccttccc  2520
gaagcgcgga cagacctgtg tggtgcacta taccggaatg ctcgaagatg gaaagaagtt  2580
tgacagctcc agggaccgca acaagccttt caagtttatg cttggaaagc aggaagtcat  2640
ccggggctgg gaagagggag tcgcccagat gagcgtcggc cagcgggcca agctgacgat  2700
ctcccctgac tatgcctacg gcgctaccgg ccatcccgga atcattccgc cgcacgcaac  2760
cctcgtgttc gacgtggaat tgctcaagct ggaatgaggc ggccgcgtcg accgagcatc  2820
ttaccgccat ttatacccat atttgttctg tttttcttga tttgggtata catttaaatg  2880
ttaatagaac aaaatggtgg ggcaatcatt tacattttta gggatatgta attactagtt  2940
caggtgtatt gccacaagac aaacatgtta agaaactttc ccgttattta cgctctgttc  3000
ctgttaatca acctctggat tacaaaattt gtgaaagatt gactgatatt cttaactatg  3060
ttgctccttt tacgctgtgt ggatatgctg ctttatagcc tctgtatcta gctattgctt  3120
cccgtacggc tttcgttttc tcctccttgt ataaatcctg gttgctgtct cttttagagg  3180
agttgtggcc cgttgtccgt caacgtggcg tggtgtgctc tgtgtttgct gacgcaaccc  3240
ccactggctg gggcattgcc accacctgtc aactcctttc tgggactttc gctttccccc  3300
tcccgatcgc cacggcagaa ctcatcgccg cctgccttgc ccgctgctgg acaggggcta  3360
ggttgctggg cactgataat tccgtggtgt tgtcatcgaa ttcggtacct ttttaaaaga  3420
aaagggggga ctggaagggc taattcactc ccaacgaaga caagatatca taacttcgta  3480
tagcatacat tatacgaagt tataatttat ttgtgaaatt tgtgatgcta ttgctttatt  3540
tgtaaccata tgtttatttg tgaaatttgt gatgctattg ctttatttgt aaccattgct  3600
ttttgcttgt actgggtctc tctggttaga ccagatctga gcctgggagc tctctggcta  3660
actagggaac ccactgctta agcctcaata aagcttgcct cgaccagcct cgactgtgcc  3720
ttctagttgc cagccatctg ttgtttgccc ctcccccgtg ccttccttga ccctggaagg  3780
tgccactccc actgtccttt cctaataaaa tgaggaaatt gcatcgcatt gtctgagtag  3840
gtgtcattct attctggggg gtggggtggg gcaggacagc aagggggagg attgggaaga  3900
caatagcagg catgctgggg atgcggtggg ctctatggcc tgcagctgca ttaatgaatc  3960
ggccaacgcg cggggagagg cggtttgcgt attgggcgct cttccgcttc ctcgctcact  4020
gactcgctgc gctcggtcgt tcggctgcgg cgagcggtat cagctcactc aaaggcggta  4080
atacggttat ccacagaatc aggggataac gcaggaaaga acatgtgagc aaaaggccag  4140
caaaaggcca ggaaccgtaa aaaggccgcg ttgctggcgt ttttccatag gctccgcccc  4200
cctgacgagc atcacaaaaa tcgacgctca agtcagaggt ggcgaaaccc gacaggacta  4260
taaagatacc aggcgtttcc ccctggaagc tccctcgtgc gctctcctgt tccgaccctg  4320
```

-continued

```
ccgcttaccg gatacctgtc cgcctttctc ccttcgggaa gcgtggcgct ttctcatagc  4380
tcacgctgta ggtatctcag ttcggtgtag gtcgttcgct ccaagctggg ctgtgtgcac  4440
gaaccccccg ttcagcccga ccgctgcgcc ttatccggta actatcgtct tgagtccaac  4500
ccggtaagac acgacttatc gccactggca gcagccactg gtaacaggat tagcagagcg  4560
aggtatgtag gcggtgctac agagttcttg aagtggtggc ctaactacgg ctacactaga  4620
aggacagtat ttggtatctg cgctctgctg aagccagtta ccttcggaaa aagagttggt  4680
agctcttgat ccggcaaaca aaccaccgct ggtagcggtg gtttttttgt ttgcaagcag  4740
cagattacgc gcagaaaaaa aggatctcaa gaagatcctt tgatcttttc tacggggtct  4800
gacgctcagt ggaacgaaaa ctcacgttaa gggattttgg tcatgagatt atcaaaaagg  4860
atcttcacct agatcctttt aaattaaaaa tgaagtttta aatcaatcta aagtatatat  4920
gagtaaactt ggtctgacag ttaccaatgc ttaatcagtg aggcacctat ctcagcgatc  4980
tgtctatttc gttcatccat agttgcctga ctccccgtcg tgtagataac tacgatacgg  5040
gagggcttac catctggccc cagtgctgca atgataccgc gagacccacg ctcaccggct  5100
ccagatttat cagcaataaa ccagccagcc ggaagggccg agcgcagaag tggtcctgca  5160
actttatccg cctccatcca gtctattaat tgttgccggg aagctagagt aagtagttcg  5220
ccagttaata gtttgcgcaa cgttgttgcc attgctacag gcatcgtggt gtcacgctcg  5280
tcgtttggta tggcttcatt cagctccggt tcccaacgat caaggcgagt tacatgatcc  5340
cccatgttgt gcaaaaaagc ggttagctcc ttcggtcctc cgatcgttgt cagaagtaag  5400
ttggccgcag tgttatcact catggttatg gcagcactgc ataattctct tactgtcatg  5460
ccatccgtaa gatgcttttc tgtgactggt gagtactcaa ccaagtcatt ctgagaatag  5520
tgtatgcggc gaccgagttg ctcttgcccg gcgtcaatac gggataatac cgcgccacat  5580
agcagaactt taaaagtgct catcattgga aaacgttctt cggggcgaaa actctcaagg  5640
atcttaccgc tgttgagatc cagttcgatg taacccactc gtgcacccaa ctgatcttca  5700
gcatctttta ctttcaccag cgtttctggg tgagcaaaaa caggaaggca aaatgccgca  5760
aaaaagggaa taagggcgac acggaaatgt tgaatactca tactcttcct ttttcaatat  5820
tattgaagca tttatcaggg ttattgtctc atgagcggat acatatttga atgtatttag  5880
aaaaataaac aaataggggt tccgcgcaca tttccccgaa aagtgccacc tgacgtcaat  5940
gtagtcttat gcaatactct tgtagtcttg caacatggta acgatgagtt agcaacatgc  6000
cttacaagga gagaaaaagc accgtgcatg ccgattggtg gaagtaaggt ggtacgatcg  6060
tgccttatta ggaaggcaac agacgggtct gacatggatt ggacgaacca ctgaattgcc  6120
gcattgcaga gatattgtat ttaagtgcct agctcgatac ataaacgggt ctctctggtt  6180
agaccagatc tgagcctggg agctctctgg ctaactaggg aacccactgc ttaagcctca  6240
ataaagcttg ccttgagtgc ttcaagtagt gtgtgcccgt ctgttgtgtg actctggtaa  6300
ctagagatcc ctcagaccct tttagtcagt gtggaaaatc tctagcagtg gcgcccgaac  6360
agggacttga aagcgaaagg gaaaccagag gagctctctc gacgcaggac tcggcttgct  6420
gaagcgcgca cggcaagagg cgaggggcgg cgactggtga gtacgccaaa aattttgact  6480
agcggaggct agaaggagag agatgggtgc gagagcgtca gtattaagcg ggggagaatt  6540
agatcgcgat gggaaaaaat tcggttaagg ccagggggaa agaaaaaata taaattaaaa  6600
catatagtat gggcaagcag ggagctagaa cgattcgcag ttaatcctgg cctgttagaa  6660
acatcagaag gctgtagaca aatactggga cagctacaac catcccttca gacaggatca  6720
gaagaactta gatcattata taatacagta gcaaccctct attgtgtgca tcaaaggata  6780
gagataaaag acaccaagga agctttagac aagatagagg aagagcaaaa caaaagtaag  6840
accaccgcac agcaagcggc cctgatcttc agacctggag gaggagatat gagggacaat  6900
tggagaagtg aattatataa atataaagta gtaaaaattg aaccattagg agtagcaccc  6960
accaaggcaa agagaagagt ggtgcagaga gaaaaaagag cagtgggaat aggagctttg  7020
ttccttgggt tcttgggagc agcaggaagc actatgggcg cagcgtcaat gacgctgacg  7080
gtacaggcca gacaattatt gtctggtata gtgcagcagc agaacaattt gctgagggct  7140
attgaggcgc aacagcatct gttgcaactc acagtctggg gcatcaagca gctccaggca  7200
agaatcctgg ctgtggaaag atacctaaag gatcaacagc tcctggggat ttggggttgc  7260
tctggaaaac tcatttgcac cactgctgtg ccttggaatg ctagttggag taatgaatct  7320
ctggaacaga tttggaatca cacgacctgg atggagtggg acagagaaat taacaattac  7380
acaagcttaa tacactcctt aattgaagaa tcgcaaaacc agcaagaaaa gaatgaacaa  7440
gaattattgg aattagataa atgggcaagt ttgtggaatt ggtttaacat aacaaattgg  7500
ctgtggtata taaaattatt cataatgata gtaggaggct tggtaggttt aagaatagtt  7560
tttgctgtac tttctatagt gaatagagtt aggcagggat attcaccatt atcgtttcag  7620
acccacctcc caaccccgag gggacccgac aggcccgaag gaatagaaga agaaggtgga  7680
gagagagaca gagacagatc cattcgatta gtgaacggat ctcgacggta tcggt       7735
```

MULTIPARTITE SIGNALING PROTEINS AND USES THEREOF

CROSS REFERENCE TO RELATED APPLICATIONS

This application is a divisional of U.S. application Ser. No. 16/573,254, filed Sep. 17, 2019; which is a continuation of U.S. application Ser. No. 16/219,640, now U.S. Pat. No. 10,457,731, issued Oct. 29, 2019; which is a continuation of U.S. application Ser. No. 14/908,734, now U.S. Pat. No. 10,196,444, issued on Feb. 5, 2019; which is the National Stage of International Application No. PCT/US2014/047852, filed Jul. 23, 2014; and which claims the benefit under 35 U.S.C. § 119(e) of U.S. Provisional Application No. 61/934,092, filed Jan. 31, 2014; and U.S. Provisional Application No. 61/859,697, filed Jul. 29, 2013, each of which is incorporated by reference in its entirety.

STATEMENT REGARDING SEQUENCE LISTING

The Sequence Listing associated with this application is provided in XML format in lieu of a paper copy, and is hereby incorporated by reference into the specification. The name of the file containing the Sequence Listing is BLUE-036.D1 [2022.11.10] Sequence Listing 137080-00109.XML and was created on Nov. 9, 2022. The file is 376,270 bytes in size and is being submitted electronically via EFS-Web.

BACKGROUND

Technical Field

The present disclosure relates to compositions and methods for using multi-component proteins in immunotherapy and, more particularly, using chemically induced multimerization to generate chimeric antigen receptor proteins for modulating spatial and temporal control of cellular signal initiation and downstream responses during adoptive immunotherapy.

Description of the Related Art

Cellular therapy is emerging as a powerful paradigm for delivering complex signals for biological action. In contrast to small molecule and biologic drug compositions, cells have the potential to execute unique therapeutic tasks owing to their myriad sensory and response programs and increasingly defined mechanisms of genetic control. To achieve such therapeutic value, cells need to be outfitted with machinery for sensing and integrating chemical and/or biological information associated with local physiological environments.

The most clinically advanced example of engineered sensory-response machinery is chimeric antigen receptors (CARs) in genetically engineered T cells for use in adoptive cellular immunotherapy (see June et al., *Nat. Biotechnol.* 30:611, 2012; Restifo et al., *Nat. Rev. Immunol.* 12:269, 2012). Antigen binding stimulates the signaling domains on the intracellular segment of the CAR, thereby transducing signals that unleash inflammatory and cytotoxicity mechanisms. CAR-based adoptive cellular immunotherapy has been used to treat cancer patients with tumors refractory to conventional standard-of-care treatments (see Grupp et al., *N. Engl. J. Med.* 368:1509, 2013; Kalos et al., *Sci. Transl. Med.* 3:95ra73, 2011).

In addition to targeting and initiating T cell activation, an effective adoptive cellular immunotherapy would preferably also modulate T cell expansion and persistence, as well as the strength and quality of T cell signaling. But, current CAR-mediated T cell responses do not realize the full potential of T cell activation and proliferation. Improvement of CAR function has been achieved by including costimulatory signaling domains into the CAR structure (see, e.g., Kowolik et al., *Cancer Res.* 66:10995, 2006; Milone et al., *Mol. Ther.* 17:1453, 2009; Pule et al., *Mol. Ther.* 12:933, 2005; Carpenito et al., *Proc. Nat'l Acad. Sci. U.S.A.* 106: 3360, 2009), but the clinical results have been mixed (see, e.g., Brentjens et al., *Blood* 118:4817, 2011; Till et al., *Blood* 119:3940, 2012; Kochenderfer and Rosenberg, *Nat. Rev. Clin. Oncol.* 10:267, 2013). Others have included, in addition to a CAR, co-expression of costimulatory ligands (see, e.g., Stephan et al., *Nat. Med.* 13:1440, 2007), costimulatory receptors (see, e.g., Duong et al., *Immunother.* 3:33, 2011; Wilkie et al., *J. Clin. Immunol.* 32:1059, 2012), and cytokines (see, e.g., Hsu et al., *J. Immunol.* 175:7226, 2005; Quintarelli et al., *Blood* 110:2793, 2007).

A concern with the use of CARs is toxicity, which arises in two forms: one is the targeted destruction of normal tissue and the second is cytokine-release associated adverse events (e.g., cytokine storm). For example, collateral damage observed with CD19-targeted CARs is B-cell aplasia (Kalos et al., 2011; Kochenderfer et al., *Blood* 119:2709, 2012). Such off-target effects could be very dangerous, particularly if the target antigen is found on other tissues, such as the heart or lung. The cytokine storms associated with large numbers of activated T cells can be life threatening (Kalos et al., 2011; Kochenderfer et al., 2012). Unlike conventional drug treatments where reducing drug dosage can control toxicity, the proliferation of T cells cannot be controlled with current CAR technologies and, therefore, immunopathology will result once a threshold level of T cells is reached.

In view of the limitations associated with CAR-mediated T cell responses, there is a need in the art for alternative compositions and methods useful for immunotherapy in which modulation of immune cell signal initiation and expansion is controllable. The present disclosure meets such needs, and further provides other related advantages.

SUMMARY OF THE INVENTION

The present disclosure describes non-natural cell compositions having signal transduction systems that are controlled—both in their activation and deactivation—by pharmacological agents. Numerous pharmacologically controlled, multipartite signal transduction systems are contemplated herein.

In various embodiments, a non-natural cell is provided, comprising: a first nucleic acid molecule encoding a first fusion protein comprising a first multimerization domain, a hydrophobic domain, and an actuator domain, wherein the first multimerization domain localizes extracellularly when the first fusion protein is expressed; and a second nucleic acid molecule encoding a second fusion protein comprising a binding domain and a second multimerization domain, wherein the second fusion protein localizes extracellularly when expressed; wherein a first bridging factor promotes the formation of a polypeptide complex on the non natural cell surface with the bridging factor associated with and disposed between the multimerization domains of the first and second fusion proteins.

In a particular embodiment, the first and second multimerization domains are the same or different.

In an additional embodiment, the multimerization domains of the first and second fusion proteins associate with a bridging factor selected from rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

In a further embodiment, the first and second multimerization domains are a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In a certain embodiment, the first multimerization domain comprises a first FKBP polypeptide or variant thereof, and the second multimerization domain comprises a first FRB polypeptide or variant thereof.

In a particular embodiment, the first multimerization domain comprises a first FRB polypeptide or variant thereof, and the second multimerization domain comprises a first FKBP polypeptide or variant thereof.

In one embodiment, the bridging factor is sirolimus, everolimus, novolimus, pimecrolimus, ridaforolimus, tacrolimus, temsirolimus, umirolimus, or zotarolimus.

In an additional embodiment, the first nucleic acid molecule encodes a first fusion protein further comprising a third multimerization domain.

In a further embodiment, the third multimerization domain of the first fusion protein is a binding domain for a bridging factor selected from rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, Tmp-SLF or a derivative thereof, or any combination thereof.

In a particular embodiment, a second bridging factor promotes the association of at least two first fusion proteins with the bridging factor associated with and disposed between the third multimerization domains of the first fusion proteins.

In a particular embodiment, the protein complex is a homocomplex comprising at least two first fusion proteins.

In a further embodiment, the first fusion protein has at least one multimerization domain of FKBP, DHFR or GyrB.

In a certain embodiment, the binding domain of the polypeptide complex specifically binds to a target located on a target cell surface.

In an additional embodiment, the protein complex is a heterocomplex comprising one or more first fusion proteins and one or more second fusion proteins.

In an additional embodiment, the binding domain of the protein heterocomplex specifically binds to a target located on a target cell surface.

In a particular embodiment, the hydrophobic domain is a transmembrane domain.

In another particular embodiment, the transmembrane domain is a CD4, CD8 or CD28 transmembrane domain.

In one embodiment, the actuator domain comprises a lymphocyte receptor signaling domain.

In a certain embodiment, the actuator domain comprises one or a plurality of immunoreceptor tyrosine-based activation motifs (ITAMs).

In a certain embodiment, the actuator domain comprises CD3ε, CD3δ, CD3ζ, pTα, TCRα, TCRβ, FcRα, FcRβ, FcRγ, NKG2D, CD22, CD79A, or CD79B, or any combination thereof.

In a particular embodiment, the first nucleic acid molecule encodes the first fusion protein further comprising a different actuator domain, a costimulatory domain, an adhesion factor, or any combination thereof.

In a further embodiment, the costimulatory domain is selected from CD27, CD28, CD30, CD40, LAT, Zap70, ICOS, DAP10, 4-1BB, CARD11, HVEM, LAG3, SLAMF1, Lck, Fyn, Slp76, TRIM, OX40, or any combination thereof.

In a particular embodiment, the actuator domain comprises a cytoplasmic portion that associates with a cytoplasmic signaling protein.

In one embodiment, the cytoplasmic signaling protein is a lymphocyte receptor or signaling domain thereof, a protein comprising a plurality of immunoreceptor tyrosine-based activation motifs (ITAMs), a costimulatory domain, an adhesion factor, or any combination thereof.

In an additional embodiment, the lymphocyte receptor or signaling domain thereof is CD3ε, CD3δ, CD3ζ, pTα, TCRα, TCRβ, FcRα, FcRβ, FcRγ, NKG2D, CD22, CD79A, or CD79B, or any combination thereof.

In a further embodiment, the costimulatory domain is selected from CD27, CD28, CD30, CD40, LAT, Zap70, ICOS, DAP10, 4-1BB, CARD11, HVEM, LAG3, SLAMF1, Lck, Fyn, Slp76, TRIM, OX40, or any combination thereof.

In a particular embodiment, a non-natural cell overexpresses a costimulatory factor, an immunomodulatoy factor, an agonist for a costimulatory factor, an agonist for an immunomodulatoy factor, or any combination thereof.

In one embodiment, the second nucleic acid molecule further encodes a secretion signal such that the second fusion protein is secreted from the non natural cell when expressed, and optionally further encodes an anchor domain.

In a certain embodiment, the binding domain of the second fusion protein is a single chain antibody variable region, a receptor ectodomain, or a ligand.

In an additional embodiment, the single chain antibody variable region is a domain antibody, sFv, scFv, F(ab')2, or Fab.

In a particular embodiment, the binding domain of the second fusion protein is amino terminal to the multimerization domain.

In one embodiment, the binding domain of the second fusion protein is carboxy terminal to the multimerization domain.

In a further embodiment, the second nucleic acid molecule encoding the second fusion protein further comprises a sequence encoding a linker disposed between the binding domain and the second multimerization domain.

In a particular embodiment, the cell further comprises a third nucleic acid molecule encoding a third fusion protein comprising a binding domain and a second multimerization domain, wherein the third fusion protein localizes extracellularly when expressed.

In a related particular embodiment, the fusion proteins comprising a binding domain have one, two, three, or four binding domains.

In an additional embodiment, the one, two, three, or four binding domains are specific for one target or up to four different targets.

In a certain embodiment, the binding domain is specific for a target that is an antigen associated with a cancer, an inflammatory disease, an autoimmune disease, or a graft versus host disease.

In a particular embodiment, the cancer is a solid malignancy or a hematologic malignancy.

In an additional embodiment, the hematologic malignancy associated antigen target is CD19, CD20, CD22, CD33, or CD37.

In one embodiment, the binding domain specifically binds to a target selected from α-folate receptor, αvβ6 integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, EGFR family including ErbB2 (HER2), EGFRvIII, EPCAM, EphA2, EpCAM, FAP, FBP, fetal acetylcholine receptor, Fzd7, GD2, GD3, Glypican-3 (GPC3), h5T4, IL-11R□, IL13R-α2, KDR, κ light chain, λ light chain, LeY, LlCAM, MAGE-A1, mesothelin, MHC presented peptides, MUC1, MUC16, NCAM, NKG2D ligands, Notch1, Notch2/3, NY-ESO-1, PRAME, PSCA, PSMA, Survivin, TAG-72, TEMs, TERT, VEGFR2, and ROR1.

In a certain embodiment, the first bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In one embodiment, the second bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In a further embodiment, the encoded first fusion protein comprises a first multimerization domain of FRB T2098L, a transmembrane domain, a costimulatory domain of 4-1BB, and actuator domain of CD3ζ; wherein the second encoded fusion protein comprises a binding domain of an scFv specific for CD19 and a second multimerization domain of FKBP12; and wherein the first bridging factor that promotes the formation of a polypeptide complex on the non natural cell surface is rapalog AP21967.

In a particular embodiment, the first fusion protein has an amino acid sequence as set forth in SEQ ID NO.:15 and the second fusion protein has an amino acid sequence as set forth in SEQ ID NO.:1.

In various embodiments, a method for treating a hyperproliferative, inflammatory, autoimmune, or graft-versus-host disease is provided, comprising: administering a recombinant cell comprising a first and a second nucleic acid molecule, wherein the first nucleic acid molecule encodes a first fusion protein comprising a first multimerization domain, a hydrophobic domain, and an actuator domain, wherein the first multimerization domain localizes extracellularly when the first fusion protein is expressed, and the second nucleic acid molecule encodes a second fusion protein comprising a binding domain and a second multimerization domain, wherein the second fusion protein localizes extracellularly when expressed; and administering a bridging factor, wherein the bridging factor promotes the formation of a polypeptide complex on the recombinant cell surface with the bridging factor associated with and disposed between the multimerization domains of the first and second fusion proteins; wherein the binding domain of the polypeptide complex specifically binds a cell surface target on a hyperproliferative, inflammatory, autoimmune, or graft-versus-host disease cell to promote an immunomodulatory response and thereby treats the hyperproliferative, inflammatory, autoimmune, or graft-versus-host disease.

In various embodiments, a method for treating a hyperproliferative, inflammatory, autoimmune, or graft-versus-host disease, comprising: administering a non-natural cell comprising a first nucleic acid molecule encoding a first fusion protein comprising a first multimerization domain, a hydrophobic domain, and an actuator domain, wherein the first multimerization domain localizes extracellularly when the first fusion protein is expressed; administering a second fusion protein comprising a binding domain and a second multimerization domain; and administering a bridging factor, wherein the bridging factor promotes the formation of a polypeptide complex on the recombinant cell surface with the bridging factor associated with and disposed between the multimerization domains of the first and second fusion proteins; wherein the binding domain of the polypeptide complex specifically binds a cell surface target on a hyperproliferative, inflammatory, autoimmune, or graft-versus-host disease cell to promote an immunomodulatory response and thereby treats the hyperproliferative, inflammatory, autoimmune, or graft-versus-host disease.

In a further embodiment, the first and second multimerization domains are the same or different.

In an additional embodiment, the multimerization domains of the first and second fusion proteins associate with a bridging factor selected from rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

In a particular embodiment, the first and second multimerization domains are a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In a particular embodiment, the first multimerization domain comprises a first FKBP polypeptide or variant thereof, and the second multimerization domain comprises a first FRB polypeptide or variant thereof.

In one embodiment, the first multimerization domain comprises a first FRB polypeptide or variant thereof, and the second multimerization domain comprises a first FKBP polypeptide or variant thereof.

In a certain embodiment, the bridging factor is sirolimus, everolimus, novolimus, pimecrolimus, ridaforolimus, tacrolimus, temsirolimus, umirolimus, or zotarolimus.

In another certain embodiment, the first nucleic acid molecule encodes a first fusion protein further comprising a third multimerization domain.

In a particular embodiment, the third multimerization domain of the first fusion protein is a binding domain for a bridging factor selected from rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, Tmp-SLF or a derivative thereof, or any combination thereof.

In one embodiment, a second bridging factor promotes the association of at least two first fusion proteins with the bridging factor associated with and disposed between the third multimerization domains of the first fusion proteins.

In an additional embodiment, the protein complex is a homocomplex comprising at least two first fusion proteins.

In an additional embodiment, the first fusion protein has at least one multimerization domain of FKBP, DHFR or GyrB.

In a particular embodiment, the binding domain of the polypeptide complex specifically binds to a target located on a target hyperproliferative disease cell surface.

In a further embodiment, the protein complex is a heterocomplex comprising one or more first fusion proteins and one or more second fusion proteins.

In a further embodiment, the binding domain of the protein heterocomplex specifically binds to a target located on a target hyperproliferative disease cell surface.

In one further embodiment, the hydrophobic domain is a transmembrane domain.

In a particular embodiment, the transmembrane domain is a CD4, CD8 or CD28 transmembrane domain.

In another particular embodiment, the actuator domain comprises a lymphocyte receptor signaling domain.

In yet another particular embodiment, the actuator domain comprises a plurality of immunoreceptor tyrosine-based activation motifs (ITAMs).

In still yet another particular embodiment, the actuator domain comprises CD3ε, CD3δ, CD3ζ, pTα, TCRα, TCRβ, FcRα, FcRβ, FcRγ, NKG2D, CD22, CD79A, or CD79B, or any combination thereof.

In a certain embodiment, the first nucleic acid molecule encodes the first fusion protein further comprising a different actuator domain, a costimulatory domain, an adhesion factor, or any combination thereof.

In a further embodiment, the costimulatory domain is selected from CD27, CD28, CD30, CD40, LAT, Zap70, ICOS, DAP10, 4-1BB, CARD11, HVEM, LAG3, SLAMF1, Lck, Fyn, Sip76, TRIM, OX40, or any combination thereof.

In an additional embodiment, the actuator domain comprises a cytoplasmic portion that associates with a cytoplasmic signaling protein.

In one particular embodiment, the cytoplasmic signaling protein is a lymphocyte receptor or signaling domain thereof, a protein comprising one or a plurality of immunoreceptor tyrosine-based activation motifs (ITAMs), a costimulatory domain, an adhesion factor, or any combination thereof.

In a particular embodiment, the lymphocyte receptor or signaling domain thereof is CD3ε, CD3δ, CD3ζ, pTα, TCRα, TCRβ, FcRα, FcRβ, FcRγ, NKG2D, CD22, CD79A, or CD79B, or any combination thereof.

In one embodiment, the costimulatory domain is selected from CD27, CD28, CD30, CD40, LAT, Zap70, ICOS, DAP10, 4-1BB, CARD11, HVEM, LAG3, SLAMF1, Lck, Fyn, Slp76, TRIM, OX40, or any combination thereof.

In another embodiment, the cytoplasmic signaling protein is combination of CD3(and 4-1BB or a combination of CD3(and OX40.

In yet another embodiment, the non-natural cell is further overexpressing a costimulatory factor, an immunomodulatoy factor, an agonist for a costimulatory factor, an agonist for an immunomodulatoy factor, or any combination thereof.

In a certain embodiment, the binding domain of the second fusion protein is a single chain antibody variable region, a receptor ectodomain, or a ligand.

In one certain embodiment, the single chain antibody variable region is a domain antibody, sFv, scFv, F(ab')2, or Fab.

In a particular embodiment, the binding domain of the second fusion protein is amino terminal to the multimerization domain.

In an additional embodiment, the binding domain of the second fusion protein is carboxy terminal to the multimerization domain.

In a particular embodiment, the second fusion protein further comprises a linker disposed between the binding domain and the second multimerization domain.

In an additional embodiment, the cell further comprises a third nucleic acid molecule encoding a third fusion protein comprising a binding domain and a second multimerization domain, wherein the third fusion protein localizes extracellularly when expressed.

In a certain embodiment, the fusion proteins comprising a binding domain have one, two, three, or four binding domains.

In one embodiment, the one, two, three, or four binding domains are specific for one target or up to four different targets.

In a particular embodiment, the binding domain is specific for a target that is an antigen associated with a cancer.

In a further embodiment, the cancer is a solid malignancy or a hematologic malignancy.

In a further embodiment, the hematologic malignancy associated antigen target is CD19, CD20, CD22, CD33, or CD37.

In one embodiment, the binding domain specifically binds to a target selected from α-folate receptor, αvβ6 integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, EGFR family including ErbB2 (HER2), EGFRvIII, EPCAM, EphA2, EpCAM, FAP, FBP, fetal acetylcholine receptor, Fzd7, GD2, GD3, Glypican-3 (GPC3), h5T4, IL-11R□, IL13R-α2, KDR, κ light chain, λ light chain, LeY, LlCAM, MAGE-A1, mesothelin, MHC presented peptides, MUC1, MUC16, NCAM, NKG2D ligands, Notch1, Notch2/3, NY-ESO-1, PRAME, PSCA, PSMA, Survivin, TAG-72, TEMs, TERT, VEGFR2, and ROR1.

In a particular embodiment, the first bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In a particular embodiment, the second bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In an additional embodiment, the first fusion protein comprises a first multimerization domain of FRB T2098L, a transmembrane domain, a costimulatory domain of 4-1BB, and actuator domain of CD3ζ; wherein the second fusion protein comprises a binding domain of an scFv specific for CD19 and a second multimerization domain of FKBP12; and wherein the first bridging factor that promotes the formation of a polypeptide complex on the non natural cell surface is rapalog AP21967.

In one embodiment, the first fusion protein has an amino acid sequence as set forth in SEQ ID NO.:15 and the second fusion protein has an amino acid sequence as set forth in SEQ ID NO.:1.

In a particular embodiment, the method further comprises administering an agent that antagonizes or blocks an inhibitor of T-cell activation.

In a further embodiment, the agent antagonizes or blocks a T-cell ligand.

In a particular embodiment, the agent antagonizes or blocks a T-cell receptor.

In an additional embodiment, the agent that antagonizes or blocks an inhibitor of T-cell activation is an anti-PD1 antibody or antigen binding fragment thereof, anti-PD-L1 antibody or antigen binding fragment thereof, or an anti CTLA4 antibody or antigen binding fragment thereof or an engineered homing endonuclease that targets PD-1.

In a particular embodiment, the method further comprises administering a cytokine agonist.

In various embodiments, a fusion polypeptide heterocomplex is provided, comprising: a first fusion protein comprising a first multimerization domain, a hydrophobic domain, and an actuator domain; a second fusion protein comprising an extracellular binding domain and second multimerization domain; and a bridging factor; wherein the first fusion protein, second fusion protein, and bridging factor associate to form a polypeptide heterocomplex with the bridging factor associated with and disposed between the multimerization domains of the first and second fusion proteins.

In one embodiment, the binding domain is a single chain antibody variable region, a receptor ectodomain, or a ligand.

In a further embodiment, the single chain antibody variable region is a domain antibody, sFv, scFv, F(ab')2, or Fab.

In one embodiment, the binding domain is amino terminal to the multimerization domain.

In a particular embodiment, the binding domain is carboxy terminal to the multimerization domain.

In a particular embodiment, the first multimerization domain comprises a first FKBP polypeptide or variant thereof, and the second multimerization domain comprises a first FRB polypeptide or variant thereof.

In a certain embodiment, the first multimerization domain comprises a first FRB polypeptide or variant thereof, and the second multimerization domain comprises a first FKBP polypeptide or variant thereof.

In an additional embodiment, the hydrophobic domain is a transmembrane domain.

In a certain embodiment, the actuator domain comprises a lymphocyte receptor chain.

In one embodiment, the bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In an additional embodiment, the second fusion protein further comprises an anchor domain.

In a particular embodiment, the anchor domain is a transmembrane domain.

In a further embodiment, the second fusion protein further comprises a sub-threshold signaling domain.

In a particular embodiment, the anchor domain is a GPI signal sequence.

In one embodiment, the GPI signal sequence has been altered and the second fusion protein further comprises a GPI molecule.

In a further embodiment, the binding domain is specific for a target that is an antigen associated with a cancer, an inflammatory disease, an autoimmune disease, or a graft versus host disease.

In an additional embodiment, the cancer is a hematologic malignancy having an antigen target of CD19, CD20, CD22, CD33, or CD37.

In various embodiments, a nucleic acid molecule is provided that encodes any one or more of the fusion proteins contemplated herein.

In a further embodiment, the nucleic acid molecule is disposed between 5' and 3' polynucleotide sequences homologous to a genomic locus.

In various embodiments, an expression vector is provided, containing a nucleic acid contemplated herein.

In a particular embodiment, the first and second fusion proteins are encoded as a polycistronic message or as a single protein separated by a 2A peptide.

In a particular embodiment, the polycistronic message comprises an internal ribosome entry site (IRES) between the nucleotide sequences that encode the fusion proteins.

In various embodiments, a non-natural cell is provided, comprising: a first nucleic acid molecule encoding a first fusion protein comprising a binding domain that binds a receptor on a T cell and a first multimerization domain, wherein the first fusion protein is secreted from the cell; and a second nucleic acid molecule encoding a second fusion protein comprising a binding domain that binds a target located on a target cell surface and a second multimerization domain, wherein the second fusion protein is secreted from the cell; wherein a bridging factor promotes the formation of a polypeptide complex with the bridging factor associated with and disposed between the multimerization domains of the first and second fusion proteins.

In a certain embodiment, the first and second multimerization domains are the same or different.

In an additional embodiment, the multimerization domains of the first and second fusion proteins associate with a bridging factor selected from rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

In a particular embodiment, the first and second multimerization domains are a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In a further embodiment, the first multimerization domain comprises a first FKBP polypeptide or variant thereof, and the second multimerization domain comprises a first FRB polypeptide or variant thereof.

In a particular embodiment, the first multimerization domain comprises a first FRB polypeptide or variant thereof, and the second multimerization domain comprises a first FKBP polypeptide or variant thereof.

In one embodiment, the bridging factor is sirolimus, everolimus, novolimus, pimecrolimus, ridaforolimus, tacrolimus, temsirolimus, umirolimus, or zotarolimus.

In a particular embodiment, a non-natural cell further overexpresses a costimulatory factor, an immunomodulatoy factor, an agonist for a costimulatory factor, an agonist for an immunomodulatoy factor, or any combination thereof.

In a certain embodiment, the binding domain of the first fusion protein and the binding domain of the second fusion protein are each independently selected from the group consisting of: a single chain antibody variable region, a receptor ectodomain, or a ligand.

In a further embodiment, the single chain antibody variable region is a domain antibody, sFv, scFv, F(ab')2, or Fab.

In an additional embodiment, the binding domain of the first fusion protein is amino terminal to the first multimerization domain.

In one embodiment, the binding domain of the first fusion protein is carboxy terminal to the first multimerization domain.

In an additional embodiment, the binding domain of the second fusion protein is amino terminal to the second multimerization domain.

In a particular embodiment, the binding domain of the second fusion protein is carboxy terminal to the second multimerization domain.

In one embodiment, the first nucleic acid molecule encoding the first fusion protein further comprises a sequence encoding a linker disposed between the binding domain and the first multimerization domain.

In a particular embodiment, the second nucleic acid molecule encoding the second fusion protein further comprises a sequence encoding a linker disposed between the binding domain and the second multimerization domain.

In a particular embodiment, the binding domain of the second nucleic acid molecule is specific for a target that is an antigen associated with a cancer, an inflammatory disease, an autoimmune disease, or a graft versus host disease.

In a certain embodiment, the cancer is a solid malignancy or a hematologic malignancy.

In a certain embodiment, the hematologic malignancy associated antigen target is CD19, CD20, CD22, CD33, or CD37.

In one embodiment, the binding domain of the second nucleic acid molecule specifically binds to a target selected from α-folate receptor, αvβ6 integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, EGFR family including ErbB2 (HER2), EGFRvIII, EPCAM, EphA2, EpCAM, FAP, FBP, fetal acetylcholine receptor, Fzd7, GD2, GD3, Glypican-3 (GPC3), h5T4, IL-11R□, IL13R-α2, KDR, κ light chain, λ light chain, LeY, L1CAM, MAGE-A1, mesothelin, MHC presented peptides, MUC1, MUC16, NCAM, NKG2D ligands, Notch1, Notch2/3, NY-ESO-1, PRAME, PSCA, PSMA, Survivin, TAG-72, TEMs, TERT, VEGFR2, and ROR1.

In an additional embodiment, the bridging factor is rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In a particular embodiment, the first nucleic acid encodes a first fusion protein comprising a binding domain of an scFv specific for CD3 and a first multimerization domain of FRB T2098L; wherein the second nucleic acid encodes a second fusion protein comprising a binding domain of an scFv specific for CD19 and a second multimerization domain of FKBP12; and wherein the bridging factor that promotes the formation of a polypeptide complex is rapalog AP21967.

In a further embodiment, the first nucleic acid encodes a first fusion protein comprising a binding domain of an scFv specific for CD3 and a first multimerization domain of FRB T2098L; wherein the second nucleic acid encodes a second fusion protein comprising a binding domain of an scFv specific for BCMA and a second multimerization domain of FKBP12; and wherein the bridging factor that promotes the formation of a polypeptide complex is rapalog AP21967.

In various embodiments, a method for treating a hyperproliferative, inflammatory, autoimmune, or graft-versus-host disease, is provided comprising: administering a non-natural cell contemplated herein and administering a bridging factor, wherein the bridging factor promotes the formation of a polypeptide complex with the bridging factor associated with and disposed between the multimerization domains of the first and second fusion proteins; wherein the binding domain of the second fusion polypeptide specifically binds a cell surface target on a hyperproliferative disease cell to promote an immunomodulatory response and thereby treats the hyperproliferative disease.

In various embodiments, a method for treating a hyperproliferative, inflammatory, autoimmune, or graft-versus-host disease, is provided comprising: administering a first fusion protein comprising a binding domain that binds a receptor on a T cell and a first multimerization domain; and a second fusion protein comprising a binding domain that binds a cell surface target on a hyperproliferative, inflammatory, autoimmune, or graft-versus-host disease cell and a second multimerization domain; and administering a bridging factor that promotes the formation of a polypeptide complex with the bridging factor associated with and disposed between the multimerization domains of the first and second fusion proteins; thereby treating the hyperproliferative, inflammatory, autoimmune, or graft-versus-host disease.

In various embodiments, a fusion polypeptide heterocomplex is provided, comprising: a first fusion protein comprising a binding domain that binds a receptor on a T cell and a first multimerization domain; a second fusion protein comprising a binding domain that binds a cell surface target on a target cell; and a bridging factor; wherein the first fusion protein, second fusion protein, and bridging factor associate to form a polypeptide heterocomplex with the bridging factor associated with and disposed between the multimerization domains of the first and second fusion proteins.

In a particular embodiment, the first and second multimerization domains are the same or different.

In a further embodiment, the multimerization domains of the first and second fusion proteins associate with a bridging factor selected from rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

In a certain embodiment, the first and second multimerization domains are a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In an additional embodiment, the first multimerization domain comprises a first FKBP polypeptide or variant thereof, and the second multimerization domain comprises a first FRB polypeptide or variant thereof.

In a certain embodiment, the first multimerization domain comprises a first FRB polypeptide or variant thereof, and the second multimerization domain comprises a first FKBP polypeptide or variant thereof.

In a particular embodiment, the bridging factor is sirolimus, everolimus, novolimus, pimecrolimus, ridaforolimus, tacrolimus, temsirolimus, umirolimus, or zotarolimus.

In one embodiment, the binding domain of the first fusion protein and the binding domain of the second fusion protein are each independently selected from the group consisting of: a single chain antibody variable region, a receptor ectodomain, or a ligand. In a further embodiment, the single chain antibody variable region is a domain antibody, sFv, scFv, F(ab')2, or Fab.

In an additional embodiment, the binding domain of the second fusion polypeptide specifically binds to a target selected from α-folate receptor, αvβ6 integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, EGFR family including ErbB2 (HER2), EGFRvIII, EPCAM, EphA2, EpCAM, FAP, FBP, fetal acetylcholine receptor, Fzd7, GD2, GD3, Glypican-3 (GPC3), h5T4, IL-11R□, IL13R-α2, KDR, κ light chain, λ light chain, LeY, L1CAM, MAGE-A1, mesothelin, MHC presented peptides, MUC1, MUC16, NCAM, NKG2D ligands, Notch1, Notch2/3, NY-ESO-1, PRAME, PSCA, PSMA, Survivin, TAG-72, TEMs, TERT, VEGFR2, and ROR1.

In a certain embodiment, the first fusion protein comprises a binding domain of an scFv specific for CD3 and a first multimerization domain of FRB T2098L; the second fusion protein comprises a binding domain of an scFv specific for CD19 and a second multimerization domain of FKBP12; and the bridging factor is rapalog AP21967.

In a particular embodiment, the first fusion protein comprises a binding domain of an scFv specific for CD3 and a first multimerization domain of FRB T2098L; the second fusion protein comprises a binding domain of an scFv specific for BCMA and a second multimerization domain of FKBP12; and the bridging factor is rapalog AP21967.

In various embodiments, a nucleic acid molecule encoding any one or more of the fusion proteins contemplated herein is provided.

In a particular embodiment, the nucleic acid molecule is disposed between 5' and 3' polynucleotide sequences homologous to a genomic locus.

In various embodiments, an expression vector containing a nucleic acid contemplated herein is provided.

In one embodiment, the expression vector comprises the first and second fusion proteins encoded as a polycistronic message or as a single protein separated by a 2A peptide.

In another embodiment, the polycistronic message comprises an internal ribosome entry site (IRES) between the nucleotide sequences that encode the fusion proteins.

BRIEF DESCRIPTION THE DRAWINGS

FIG. 1A-1M show schematics of various types of multipartite signaling complexes of this disclosure.

Figure 5:
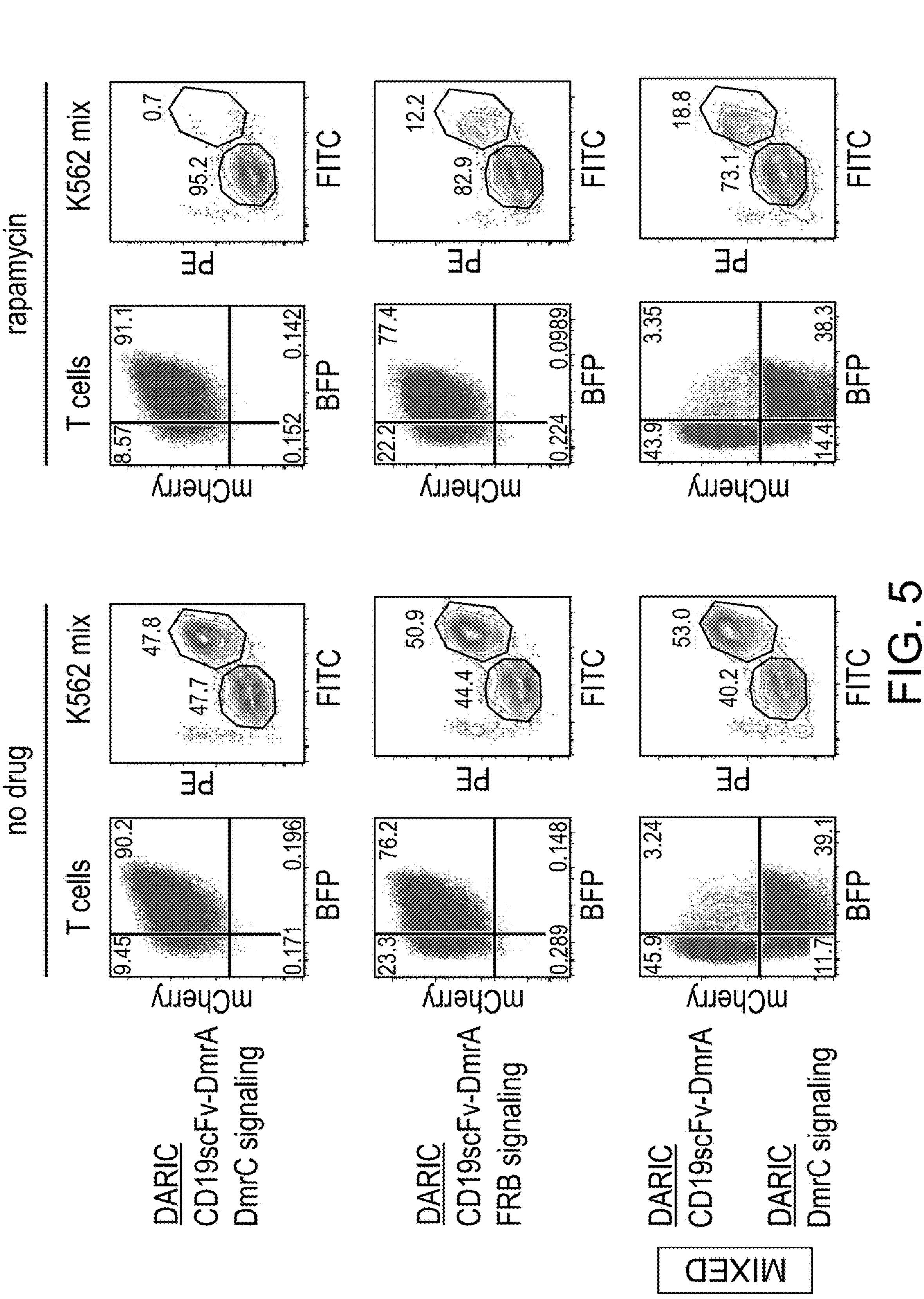
Figure 5:
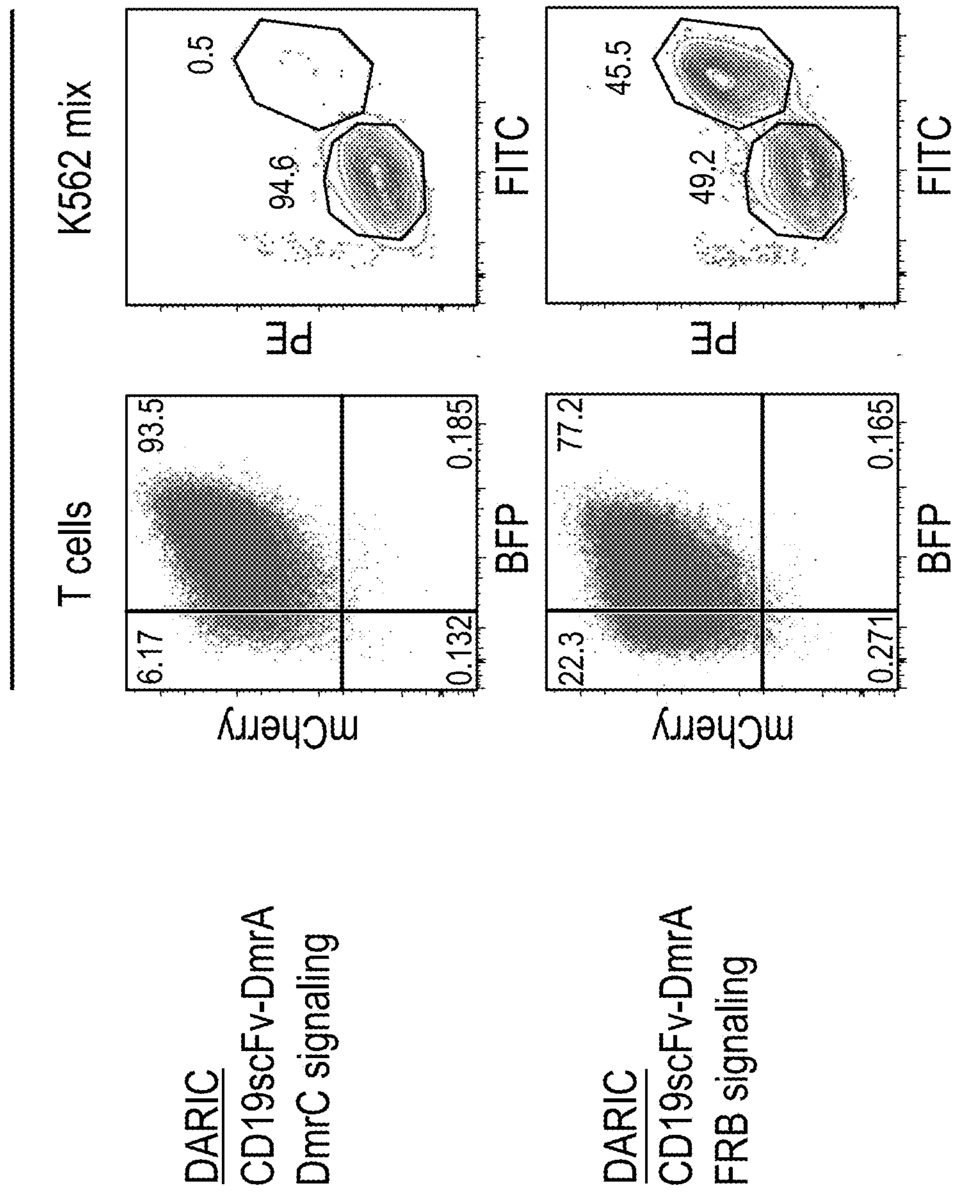

FIG. 5 shows that use of independent multimerization domains having different specificities for bridging components allows for directed cytotoxic activity of human T cells expressing a multipartite signaling complex of this disclosure. In addition, this figure shows that human T cells expressing a multipartite signaling complex of this disclosure can be cytotoxic even when the DARIC binding and signaling components are individually expressed in separate cells.

Figure 6:
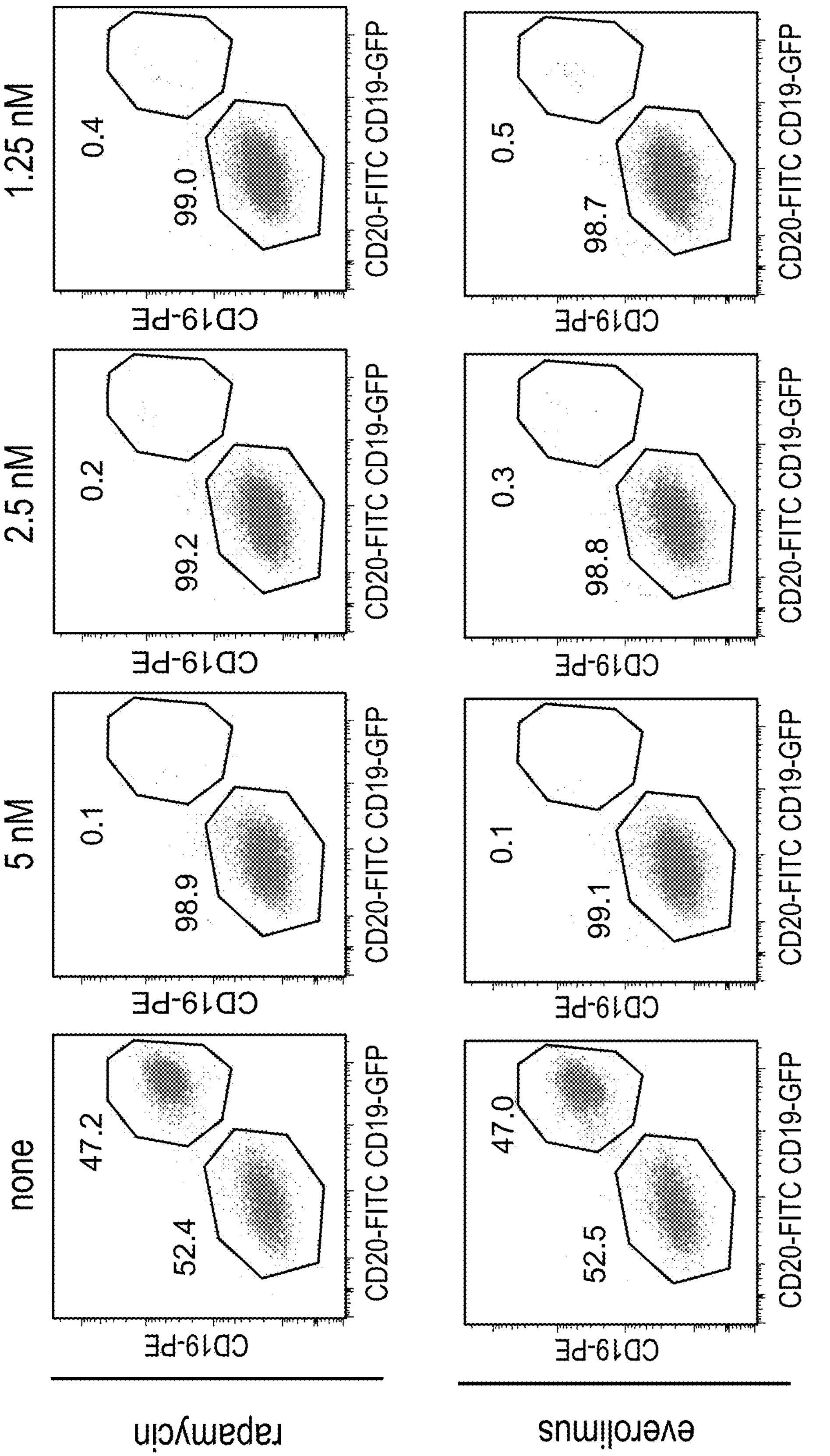
Figure 6:
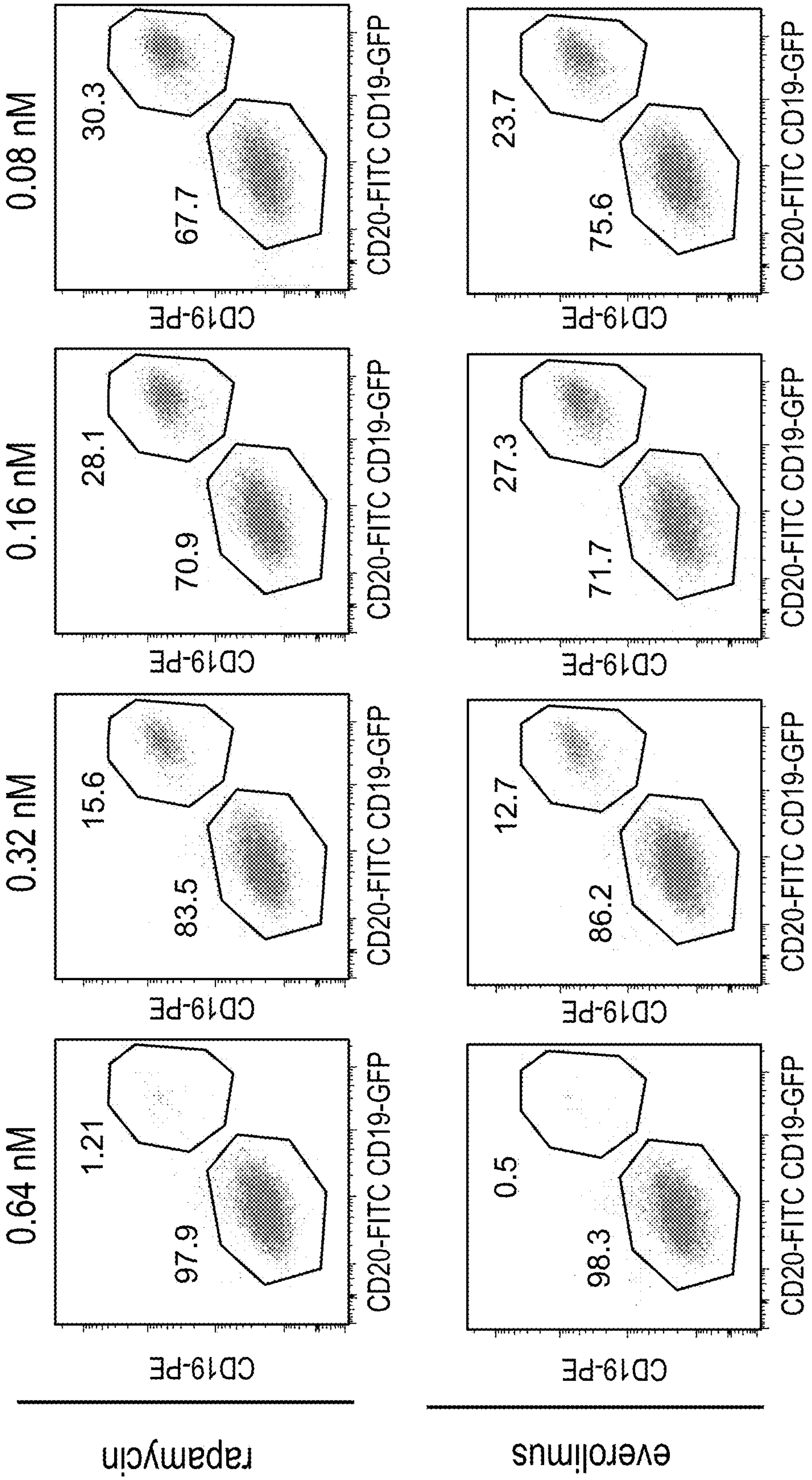

FIG. 6 shows that bridging factors can function in the DARIC system at clinically relevant concentrations.

Figure 7:
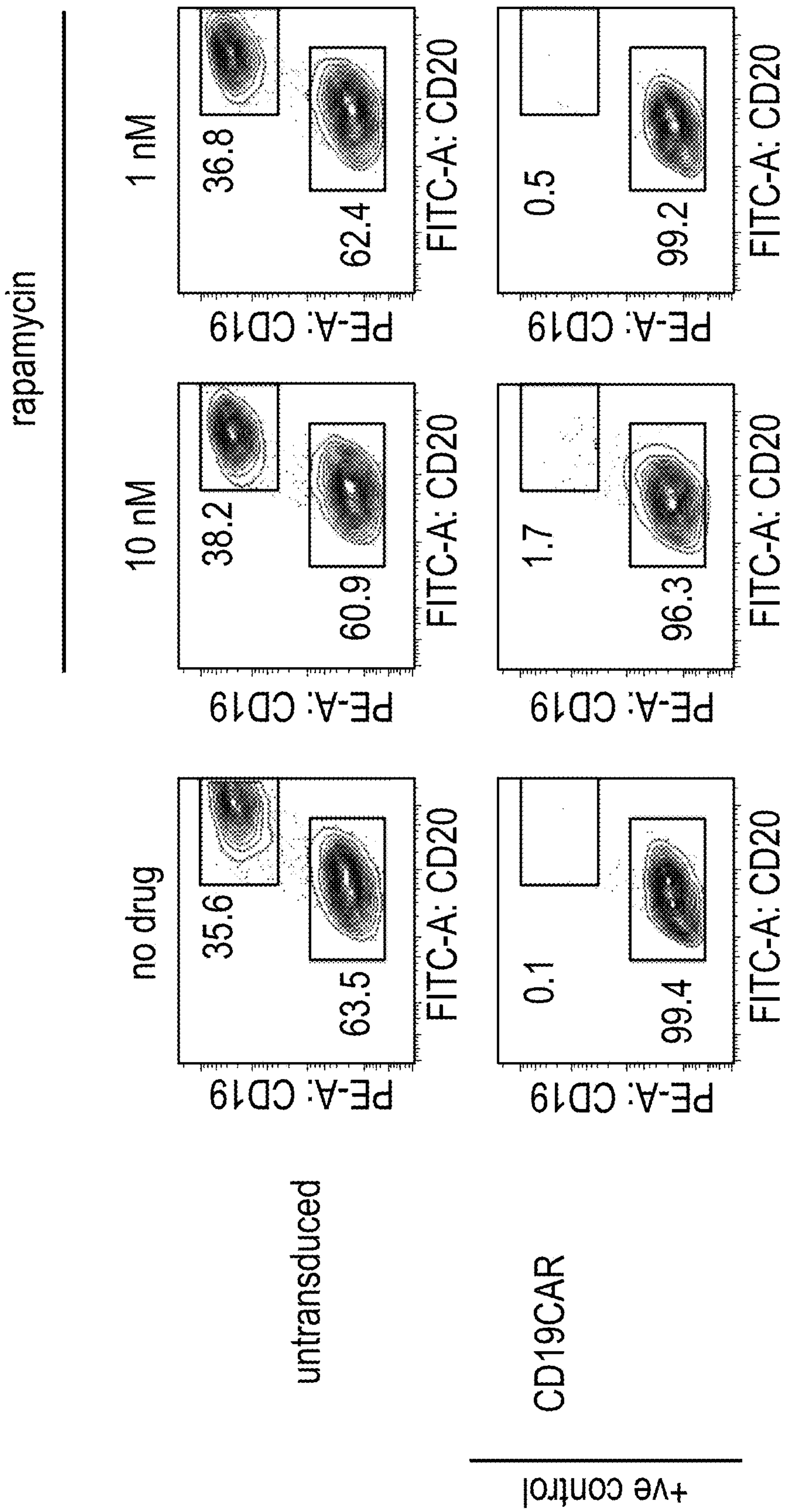
Figure 7:
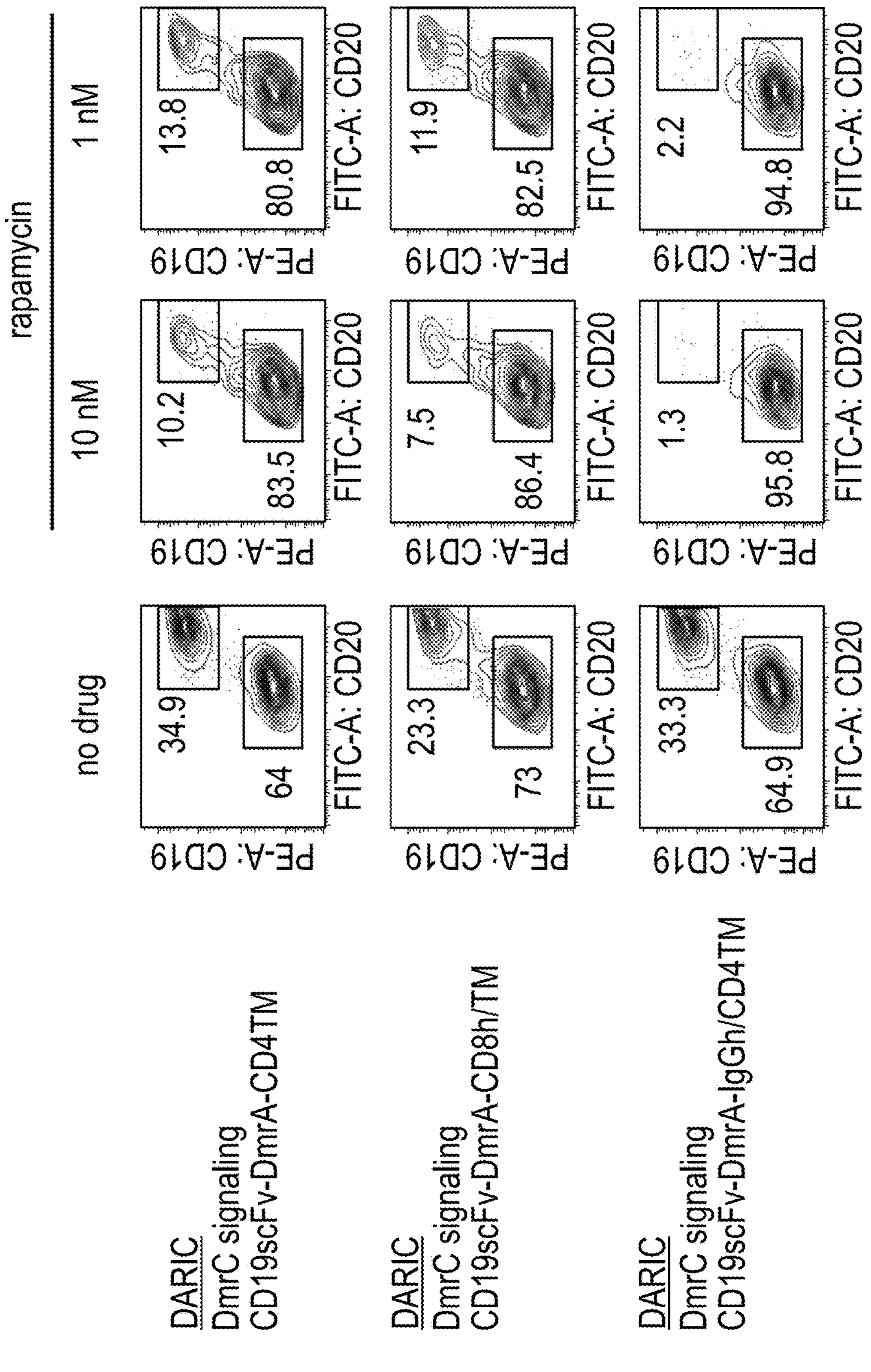

FIG. 7 shows that a DARIC binding component can be released from a cell or tethered to the cell surface and still functionally associate with a DARIC signaling component to form a multipartite signaling complex of this disclosure.

Figure 8:
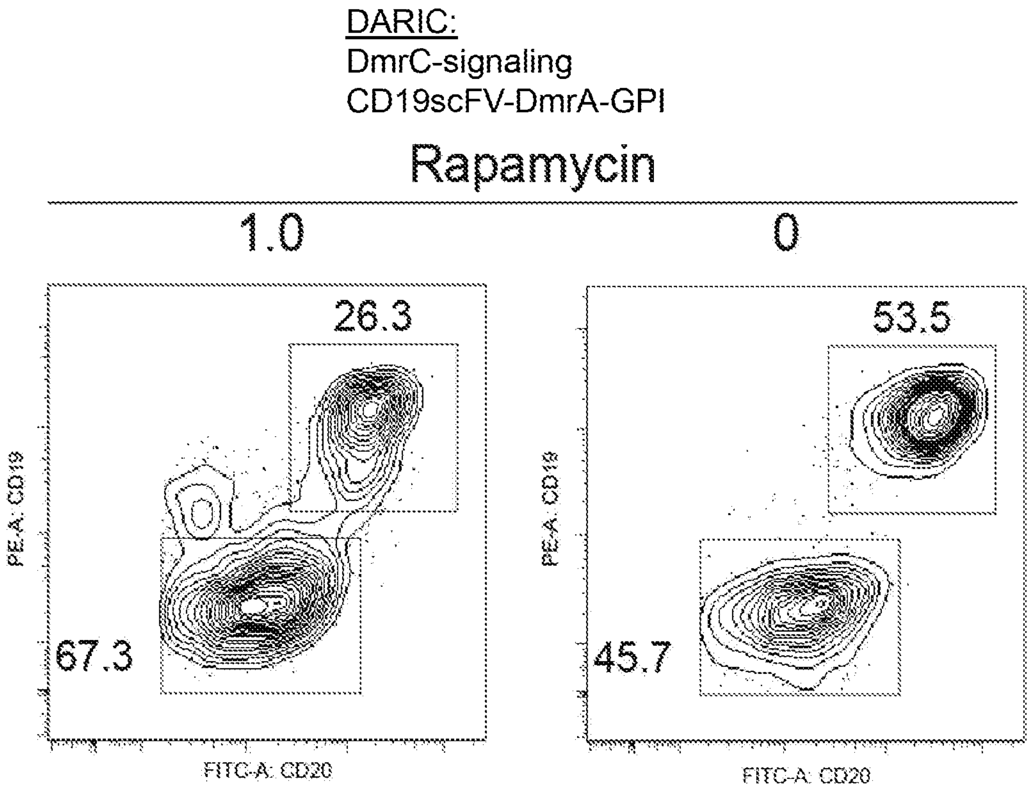

FIG. 8 shows that a DARIC binding component may be tethered to the cell surface via GPI-anchor and still functionally associate with a DARIC signaling component in the presence of a bridging factor to form a multipartite signaling complex of this disclosure.

Figure 9:
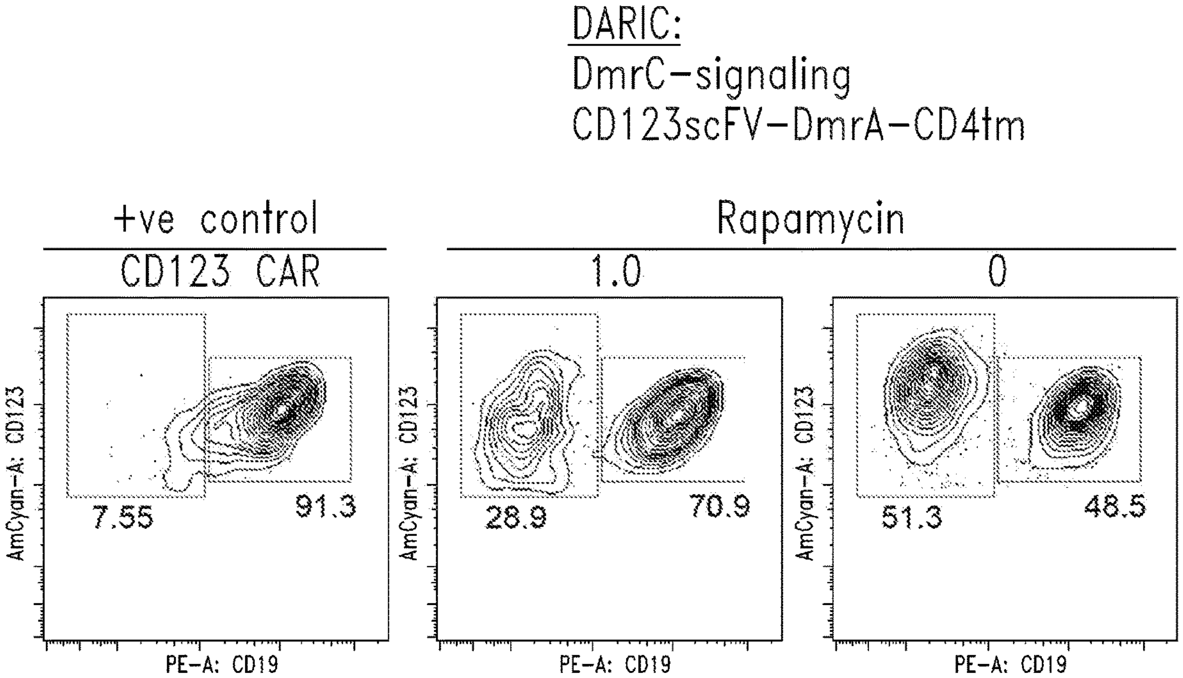

FIG. 9 shows a DARIC system targeting an additional model antigen, CD123, that may be used either to eradicate a myeloid cancer, or in a conditioning regimen to ablate myeloid cells prior to a bone marrow transplant.

Figure 10:
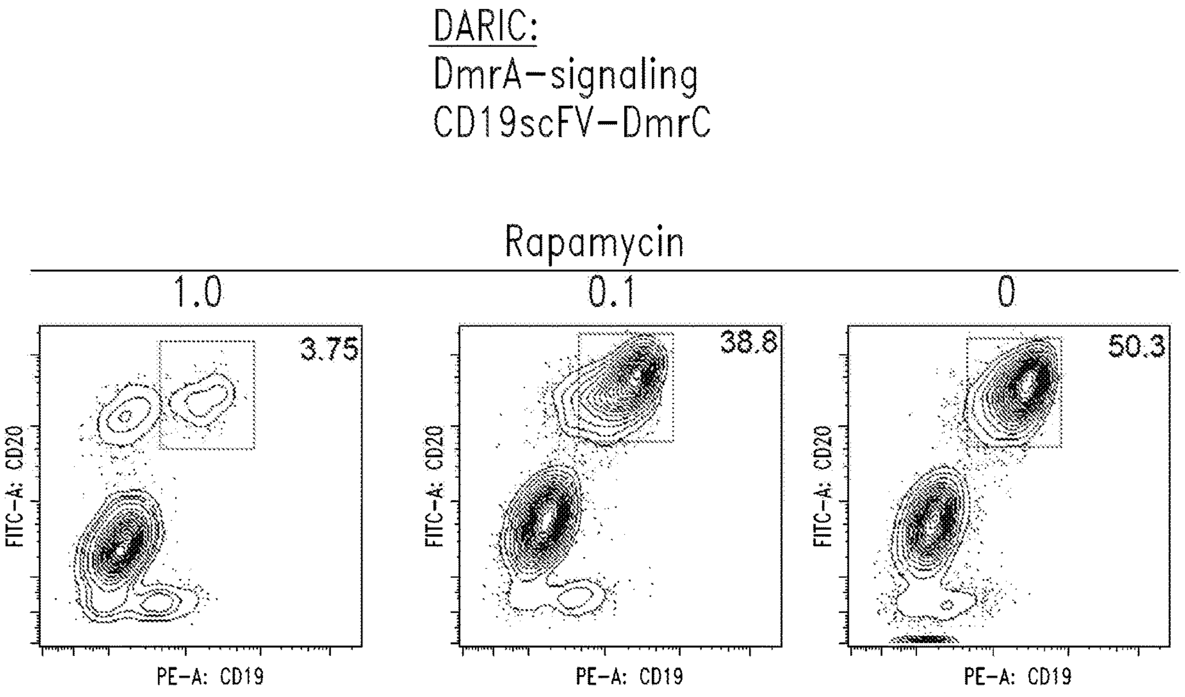
Figure 11:
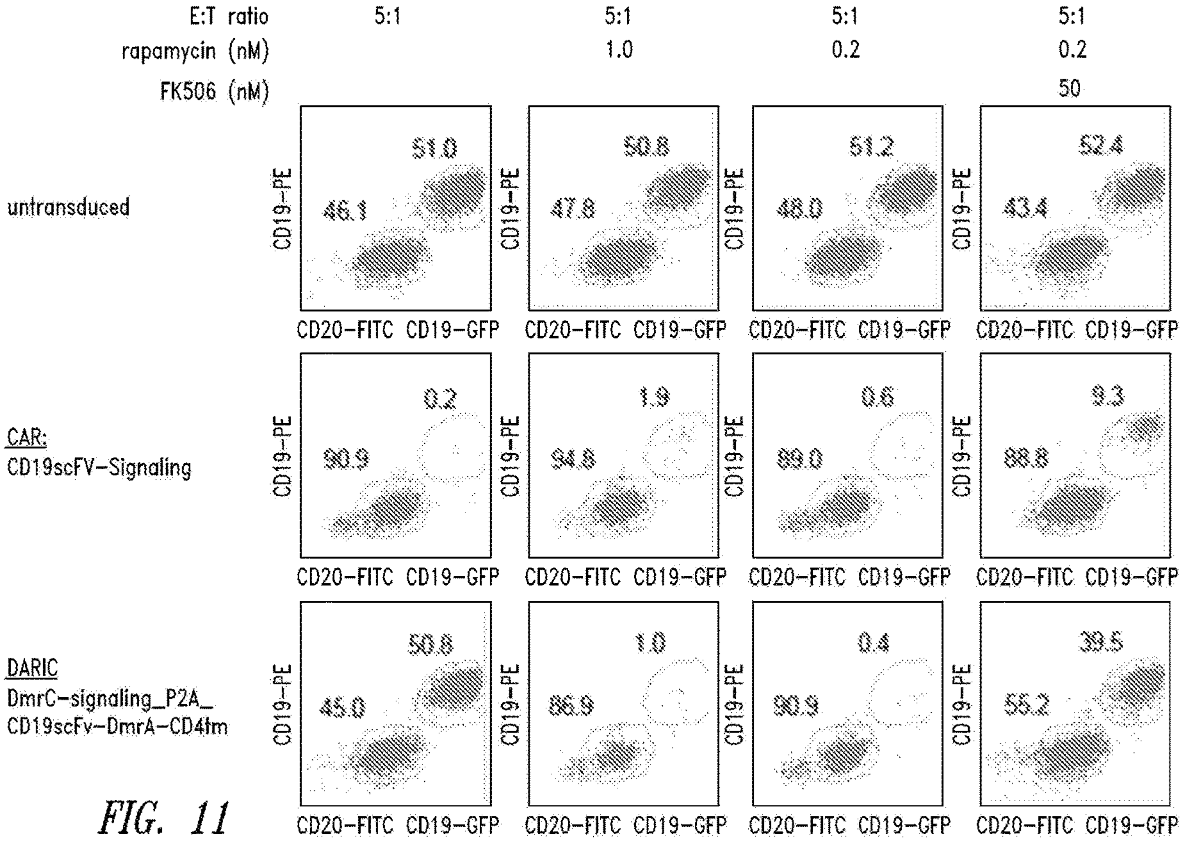

FIG. 10 shows that the FRB and FKBP12 multimerization domains may be appended to the DARIC binding component or signaling component and still form a functional multipartite signaling complex in the presence of a bridging factor.

Figure 11:
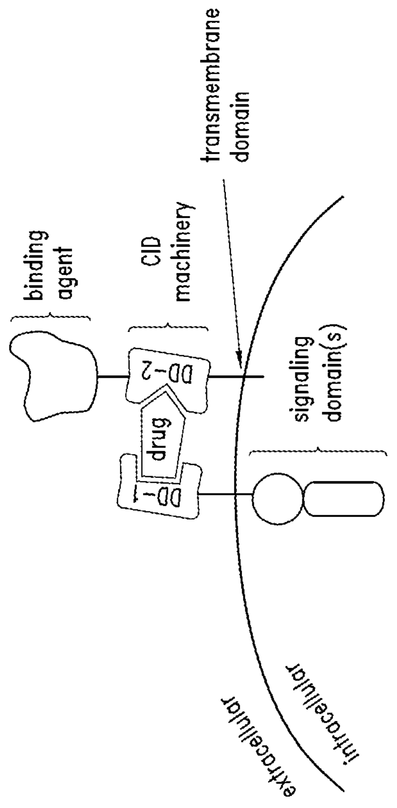

FIG. 11 shows that the coupling of the DARIC binding and signaling components can be deactivated by the addition of an anti-bridging factor, a monovalent drug that binds only to one of the multimerization domains and thereby blocks the activation of the cell.

DETAILED DESCRIPTION

In one embodiment, multi-component fusion proteins for use in modulating a biological response to immunotherapy, such as adoptive immunotherapy, are provided. By way of background, signal transduction by cell surface receptors converts extracellular information into intracellular responses and requires machinery for both ligand recognition and transmembrane signal transduction. Cell surface receptors recognize ligands through the use of an extracellular binding domain and, upon ligand binding, transduce signals across the plasma membrane via membrane spanning domains connected with intracellular signaling domains. These occur either as single-chain units, where binding and signaling are linked directly, or through multi-chain contacts whereby cell surface binding of ligand allows intracellular interactions of signaling domains with other proteins to mediate cell signal transduction.

An advantage of the compositions and methods contemplated herein is to provide both spatial and temporal control over such signal transduction binding and signaling activities. In one embodiment, this disclosure provides a binding component and a signaling component that are each expressed as separate fusion proteins, but contain an extracellular multimerization mechanism (bridging factor) for recoupling of the two functional components on a cell surface—referred to herein as DARIC binding and signaling components—which provides temporal control. Since the binding component is either secreted, expressed on the surface, or delivered in a recombinant form, it is then present in the extracellular environment without being basally coupled to any cell signal transduction machinery. The transmembrane signaling fusion protein to be expressed by the cell of interest comprises one or more intracellular signaling (actuator) domains fused via a transmembrane domain to an extracellular multimerization domain, such as a FRB or FKBP12 protein (whichever is not present on the binding component). Only upon the application of the FRB/FKBP12 coupling drug (e.g., rapamycin or a rapalog thereof) do the binding and signaling components form a complex that is capable of initiating signal transduction.

In a particular embodiment, a deconstructed drug regulated bispecific T cell engager (BiTE) expressed as separate fusion proteins is provided. See FIG. 1L. The BiTE comprises a DARIC signaling component comprising a binding agent that binds a T cell receptor and a first multimerization domain; and a DARIC binding component comprising a binding agent that binds an antigen on a target cell and a second multimerization domain, such as a FRB or FKBP12 protein (whichever is not present on the binding component). Only upon the application of the FRB/FKBP12 coupling drug (e.g., rapamycin or a rapalog thereof) do the BiTE components form a complex that is capable of initiating signal transduction.

But, the temporal control achieved through the multimerization mechanism described herein only primes the machinery for signaling. The chemically induced multimerization reconstitutes a signaling-potentiated receptor, but it does not activate downstream signaling because there is no aggregation of intracellular signaling components. Spatial control is, therefore, achieved on the basis of the presence or absence of a target recognized by the binding domain on the binding component. Since the binding component fusion protein is secreted to the outside of the cell (or applied extraneously), it accumulates only where target is present, such that cells will only become activated when both target (e.g., cell surface antigen) and the bridging factor are present.

In certain embodiments, a recombinant cell comprising a first nucleic acid molecule encoding a first fusion protein comprising a first multimerization domain, a hydrophobic domain, and an actuator domain, wherein the first multimerization domain localizes extracellularly when the first fusion protein is expressed is administered to a subject having a hyperproliferative disease (e.g., cancer), an inflammatory disease, an autoimmune disease, or a graft-versus-host disease. Such a fusion protein can be referred to as a DARIC signaling component, which may be expressed as one or more transmembrane protein(s). A DARIC signaling component may contain more than one multimerization domain, including a multimerization domain that promotes homodimerization in the presence of homo-bivalent bridging factor. In such an embodiment (see FIG. 1*c*), the administration of a bridging factor will promote some level of basal signaling in the absence of binding to an extracellular target—for example, as a way to drive cell proliferation in vitro or in vivo prior to activation with a DARIC binding component (which in this context functions like a drug). For T cells, it is known that lower level activation promotes proliferation, whereas the higher order multimerization (as would occur by high density of antigen on a target cell and heterodimerization of the DARIC components with a bridging component) would lead to activation of a cytotoxicity response.

In further embodiments, a subject receiving a recombinant (non-natural) cell (e.g., T cell) expressing a DARIC signaling component may be further administered, simultaneously or sequentially, a fusion protein comprising a binding domain and a multimerization domain—a DARIC binding component—and a bridging factor (e.g., rapamycin or rapalog thereof) to promote the formation of a polypeptide complex on the non-natural cell surface with the bridging factor associated with and disposed between the multimerization domains of the first and second fusion proteins (DARIC signaling and binding components, respectively). In certain embodiments, a nucleic acid molecule further encodes a fusion protein comprising a secretion signal, a binding domain and a multimerization domain, wherein the fusion protein (DARIC binding component) is secreted from the non-natural cell when expressed. In some embodiments, a nucleic acid molecule further encodes a fusion protein comprising a secretion signal, a binding domain and a multimerization domain, wherein the expressed fusion protein (DARIC binding component) is secreted and tethered or anchored to the cell surface of the non-natural cell (see FIG. 1I-K). The DARIC binding component will specifically bind to a target cell (e.g., cancer, autoimmune) either before or after associating with the DARIC signaling component through the bridging factor, wherein the tripartite association of the two DARIC components and bridging factor will trigger a cellular response that treats the hyperproliferative, inflammatory, autoimmune, or graft-versus-host disease. For example, the presence at least one DARIC binding component and a cell surface target would lead to increasing signals proportional to the density of target due to multimerization.

In a further embodiment, the DARIC signaling component may be created by leveraging existing activating receptors on the cell (e.g., T cell) surface using a drug regulated bi-specific engager (BiTE). In this instance, both DARIC components are secreted: a binding component that binds to a target cell, and a signaling component that binds to a receptor (e.g., the TCR/CD3 complex) on a T cell. In one embodiment, a non-natural cell secretes both components. In another embodiment, one or more non-natural cells secretes one or more of the components.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the terms "about" means (1) ±1%, ±2%, ±3%, ±4%, ±5%, ±10%, ±15%, or ±20% of the indicated range, value or structure; (2) a value includes the inherent variation of error for the method being employed to determine the value; or (3) a value includes the variation that exists among replicate experiments, unless otherwise indicated. It should be understood that the terms "a" and "an" as used herein refer to "one or more" of the enumerated components. The use of the alternative (e.g., "or") should be understood to mean either one, both, or any combination thereof of the alternatives or enumerated components. As used herein, the terms "include," "have" and "comprise" are used synonymously, which terms and variants thereof are intended to be construed as non-limiting.

As used herein, a protein or polypeptide "consists essentially of" several domains (e.g., a binding domain, a linker or spacer, a hydrophobic domain, a multimerization domain, an actuator domain) when the portions outside of the several domains (e.g., amino acids at the amino- or carboxy-terminus or between two domains), in combination, contribute to at most 20% (e.g., at most 15%, 10%, 8%, 6%, 5%, 4%, 3%, 2% or 1%) of the length of the protein or polypeptide and do not substantially affect (i.e., do not alter the activity by more than 50%, such as no more than 40%, 30%, 25%, 20%, 15%, 10%, 5%, 4%, 3%, 2%, 1%) the activities of one or more of the various domains (e.g., the target binding affinity of the binding domain, the capability of the multimerization domain to facilitate complex formation, and the capability of the actuator domain to transmit functional signals to a cell). In certain embodiments, a protein (e.g., a single chain polypeptide) consists essentially of a binding domain that specifically binds a target, a linker, and a multimerization domain, wherein the protein may comprise junction amino acids at the amino- and/or carboxy-terminus of the protein or between two different domains (e.g., between the binding domain and the multimerization domain, between the multimerization domain and the linker).

A "fusion protein" or "chimeric protein," as used herein, refers to a protein that includes polypeptide components derived from one or more parental proteins or polypeptides and does not naturally occur in a host cell. A fusion protein will contain two or more naturally-occurring amino acid sequences that are linked together in a way that does not occur naturally. For example, a fusion protein may have two or more portions from the same protein linked in a way not normally found in a cell, or a fusion protein may have portions from two, three, four, five or more different proteins linked in a way not normally found in a cell. A fusion protein can be encoded by a nucleic acid molecule wherein a nucleotide sequence encoding one protein or portion thereof is appended in frame with, and optionally separated by nucleotides that encode a linker, spacer or junction amino acids, a nucleic acid molecule that encodes one or more different proteins or a portion thereof. In certain embodiments, a nucleic acid molecule encoding a fusion protein is introduced into a host cell and expressed.

As used herein, the term "host" refers to a cell (e.g., T cell) or microorganism that may be genetically modified with an exogenous nucleic acid molecule to produce a polypeptide of interest (e.g., DARIC binding or signaling components). In certain embodiments, a host cell may optionally already possess or be modified to include other genetic modifications that confer desired properties related or unrelated to fusion protein biosynthesis (e.g., deleted, altered or truncated TCR; increased costimulatory factor expression). In certain embodiments, a host cell is a human T cell or a human T cell with TCRα, TCRβ, or both knocked out with a site-specific nuclease (e.g., a LAGLIDADG homing endonuclease, LHE).

As used herein, "recombinant" or "non-natural" refers to an organism, microorganism, cell, nucleic acid molecule, or vector that has at least one engineered genetic alteration or has been modified by the introduction of a heterologous nucleic acid molecule, or refers to a cell that has been altered such that the expression of an endogenous nucleic acid molecule or gene can be controlled. Recombinant also refers to a cell that is derived from a non-natural cell or is progeny of a non-natural cell having one or more such modifications. Genetic alterations include, for example, modifications introducing expressible nucleic acid molecules encoding proteins, or other nucleic acid molecule additions, deletions, substitutions or other functional alteration of a cell's genetic material. For example, recombinant cells may express genes or other nucleic acid molecules that are not found in identical or homologous form within a native (wild-type) cell (e.g., a fusion or chimeric protein), or may provide an altered expression pattern of endogenous genes, such as being over-expressed, under-expressed, minimally expressed, or not expressed at all.

Recombinant methods for expression of exogenous or heterologous nucleic acids in cells are well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, MD (1999). Exemplary exogenous proteins or enzymes to be expressed include scFv, CD3ζ, FKBP, FRB, cytokines, or any combination thereof. Genetic modifications to nucleic acid molecules encoding fusion proteins can confer a biochemical or metabolic capability to a recombinant or non-natural cell that is altered from its naturally occurring state.

As used herein, the term "endogenous" or "native" refers to a gene, protein, compound or activity that is normally present in a host cell. The term "homologous" or "homolog" refers to a molecule or activity from an exogenous (non-native) source that is the same or similar molecule or activity as that found in or derived from a host cell, species or strain.

As used herein, "heterologous" nucleic acid molecule, construct or sequence refers to a nucleic acid molecule or portion of a nucleic acid molecule sequence that is not native to a cell in which it is expressed, a nucleic acid molecule or portion of a nucleic acid molecule native to a host cell that has been altered or mutated, or a nucleic acid molecule with an altered expression as compared to the native expression levels under similar conditions. For example, a heterologous control sequence (e.g., promoter, enhancer) may be used to regulate expression of a gene or a nucleic acid molecule in a way that is different than the gene or a nucleic acid molecule that is normally expressed in nature or culture. In certain embodiments, a heterologous nucleic acid molecule may be homologous to a native host cell gene, but may have an altered expression level or have a different sequence or both. In other embodiments, heterologous or exogenous nucleic acid molecules may not be endogenous to a host cell or host genome (e.g., fusion protein), but instead may have been introduced into a host cell by transformation (e.g., transfection, electroporation), wherein the added molecule may integrate into the host genome or can exist as extra-chromosomal genetic material either transiently (e.g., mRNA) or stably for more than one generation (e.g., episomal viral vector, plasmid or other self-replicating vector).

In certain embodiments, more than one heterologous or exogenous nucleic acid molecule can be introduced into a host cell as separate nucleic acid molecules, as a polycistronic nucleic acid molecule, as a single nucleic acid molecule encoding a fusion protein, or any combination thereof, and still be considered as more than one heterologous or exogenous nucleic acid. When two or more exogenous nucleic acid molecules are introduced into a host cell, it is understood that the two more exogenous nucleic acid molecules can be introduced as a single nucleic acid molecule (e.g., on a single vector), on separate vectors, as single or multiple mRNA molecules, integrated into the host chromosome at a single site or multiple sites, and each of these embodiments is still to be considered two or more exogenous nucleic acid molecules. Thus, the number of referenced heterologous nucleic acid molecules or protein activities refers to the number of encoding nucleic acid molecules or the number of protein activities, not the number of separate nucleic acid molecules introduced into a host cell.

For example, a cell can be modified to express two or more heterologous or exogenous nucleic acid molecules, which may be the same or different, that encode one or more fusion proteins, as disclosed herein. In certain embodiments, a host cell will contain a first nucleic acid molecule encoding a first fusion protein and a separate second nucleic acid molecule encoding a second fusion protein, or a host cell will contain a single polycistronic nucleic acid molecule that encodes a first fusion protein and second fusion protein, or single nucleic acid molecule that encodes a first fusion protein, a self-cleaving amino acid sequence and a second fusion protein.

Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S), for example, ENLYFQG and ENLYFQS, wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a *Thosea asigna* virus (TaV) 2A peptide, a porcine teschovirus-1 (PTV-1) 2A peptide, a Theilovirus 2A peptide, and an encephalomyocarditis virus 2A peptide.

A "polypeptide complex" or "protein complex," as used herein, refers to a dimer, trimer, or higher order multimer formed by at least two different single chain polypeptides, comprising at least one chain having a binding domain specific for a target and one chain having an actuator domain. This term does not include an antibody formed from four single chain polypeptides (i.e., two light chains and two heavy chains). A "dimer" refers to a biological entity that contains two subunits associated with each other, and a "polypeptide complex" refers to a biological entity that includes at least two proteins subunits and a bridging factor associated with each other, via one or more forms of intramolecular forces, including covalent bonds (e.g., disulfide bonds) and other interactions (e.g., electrostatic interactions, salt bridges, hydrogen bonding, and hydrophobic interactions), and is stable under appropriate conditions (e.g., under physiological conditions, in an aqueous solution suitable for expressing, purifying, and/or storing recombinant proteins, or under conditions for non-denaturing and/or non-reducing electrophoresis).

A "single chain polypeptide" is a single, linear and contiguous arrangement of covalently linked amino acids. It does not include two polypeptide chains that link together in a non-linear fashion, such as via an interchain disulfide bond (e.g., a half immunoglobulin molecule in which a light chain links with a heavy chain via a disulfide bond). In certain embodiments, a single chain polypeptide may have or form one or more intrachain disulfide bonds. In certain other embodiments, two or more single chain polypeptides (e.g., fusion proteins) may associate via an interchain disulfide bond to provide a potentially active complex, provided the complex is made up of at least one non-natural protein, such as fusion or chimeric proteins and is not a natural antibody.

A "multimerization domain," as used herein, refers to a polypeptide molecule that preferentially interacts or associates with another different polypeptide molecule directly or via a bridging molecule, wherein the interaction of the different multimerization domains substantially contribute to or efficiently promote multimerization (i.e., the formation of a dimer, trimer, or multipartite complex, which may be a homodimer, heterodimer, homotrimer, heterotrimer, homomultimer, heteromultimer). Representative multimerization domains of the present disclosure include an FKBP, FRB, calcineurin, cyclophilin, bacterial DHFR, PYL1, ABI1, GIB1, GAI, or variants thereof, as provided herein.

In certain embodiments, a polypeptide complex comprises (i) a first fusion protein having a first multimerization domain and (ii) second fusion protein having a second multimerization domain that is not the same as the first multimerization domain, wherein the first and second multimerization domains substantially contribute to or efficiently promote formation of the polypeptide complex in the presence of a bridging factor. The interaction(s) between the first and second multimerization domains substantially contributes to or efficiently promotes the multimerization of the first and second fusion proteins if there is a statistically significant reduction in the association between the first and second fusion proteins in the absence of the first multimerization domain, the second multimerization domain, or the bridging factor. In certain embodiments, when the first and second fusion proteins are co-expressed, at least about 60%, for instance, at least about 60% to about 70%, at least about 70% to about 80%, at least about 80% to about 90%, 91%, 92%, 93%, 94%, 95%, 96%, 97%, 98%, 99%, or 100%, and at least about 90% to about 92%, 93%, 94%, 95%, 96%, 97%, 98%, or 99% of the first and second single chain polypeptides form multimers with each other in the presence of a bridging factor.

As used herein, "hydrophobic domain" refers to an amino acid sequence having a three-dimensional structure that is thermodynamically stable in a cell membrane. The structure of a hydrophobic domain may comprise an alpha helix, a beta barrel, a beta sheet, a beta helix, or any combination thereof. In certain embodiments, a hydrophobic domain is a transmembrane domain, such as one derived from an integral membrane protein (e.g., receptor, cluster of differentiation (CD) molecule, enzyme, transporter, cell adhesion molecule, or the like).

As used herein, "anchor domain" refers to an amino acid sequence or other molecule that promotes tethering, anchoring or association of a fusion protein of this disclosure with a cell surface. Exemplary anchor domains include an amino acid sequence with a structure that is stable in a cell membrane or an amino acid sequence that promotes the addition of a glycolipid (also known as glycosyl phosphatidylinositols or GPIs), or the like. By way of background, a GPI molecule is post-translationally attached to a protein target by a transamidation reaction, which results in the cleavage of a carboxy-terminal GPI signal sequence (see, e.g., White et al., *J. Cell Sci.* 113:721, 2000) and the simultaneous transfer of the already synthesized GPI anchor molecule to the newly formed carboxy-terminal amino acid (see www.ncbi.nlm.nih.gov/books/NBK20711 for exemplary GPI anchors, which GPI anchors are incorporated by reference in their entirety. In certain embodiments, an anchor domain is a hydrophobic domain (e.g., transmembrane domain) or a GPI signal sequence. In some embodiments, a nucleic acid molecule encoding a fusion protein of this disclosure with an anchor domain results in a fusion protein further comprising a GPI molecule.

An "actuator domain," as used herein, directly or indirectly, promotes a biological or physiological response in a cell when receiving the appropriate signal. In certain embodiments, the actuator domain is part of a protein or protein complex that receives a signal when bound or it binds to a target molecule and the binding triggers a signal from the actuator domain. The actuator domain may directly promote a cellular response when it contains signaling domains or motifs, such as an immunoreceptor tyrosine-based activation motif (ITAM). In other embodiments, an actuator domain will indirectly promote a cellular response by associating with one or more other proteins that directly promote a cellular response. Exemplary actuator domains include CD2, CD3ε, CD3δ, CD3ζ, pTα, TCRα, TCRβ, FcRα, FcRβ, FcRγ, NKG2D, CD79A, CD79B, CD22, CD27, CD28, CD30, CD40, LAT, Zap70, ICOS, DAP10, 4-1BB, CARD11, HVEM, LAG3, SLAMF1, Lck, Fyn, Slp76, TRIM, OX40, or any combination thereof.

In particular embodiments, a "transmembrane domain" refers to a portion of the signaling component that fuses an extracellular multimerization domain and one or more intracellular signaling domains and anchors the signaling component to the plasma membrane of the T cell. In certain embodiments, a "transmembrane domain" refers to a portion of the binding component that is fused to an extracellular multimerization domain and anchors the binding component to the plasma membrane of the T cell. The transmembrane domain may be derived either from a natural, synthetic, semi-synthetic, or recombinant source. Illustrative transmembrane domains may be derived from (i.e., comprise at least the transmembrane region(s) of) the alpha, beta or zeta chain of the T-cell receptor, CD3ε, CD3ζ, CD4, CD5, CD8α, CD9, CD 16, CD22, CD27, CD28, CD33, CD37, CD45, CD64, CD80, CD86, CD 134, CD137, CD152, CD 154, and PD1. In various embodiments, a transmembrane domain of a binding component and/or signaling component is fused to a short oligo- or polypeptide linker, preferably between 1, 2, 3, 4, 5, 6, 7, 8, 9, or 10 amino acids in length and that optionally links the transmembrane domain and the intracellular signaling domain of the signaling component.

A "binding domain" (also referred to as a "binding region," "binding agent," or "binding moiety"), as used herein, refers to a protein, polypeptide, oligopeptide, or peptide that possesses the ability to specifically recognize and bind to a target (e.g., CD19, CD20). A binding domain includes any naturally occurring, synthetic, semi-synthetic, or recombinantly produced binding partner for a biological molecule or another target of interest. Exemplary binding domains include single chain antibody variable regions (e.g., domain antibodies, sFv, scFv, Fab), receptor ectodomains (e.g., c-Met), or ligands (e.g., cytokines, chemokines, or cell surface associated ligands). In particular embodiments, a binding domain comprises an antibody or antigen binding fragment thereof, including but not limited to a Camel Ig (a camelid antibody (VHH)), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody). A variety of assays are known for identifying binding domains of the present disclosure that specifically bind a particular target, including Western blot, ELISA, and Biacore analysis.

A binding domain and a fusion protein thereof "specifically binds" a target if it binds the target with an affinity or $K_a$ (i.e., an equilibrium association constant of a particular binding interaction with units of 1/M) equal to or greater than $10^5$ $M^{-1}$, while not significantly binding other components present in a test sample. Binding domains (or fusion proteins thereof) may be classified as "high affinity" binding domains (or fusion proteins thereof) and "low affinity" binding domains (or fusion proteins thereof). "High affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding domains refer to those binding domains with a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M). Affinities of binding domain polypeptides and fusion proteins according to the present disclosure can be readily determined using conventional techniques (see, e.g., Scatchard et al. (1949) Ann. N.Y. Acad. Sci. 51:660; and U.S. Pat. Nos. 5,283,173, 5,468,614, or the equivalent).

"T cell receptor" (TCR) is a molecule found on the surface of T cells that, along with CD3, is generally responsible for recognizing antigens bound to major histocompatibility complex (MHC) molecules. It consists of a disulfide-linked heterodimer of the highly variable α and β chains in most T cells. In other T cells, an alternative receptor made up of variable γ and δ chains is expressed. Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see, Abbas and Lichtman, *Cellular and Molecular Immunology* (5th Ed.), Editor: Saunders, Philadelphia, 2003; Janeway et al., *Immunobiology: The Immune System in Health and Disease,* $4^{th}$ Ed., Current Biology Publications, p148, 149, and 172, 1999). TCR as used in the present disclosure may be from one or various animal species, including human, mouse, rat, or other mammals.

"CD3" is known in the art as a multi-protein complex of six chains (see, Abbas and Lichtman, 2003; Janeway et al., p172 and 178, 1999). In mammals, the complex comprises a CD3γ chain, a CD3δ chain, two CD3ε chains, and a homodimer of CD3ζ chains. The CD37, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. It is believed the ITAMs are important for the signaling capacity of a TCR complex. CD3 as used in the present disclosure may be from one or various animal species, including human, mouse, rat, or other mammals.

"TCR complex," as used herein, refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3P chains, a homodimer of CD3ζ chains, a TCRγ chain, and a TCRδ chain.

"A component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

Terms understood by those in the art of antibody technology are each given the meaning acquired in the art, unless expressly defined differently herein. Antibodies are known to have variable regions, a hinge region, and constant domains. Immunoglobulin structure and function are reviewed, for example, in Harlow et al., Eds., Antibodies: A Laboratory Manual, Chapter 14 (Cold Spring Harbor Laboratory, Cold Spring Harbor, 1988).

For example, the terms "VL" and "VH" refer to the variable binding region from an antibody light and heavy chain, respectively. The variable binding regions are made up of discrete, well-defined sub-regions known as "complementarity determining regions" (CDRs) and "framework regions" (FRs). The term "CL" refers to an "immunoglobulin light chain constant region" or a "light chain constant region," i.e., a constant region from an antibody light heavy chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 of the heavy chain linked to the light chain via an inter-chain disulfide bond.

As used herein, "an Fc region constant domain portion" or "Fc region portion" refers to the heavy chain constant region segment of the Fc fragment (the "fragment crystallizable" region or Fc region) from an antibody, which can include one or more constant domains, such as CH2, CH3, CH4, or any combination thereof. In certain embodiments, an Fc region portion includes the CH2 and CH3 domains of an IgG, IgA, or IgD antibody and any combination thereof, or the CH3 and CH4 domains of an IgM or IgE antibody and any combination thereof. In one embodiment, the CH2CH3 or the CH3CH4 structures are from the same antibody isotype, such as IgG, IgA, IgD, IgE, or IgM. By way of background, the Fc region is responsible for the effector functions of an immunoglobulin, such as ADCC (antibody-dependent cell-mediated cytotoxicity), ADCP (antibody-dependent cellular phagocytosis), CDC (complement-dependent cytotoxicity) and complement fixation, binding to Fc receptors (e.g., CD16, CD32, FcRn), greater half-life in vivo relative to a polypeptide lacking an Fc region, protein A binding, and perhaps even placental transfer (see Capon et al., Nature, 337:525 (1989)).

A "linker" or "spacer" refers to an amino acid sequence that connects two proteins, polypeptides, peptides, domains, regions, or motifs and may provide a spacer function compatible with interaction of the two sub-binding (e.g., multimerization) domains so that the resulting polypeptide retains a specific binding affinity to a target molecule or retains signaling activity (e.g., actuator domain activity). In certain embodiments, a linker is comprised of about two to about 35 amino acids, for instance, or about four to about 20 amino acids or about eight to about 15 amino acids or about 15 to about 25 amino acids. In other embodiments, a spacer may have a particular structure, such as an antibody CH2CH3 domain, hinge domain or the like. In one embodiment, a spacer comprises the CH2 and CH3 domains of IgG1 or IgG4.

"Junction amino acids" or "junction amino acid residues" refer to one or more (e.g., about 2-10) amino acid residues between two adjacent motifs, regions or domains of a polypeptide, such as between a binding domain and an adjacent multimerization domain or between a hydrophobic region and an adjacent multimerization domain or between a peptide linker or spacer that links two motifs, regions or domains and an adjacent actuator domain. Junction amino acids may result from the construct design of a fusion protein (e.g., amino acid residues resulting from the use of a restriction enzyme site during the construction of a nucleic acid molecule encoding a fusion protein).

An "altered domain" or "altered protein" refers to a motif, region, domain, peptide, polypeptide, or protein with a sequence identity to a wild type motif, region, domain, peptide, polypeptide, or protein (e.g., a wild type human FKBP12, FRP, ITAM, CD3ζ, TCR) of at least 75% (e.g., 80%, 82%, 84%, 86%, 88%, 90%, 91%, 92%, 93%, 94%, 95%, 96%, 97%, 98%, 99%, or 99.5%). For example, an "altered FKBP" refers to a FKBP with a sequence identity to a wild type FKBP (e.g., a human FKBP) of at least 75% (e.g., 80%, 82%, 84%, 86%, 88%, 90%, 91%, 92%, 93%, 94%, 95%, 96%, 97%, 98%, 99%, or 99.5%). Similarly, an "altered CD3ζ" refers to a CD3ζ with a sequence identity to a wild type CD3ζ (e.g., a human CD3ζ) of at least 75% (e.g., 80%, 82%, 84%, 86%, 88%, 90%, 91%, 92%, 93%, 94%, 95%, 96%, 97%, 98%, 99%, or 99.5%).

As used herein, "nucleic acid" or "nucleic acid molecule" refers to any of deoxyribonucleic acid (DNA), ribonucleic acid (RNA), oligonucleotides, fragments generated, for example, by the polymerase chain reaction (PCR) or by in vitro translation, and fragments generated by any of ligation, scission, endonuclease action, or exonuclease action. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, morpholino, or the like. The term "nucleic acid molecule" also includes "peptide nucleic acids" (PNAs), which comprise naturally occurring or modified nucleic acid bases attached to a polyamide backbone. Nucleic acid molecules can be either single stranded or double stranded.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In other embodiments, a mutation is a substitution of one or more nucleotides or residues.

The term "construct" refers to any polynucleotide that contains a recombinant nucleic acid. A construct may be present in a vector (e.g., a bacterial vector, a viral vector) or may be integrated into a genome. A "vector" is a nucleic acid molecule that is capable of transporting another nucleic acid. Vectors may be, for example, plasmids, cosmids, viruses, a RNA vector or a linear or circular DNA or RNA molecule that may include chromosomal, non-chromosomal, semi-synthetic or synthetic nucleic acids. Exemplary vectors are those capable of autonomous replication (episomal vector) and/or expression of nucleic acids to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

"Lentiviral vector," as used herein, means HIV-based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells.

"Integrative lentiviral vectors (or LV)," as used herein, means such vectors as examples of those that are able to integrate into the genome of a target cell.

By "non-integrative lentiviral vectors" (or NILV) is meant efficient gene delivery vectors that do not integrate into the genome of a target cell through the action of the viral integrase. In one embodiment, a NILV refers to a lentivirus having an integrase protein mutated to specifically decrease its integrase activity. Illustrative mutations in the HIV-1 pol gene suitable to reduce integrase activity include, but are not limited to: H12N, H12C, H16C, H16V, S81 R, D41A, K42A, H51A, Q53C, D55V, D64E, D64V, E69A, K71A, E85A, E87A, D116N, D1161, D116A, N120G, N120I, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values are generated by the NCBI BLAST2.0 software as defined by Altschul et al. (1997) "Gapped BLAST and PSI-BLAST: a new generation of protein database search programs," Nucleic Acids Res. 25:3389-3402, with the parameters set to default values.

In certain embodiments, an altered immunoglobulin domain only contains conservative amino acid substitutions of a wild type immunoglobulin domain. In certain other embodiments, an altered immunoglobulin domain only contains non-conservative amino acid substitutions of a wild type immunoglobulin domain. In yet other embodiments, an altered immunoglobulin domain contains both conservative and non-conservative amino acid substitutions.

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, MA (1990), p. 8). In certain embodiments, a conservative substitution includes a leucine to serine substitution.

As used herein, the term "derivative" refers to a modification of one or more amino acid residues of a peptide by chemical or biological means, either with or without an enzyme, e.g., by glycosylation, alkylation, acylation, ester formation, or amide formation. Generally, a "derivative" differs from an "analogue" in that a parent polypeptide may be the starting material to generate a "derivative," whereas the parent polypeptide may not necessarily be used as the starting material to generate an "analogue." A derivative may have different chemical, biological or physical properties of the parent polypeptide. For example, a derivative may be more hydrophilic or it may have altered reactivity (e.g., a CDR having an amino acid change that alters its affinity for a target, or FKBP having an amino acid change that alters its affinity for rapamycin or a rapalog thereof) as compared to the parent polypeptide.

A "receptor" is a protein present in the plasma membrane or in the cytoplasm of a cell to which a signal molecule (i.e., a ligand, such as a hormone, neurotransmitter, toxin, cytokine) may bind or attach. The binding of the single molecule to the receptor may result in a conformational change of the receptor, which can initiate a cellular response. However, some ligands merely block receptors without inducing any response (e.g., antagonists). Some receptor proteins are peripheral membrane proteins, many hormone and neurotransmitter receptors are transmembrane proteins that are embedded in the phospholipid bilayer of cell membranes, and another major class of receptors are intracellular proteins such as those for steroid and intracrine peptide hormone receptors.

As used herein, the term "isolated" refers to a substance that has been removed from the source in which it naturally occurs. A substance need not be purified in order to be isolated. For example, a protein produced in a host cell is considered isolated when it is removed or released from the cell. A protein contained within a crude cell lysate fraction is considered "isolated" for purposes of the present disclosure. Further, an "isolated nucleic acid molecule" refers to a polynucleotide molecule in the form of a separate fragment or as a component of a larger nucleic acid construct, which has been separated from its source cell, including the chromosome it normally resides in, at least once. For example, a DNA molecule that encodes a recombinant polypeptide, peptide, or variant thereof, which has been separated from the genomic DNA of a cell, is an isolated nucleic acid molecule. Another example of an isolated nucleic acid molecule is a bacteriophage promoter (e.g., T5 or T7), or nucleic acid expression control sequence, which can be cloned into a vector capable of replication in a suitable host cell. Still another example of an isolated nucleic acid molecule is a chemically synthesized or PCR synthesized nucleic acid molecule.

As used herein, the term "purified" refers to a substance that has been rendered at least partially free of contaminants and other materials that typically accompany it. Substances can be purified to varying degrees. A substance is "substantially pure" when a preparation or composition of the substance contains less than about 1% contaminants. A substance is "essentially pure" when a preparation or composition of the substance contains less than about 5% contaminants. A substance is "pure" when a preparation or composition of the substance contains less than about 2% contaminants. For substances that are "purified to homogeneity," contaminants cannot be detected with conventional analytical methods.

"Treatment," "treating" or "ameliorating" refers to either a therapeutic treatment or prophylactic/preventative treatment. A treatment is therapeutic if at least one symptom of disease in an individual receiving treatment improves or a treatment may delay worsening of a progressive disease in an individual, or prevent onset of additional associated diseases.

A "therapeutically effective amount (or dose)" or "effective amount (or dose)" of a specific binding molecule or compound refers to that amount of the compound sufficient to result in amelioration of one or more symptoms of the disease being treated in a statistically significant manner. When referring to an individual active ingredient, administered alone, a therapeutically effective dose refers to that ingredient alone. When referring to a combination, a therapeutically effective dose refers to combined amounts of the active ingredients that result in the therapeutic effect, whether administered serially or simultaneously.

The term "pharmaceutically acceptable" refers to molecular entities and compositions that do not produce allergic or other serious adverse reactions when administered using routes well known in the art.

A "subject in need" refers to a subject at risk of, or suffering from, a disease, disorder or condition that is amenable to treatment or amelioration with a non-natural cell, polypeptide complex or a composition thereof provided herein. In certain embodiments, a subject is a human.

Additional definitions are provided throughout the present disclosure.

In certain aspects, the instant disclosure is directed to a non-natural cell, comprising (a) a first nucleic acid molecule encoding a first fusion protein comprising a first multimerization domain, a hydrophobic domain, and an actuator domain, wherein the first multimerization domain localizes extracellularly when the first fusion protein is expressed; and (b) a second nucleic acid molecule encoding a second fusion protein comprising a binding domain and a second multimerization domain, wherein the second fusion protein localizes extracellularly, either secreted from the cell or anchored to the cell surface, when expressed; wherein a first bridging factor promotes the formation of a polypeptide complex on the non-natural cell surface with the bridging factor associated with and disposed between the multimerization domains of the first and second fusion proteins. In certain embodiments, the second fusion protein (e.g., DARIC binding component) further comprises an anchor domain (e.g., transmembrane domain, GPI signal sequence), wherein the extracellularly localized second fusion protein is tethered or anchored to the surface of the non-natural cell. In certain embodiments, a fusion protein is anchored to the surface of a non-natural cell by a transmembrane domain, such as a transmembrane domain from CD4, CD8, CD28 or the like. In some embodiments, a fusion protein is anchored to the surface of a non-natural cell by a GPI molecule.

In a further embodiment, a first fusion protein, rather than comprising its own hydrophobic and actuator domains, instead comprises a binding domain that binds to a transmembrane protein expressed on the surface of a T cell that comprises a hydrophobic and actuator domain (e.g., TCR/CD3 or the like).

In further aspects, the instant disclosure is directed to a first non-natural cell comprising a heterologous nucleic acid molecule encoding a first fusion protein comprising a first multimerization domain, a hydrophobic domain, and an actuator domain, wherein the first multimerization domain localizes extracellularly when the first fusion protein is expressed; and a second non-natural cell comprising a heterologous a second nucleic acid molecule encoding a second fusion protein comprising a binding domain and a second multimerization domain, wherein the second fusion protein is released extracellularly when expressed; wherein a first bridging factor promotes the formation of a polypeptide complex on the first non-natural cell surface with the bridging factor associated with and disposed between the multimerization domains of the first and second fusion proteins.

In certain embodiments, the first and second multimerization domains are the same or different. Exemplary bridging factors that associate with multimerization domains and are useful with the fusion proteins of this disclosure include rapamycin (sirolimus) or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

Exemplary rapamycin analogs (rapalogs) include those disclosed in U.S. Pat. No. 6,649,595, which rapalog structures are incorporated herein by reference. In certain embodiments, a bridging factor is a rapalog with substantially reduced immunosuppressive effect as compared to rapamycin. A "substantially reduced immunosuppressive effect" refers to a rapalog having at least less than 0.1 to 0.005 times the immunosuppressive effect observed or expected for an equimolar amount of rapamycin, as measured either clinically or in an appropriate in vitro (e.g., inhibition of T cell proliferation) or in vivo surrogate of human immunosuppressive activity. Alternatively, "substantially reduced immunosuppressive effect" refers to a rapalog having an $EC_{50}$ value in such an in vitro assay that is at least 10 to 250 times larger than the $EC_{50}$ value observed for rapamycin in the same assay. Other exemplary rapalogs include everolimus, novolimus, pimecrolimus, ridaforolimus, tacrolimus, temsirolimus, umirolimus, and zotarolimus.

In certain embodiments, multimerization domains will associate with a bridging factor being a rapamycin or rapalog thereof. For example, the first and second multimerization domains are a pair selected from FKBP and FRB. FRB domains are polypeptide regions (protein "domains") that are capable of forming a tripartite complex with an FKBP protein and rapamycin or rapalog thereof. FRB domains are present in a number of naturally occurring proteins, including mTOR proteins (also referred to in the literature as FRAP, RAPT1, or RAFT) from human and other species; yeast proteins including Tor1 and Tor2; and a Candida FRAP homolog. Information concerning the nucleotide sequences, cloning, and other aspects of these proteins is already known in the art. For example, a protein sequence accession number for a human mTOR is GenBank Accession No. L34075.1 (Brown et al., *Nature* 369:756, 1994).

FRB domains for use in the fusion proteins of this disclosure generally contain at least about 85 to about 100 amino acid residues. In certain embodiments, an FRB amino acid sequence for use in fusion proteins of this disclosure will comprise a 93 amino acid sequence Ile-2021 through Lys-2113 and a mutation of T2098L, based the amino acid sequence of GenBank Accession No. L34075.1. A FRB domain for use in fusion proteins of this disclosure will be capable of binding to a complex of an FKBP protein bound to rapamycin or a rapalog thereof of this disclosure. In certain embodiments, a peptide sequence of an FRB domain comprises (a) a naturally occurring peptide sequence spanning at least the indicated 93 amino acid region of human mTOR or corresponding regions of homologous proteins; (b) a variant of a naturally occurring FRB in which up to about ten amino acids, or about 1 to about 5 amino acids or about 1 to about 3 amino acids, or in some embodiments just one amino acid, of the naturally-occurring peptide have been deleted, inserted, or substituted; or (c) a peptide encoded by a nucleic acid molecule capable of selectively hybridizing to a DNA molecule encoding a naturally occurring FRB domain or by a DNA sequence which would be capable, but for the degeneracy of the genetic code, of selectively hybridizing to a DNA molecule encoding a naturally occurring FRB domain.

FKBPs (FK506 binding proteins) are the cytosolic receptors for macrolides, such as FK506, FK520 and rapamycin, and are highly conserved across species lines. For the purpose of this disclosure, FKBPs are proteins or protein domains that are capable of binding to rapamycin or to a rapalog thereof and further forming a tripartite complex with an FRB-containing protein or fusion protein. An FKBP domain may also be referred to as a "rapamycin binding domain". Information concerning the nucleotide sequences, cloning, and other aspects of various FKBP species is known in the art (see, e.g., Staendart et al., *Nature* 346:671, 1990 (human FKBP12); Kay, *Biochem. J.* 314:361, 1996). Homologous FKBP proteins in other mammalian species, in yeast, and in other organisms are also known in the art and may be used in the fusion proteins disclosed herein. The size of FKBP domains for use in this invention varies, depending on which FKBP protein is employed. An FKBP domain of a fusion protein of this disclosure will be capable of binding to rapamycin or a rapalog thereof and participating in a tripartite complex with an FRB-containing protein (as may be determined by any means, direct or indirect, for detecting such binding).

The peptide sequence of an FKBP domain of an FKBP fusion protein of this invention comprises (a) a naturally occurring FKBP peptide sequence, preferably derived from the human FKBP12 protein (GenBank Accession No. AAA58476.1) or a peptide sequence derived therefrom, from another human FKBP, from a murine or other mammalian FKBP, or from some other animal, yeast or fungal FKBP; (b) a variant of a naturally occurring FKBP sequence in which up to about ten amino acids, or about 1 to about 5 amino acids or about 1 to about 3 amino acids, or in some embodiments just one amino acid, of the naturally-occurring peptide have been deleted, inserted, or substituted; or (c) a peptide sequence encoded by a nucleic acid molecule capable of selectively hybridizing to a DNA molecule encoding a naturally occurring FKBP or by a DNA sequence which would be capable, but for the degeneracy of the genetic code, of selectively hybridizing to a DNA molecule encoding a naturally occurring FKBP.

Other multimerization domain pairs include FKBP and calcineurin, FKBP and cyclophilin, FKBP and bacterial DHFR, calcineurin and cyclophilin, PYL1 and ABI1, or GIB1 and GAI, or variants thereof.

In yet other embodiments, an anti-bridging factor blocks the association of at least two first fusion proteins with the bridging factor. For example, cyclosporin or FK506 could be used as anti-bridging factors to titrate out rapamycin and, therefore, stop signaling since only one multimerization domain is bound. In certain embodiments, an anti-bridging factor (e.g., cyclosporine, FK506) is an immunosuppressive agent. For example, an immunosuppressive anti-bridging factor may be used to block or minimize the function of the fusion proteins of the instant disclosure and at the same time inhibit or block an unwanted or pathological inflammatory response in a clinical setting.

In certain embodiments, a first fusion protein (e.g., DARIC signaling component) has a first multimerization domain comprising a first FKBP polypeptide or variant thereof, and a second fusion protein (e.g., DARIC binding component) has a second multimerization domain comprising a first FRB polypeptide or variant thereof. In other embodiments, a first fusion protein (e.g., DARIC signaling component) has a first multimerization domain comprising a first FRB polypeptide or variant thereof, and a second fusion protein (e.g., DARIC binding component) has a second multimerization domain comprising a first FKBP polypeptide or variant thereof. In any of these embodiments, the second fusion protein further comprises an anchor domain (e.g., transmembrane domain, GPI signal sequence) and optionally a sub-threshold signaling domain. In some embodiments, a second fusion protein contains a GPI molecule, wherein the GPI signal sequence has been removed or altered to attach the GPI molecule.

In certain embodiments, a first nucleic acid molecule encoding a first fusion protein comprising a first multimerization domain, a third multimerization domain, a hydrophobic domain, and an actuator domain, wherein the first and third multimerization domains localize extracellularly when the first fusion protein is expressed in a cell. In certain embodiments, the third multimerization domain of the first fusion protein is a binding domain for a bridging factor selected from rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, Tmp-SLF or a derivative thereof, or any combination thereof.

In still further embodiments, a second bridging factor promotes the association of at least two first fusion proteins with the bridging factor associated with and disposed between the third multimerization domains of the first fusion proteins. In certain embodiments, a protein complex that is formed is a homocomplex comprising at least two first fusion proteins, wherein the multimerization domains may be DHFR (with the bridging molecule being methotrexate) or GyrB (with the bridging molecule being coumermycin) or FKBP (with the bridging molecule being AP1903 or AP20187). In certain other embodiments, a protein complex is a heterocomplex comprising one or more first fusion proteins and one or more second fusion proteins.

In certain embodiments, a hydrophobic domain is a transmembrane domain, such as a transmembrane domain from CD4, CD8, CD28, or the like. In some embodiments, a fusion protein (e.g., DARIC binding component) comprises an anchor domain, such as a transmembrane domain or GPI signal sequence. In further embodiments, a fusion protein (e.g., DARIC binding component) contains a GPI molecule, wherein the GPI signal sequence has been removed or altered to attach the GPI molecule.

In further embodiments, the actuator domain comprises a lymphocyte receptor signaling domain or comprises an amino acid sequences having one or a plurality of immunoreceptor tyrosine-based activation motifs (ITAMs). In still further embodiments, an actuator domain comprises a cytoplasmic portion that associates with a cytoplasmic signaling protein, wherein the cytoplasmic signaling protein is a lymphocyte receptor or signaling domain thereof, a protein comprising a plurality of immunoreceptor tyrosine-based activation motifs (ITAMs), a costimulatory domain, an adhesion factor, or any combination thereof. Exemplary actuator domains include, but are not limited to, CD2, CD3ε, CD3δ, CD3ζ, pTα, TCRα, TCRβ, FcRα, FcRβ, FcRγ, NKG2D, CD22, CD79A, and CD79B, CD27, CD28, CD30, CD40, LAT, Zap70, ICOS, DAP10, 4-1BB, CARD11, HVEM, LAG3, SLAMF1, Lck, Fyn, Slp76, TRIM, OX40, or any combination thereof. In yet further embodiments, a first nucleic acid molecule encodes the first fusion protein further comprising one or more different actuator domains, costimulatory domains, adhesion factors, or any combination thereof. As used herein, the term, "costimulatory signaling domain," or "costimulatory domain", refers to an intracellular signaling domain of a costimulatory factor. Exemplary costimulatory domains include, but are not limited to intracellular signaling domains from CD2, CD27, CD28, CD30, CD40, LAT, Zap70, ICOS, DAP10, 4-1BB, CARD11, HVEM, LAG3, SLAMF1, Lck, Fyn, Slp76, TRIM, and OX40.

In certain embodiments, a non-natural cell further overexpresses a costimulatory factor, an immunomodulatory factor, an agonist for a costimulatory factor, an agonist for an immunomodulatoy factor, or any combination thereof. In a related embodiment, cofactor IL-12 is overexpressed or supplied to the cell.

Fusion protein binding domains useful in the instant invention include those known in the art or as described herein, or those generated by a variety of methods known in the art (see, e.g., U.S. Pat. Nos. 6,291,161 and 6,291,158). For example, fusion protein binding domains may be identified by screening a Fab phage library for Fab fragments that specifically bind to a target of interest (see Hoet et al., *Nat. Biotechnol.* 23:344, 2005). Additionally, traditional strategies for hybridoma development, such as using a target antigen as an immunogen in convenient systems (e.g., mice, HuMAb Mouse®, TC Mouse™, KM-Mouse®, llamas, sheep, chicken, rats, hamsters, rabbits, etc.), can be used to develop anti-target antibodies having target-specific binding domains of interest.

Sources of further binding domains include target-specific antibody variable domains from various species (which can be formatted as antibodies, sFvs, scFvs, Fabs, or soluble VH domain or domain antibodies), including human, rodent, avian, and ovine. Additional sources of binding domains include variable domains of antibodies from other species, such as camelid (from camels, dromedaries, or llamas (Ghahroudi et al., *FEBS Letters* 414:521, 1997; Vincke et al., *J. Biol. Chem.* 284:3273, 2009; and Hamers-Casterman et al., *Nature* 363:446, 1993; and Nguyen et al., *J. Mol. Biol.* 275:413, 1998), nurse sharks (Roux et al., *Proc. Nat'l. Acad. Sci.* (*USA*) 95:11804, 1998), spotted ratfish (Nguyen et al., *Immunogenetics* 54:39, 2002), or lamprey (Herrin et al., *Proc. Nat'l. Acad. Sci.* (*USA*) 105:2040, 2008 and Alder et al., *Nature Immunol.* 9:319, 2008). These antibodies can apparently form antigen-binding regions using only heavy chain variable region, i.e., these functional antibodies are homodimers of heavy chains only (referred to as "heavy chain antibodies") (Jespers et al., *Nat. Biotechnol.* 22:1161, 2004; Cortez-Retamozo et al., *Cancer Res.* 64:2853, 2004; Baral et al., *Nature Med.* 12:580, 2006, and Barthelemy et al., *J. Biol. Chem.* 283:3639, 2008).

Other alternative sources of target-specific binding domains includes sequences that encode random peptide libraries or sequences that encode an engineered diversity of amino acids in loop regions of alternative non-antibody scaffolds, such as fibrinogen domains (see, e.g., Weisel et al. (1985) Science 230:1388), Kunitz domains (see, e.g., U.S. Pat. No. 6,423,498), ankyrin repeat proteins (also known as DARPins; Binz et al., *J. Mol. Biol.* 332:489, 2003 and Binz et al., *Nat. Biotechnol.* 22:575, 2004), fibronectin binding domains (also known as adnectins or monobodies; Richards et al., *J. Mol. Biol.* 326:1475, 2003; Parker et al., *Protein Eng. Des. Sel.* 18:435, 2005 and Hackel et al., *J. Mol. Biol.* 381:1238, 2008), cysteine-knot miniproteins (Vita et al., *Proc. Nat'l. Acad. Sci.* (*USA*) 92:6404, 1995; Martin et al., *Nat. Biotechnol.* 21:71, 2002 and Huang et al., *Structure* 13:755, 2005), tetratricopeptide repeat domains (Main et al., *Structure* 11:497, 2003 and Cortajarena et al., *ACS Chem. Biol.* 3:161, 2008), leucine-rich repeat domains (Stumpp et al., *J. Mol. Biol.* 332:471, 2003), anticalins (Skerra, *FEBS J.* 275:2677, 2008), lipocalin domains (see, e.g., PCT Publication No. WO 2006/095164, Beste et al., *Proc. Nat'l. Acad. Sci.* (*USA*) 96:1898, 1999 and Schönfeld et al., *Proc. Nat'l. Acad. Sci.* (*USA*) 106:8198, 2009), armadillo repeat proteins (ArmRPs; Varadamsetty et al., *J. Mol. Biol.* 424:68, 2012), diabodies (Manzke et al., *Int. J. Cancer* 82:700, 1999), repebodies (Lee et al., *Proc. Nat'l. Acad. Sci. U.S.A.* 109:3299, 2012), minibodies (Hu et al., *Cancer Res.* 56:3055, 1996), cyclotides (Craik et al., *J. Mol. Biol.* 294:1327, 1999), V-like domains (see, e.g., US Patent Application Publication No. 2007/0065431), C-type lectin domains (Zelensky and Gready, *FEBS J.* 272:6179, 2005; Beavil et al.I,

*Proc. Nat'l. Acad. Sci.* (USA) 89:753, 1992 and Sato et al., *Proc. Nat'l. Acad. Sci.* (*USA*) 100:7779, 2003), mAb$^2$ or Fcab™ (see, e.g., PCT Publication Nos. WO 2007/098934; WO 2006/072620), or the like (Nord et al., *Protein Eng.* 8:601, 1995; Nord et al., *Nat. Biotechnol.* 15:772, 1997; Nord et al., *Eur. J. Biochem.* 268:4269, 2001; and Binz et al. (2005) *Nat. Biotechnol.* 23:1257, 2005).

In certain embodiments, the binding domain of the second fusion protein is a single chain antibody variable region, a receptor ectodomain, or a ligand. In further embodiments, the single chain antibody variable region is a domain antibody, sFv, scFv, F(ab')$_2$, or Fab. In still further embodiments, the binding domain of the second fusion protein is amino or carboxy terminal to the multimerization domain.

In certain further aspects, a non-natural cell comprises a nucleic acid molecule that encodes a fusion comprising a binding domain and multimerization domain, and optionally an anchor domain (e.g., transmembrane domain, GPI signal sequence) or an anchor domain with a sub-threshold signaling domain, wherein the binding domain specifically binds to a target located on a target cell surface. In further embodiments, a binding domain is specific for a target that is an antigen associated with a cancer (e.g., solid malignancy, hematologic malignancy), an inflammatory disease, an autoimmune disease, or a graft versus host disease. Exemplary target antigens include, but are not limited to, α-folate receptor, $\alpha_v\beta_6$ integrin, BCMA, B7-H3, B7-H6, CAIX, CD19, CD20, CD22, CD30, CD33, CD3γ, CD44, CD44v6, CD44v7/8, CD70, CD123, CD138, CD171, CEA, DLL4, EGP-2, EGP-40, CSPG4, EGFR, EGFR family including ErbB2 (HER2), EGFRvIII, EPCAM, EphA2, EpCAM, FAP, FBP, fetal acetylcholine receptor, Fzd7, GD2, GD3, Glypican-3 (GPC3), h5T4, IL-11Rα, IL13R-α2, KDR, κ light chain, λ light chain, LeY, L1CAM, MAGE-A1, mesothelin, MHC presented peptides, MUC1, MUC16, NCAM, NKG2D ligands, Notch1, Notch2/3, NY-ESO-1, PRAME, PSCA, PSMA, Survivin, TAG-72, TEMs, TERT, VEGFR2, and ROR1.

In certain embodiments, such a binding fusion protein (DARIC binding component) forms a tripartite complex with DARIC signaling component and a bridging factor to form a polypeptide complex. Exemplary bridging factors for such a complex include rapamycin or a rapalog thereof, coumermycin or a derivative thereof, gibberellin or a derivative thereof, ABA or a derivative thereof, methotrexate or a derivative thereof, cyclosporin A or a derivative thereof, FKCsA or a derivative thereof, or Tmp-SLF or a derivative thereof.

In other embodiments, the instant disclosure is directed to a non-natural cell comprising (a) a heterologous first nucleic acid molecule encoding a first fusion protein comprising a first multimerization domain, a hydrophobic domain, and an actuator domain, wherein the first multimerization domain localizes extracellularly when the first fusion protein is expressed; and (b) a second nucleic acid molecule encoding a second fusion protein comprising a binding domain, a second multimerization domain and an anchor domain (e.g., transmembrane domain, GPI molecule), wherein the second fusion protein localizes to the cell surface when expressed; wherein a first bridging factor promotes the formation of a polypeptide complex on the non-natural cell surface with the bridging factor associated with and disposed between the multimerization domains of the first and second fusion proteins. In certain embodiments, the second fusion protein further comprises an intracellularly localized sub-threshold signaling domain.

As used herein, a "sub-threshold signaling domain" is not capable of inducing or activating a sufficiently robust signal transduction cascade in the presence of one or more other sub-threshold signaling domains, but can induce or activate a signal transduction cascade or adjust a signal qualitatively in the presence of an actuator domain. For example, a second fusion protein tethered to a cell surface that associates with another second fusion protein tethered to a cell surface will not induce or will minimally activate signal transduction. Exemplary sub-threshold signaling domains include costimulatory domains, such as CD28, CD2, CD4, CD5, CD8, CD9, CD27, CD44, CD46, CD81, CD137, LFA-1, ICAM-1, VLA-4, OX40, 4-1BB, LIGHT, SLAM, ICOS, CTLA-4, PD-1, or the like.

In particular embodiments, an encoded first fusion protein comprises a first multimerization domain of FRB T2098L, a transmembrane domain, a costimulatory domain of 4-1BB, and actuator domain of CD3ζ; wherein the second encoded fusion protein comprises a binding domain of an scFv specific for CD19 and a second multimerization domain of FKBP12, and optionally an anchor domain (e.g., transmembrane domain, GPI signal sequence) or an anchor domain with a sub-threshold signaling domain; and wherein the first bridging factor that promotes the formation of a polypeptide complex on the non-natural cell surface is rapalog AP21967. An exemplary first fusion protein has an amino acid sequence as set forth in SEQ ID NO.:15 and an exemplary second fusion protein has an amino acid sequence as set forth in SEQ ID NO.:1 or 56.

In certain embodiments, a DARIC binding component may have multiple binding domains. For example, a non-natural cell further comprises a third nucleic acid molecule encoding a third fusion protein comprising a binding domain and a second multimerization domain, optionally an anchor domain (e.g., transmembrane domain, GPI signal sequence) or an anchor domain with a sub-threshold signaling domain, wherein the third fusion protein localizes extracellularly when expressed. In related embodiments, the fusion proteins comprise a binding domain have one, two, three, or four binding domains, wherein the one, two, three, or four binding domains are specific for one target or up to four different targets.

In any of the aforementioned embodiments, a second nucleic acid molecule encoding a second (binding) fusion protein may further comprise a sequence encoding a linker, spacer or junction amino acids disposed between the binding domain and the second multimerization domain. In certain embodiments, a second nucleic acid molecule encoding a second fusion protein (e.g., DARIC binding component) further comprises an anchor domain (e.g., transmembrane domain, GPI signal sequence) and optionally a sub-threshold signaling domain. In further embodiments, a second fusion protein (e.g., DARIC binding component) contains a GPI molecule, wherein the GPI signal sequence has been removed or altered to attach the GPI molecule.

Exemplary diseases or disorders associated with excess receptor-mediated signal transduction include cancer (e.g., solid malignancy and hematologic malignancy), autoimmune or inflammatory diseases or conditions, sepsis resulting from bacterial infection, and viral infection.

In one aspect, the present disclosure provides a method for directing T cell activation, comprising administering to a subject in need thereof an effective amount of a DARIC binding component or a pharmaceutical composition thereof that specifically binds a target, such as a cell surface target that is a tumor-specific antigen or other antigen of choice at a site or cell where T cell activation is desired.

Pharmaceutically acceptable carriers for therapeutic use are also well known in the pharmaceutical art, and are described, for example, in the *Physicians Desk Reference,* 62nd edition. Oradell, NJ: Medical Economics Co., 2008; Goodman & Gilman's *The Pharmacological Basis of Therapeutics*, Eleventh Edition. McGraw-Hill, 2005; *Remington: The Science and Practice of Pharmacy,* 20th Edition. Baltimore, MD: Lippincott Williams & Wilkins, 2000; and *The Merck Index*, Fourteenth Edition. Whitehouse Station, NJ: Merck Research Laboratories, 2006; each of which is hereby incorporated by reference in relevant parts. Exemplary pharmaceutically acceptable carriers include sterile saline and phosphate buffered saline at physiological pH. Preservatives, stabilizers, dyes and the like may be provided in the pharmaceutical composition. In addition, antioxidants and suspending agents may also be used.

Pharmaceutical compositions may also contain diluents such as buffers, antioxidants such as ascorbic acid, low molecular weight (less than about 10 residues) polypeptides, proteins, amino acids, carbohydrates (e.g., glucose, sucrose, dextrins), chelating agents (e.g., EDTA), glutathione and other stabilizers and excipients. Neutral buffered saline or saline mixed with nonspecific serum albumin are exemplary diluents.

In another aspect, the present disclosure provides a method for inhibiting growth, metastasis or metastatic growth of a malignancy (e.g., a solid malignancy or a hematologic malignancy), comprising administering to a subject in need thereof an effective amount of a cell encoding a polypeptide complex provided herein or a composition thereof.

A wide variety of cancers, including solid malignancy and hematologic malignancy, are amenable to the compositions and methods disclosed herein. Types of cancer that may be treated include adenocarcinoma of the breast, prostate, pancreas, colon and rectum; all forms of bronchogenic carcinoma of the lung (including squamous cell carcinoma, adenocarcinoma, small cell lung cancer and non-small cell lung cancer); myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; non-Hodgkin's lymphoma; plasmacytoma; reticuloendotheliosis; melanoma; renal cell carcinoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor.

Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; and glioblastoma multiforme. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Additional exemplary cancers that are also amenable to the compositions and methods disclosed herein are B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia and chronic myoblastic leukemia) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt lymphoma/leukemia, B-cell proliferations of uncertain malignant potential, lymphomatoid granulomatosis, and post-transplant lymphoproliferative disorder.

In certain embodiments, cells encoding polypeptide complexes useful for inhibiting growth of a solid malignancy or metastasis or metastatic growth of a solid malignancy or a hematologic malignancy include those that specifically bind to a tumor or cancer antigen and a second target antigen on the cancer cell.

In another aspect, the present disclosure provides a method for treating an autoimmune or inflammatory disease, disorder or condition, comprising administering to a subject in need thereof an effective amount of a cell encoding a polypeptide complex provided herein or a composition thereof.

Exemplary autoimmune or inflammatory diseases, disorders or conditions that may be treated by the fusion proteins and compositions and unit dose forms thereof include inflammatory bowel disease (e.g., Crohn's disease or ulcerative colitis), diabetes mellitus (e.g., type I diabetes), dermatomyositis, polymyositis, pernicious anaemia, primary biliary cirrhosis, acute disseminated encephalomyelitis (ADEM), Addison's disease, ankylosing spondylitis, antiphospholipid antibody syndrome (APS), autoimmune hepatitis, Goodpasture's syndrome, Graves' disease, Guillain-Barré syndrome (GBS), Hashimoto's disease, idiopathic thrombocytopenic purpura, systemic lupus erythematosus, lupus nephritis, neuropsychiatric lupus, multiple sclerosis (MS), myasthenia gravis, pemphigus vulgaris, asthma, psoriatic arthritis, rheumatoid arthritis, Sjögren's syndrome, temporal arteritis (also known as "giant cell arteritis"), autoimmune hemolytic anemia, Bullous pemphigoid, vasculitis, coeliac disease, chronic obstructive pulmonary disease, endometriosis, Hidradenitis suppurativa, interstitial cystitis, morphea, scleroderma, narcolepsy, neuromyotonia, vitiligo, and autoimmune inner ear disease.

In certain embodiments, a method for treating a hyperproliferative, inflammatory, autoimmune, or graft-versus-host disease, comprises (a) administering a recombinant cell comprising a first and a second nucleic acid molecule, wherein the first nucleic acid molecule encodes a first fusion protein comprising a first multimerization domain, a hydrophobic domain, and an actuator domain, wherein the first multimerization domain localizes extracellularly when the first fusion protein is expressed, and the second nucleic acid molecule encodes a second fusion protein comprising a binding domain and a second multimerization domain, wherein the second fusion protein localizes extracellularly when expressed; and (c) administering a bridging factor, wherein the bridging factor promotes the formation of a polypeptide complex on the recombinant cell surface with the bridging factor associated with and disposed between the multimerization domains of the first and second fusion proteins; wherein the binding domain of the polypeptide complex specifically binds a cell surface target on a hyperproliferative disease cell to promote an immunomodulatory response and thereby treats the hyperproliferative disease.

In particular embodiments, a method for treating a hyperproliferative, inflammatory, autoimmune, or graft-versus-host disease, comprises (a) administering one or more recombinant cells comprising a first nucleic acid molecule and a second nucleic acid molecule, wherein the first nucleic acid molecule encodes a first fusion protein comprising a binding agent that binds a receptor expressed on a T cell and first multimerization domain, and the second nucleic acid molecule encodes a second fusion protein comprising a binding agent that binds a cell surface target on a hyperproliferative disease cell and a second multimerization domain, and (c) administering a bridging factor, wherein the bridging factor promotes the formation of a polypeptide complex, e.g., a BiTE, with the bridging factor associated with and disposed between the multimerization domains of the first and second fusion proteins; wherein the binding agent of the first fusion protein binds a receptor on a T cell and the binding agent of the second fusion protein binds a cell surface target on a hyperproliferative disease cell to promote an immunomodulatory response and thereby treats the hyperproliferative disease.

In other embodiments, a method for treating a hyperproliferative, inflammatory, autoimmune, or graft-versus-host disease, comprises (a) administering a non-natural cell comprising a first nucleic acid molecule encoding a first fusion protein comprising a first multimerization domain, a hydrophobic domain, and an actuator domain, wherein the first multimerization domain localizes extracellularly when the first fusion protein is expressed; (b) administering a second fusion protein comprising a binding domain and a second multimerization domain, optionally comprising an anchor domain (e.g., transmembrane domain, GPI signal sequence) or an anchor domain with a sub-threshold signaling domain; and (c) administering a bridging factor, wherein the bridging factor promotes the formation of a polypeptide heterocomplex on the recombinant cell surface with the bridging factor associated with and disposed between the multimerization domains of the first and second fusion proteins; wherein the binding domain of the polypeptide heterocomplex specifically binds a cell surface target on a hyperproliferative disease cell to promote an immunomodulatory response and thereby treats the hyperproliferative disease.

Any of the aforementioned non-natural cells, fusion proteins, bridging factors and other accessory molecules may be used in the methods of treatment of this disclosure. In certain embodiments, a method further comprises administering an agent that antagonizes or blocks an inhibitor of T cell activation, such as an agent that antagonizes or blocks a T cell ligand or a T cell receptor. In certain embodiments, an agent that antagonizes or blocks an inhibitor of T cell activation is an anti-PD1 antibody, anti-PD-L1 antibody, or an anti-CTLA4 antibody or antigen binding fragment thereof, or an engineered homing endonuclease that targets PD-1. In further embodiments, the method further comprises administering a cytokine agonist.

The cells, fusion proteins, bridging factors, other accessory molecules or compositions thereof of the present disclosure may be administered orally, topically, transdermally, parenterally, by inhalation spray, vaginally, rectally, or by intracranial injection, or any combination thereof. In certain embodiments, fusion proteins, bridging factors, or compositions thereof are administered parenterally. The term "parenteral," as used herein, includes subcutaneous injections, intravenous, intramuscular, intracisternal injection, or infusion techniques. Administration by intravascular, intravenous, intraarterial, intradermal, intramusclar, intramammary, intraperitoneal, intrathecal, retrobulbar, intrapulmonary injection and/or surgical implantation at a particular site is contemplated as well. In certain embodiments, fusion proteins, bridging factors, or compositions thereof are administered by injection, such as intravenously.

Also contemplated is the administration of recombinant cells with a bridging factor, recombinant cells with a fusion protein and a bridging factor, or compositions thereof in combination with a second agent. A second agent may be one accepted in the art as a standard treatment for a particular disease state or disorder, such as in cancer, inflammation, autoimmunity, and infection. Exemplary second agents contemplated include recombinant cells with a bridging factor, recombinant cells with a fusion protein and a bridging factor, or compositions thereof that bind to targets different from those that the primary protein complex binds, polyclonal antibodies, monoclonal antibodies, immunoglobulin-derived fusion proteins, chemotherapeutics, ionizing radiation, steroids, NSAIDs, anti-infective agents, or other active and ancillary agents, or any combination thereof.

Second agents useful in combination with recombinant cells with a bridging factor, recombinant cells with a fusion protein and a bridging factor, or compositions thereof provided herein may be steroids, NSAIDs, mTOR inhibitors (e.g., rapamycin (sirolimus), temsirolimus, deforolimus, everolimus, zotarolimus, curcumin, farnesylthiosalicylic acid), calcineurin inhibitors (e.g., cyclosporine, tacrolimus), anti-metabolites (e.g., mycophenolic acid, mycophenolate mofetil), polyclonal antibodies (e.g., anti-thymocyte globulin), monoclonal antibodies (e.g., daclizumab, basiliximab), and CTLA4-Ig fusion proteins (e.g., abatacept or belatacept).

Second agents useful for inhibiting growth of a solid malignancy, inhibiting metastasis or metastatic growth of a solid malignancy, or treating or ameliorating a hematologic malignancy include chemotherapeutic agents, ionizing radiation, and other anti-cancer drugs. Examples of chemotherapeutic agents contemplated as further therapeutic agents include alkylating agents, such as nitrogen mustards (e.g., mechlorethamine, cyclophosphamide, ifosfamide, melphalan, and chlorambucil); bifunctional chemotherapeutics (e.g., bendamustine); nitrosoureas (e.g., carmustine (BCNU), lomustine (CCNU), and semustine (methyl-CCNU)); ethyleneimines and methyl-melamines (e.g., triethylenemelamine (TEM), triethylene thiophosphoramide (thiotepa), and hexamethylmelamine (HMM, altretamine));

alkyl sulfonates (e.g., buslfan); and triazines (e.g., dacabazine (DTIC)); antimetabolites, such as folic acid analogues (e.g., methotrexate, trimetrexate, and pemetrexed (multi-targeted antifolate)); pyrimidine analogues (such as 5-fluorouracil (5-FU), fluorodeoxyuridine, gemcitabine, cytosine arabinoside (AraC, cytarabine), 5-azacytidine, and 2,2'-difluorodeoxycytidine); and purine analogues (e.g, 6-mercaptopurine, 6-thioguanine, azathioprine, 2'-deoxycoformycin (pentostatin), erythrohydroxynonyladenine (EHNA), fludarabine phosphate, 2-chlorodeoxyadenosine (cladribine, 2-CdA)); Type I topoisomerase inhibitors such as camptothecin (CPT), topotecan, and irinotecan; natural products, such as epipodophylotoxins (e.g., etoposide and teniposide); and vinca alkaloids (e.g., vinblastine, vincristine, and vinorelbine); anti-tumor antibiotics such as actinomycin D, doxorubicin, and bleomycin; radiosensitizers such as 5-bromodeozyuridine, 5-iododeoxyuridine, and bromodeoxycytidine; platinum coordination complexes such as cisplatin, carboplatin, and oxaliplatin; substituted ureas, such as hydroxyurea; and methylhydrazine derivatives such as N-methylhydrazine (MIH) and procarbazine.

Further therapeutic agents contemplated by this disclosure for treatment of autoimmune diseases are referred to as immunosuppressive agents, which act to suppress or mask the immune system of the individual being treated. Immunosuppressive agents include, for example, non-steroidal anti-inflammatory drugs (NSAIDs), analgesics, glucocorticoids, disease-modifying antirheumatic drugs (DMARDs) for the treatment of arthritis, or biologic response modifiers. Compositions in the DMARD description are also useful in the treatment of many other autoimmune diseases aside from rheumatoid arthritis.

Exemplary NSAIDs include ibuprofen, naproxen, naproxen sodium, Cox-2 inhibitors (such as Vioxx or Celebrex), and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone.

Exemplary biological response modifiers include molecules directed against cell surface markers (e.g., CD4, CD5, etc.), cytokine inhibitors, such as the TNF antagonists (e.g. etanercept (Enbrel), adalimumab (Humira) and infliximab (Remicade)), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In still further aspects, the instant disclosure provides a fusion polypeptide heterocomplex, comprising (a) a first fusion protein comprising a first multimerization domain, a hydrophobic domain, and an actuator domain; (b) a second fusion protein comprising an extracellular binding domain and second multimerization domain; and (c) a bridging factor; wherein the first fusion protein, second fusion protein, and bridging factor associate to form a polypeptide heterocomplex with the bridging factor associated with and disposed between the multimerization domains of the first and second fusion proteins. Any of the aforementioned fusion protein components and bridging factors and may be used in these embodiments.

In other aspects, the instant disclosure provides a nucleic acid molecule encoding any one or more of the aforementioned fusion proteins. Such nucleic acid molecules may be incorporated into an expression vector (e.g., lentiviral vector), wherein the first and second fusion proteins are encoded as a polycistronic message or as a single protein separated by a 2A peptide. In certain embodiments, the polycistronic message comprises an internal ribosome entry site (IRES) between the nucleotide sequences that encode the fusion proteins.

Illustrative examples of DARIC binding and signaling components are provided in SEQ ID NOs: 1-75 and below in Table 1.

TABLE 1

Exemplary DARIC Binding and Signaling Components

| SEQ ID NO. | Construct | Sequence |
|---|---|---|
| 1 | scFvCD19-FKBP protein | MGSDIQMTQTTSSLSASLGDRVTISCRASQDISKYLNWYQQKPDG<br>TVKLLIYHTSRLHSGVPSRFSGSGSGTDYSLTISNLEQEDIATYFCQ<br>QGNTLPYTFGGGTKLEITGSTSGSGKPGSGEGSTKGEVKLQESGP<br>GLVAPSQSLSVTCTVSGVSLPDYGVSWIRQPPRKGLEWLGVIWGS<br>ETTYYNSALKSRLTIIKDNSKSQVFLKMNSLQTDDTAIYYCAKHY<br>YYGGSYAMDYWGQGTSVTVSSASGGGGSGVQVETISPGDGRTFP<br>KRGQTCVVHYTGMLEDGKKFDSSRDRNKPFKFMLGKQEVIRGW<br>EEGVAQMSVGQRAKLTISPDYAYGATGHPGIIPPHATLVFDVELL<br>KLEG |
| 2 | SS-scFvCD19-FKBP mRNA | AUGCCCCUGGGCCUGCUGUGGCUGGGCCUGGCCCUGCUGGGC<br>GCCCUGCACGCCCAGGCCGGAUCCGAUAUCCAGAUGACCCAG<br>ACCACCAGCAGCCUGAGCGCCAGCCUGGGCGAUAGAGUGACC<br>AUCAGCUGCAGAGCCAGCCAGGACAUCAGCAAGUACCUGAA<br>CUGGUAUCAGCAGAAACCCGACGGCACCGUGAAGCUGCUGA<br>UCUACCACACCAGCAGACUGCACAGCGGCGUGCCCAGCAGAU<br>UUUCUGGCAGCGGCUCCGGCACCGACUACAGCCUGACCAUCU<br>CCAACCUGGAACAGGAAGAUAUCGCUACCUACUUCUGUCAG<br>CAAGGCAACACCCUGCCCUACACCUUCGGCGGAGGCACCAAG<br>CUGGAAAUCACCGGCAGCACAAGCGGCAGCGGCAAGCCUGG<br>AUCUGGCGAGGGAAGCACCAAGGGCGAAGUGAAACUGCAGG<br>AAAGCGGCCCUGGACUGGUGGCCCCAAGCCAGUCUCUGAGCG<br>UGACCUGUACCGUGUCCGGCGUGUCCCUGCCUGACUAUGGCG<br>UGUCCUGGAUCAGACAGCCCCCCAGAAAGGGCCUGGAAUGG<br>CUGGGAGUGAUCUGGGGCAGCGAGACAACCUACUACAACAG<br>CGCCCUGAAGUCCCGGCUGACCAUCAUCAAGGACAACUCCAA |

TABLE 1-continued

Exemplary DARIC Binding and Signaling Components

| SEQ ID NO. | Construct | Sequence |
|---|---|---|
| | | GAGCCAGGUGUUCCUGAAGAUGAACAGCCUGCAGACCGACG ACACCGCCAUCUACUACUGCGCCAAGCACUACUACUACGGCG GCAGCUACGCCAUGGACUACUGGGGCCAGGGCACAAGCGUG ACCGUGUCCAGCGCUAGCGGCGGAGGUGGGAGCGGAGUGCA GGUGGAAACCAUCUCCCCAGGAGACGGGCGCACCUUCCCCAA GCGCGGCCAGACCUGCGUGGUGCACUACACCGGGAUGCUUG AAGAUGGAAAGAAAUUUGAUUCCUCCCGGGACAGAAACAAG CCCUUUAAGUUUAUGCUAGGCAAGCAGGAGGUGAUCCGAGG CUGGGAAGAAGGGGUUGCCCAGAUGAGUGUGGGUCAGAGAG CCAAACUGACUAUAUCUCCAGAUUAUGCCUAUGGUGCCACU GGGCACCCAGGCAUCAUCCCACCACAUGCCACUCUCGUCUUC GAUGUGGAGCUUCUAAAACUGGAAGGCUGA |
| 3 | SS-scFvCD19-FKBP DNA | ATGCCCCTGGGCCTGCTGTGGCTGGGCCTGGCCCTGCTGGGCG CCCTGCACGCCCAGGCCGGATCCGATATCCAGATGACCCAGAC CACCAGCAGCCTGAGCGCCAGCCTGGGCGATAGAGTGACCAT CAGCTGCAGAGCCAGCCAGGACATCAGCAAGTACCTGAACTG GTATCAGCAGAAACCCGACGGCACCGTGAAGCTGCTGATCTAC CACACCAGCAGACTGCACAGCGGCGTGCCCAGCAGATTTTCTG GCAGCGGCTCCGGCACCGACTACAGCCTGACCATCTCCAACCT GGAACAGGAAGATATCGCTACCTACTTCTGTCAGCAAGGCAAC ACCCTGCCCTACACCTTCGGCGGAGGCACCAAGCTGGAAATCA CCGGCAGCACAAGCGGCAGCGGCAAGCCTGGATCTGGCGAGG GAAGCACCAAGGGCGAAGTGAAACTGCAGGAAAGCGGCCCTG GACTGGTGGCCCCAAGCCAGTCTCTGAGCGTGACCTGTACCGT GTCCGGCGTGTCCCTGCCTGACTATGGCGTGTCCTGGATCAGA CAGCCCCCCAGAAAGGGCCTGGAATGGCTGGGAGTGATCTGG GGCAGCGAGACAACCTACTACAACAGCGCCCTGAAGTCCCGG CTGACCATCATCAAGGACAACTCCAAGAGCCAGGTGTTCCTGA AGATGAACAGCCTGCAGACCGACGACACCGCCATCTACTACTG CGCCAAGCACTACTACTACGGCGGCAGCTACGCCATGGACTAC TGGGGCCAGGGCACAAGCGTGACCGTGTCCAGCGCTAGCGGC GGAGGTGGGAGCGGAGTGCAGGTGGAAACCATCTCCCCAGGA GACGGGCGCACCTTCCCCAAGCGCGGCCAGACCTGCGTGGTGC ACTACACCGGGATGCTTGAAGATGGAAAGAAATTTGATTCCTC CCGGGACAGAAACAAGCCCTTTAAGTTTATGCTAGGCAAGCA GGAGGTGATCCGAGGCTGGGAAGAAGGGGTTGCCCAGATGAG TGTGGGTCAGAGAGCCAAACTGACTATATCTCCAGATTATGCC TATGGTGCCACTGGGCACCCAGGCATCATCCCACCACATGCCA CTCTCGTCTTCGATGTGGAGCTTCTAAAACTGGAAGGCTGA |
| 4 | scFvCD19-FKBP (F36V) protein | MGSDIQMTQTTSSLSASLGDRVTISCRASQDISKYLNWYQQKPDG TVKLLIYHTSRLHSGVPSRFSGSGSGTDYSLTISNLEQEDIATYFCQ QGNTLPYTFGGGTKLEITGSTSGSGKPGSGEGSTKGEVKLQESGP GLVAPSQSLSVTCTVSGVSLPDYGVSWIRQPPRKGLEWLGVIWGS ETTYYNSALKSRLTIIKDNSKSQVFLKMNSLQTDDTAIYYCAKHY YYGGSYAMDYWGQGTSVTVSSASGGGGSGVQVETISPGDGRTFP KRGQTCVVHYTGMLEDGKKVDSSRDRNKPFKFMLGKQEVIRGW EEGVAQMSVGQRAKLTISPDYAYGATGHPGIIPPHATLVFDVELL KLEG |
| 5 | SS-scFvCD19-FKBP (F36V) mRNA | AUGCCCCUGGGCCUGCUGUGGCUGGGCCUGGCCCUGCUGGGC GCCCUGCACGCCCAGGCCGGAUCCGAUAUCCAGAUGACCCAG ACCACCAGCAGCCUGAGCGCCAGCCUGGGCGAUAGAGUGACC AUCAGCUGCAGAGCCAGCCAGGACAUCAGCAAGUACCUGAA CUGGUAUCAGCAGAAACCCGACGGCACCGUGAAGCUGCUGA UCUACCACACCAGCAGACUGCACAGCGGCGUGCCCAGCAGAU UUUCUGGCAGCGGCUCCGGCACCGACUACAGCCUGACCAUCU CCAACCUGGAACAGGAAGAUAUCGCUACCUACUUCUGUCAG CAAGGCAACACCCUGCCCUACACCUUCGGCGGAGGCACCAAG CUGGAAAUCACCGGCAGCACAAGCGGCAGCGGCAAGCCUGG AUCUGGCGAGGGAAGCACCAAGGGCGAAGUGAAACUGCAGG AAAGCGGCCCUGGACUGGUGGCCCCAAGCCAGUCUCUGAGCG UGACCUGUACCGUGUCCGGCGUGUCCCUGCCUGACUAUGGCG UGUCCUGGAUCAGACAGCCCCCCAGAAAGGGCCUGGAAUGG CUGGGAGUGAUCUGGGGCAGCGAGACAACCUACUACAACAG CGCCCUGAAGUCCCGGCUGACCAUCAUCAAGGACAACUCCAA GAGCCAGGUGUUCCUGAAGAUGAACAGCCUGCAGACCGACG ACACCGCCAUCUACUACUGCGCCAAGCACUACUACUACGGCG GCAGCUACGCCAUGGACUACUGGGGCCAGGGCACAAGCGUG ACCGUGUCCAGCGCUAGCGGCGGAGGUGGGAGCGGAGUGCA GGUGGAAACCAUCUCCCCAGGAGACGGGCGCACCUUCCCCAA GCGCGGCCAGACCUGCGUGGUGCACUACACCGGGAUGCUUG AAGAUGGAAAGAAAGUUGAUUCCUCCCGGGACAGAAACAAG |

TABLE 1-continued

Exemplary DARIC Binding and Signaling Components

| SEQ ID NO. | Construct | Sequence |
|---|---|---|
| | | CCCUUUAAGUUUAUGCUAGGCAAGCAGGAGGUGAUCCGAGG<br>CUGGGAAGAAGGGGUUGCCCAGAUGAGUGUGGGUCAGAGAG<br>CCAAACUGACUAUAUCUCCAGAUUAUGCCUAUGGUGCCACU<br>GGGCACCCAGGCAUCAUCCCACCACAUGCCACUCUCGUCUUC<br>GAUGUGGAGCUUCUAAAACUGGAAGGCUGA |
| 6 | SS-scFvCD19-FKBP (F36V) DNA | ATGCCCCTGGGCCTGCTGTGGCTGGGCCTGGCCCTGCTGGGCG<br>CCCTGCACGCCCAGGCCGGATCCGATATCCAGATGACCCAGAC<br>CACCAGCAGCCTGAGCGCCAGCCTGGGCGATAGAGTGACCAT<br>CAGCTGCAGAGCCAGCCAGGACATCAGCAAGTACCTGAACTG<br>GTATCAGCAGAAACCCGACGGCACCGTGAAGCTGCTGATCTAC<br>CACACCAGCAGACTGCACAGCGGCGTGCCCAGCAGATTTTCTG<br>GCAGCGGCTCCGGCACCGACTACAGCCTGACCATCTCCAACCT<br>GGAACAGGAAGATATCGCTACCTACTTCTGTCAGCAAGGCAAC<br>ACCCTGCCCTACACCTTCGGCGGAGGCACCAAGCTGGAAATCA<br>CCGGCAGCACAAGCGGCAGCGGCAAGCCTGGATCTGGCGAGG<br>GAAGCACCAAGGGCGAAGTGAAACTGCAGGAAAGCGGCCCTG<br>GACTGGTGGCCCCAAGCCAGTCTCTGAGCGTGACCTGTACCGT<br>GTCCGGCGTGTCCCTGCCTGACTATGGCGTGTCCTGGATCAGA<br>CAGCCCCCCAGAAAGGGCCTGGAATGGCTGGGAGTGATCTGG<br>GGCAGCGAGACAACCTACTACAACAGCGCCCTGAAGTCCCGG<br>CTGACCATCATCAAGGACAACTCCAAGAGCCAGGTGTTCCTGA<br>AGATGAACAGCCTGCAGACCGACGACACCGCCATCTACTACTG<br>CGCCAAGCACTACTACTACGGCGGCAGCTACGCCATGGACTAC<br>TGGGGCCAGGGCACAAGCGTGACCGTGTCCAGCGCTAGCGGC<br>GGAGGTGGGAGCGGAGTGCAGGTGGAAACCATCTCCCCAGGA<br>GACGGGCGCACCTTCCCCAAGCGCGGCCAGACCTGCGTGGTGC<br>ACTACACCGGGATGCTTGAAGATGGAAAGAAAGTTGATTCCTC<br>CCGGGACAGAAACAAGCCCTTTAAGTTTATGCTAGGCAAGCA<br>GGAGGTGATCCGAGGCTGGGAAGAAGGGGTTGCCCAGATGAG<br>TGTGGGTCAGAGAGCCAAACTGACTATATCTCCAGATTATGCC<br>TATGGTGCCACTGGGCACCCAGGCATCATCCCACCACATGCCA<br>CTCTCGTCTTCGATGTGGAGCTTCTAAAACTGGAAGGCTGA |
| 7 | scFvCD19-FRB (T2098L) protein | MGSDIQMTQTTSSLSASLGDRVTISCRASQDISKYLNWYQQKPDG<br>TVKLLIYHTSRLHSGVPSRFSGSGSGTDYSLTISNLEQEDIATYFCQ<br>QGNTLPYTFGGGTKLEITGSTSGSGKPGSGEGSTKGEVKLQESGP<br>GLVAPSQSLSVTCTVSGVSLPDYGVSWIRQPPRKGLEWLGVIWGS<br>ETTYYNSALKSRLTIIKDNSKSQVFLKMNSLQTDDTAIYYCAKHY<br>YYGGSYAMDYWGQGTSVTVSSASGGGGSILWHEMWHEGLEEA<br>SRLYFGERNVKGMFEVLEPLHAMMERGPQTLKETSFNQAYGRDL<br>MEAQEWCRKYMKSGNVKDLLQAWDLYYHVFRRISKG |
| 8 | SS-scFvCD19-FRB (T2098L) mRNA | AUGCCCCUGGGCCUGCUGUGGCUGGGCCUGGCCCUGCUGGGC<br>GCCCUGCACGCCCAGGCCGGAUCCGAUAUCCAGAUGACCCAG<br>ACCACCAGCAGCCUGAGCGCCAGCCUGGGCGAUAGAGUGACC<br>AUCAGCUGCAGAGCCAGCCAGGACAUCAGCAAGUACCUGAA<br>CUGGUAUCAGCAGAAACCCGACGGCACCGUGAAGCUGCUGA<br>UCUACCACACCAGCAGACUGCACAGCGGCGUGCCCAGCAGAU<br>UUUCUGGCAGCGGCUCCGGCACCGACUACAGCCUGACCAUCU<br>CCAACCUGGAACAGGAAGAUAUCGCUACCUACUUCUGUCAG<br>CAAGGCAACACCCUGCCCUACACCUUCGGCGGAGGCACCAAG<br>CUGGAAAUCACCGGCAGCACAAGCGGCAGCGGCAAGCCUGG<br>AUCUGGCGAGGGAAGCACCAAGGGCGAAGUGAAACUGCAGG<br>AAAGCGGCCCUGGACUGGUGGCCCCAAGCCAGUCUCUGAGCG<br>UGACCUGUACCGUGUCCGGCGUGUCCCUGCCUGACUAUGGCG<br>UGUCCUGGAUCAGACAGCCCCCCAGAAAGGGCCUGGAAUGG<br>CUGGGAGUGAUCUGGGGCAGCGAGACAACCUACUACAACAG<br>CGCCCUGAAGUCCCGGCUGACCAUCAUCAAGGACAACUCCAA<br>GAGCCAGGUGUUCCUGAAGAUGAACAGCCUGCAGACCGACG<br>ACACCGCCAUCUACUACUGCGCCAAGCACUACUACUACGGCG<br>GCAGCUACGCCAUGGACUACUGGGGCCAGGGCACAAGCGUG<br>ACCGUGUCCAGCGCUAGCGGCGGAGGUGGGAGCAUCCUCUG<br>GCAUGAGAUGUGGCAUGAAGGCCUGGAAGAGGCAUCUCGUU<br>UGUACUUUGGGGAAAGGAACGUGAAAGGCAUGUUUGAGGUG<br>CUGGAGCCCUUGCAUGCUAUGAUGGAACGGGGCCCCCAGAC<br>UCUGAAGGAAACAUCCUUUAAUCAGGCCUAUGGUCGAGAUU<br>UAAUGGAGGCCCAAGAGUGGUGCAGGAAGUACAUGAAAUCA<br>GGGAAUGUCAAGGACCUCCUCCAAGCCUGGGACCUCUAUUA<br>UCAUGUGUUCCGACGAAUCUCAAAGGGCUGA |
| 9 | SS-scFvCD19-FRB (T2098L) DNA | ATGCCCCTGGGCCTGCTGTGGCTGGGCCTGGCCCTGCTGGGCG<br>CCCTGCACGCCCAGGCCGGATCCGATATCCAGATGACCCAGAC<br>CACCAGCAGCCTGAGCGCCAGCCTGGGCGATAGAGTGACCAT |

TABLE 1-continued

Exemplary DARIC Binding and Signaling Components

| SEQ ID NO. | Construct | Sequence |
|---|---|---|
| | | CAGCTGCAGAGCCAGCCAGGACATCAGCAAGTACCTGAACTG GTATCAGCAGAAACCCGACGGCACCGTGAAGCTGCTGATCTAC CACACCAGCAGACTGCACAGCGGCGTGCCCAGCAGATTTTCTG GCAGCGGCTCCGGCACCGACTACAGCCTGACCATCTCCAACCT GGAACAGGAAGATATCGCTACCTACTTCTGTCAGCAAGGCAAC ACCCTGCCCTACACCTTCGGCGGAGGCACCAAGCTGGAAATCA CCGGCAGCACAAGCGGCAGCGGCAAGCCTGGATCTGGCGAGG GAAGCACCAAGGGCGAAGTGAAACTGCAGGAAAGCGGCCCTG GACTGGTGGCCCCAAGCCAGTCTCTGAGCGTGACCTGTACCGT GTCCGGCGTGTCCCTGCCTGACTATGGCGTGTCCTGGATCAGA CAGCCCCCCAGAAAGGGCCTGGAATGGCTGGGAGTGATCTGG GGCAGCGAGACAACCTACTACAACAGCGCCCTGAAGTCCCGG CTGACCATCATCAAGGACAACTCCAAGAGCCAGGTGTTCCTGA AGATGAACAGCCTGCAGACCGACGACACCGCCATCTACTACTG CGCCAAGCACTACTACTACGGCGGCAGCTACGCCATGGACTAC TGGGGCCAGGGCACAAGCGTGACCGTGTCCAGCGCTAGCGGC GGAGGTGGGAGCATCCTCTGGCATGAGATGTGGCATGAAGGC CTGGAAGAGGCATCTCGTTTGTACTTTGGGGAAAGGAACGTGA AAGGCATGTTTGAGGTGCTGGAGCCCTTGCATGCTATGATGGA ACGGGGCCCCCAGACTCTGAAGGAAACATCCTTTAATCAGGCC TATGGTCGAGATTTAATGGAGGCCCAAGAGTGGTGCAGGAAG TACATGAAATCAGGGAATGTCAAGGACCTCCTCCAAGCCTGGG ACCTCTATTATCATGTGTTCCGACGAATCTCAAAGGGCTGA |
| 13 | scFvCD19-TM-41BB-CD3z-BFP mRNA | AUGGCUCUGCCUGUGACAGCUCUGCUGCUGCCUCUGGCCCUG CUGCUCCAUGCCGCCAGACCCGGAUCCGAUAUCCAGAUGACC CAGACCACCAGCAGCCUGAGCGCCAGCCUGGGCGAUAGAGUG ACCAUCAGCUGCAGAGCCAGCCAGGACAUCAGCAAGUACCUG AACUGGUAUCAGCAGAAACCCGACGGCACCGUGAAGCUGCU GAUCUACCACACCAGCAGACUGCACAGCGGCGUGCCCAGCAG AUUUUCUGGCAGCGGCUCCGGCACCGACUACAGCCUGACCAU CUCCAACCUGGAACAGGAAGAUAUCGCUACCUACUUCUGUC AGCAAGGCAACACCCUGCCCUACACCUUCGGCGGAGGCACCA AGCUGGAAAUCACCGGCAGCACAAGCGGCAGCGGCAAGCCU GGAUCUGGCGAGGGAAGCACCAAGGGCGAAGUGAAACUGCA GGAAAGCGGCCCUGGACUGGUGGCCCCAAGCCAGUCUCUGA GCGUGACCUGUACCGUGUCCGGCGUGUCCCUGCCUGACUAUG GCGUGUCCUGGAUCAGACAGCCACCCAGAAAGGGCCUGGAA UGGCUGGGAGUGAUCUGGGGCAGCGAGACAACCUACUACAA CAGCGCCCUGAAGUCCCGGCUGACCAUCAUCAAGGACAACUC CAAGAGCCAGGUGUUCCUGAAGAUGAACAGCCUGCAGACCG ACGACACCGCCAUCUACUACUGCGCCAAGCACUACUACUACG GCGGCAGCUACGCCAUGGACUACUGGGGCCAGGGCACAAGC GUGACCGUGUCCAGCGCUAGCGCCAAGCCUACCACCACCCCU GCCCCUAGACCUCCAACACCCGCCCCAACAAUCGCCAGCCAG CCUCUGUCUCUGAGGCCCGAGGCUUGUAGACCAGCUGCUGGC GGAGCCGUGCACACCAGAGGACUGGAUUUCGCCUGCGACAU CUACAUCUGGGCCCCUCUGGCCGGCACAUGUGGCGUGCUGCU GCUGAGCCUCGUGAUCACCAUGCAUAAACGGGGCAGAAAGA AACUCCUGUAUAUAUUCAAACAACCAUUUAUGAGACCAGUA CAAACUACUCAAGAGGAAGAUGGCUGUAGCUGCCGAUUUCC AGAAGAAGAAGAAGGAGGAUGUGAACUGCGGGUGAAGUUCA GCAGAAGCGCCGACGCCCCUGCCUACCAGCAGGGCCAGAAUC AGCUGUACAACGAGCUGAACCUGGGCAGAAGGGAAGAGUAC GACGUCCUGGAUAAGCGGAGAGGCCGGGACCCUGAGAUGGG CGGCAAGCCUCGGCGGAAGAACCCCCAGGAAGGCCUGUAUA ACGAACUGCAGAAAGACAAGAUGGCCGAGGCCUACAGCGAG AUCGGCAUGAAGGGCGAGCGGAGGCGGGGCAAGGGCCACGA CGGCCUGUAUCAGGGCCUGUCCACCGCCACCAAGGAUACCUA CGACGCCCUGCACAUGCAGGCCCUGCCCCCAAGGGGCGGCCG CUCCGGUGAGGGCAGAGGAAGUCUUCUAACAUGCGGUGACG UGGAGGAGAAUCCGGGCCCCUCUAGAAGCGAGCUGAUUAAG GAGAACAUGCACAUGAAGCUGUACAUGGAGGGCACCGUGGA CAACCAUCACUUCAAGUGCACAUCCGAGGGCGAAGGCAAGCC CUACGAGGGCACCCAGACCAUGAGAAUCAAGGUGGUCGAGG GCGGCCCUCUCCCCUUCGCCUUCGACAUCCUGGCUACUAGCU UCCUCUACGGCAGCAAGACCUUCAUCAACCACACCCAGGGCA UCCCCGACUUCUUCAAGCAGUCCUUCCCUGAGGGCUUCACAU GGGAGAGAGUCACCACAUACGAAGACGGGGGCGUGCUGACC GCUACCCAGGACACCAGCCUCCAGGACGGCUGCCUCAUCUAC AACGUCAAGAUCAGAGGGGUGAACUUCACAUCCAACGGCCC UGUGAUGCAGAAGAAAACACUCGGCUGGGAGGCCUUCACCG AGACGCUGUACCCCGCUGACGGCGGCCUGGAAGGCAGAAAC GACAUGGCCCUGAAGCUCGUGGGCGGGAGCCAUCUGAUCGC |

TABLE 1-continued

Exemplary DARIC Binding and Signaling Components

| SEQ ID NO. | Construct | Sequence |
|---|---|---|
| | | AAACAUCAAGACCACAUAUAGAUCCAAGAAACCCGCUAAGA<br>ACCUCAAGAUGCCUGGCGUCUACUAUGUGGACUACAGACUG<br>GAAAGAAUCAAGGAGGCCAACAACGAGACCUACGUCGAGCA<br>GCACGAGGUGGCAGUGGCCAGAUACUGCGACCUCCCUAGCA<br>AACUGGGGCACAAGCUUAAUUGA |
| 15 | FRB(T2098L)-TM-41BB-CD3z protein | MGSILWHEMWHEGLEEASRLYFGERNVKGMFEVLEPLHAMMER<br>GPQTLKETSFNQAYGRDLMEAQEWCRKYMKSGNVKDLLQAWD<br>LYYHVFRRISKASAKPTTTPAPRPPTPAPTIASQPLSLRPEACRPAA<br>GGAVHTRGLDFACDIYIWAPLAGTCGVLLLSLVITMHKRGRKKL<br>LYIFKQPFMRPVQTTQEEDGCSCRFPEEEEGGCELRVKFSRSADAP<br>AYQQGQNQLYNELNLGRREEYDVLDKRRGRDPEMGGKPRRKNP<br>QEGLYNELQKDKMAEAYSEIGMKGERRRGKGHDGLYQGLSTAT<br>KDTYDALHMQALPPRG |
| 16 | SS-FRB(T2098L)-TM-41BB-CD3z mRNA | AUGGCUCUGCCUGUGACAGCUCUGCUGCUGCCUCUGGCCCUG<br>CUGCUCCAUGCCGCCAGACCCGGAUCCAUCCUCUGGCAUGAG<br>AUGUGGCAUGAAGGCCUGGAAGAGGCAUCUCGUUUGUACUU<br>UGGGGAAAGGAACGUGAAAGGCAUGUUUGAGGUGCUGGAGC<br>CCUUGCAUGCUAUGAUGGAACGGGGCCCCCAGACUCUGAAG<br>GAAACAUCCUUUAAUCAGGCCUAUGGUCGAGAUUUAAUGGA<br>GGCCCAAGAGUGGUGCAGGAAGUACAUGAAAUCAGGGAAUG<br>UCAAGGACCUCCUCCAAGCCUGGGACCUCUAUUAUCAUGUG<br>UUCCGACGAAUCUCAAAGGCUAGCGCCAAGCCUACCACCACC<br>CCUGCCCCUAGACCUCCAACACCCGCCCCAACAAUCGCCAGC<br>CAGCCUCUGUCUCUGAGGCCCGAGGCUUGUAGACCAGCUGCU<br>GGCGGAGCCGUGCACACCAGAGGACUGGAUUUCGCCUGCGA<br>CAUCUACAUCUGGGCCCCUCUGGCCGGCACAUGUGGCGUGCU<br>GCUGCUGAGCCUCGUGAUCACCAUGCAUAAACGGGGCAGAA<br>AGAAACUCCUGUAUAUAUUCAAACAACCAUUUAUGAGACCA<br>GUACAAACUACUCAAGAGGAAGAUGGCUGUAGCUGCCGAUU<br>UCCAGAAGAAGAAGAAGGAGGAUGUGAACUGCGGGUGAAGU<br>UCAGCAGAAGCGCCGACGCCCCUGCCUACCAGCAGGGCCAGA<br>AUCAGCUGUACAACGAGCUGAACCUGGGCAGAAGGGAAGAG<br>UACGACGUCCUGGAUAAGCGGAGAGGCCGGGACCCUGAGAU<br>GGGCGGCAAGCCUCGGCGGAAGAACCCCCAGGAAGGCCUGU<br>AUAACGAACUGCAGAAAGACAAGAUGGCCGAGGCCUACAGC<br>GAGAUCGGCAUGAAGGGCGAGCGGAGGCGGGGCAAGGGCCA<br>CGACGGCCUGUAUCAGGGCCUGUCCACCGCCACCAAGGAUAC<br>CUACGACGCCCUGCACAUGCAGGCCCUGCCCCCAAGGGGC |
| 17 | SS-FRB(T2098L)-TM-41BB-CD3z DNA | ATGGCTCTGCCTGTGACAGCTCTGCTGCTGCCTCTGGCCCTGCT<br>GCTCCATGCCGCCAGACCCGGATCCATCCTCTGGCATGAGATG<br>TGGCATGAAGGCCTGGAAGAGGCATCTCGTTTGTACTTTGGGG<br>AAAGGAACGTGAAAGGCATGTTTGAGGTGCTGGAGCCCTTGC<br>ATGCTATGATGGAACGGGGCCCCCAGACTCTGAAGGAAACAT<br>CCTTTAATCAGGCCTATGGTCGAGATTTAATGGAGGCCCAAGA<br>GTGGTGCAGGAAGTACATGAAATCAGGGAATGTCAAGGACCT<br>CCTCCAAGCCTGGGACCTCTATTATCATGTGTTCCGACGAATCT<br>CAAAGGCTAGCGCCAAGCCTACCACCACCCCTGCCCCTAGACC<br>TCCAACACCCGCCCCAACAATCGCCAGCCAGCCTCTGTCTCTG<br>AGGCCCGAGGCTTGTAGACCAGCTGCTGGCGGAGCCGTGCAC<br>ACCAGAGGACTGGATTTCGCCTGCGACATCTACATCTGGGCCC<br>CTCTGGCCGGCACATGTGGCGTGCTGCTGCTGAGCCTCGTGAT<br>CACCATGCATAAACGGGGCAGAAAGAAACTCCTGTATATATTC<br>AAACAACCATTTATGAGACCAGTACAAACTACTCAAGAGGAA<br>GATGGCTGTAGCTGCCGATTTCCAGAAGAAGAAGAAGGAGGA<br>TGTGAACTGCGGGTGAAGTTCAGCAGAAGCGCCGACGCCCCT<br>GCCTACCAGCAGGGCCAGAATCAGCTGTACAACGAGCTGAAC<br>CTGGGCAGAAGGGAAGAGTACGACGTCCTGGATAAGCGGAGA<br>GGCCGGGACCCTGAGATGGGCGGCAAGCCTCGGCGGAAGAAC<br>CCCCAGGAAGGCCTGTATAACGAACTGCAGAAAGACAAGATG<br>GCCGAGGCCTACAGCGAGATCGGCATGAAGGGCGAGCGGAGG<br>CGGGGCAAGGGCCACGACGGCCTGTATCAGGGCCTGTCCACC<br>GCCACCAAGGATACCTACGACGCCCTGCACATGCAGGCCCTGC<br>CCCCAAGGGGC |
| 18 | SS-FRB(T2098L)-spacer-TM-41BB-CD3z DNA | ATGGCTCTGCCTGTGACAGCTCTGCTGCTGCCTCTGGCCCTGCT<br>GCTCCATGCCGCCAGACCCGGATCCATCCTCTGGCATGAGATG<br>TGGCATGAAGGCCTGGAAGAGGCATCTCGTTTGTACTTTGGGG<br>AAAGGAACGTGAAAGGCATGTTTGAGGTGCTGGAGCCCTTGC<br>ATGCTATGATGGAACGGGGCCCCCAGACTCTGAAGGAAACAT<br>CCTTTAATCAGGCCTATGGTCGAGATTTAATGGAGGCCCAAGA<br>GTGGTGCAGGAAGTACATGAAATCAGGGAATGTCAAGGACCT |

TABLE 1-continued

Exemplary DARIC Binding and Signaling Components

| SEQ ID NO. | Construct | Sequence |
|---|---|---|
| | | CCTCCAAGCCTGGGACCTCTATTATCATGTGTTCCGACGAATCT<br>CAAAGGCTAGCGAGAGCAAGTACGGACCGCCCTGCCCACCTT<br>GCCCTGCCCCCGAGTTCCTGGGCGGACCCAGCGTGTTCCTGTT<br>CCCACCCAAGCCCAAGGACACCCTGATGATCAGCCGGACCCCC<br>GAGGTGACCTGCGTGGTGGTGGACGTGAGCCAGGAAGATCCC<br>GAGGTCCAGTTCAATTGGTACGTGGACGGCGTGGAAGTGCAC<br>AACGCCAAGACCAAGCCCAGAGAGGAACAGTTCAACAGCACC<br>TACCGGGTGGTGTCTGTGCTGACCGTGCTGCACCAGGACTGGC<br>TGAACGGCAAAGAATACAAGTGCAAGGTGTCCAACAAGGGCC<br>TGCCCAGCAGCATCGAAAAGACCATCAGCAAGGCCAAGGGCC<br>AGCCTCGCGAGCCCCAGGTGTACACCCTGCCTCCCTCCCAGGA<br>AGAGATGACCAAGAACCAGGTGTCCCTGACCTGCCTGGTGAA<br>GGGCTTCTACCCCAGCGACATCGCCGTGGAGTGGGAGAGCAA<br>CGGCCAGCCTGAGAACAACTACAAGACCACCCCTCCCGTGCTG<br>GACAGCGACGGCAGCTTCTTCCTGTACAGCCGGCTGACCGTGG<br>ACAAGAGCCGGTGGCAGGAAGGCAACGTCTTTAGCTGCAGCG<br>TGATGCACGAGGCCCTGCACAACCACTACACCCAGAAGAGCC<br>TGAGCCTGTCCCTGGGCAAGATGCATAAACGGGGCAGAAAGA<br>AACTCCTGTATATATTCAAACAACCATTTATGAGACCAGTACA<br>AACTACTCAAGAGGAAGATGGCTGTAGCTGCCGATTTCCAGAA<br>GAAGAAGAAGGAGGATGTGAACTGCGGGTGAAGTTCAGCAGA<br>AGCGCCGACGCCCCTGCCTACCAGCAGGGCCAGAATCAGCTGT<br>ACAACGAGCTGAACCTGGGCAGAAGGGAAGAGTACGACGTCC<br>TGGATAAGCGGAGAGGCCGGGACCCTGAGATGGGCGGCAAGC<br>CTCGGCGGAAGAACCCCCAGGAAGGCCTGTATAACGAACTGC<br>AGAAAGACAAGATGGCCGAGGCCTACAGCGAGATCGGCATGA<br>AGGGCGAGCGGAGGCGGGGCAAGGGCCACGACGGCCTGTATC<br>AGGGCCTGTCCACCGCCACCAAGGATACCTACGACGCCCTGCA<br>CATGCAGGCCCTGCCCCCAAGGGGC |
| 19 | FKBP(F36V)-TM-41BB-CD3z protein | MGSGVQVETISPGDGRTFPKRGQTCVVHYTGMLEDGKKVDSSRD<br>RNKPFKFMLGKQEVIRGWEEGVAQMSVGQRAKLTISPDYAYGA<br>TGHPGIIPPHATLVFDVELLKLEASAKPTTTPAPRPPTPAPTIASQPL<br>SLRPEACRPAAGGAVHTRGLDFACDIYIWAPLAGTCGVLLLSLVI<br>TMHKRGRKKLLYIFKQPFMRPVQTTQEEDGCSCRFPEEEEGGCEL<br>RVKFSRSADAPAYQQGQNQLYNELNLGRREEYDVLDKRRGRDP<br>EMGGKPRRKNPQEGLYNELQKDKMAEAYSEIGMKGERRRGKGH<br>DGLYQGLSTATKDTYDALHMQALPPRG |
| 20 | SS-FKBP(F36V)-TM-41BB-CD3z mRNA | AUGGCUCUGCCUGUGACAGCUCUGCUGCUGCCUCUGGCCCUG<br>CUGCUCCAUGCCGCCAGACCCGGAUCCGGAGUGCAGGUGGAA<br>ACCAUCUCCCCAGGAGACGGGCGCACCUUCCCCAAGCGCGGC<br>CAGACCUGCGUGGUGCACUACACCGGGAUGCUUGAAGAUGG<br>AAAGAAAGUUGAUUCCUCCCGGGACAGAAACAAGCCCUUUA<br>AGUUUAUGCUAGGCAAGCAGGAGGUGAUCCGAGGCUGGGAA<br>GAAGGGGUUGCCCAGAUGAGUGUGGGUCAGAGAGCCAAACU<br>GACUAUAUCUCCAGAUUAUGCCUAUGGUGCCACUGGGCACC<br>CAGGCAUCAUCCCACCACAUGCCACUCUCGUCUUCGAUGUGG<br>AGCUUCUAAAACUGGAAGCUAGCGCCAAGCCUACCACCACCC<br>CUGCCCCUAGACCUCCAACACCCGCCCCAACAAUCGCCAGCC<br>AGCCUCUGUCUCUGAGGCCCGAGGCUUGUAGACCAGCUGCU<br>GGCGGAGCCGUGCACACCAGAGGACUGGAUUUCGCCUGCGA<br>CAUCUACAUCUGGGCCCCUCUGGCCGGCACAUGUGGCGUGCU<br>GCUGCUGAGCCUCGUGAUCACCAUGCAUAAACGGGGCAGAA<br>AGAAACUCCUGUAUAUAUUCAAACAACCAUUUAUGAGACCA<br>GUACAAACUACUCAAGAGGAAGAUGGCUGUAGCUGCCGAUU<br>UCCAGAAGAAGAAGAAGGAGGAUGUGAACUGCGGGUGAAGU<br>UCAGCAGAAGCGCCGACGCCCCUGCCUACCAGCAGGGCCAGA<br>AUCAGCUGUACAACGAGCUGAACCUGGGCAGAAGGGAAGAG<br>UACGACGUCCUGGAUAAGCGGAGAGGCCGGGACCCUGAGAU<br>GGGCGGCAAGCCUCGGCGGAAGAACCCCCAGGAAGGCCUGU<br>AUAACGAACUGCAGAAAGACAAGAUGGCCGAGGCCUACAGC<br>GAGAUCGGCAUGAAGGGCGAGCGGAGGCGGGGCAAGGGCCA<br>CGACGGCCUGUAUCAGGGCCUGUCCACCGCCACCAAGGAUAC<br>CUACGACGCCCUGCACAUGCAGGCCCUGCCCCCAAGGGGC |
| 21 | SS-FKBP(F36V)-TM-41BB-CD3z DNA | ATGGCTCTGCCTGTGACAGCTCTGCTGCTGCCTCTGGCCCTGCT<br>GCTCCATGCCGCCAGACCCGGATCCGGAGTGCAGGTGGAAAC<br>CATCTCCCCAGGAGACGGGCGCACCTTCCCCAAGCGCGGCCAG<br>ACCTGCGTGGTGCACTACACCGGGATGCTTGAAGATGGAAAG<br>AAAGTTGATTCCTCCCGGGACAGAAACAAGCCCTTTAAGTTTA<br>TGCTAGGCAAGCAGGAGGTGATCCGAGGCTGGGAAGAAGGGG<br>TTGCCCAGATGAGTGTGGGTCAGAGAGCCAAACTGACTATATC<br>TCCAGATTATGCCTATGGTGCCACTGGGCACCCAGGCATCATC |

TABLE 1-continued

Exemplary DARIC Binding and Signaling Components

| SEQ ID NO. | Construct | Sequence |
|---|---|---|
| | | CCACCACATGCCACTCTCGTCTTCGATGTGGAGCTTCTAAAAC<br>TGGAAGCTAGCGCCAAGCCTACCACCACCCCTGCCCCTAGACC<br>TCCAACACCCGCCCCAACAATCGCCAGCCAGCCTCTGTCTCTG<br>AGGCCCGAGGCTTGTAGACCAGCTGCTGGCGGAGCCGTGCAC<br>ACCAGAGGACTGGATTTCGCCTGCGACATCTACATCTGGGCCC<br>CTCTGGCCGGCACATGTGGCGTGCTGCTGCTGAGCCTCGTGAT<br>CACCATGCATAAACGGGGCAGAAAGAAACTCCTGTATATATTC<br>AAACAACCATTTATGAGACCAGTACAAACTACTCAAGAGGAA<br>GATGGCTGTAGCTGCCGATTTCCAGAAGAAGAAGAAGGAGGA<br>TGTGAACTGCGGGTGAAGTTCAGCAGAAGCGCCGACGCCCCT<br>GCCTACCAGCAGGGCCAGAATCAGCTGTACAACGAGCTGAAC<br>CTGGGCAGAAGGGAAGAGTACGACGTCCTGGATAAGCGGAGA<br>GGCCGGGACCCTGAGATGGGCGGCAAGCCTCGGCGGAAGAAC<br>CCCCAGGAAGGCCTGTATAACGAACTGCAGAAAGACAAGATG<br>GCCGAGGCCTACAGCGAGATCGGCATGAAGGGCGAGCGGAGG<br>CGGGGCAAGGGCCACGACGGCCTGTATCAGGGCCTGTCCACC<br>GCCACCAAGGATACCTACGACGCCCTGCACATGCAGGCCCTGC<br>CCCCAAGGGGC |
| 22 | SS-FKBP(F36V)-spacer-TM-41BB-CD3z DNA | ATGGCTCTGCCTGTGACAGCTCTGCTGCTGCCTCTGGCCCTGCT<br>GCTCCATGCCGCCAGACCCGGATCCGGAGTGCAGGTGGAAAC<br>CATCTCCCCAGGAGACGGGCGCACCTTCCCCAAGCGCGGCCAG<br>ACCTGCGTGGTGCACTACACCGGGATGCTTGAAGATGGAAAG<br>AAAGTTGATTCCTCCCGGGACAGAAACAAGCCCTTTAAGTTTA<br>TGCTAGGCAAGCAGGAGGTGATCCGAGGCTGGGAAGAAGGGG<br>TTGCCCAGATGAGTGTGGGTCAGAGAGCCAAACTGACTATATC<br>TCCAGATTATGCCTATGGTGCCACTGGGCACCCAGGCATCATC<br>CCACCACATGCCACTCTCGTCTTCGATGTGGAGCTTCTAAAAC<br>TGGAAGCTAGCGAGAGCAAGTACGGACCGCCCTGCCCACCTT<br>GCCCTGCCCCCGAGTTCCTGGGCGGACCCAGCGTGTTCCTGTT<br>CCCACCCAAGCCCAAGGACACCCTGATGATCAGCCGGACCCCC<br>GAGGTGACCTGCGTGGTGGTGGACGTGAGCCAGGAAGATCCC<br>GAGGTCCAGTTCAATTGGTACGTGGACGGCGTGGAAGTGCAC<br>AACGCCAAGACCAAGCCCAGAGAGGAACAGTTCAACAGCACC<br>TACCGGGTGGTGTCTGTGCTGACCGTGCTGCACCAGGACTGGC<br>TGAACGGCAAAGAATACAAGTGCAAGGTGTCCAACAAGGGCC<br>TGCCCAGCAGCATCGAAAAGACCATCAGCAAGGCCAAGGGCC<br>AGCCTCGCGAGCCCCAGGTGTACACCCTGCCTCCCTCCCAGGA<br>AGAGATGACCAAGAACCAGGTGTCCCTGACCTGCCTGGTGAA<br>GGGCTTCTACCCCAGCGACATCGCCGTGGAGTGGGAGAGCAA<br>CGGCCAGCCTGAGAACAACTACAAGACCACCCCTCCCGTGCTG<br>GACAGCGACGGCAGCTTCTTCCTGTACAGCCGGCTGACCGTGG<br>ACAAGAGCCGGTGGCAGGAAGGCAACGTCTTTAGCTGCAGCG<br>TGATGCACGAGGCCCTGCACAACCACTACACCCAGAAGAGCC<br>TGAGCCTGTCCCTGGGCAAGATGCATAAACGGGGCAGAAAGA<br>AACTCCTGTATATATTCAAACAACCATTTATGAGACCAGTACA<br>AACTACTCAAGAGGAAGATGGCTGTAGCTGCCGATTTCCAGAA<br>GAAGAAGAAGGAGGATGTGAACTGCGGGTGAAGTTCAGCAGA<br>AGCGCCGACGCCCCTGCCTACCAGCAGGGCCAGAATCAGCTGT<br>ACAACGAGCTGAACCTGGGCAGAAGGGAAGAGTACGACGTCC<br>TGGATAAGCGGAGAGGCCGGGACCCTGAGATGGGCGGCAAGC<br>CTCGGCGGAAGAACCCCCAGGAAGGCCTGTATAACGAACTGC<br>AGAAAGACAAGATGGCCGAGGCCTACAGCGAGATCGGCATGA<br>AGGGCGAGCGGAGGCGGGGCAAGGGCCACGACGGCCTGTATC<br>AGGGCCTGTCCACCGCCACCAAGGATACCTACGACGCCCTGCA<br>CATGCAGGCCCTGCCCCCAAGGGGC |
| 23 | FKBP-TM-41BB-CD3z protein | MGSGVQVETISPGDGRTFPKRGQTCVVHYTGMLEDGKKFDSSRD<br>RNKPFKFMLGKQEVIRGWEEGVAQMSVGQRAKLTISPDYAYGA<br>TGHPGIIPPHATLVFDVELLKLEASAKPTTTPAPRPPTPAPTIASQPL<br>SLRPEACRPAAGGAVHTRGLDFACDIYIWAPLAGTCGVLLLSLVI<br>TMHKRGRKKLLYIFKQPFMRPVQTTQEEDGCSCRFPEEEEGGCEL<br>RVKFSRSADAPAYQQGQNQLYNELNLGRREEYDVLDKRRGRDP<br>EMGGKPRRKNPQEGLYNELQKDKMAEAYSEIGMKGERRRGKGH<br>DGLYQGLSTATKDTYDALHMQALPPRG |
| 24 | FKBP-TM-41BB-CD3z mRNA | AUGGCUCUGCCUGUGACAGCUCUGCUGCUGCCUCUGGCCCUG<br>CUGCUCCAUGCCGCCAGACCCGGAUCCGGAGUGCAGGUGGAA<br>ACCAUCUCCCCAGGAGACGGGCGCACCUUCCCCAAGCGCGGC<br>CAGACCUGCGUGGUGCACUACACCGGGAUGCUUGAAGAUGG<br>AAAGAAAUUUGAUUCCUCCCGGGACAGAAACAAGCCCUUUA<br>AGUUUAUGCUAGGCAAGCAGGAGGUGAUCCGAGGCUGGGAA<br>GAAGGGGUUGCCCAGAUGAGUGUGGGUCAGAGAGCCAAACU<br>GACUAUAUCUCCAGAUUAUGCCUAUGGUGCCACUGGGCACC |

TABLE 1-continued

Exemplary DARIC Binding and Signaling Components

| SEQ ID NO. | Construct | Sequence |
|---|---|---|
| | | CAGGCAUCAUCCCACCACAUGCCACUCUCGUCUUCGAUGUGG<br>AGCUUCUAAAACUGGAAGCUAGCGCCAAGCCUACCACCACCC<br>CUGCCCCUAGACCUCCAACACCCGCCCCAACAAUCGCCAGCC<br>AGCCUCUGUCUCUGAGGCCCGAGGCUUGUAGACCAGCUGCU<br>GGCGGAGCCGUGCACACCAGAGGACUGGAUUUCGCCUGCGA<br>CAUCUACAUCUGGGCCCCUCUGGCCGGCACAUGUGGCGUGCU<br>GCUGCUGAGCCUCGUGAUCACCAUGCAUAAACGGGGCAGAA<br>AGAAACUCCUGUAUAUAUUCAAACAACCAUUUAUGAGACCA<br>GUACAAACUACUCAAGAGGAAGAUGGCUGUAGCUGCCGAUU<br>UCCAGAAGAAGAAGAAGGAGGAUGUGAACUGCGGGUGAAGU<br>UCAGCAGAAGCGCCGACGCCCCUGCCUACCAGCAGGGCCAGA<br>AUCAGCUGUACAACGAGCUGAACCUGGGCAGAAGGGAAGAG<br>UACGACGUCCUGGAUAAGCGGAGAGGCCGGGACCCUGAGAU<br>GGGCGGCAAGCCUCGGCGGAAGAACCCCCAGGAAGGCCUGU<br>AUAACGAACUGCAGAAAGACAAGAUGGCCGAGGCCUACAGC<br>GAGAUCGGCAUGAAGGGCGAGCGGAGGCGGGGCAAGGGCCA<br>CGACGGCCUGUAUCAGGGCCUGUCCACCGCCACCAAGGAUAC<br>CUACGACGCCCUGCACAUGCAGGCCCUGCCCCCAAGGGGC |
| 25 | FKBP-TM-41BB-CD3z DNA | ATGGCTCTGCCTGTGACAGCTCTGCTGCTGCCTCTGGCCCTGCT<br>GCTCCATGCCGCCAGACCCGGATCCGGAGTGCAGGTGGAAAC<br>CATCTCCCCAGGAGACGGGCGCACCTTCCCCAAGCGCGGCCAG<br>ACCTGCGTGGTGCACTACACCGGGATGCTTGAAGATGGAAAG<br>AAATTTGATTCCTCCCGGGACAGAAACAAGCCCTTTAAGTTTA<br>TGCTAGGCAAGCAGGAGGTGATCCGAGGCTGGGAAGAAGGGG<br>TTGCCCAGATGAGTGTGGGTCAGAGAGCCAAACTGACTATATC<br>TCCAGATTATGCCTATGGTGCCACTGGGCACCCAGGCATCATC<br>CCACCACATGCCACTCTCGTCTTCGATGTGGAGCTTCTAAAAC<br>TGGAAGCTAGCGCCAAGCCTACCACCACCCCTGCCCCTAGACC<br>TCCAACACCCGCCCCAACAATCGCCAGCCAGCCTCTGTCTCTG<br>AGGCCCGAGGCTTGTAGACCAGCTGCTGGCGGAGCCGTGCAC<br>ACCAGAGGACTGGATTTCGCCTGCGACATCTACATCTGGGCCC<br>CTCTGGCCGGCACATGTGGCGTGCTGCTGCTGAGCCTCGTGAT<br>CACCATGCATAAACGGGGCAGAAAGAAACTCCTGTATATATTC<br>AAACAACCATTTATGAGACCAGTACAAACTACTCAAGAGGAA<br>GATGGCTGTAGCTGCCGATTTCCAGAAGAAGAAGAAGGAGGA<br>TGTGAACTGCGGGTGAAGTTCAGCAGAAGCGCCGACGCCCCT<br>GCCTACCAGCAGGGCCAGAATCAGCTGTACAACGAGCTGAAC<br>CTGGGCAGAAGGGAAGAGTACGACGTCCTGGATAAGCGGAGA<br>GGCCGGGACCCTGAGATGGGCGGCAAGCCTCGGCGGAAGAAC<br>CCCCAGGAAGGCCTGTATAACGAACTGCAGAAAGACAAGATG<br>GCCGAGGCCTACAGCGAGATCGGCATGAAGGGCGAGCGGAGG<br>CGGGGCAAGGGCCACGACGGCCTGTATCAGGGCCTGTCCACC<br>GCCACCAAGGATACCTACGACGCCCTGCACATGCAGGCCCTGC<br>CCCCAAGGGGC |
| 26 | FKBP-spacer-TM-41BB-CD3z DNA | ATGGCTCTGCCTGTGACAGCTCTGCTGCTGCCTCTGGCCCTGCT<br>GCTCCATGCCGCCAGACCCGGATCCGGAGTGCAGGTGGAAAC<br>CATCTCCCCAGGAGACGGGCGCACCTTCCCCAAGCGCGGCCAG<br>ACCTGCGTGGTGCACTACACCGGGATGCTTGAAGATGGAAAG<br>AAATTTGATTCCTCCCGGGACAGAAACAAGCCCTTTAAGTTTA<br>TGCTAGGCAAGCAGGAGGTGATCCGAGGCTGGGAAGAAGGGG<br>TTGCCCAGATGAGTGTGGGTCAGAGAGCCAAACTGACTATATC<br>TCCAGATTATGCCTATGGTGCCACTGGGCACCCAGGCATCATC<br>CCACCACATGCCACTCTCGTCTTCGATGTGGAGCTTCTAAAAC<br>TGGAAGCTAGCGAGAGCAAGTACGGACCGCCCTGCCCACCTT<br>GCCCTGCCCCCGAGTTCCTGGGCGGACCCAGCGTGTTCCTGTT<br>CCCACCCAAGCCCAAGGACACCCTGATGATCAGCCGGACCCCC<br>GAGGTGACCTGCGTGGTGGTGGACGTGAGCCAGGAAGATCCC<br>GAGGTCCAGTTCAATTGGTACGTGGACGGCGTGGAAGTGCAC<br>AACGCCAAGACCAAGCCCAGAGAGGAACAGTTCAACAGCACC<br>TACCGGGTGGTGTCTGTGCTGACCGTGCTGCACCAGGACTGGC<br>TGAACGGCAAAGAATACAAGTGCAAGGTGTCCAACAAGGGCC<br>TGCCCAGCAGCATCGAAAAGACCATCAGCAAGGCCAAGGGCC<br>AGCCTCGCGAGCCCCAGGTGTACACCCTGCCTCCCTCCCAGGA<br>AGAGATGACCAAGAACCAGGTGTCCCTGACCTGCCTGGTGAA<br>GGGCTTCTACCCCAGCGACATCGCCGTGGAGTGGGAGAGCAA<br>CGGCCAGCCTGAGAACAACTACAAGACCACCCCTCCCGTGCTG<br>GACAGCGACGGCAGCTTCTTCCTGTACAGCCGGCTGACCGTGG<br>ACAAGAGCCGGTGGCAGGAAGGCAACGTCTTTAGCTGCAGCG<br>TGATGCACGAGGCCCTGCACAACCACTACACCCAGAAGAGCC<br>TGAGCCTGTCCCTGGGCAAGATGCATAAACGGGGCAGAAAGA<br>AACTCCTGTATATATTCAAACAACCATTTATGAGACCAGTACA<br>AACTACTCAAGAGGAAGATGGCTGTAGCTGCCGATTTCCAGAA |

TABLE 1-continued

Exemplary DARIC Binding and Signaling Components

| SEQ ID NO. | Construct | Sequence |
|---|---|---|
| | | GAAGAAGAAGGAGGATGTGAACTGCGGGTGAAGTTCAGCAGA AGCGCCGACGCCCCTGCCTACCAGCAGGGCCAGAATCAGCTGT ACAACGAGCTGAACCTGGGCAGAAGGGAAGAGTACGACGTCC TGGATAAGCGGAGAGGCCGGGACCCTGAGATGGGCGGCAAGC CTCGGCGGAAGAACCCCCAGGAAGGCCTGTATAACGAACTGC AGAAAGACAAGATGGCCGAGGCCTACAGCGAGATCGGCATGA AGGGCGAGCGGAGGCGGGGCAAGGGCCACGACGGCCTGTATC AGGGCCTGTCCACCGCCACCAAGGATACCTACGACGCCCTGCA CATGCAGGCCCTGCCCCCAAGGGGC |
| 37 | SS-2xDmrB-DmrC-TM-41BB-CD3z protein | MALPVTALLLPLALLLHAARPGSGGVQVETISPGDGRTFPKRGQT CVVHYTGMLEDGKKVDSSRDRNKPFKFMLGKQEVIRGWEEGVA QMSVGQRAKLTISPDYAYGATGHPGIIPPHATLVFDVEFLKLESGT SGTSGVQVETISPGDGRTFPKRGQTCVVHYTGMLEDGKKVDSSR DRNKPFKFMLGKQEVIRGWEEGV |
| 38 | SS-2xDmrB-DmrC-TM-41BB-CD3z mRNA | AUGGCUCUGCCUGUGACAGCUCUGCUGCUGCCUCUGGCCCUG CUGCUCCAUGCCGCCAGACCCGGAUCCGGCGGUGUCCAAGUC GAAACUAUAUCGCCUGGCGAUGGCAGAACGUUUCCCAAACG UGGCCAGACCUGUGUCGUACACUAUACCGGCAUGCUAGAGG AUGGGAAAAAGGUUGAUUCCAGUCGCGAUCGGAACAAACCG UUUAAAUUCAUGUUGGGGAAGCAAGAGGUUAUCAGGGGAUG GGAAGAGGGUGUCGCGCAAAUGUCGGUUGGGCAACGUGCGA AACUCACAAUUUCCCCGGAUUACGCAUACGGAGCUACCGGAC ACCCUGGGAUUAUCCCACCGCAUGCGACGCUAGUGUUUGAC GUAGAGUUCUUGAAGCUCGAAUCAGGUACAAGCGGCACUUC UGGCGUACAGGUUGAGACAAUUAGUCCCGGAGACGGACGUA CAUUCCCAAAGAGAGGGCAAACUUGCGUAGUCCAUUACACU GGAAUGUUGGAAGACGGCAAGAAAGUGGACAGUUCAAGAGA CCGCAAUAAGCCUUUCAAGUUUAUGCUCGGAAAACAGGAAG UCAUACGCGGUUGGGAGGAAGGCGUGGCUCAGAUGAGCGUC GGACAGAGGGCAAAGUUGACCAUCAGUCCCGACUAUGCGUA UGGCGCGACAGGCCAUCCCGGAAUCAUACCUCCCCACGCAAC CUUGGUAUUCGAUGUCGAACUGCUCAAAUUAGAGGGUAGUA GAUCCAUCCUCUGGCAUGAGAUGUGGCAUGAAGGCCUGGAA GAGGCAUCUCGUUUGUACUUUGGGGAAAGGAACGUGAAAGG CAUGUUUGAGGUGCUGGAGCCCUUGCAUGCUAUGAUGGAAC GGGGCCCCCAGACUCUGAAGGAAACAUCCUUUAAUCAGGCC UAUGGUCGAGAUUUAAUGGAGGCCCAAGAGUGGUGCAGGAA GUACAUGAAAUCAGGGAAUGUCAAGGACCUCCUCCAAGCCU GGGACCUCUAUUAUCAUGUGUUCCGACGAAUCUCAAAGGCU AGCGCCAAGCCUACCACCACCCCUGCCCCUAGACCUCCAACA CCCGCCCCAACAAUCGCCAGCCAGCCUCUGUCUCUGAGGCCC GAGGCUUGUAGACCAGCUGCUGGCGGAGCCGUACACACCAG AGGACUGGAUUUCGCCUGCGACAUCUACAUCUGGGCCCCUCU GGCCGGCACAUGUGGCGUGCUGCUGCUGAGCCUCGUGAUCA CCAUGCAUAAACGGGGCAGAAAGAAACUCCUGUAUAUAUUC AAACAACCAUUUAUGAGACCAGUACAAACUACUCAAGAGGA AGAUGGCUGUAGCUGCCGAUUUCCAGAAGAAGAAGAAGGAG GAUGUGAACUGCGGGUGAAGUUCAGCAGAAGCGCCGACGCC CCUGCCUACCAGCAGGGCCAGAAUCAGCUGUACAACGAGCUG AACCUGGGCAGAAGGGAAGAGUACGACGUCCUGGAUAAGCG GAGAGGCCGGGACCCUGAGAUGGGCGGCAAGCCUCGGCGGA AGAACCCCCAGGAAGGCCUGUAUAACGAACUGCAGAAAGAC AAGAUGGCCGAGGCCUACAGCGAGAUCGGCAUGAAGGGCGA GCGGAGGCGGGGCAAGGGCCACGACGGCCUGUAUCAGGGCC UGUCCACCGCCACCAAGGAUACCUACGACGCCCUGCACAUGC AGGCCCUGCCCCCAAGGGGC |
| 39 | SS-2xDmrB-DmrC-TM-41BB-CD3z DNA | ATGGCTCTGCCTGTGACAGCTCTGCTGCTGCCTCTGGCCCTGCT GCTCCATGCCGCCAGACCCGGATCCGGCGGTGTCCAAGTCGAA ACTATATCGCCTGGCGATGGCAGAACGTTTCCCAAACGTGGCC AGACCTGTGTCGTACACTATACCGGCATGCTAGAGGATGGGAA AAAGGTTGATTCCAGTCGCGATCGGAACAAACCGTTTAAATTC ATGTTGGGGAAGCAAGAGGTTATCAGGGGATGGGAAGAGGGT GTCGCGCAAATGTCGGTTGGGCAACGTGCGAAACTCACAATTT CCCCGGATTACGCATACGGAGCTACCGGACACCCTGGGATTAT CCCACCGCATGCGACGCTAGTGTTTGACGTAGAGTTCTTGAAG CTCGAATCAGGTACAAGCGGCACTTCTGGCGTACAGGTTGAGA CAATTAGTCCCGGAGACGGACGTACATTCCCAAAGAGAGGGC AAACTTGCGTAGTCCATTACACTGGAATGTTGGAAGACGGCAA GAAAGTGGACAGTTCAAGAGACCGCAATAAGCCTTTCAAGTTT ATGCTCGGAAAACAGGAAGTCATACGCGGTTGGGAGGAAGGC GTGGCTCAGATGAGCGTCGGACAGAGGGCAAAGTTGACCATC |

TABLE 1-continued

Exemplary DARIC Binding and Signaling Components

| SEQ ID NO. | Construct | Sequence |
| --- | --- | --- |
| | | AGTCCCGACTATGCGTATGGCGCGACAGGCCATCCCGGAATCA<br>TACCTCCCCACGCAACCTTGGTATTCGATGTCGAACTGCTCAA<br>ATTAGAGGGTAGTAGATCCATCCTCTGGCATGAGATGTGGCAT<br>GAAGGCCTGGAAGAGGCATCTCGTTTGTACTTTGGGGAAAGG<br>AACGTGAAAGGCATGTTTGAGGTGCTGGAGCCCTTGCATGCTA<br>TGATGGAACGGGGCCCCCAGACTCTGAAGGAAACATCCTTTAA<br>TCAGGCCTATGGTCGAGATTTAATGGAGGCCCAAGAGTGGTGC<br>AGGAAGTACATGAAATCAGGGAATGTCAAGGACCTCCTCCAA<br>GCCTGGGACCTCTATTATCATGTGTTCCGACGAATCTCAAAGG<br>CTAGCGCCAAGCCTACCACCACCCCTGCCCCTAGACCTCCAAC<br>ACCCGCCCCAACAATCGCCAGCCAGCCTCTGTCTCTGAGGCCC<br>GAGGCTTGTAGACCAGCTGCTGGCGGAGCCGTACACACCAGA<br>GGACTGGATTTCGCCTGCGACATCTACATCTGGGCCCCTCTGG<br>CCGGCACATGTGGCGTGCTGCTGCTGAGCCTCGTGATCACCAT<br>GCATAAACGGGGCAGAAAGAAACTCCTGTATATATTCAAACA<br>ACCATTTATGAGACCAGTACAAACTACTCAAGAGGAAGATGG<br>CTGTAGCTGCCGATTTCCAGAAGAAGAAGAAGGAGGATGTGA<br>ACTGCGGGTGAAGTTCAGCAGAAGCGCCGACGCCCCTGCCTAC<br>CAGCAGGGCCAGAATCAGCTGTACAACGAGCTGAACCTGGGC<br>AGAAGGGAAGAGTACGACGTCCTGGATAAGCGGAGAGGCCGG<br>GACCCTGAGATGGGCGGCAAGCCTCGGCGGAAGAACCCCCAG<br>GAAGGCCTGTATAACGAACTGCAGAAAGACAAGATGGCCGAG<br>GCCTACAGCGAGATCGGCATGAAGGGCGAGCGGAGGCGGGGC<br>AAGGGCCACGACGGCCTGTATCAGGGCCTGTCCACCGCCACCA<br>AGGATACCTACGACGCCCTGCACATGCAGGCCCTGCCCCCAAG<br>GGGC |
| 41 | SS-scFvCD19-DmrA-fuP2A-DmrC-TM-41BB-CD3z protein | METDTLLLWVLLLWVPGSTGDYKDEGSDIQMTQTTSSLSASLGD<br>RVTISCRASQDISKYLNWYQQKPDGTVKLLIYHTSRLHSGVPSRFS<br>GSGSGTDYSLTISNLEQEDIATYFCQQGNTLPYTFGGGTKLEITGS<br>TSGSGKPGSGEGSTKGEVKLQESGPGLVAPSQSLSVTCTVSGVSL<br>PDYGVSWIRQPPRKGLEWLGVIWGSE |
| 42 | SS-scFvCD19-DmrA-fuP2A-DmrC-TM-41BB-CD3z DNA | ATGGAGACAGACACACTCCTGCTATGGGTACTGCTGCTCTGGG<br>TTCCAGGTTCCACTGGTGACTACAAGGACGAGGGATCCGATAT<br>CCAGATGACCCAGACCACCAGCAGCCTGAGCGCCAGCCTGGG<br>CGATAGAGTGACCATCAGCTGCAGAGCCAGCCAGGACATCAG<br>CAAGTACCTGAACTGGTATCAGCAGAAACCCGACGGCACCGT<br>GAAGCTGCTGATCTACCACACCAGCAGACTGCACAGCGGCGT<br>GCCCAGCAGATTTTCTGGCAGCGGCTCCGGCACCGACTACAGC<br>CTGACCATCTCCAACCTGGAACAGGAAGATATCGCTACCTACT<br>TCTGTCAGCAAGGCAACACCCTGCCCTACACCTTCGGCGGAGG<br>CACCAAGCTGGAAATCACCGGCAGCACAAGCGGCAGCGGCAA<br>GCCTGGATCTGGCGAGGGAAGCACCAAGGGCGAAGTGAAACT<br>GCAGGAAAGCGGCCCTGGACTGGTGGCCCCAAGCCAGTCTCT<br>GAGCGTGACCTGTACCGTGTCCGGCGTGTCCCTGCCTGACTAT<br>GGCGTGTCCTGGATCAGACAGCCACCCAGAAAGGGCCTGGAA<br>TGGCTGGGAGTGATCTGGGGCAGCGAGACAACCTACTACAAC<br>AGCGCCCTGAAGTCCCGGCTGACCATCATCAAGGACAACTCCA<br>AGAGCCAGGTGTTCCTGAAGATGAACAGCCTGCAGACCGACG<br>ACACCGCCATCTACTACTGCGCCAAGCACTACTACTACGGCGG<br>CAGCTACGCCATGGACTACTGGGGCCAGGGCACAAGCGTGAC<br>CGTGTCCAGCGCTAGCGGCTCAGGAGGAGTGCAGGTTGAAAC<br>CATCTCCCCAGGAGACGGGCGCACCTTCCCGAAGCGCGGACA<br>GACATGCGTGGTGCACTACACCGGGATGCTTGAAGATGGAAA<br>GAAATTCGATTCATCGCGGGACAGAAACAAGCCCTTTAAGTTT<br>ATGCTGGGCAAGCAGGAGGTCATCCGAGGCTGGGAAGAAGGG<br>GTTGCCCAGATGAGTGTCGGCCAGAGAGCCAAACTGACTATAT<br>CACCTGACTACGCCTATGGGGCCACTGGGCACCCTGGCATAAT<br>TCCGCCACACGCCACTCTCGTCTTCGATGTGGAGCTTCTAAAA<br>CTGGAAGGCGGCCGCGCTCGTTACAAGCGAAGTGTCTCAGGAT<br>CTGGCGCCACGAACTTCTCTCTGTTAAAGCAAGCAGGAGATGT<br>TGAAGAAAACCCCGGGCCTTCAAGATCCATCCTCTGGCATGAG<br>ATGTGGCATGAAGGCCTGGAAGAGGCATCTCGTTTGTACTTTG<br>GGGAAAGGAACGTGAAAGGCATGTTTGAGGTGCTGGAGCCCT<br>TGCATGCTATGATGGAACGGGGCCCCCAGACTCTGAAGGAAA<br>CATCCTTTAATCAGGCCTATGGTCGAGATTTAATGGAGGCCCA<br>AGAGTGGTGCAGGAAGTACATGAAATCAGGGAATGTCAAGGA<br>CCTCCTCCAAGCCTGGGACCTCTATTATCATGTGTTCCGACGA<br>ATCTCAAAGGCTAGCGCCAAGCCTACCACCACCCCTGCCCCTA<br>GACCTCCAACACCCGCCCCAACAATCGCCAGCCAGCCTCTGTC<br>TCTGAGGCCCGAGGCTTGTAGACCAGCTGCTGGCGGAGCCGTA<br>CACACCAGAGGACTGGATTTCGCCTGCGACATCTACATCTGGG<br>CCCCTCTGGCCGGCACATGTGGCGTGCTGCTGCTGAGCCTCGT |

TABLE 1-continued

Exemplary DARIC Binding and Signaling Components

| SEQ ID NO. | Construct | Sequence |
|---|---|---|
| | | GATCACCATGCATAAACGGGGCAGAAAGAAACTCCTGTATAT ATTCAAACAACCATTTATGAGACCAGTACAAACTACTCAAGAG GAAGATGGCTGTAGCTGCCGATTTCCAGAAGAAGAAGAAGGA GGATGTGAACTGCGGGTGAAGTTCAGCAGAAGCGCCGACGCC CCTGCCTACCAGCAGGGCCAGAATCAGCTGTACAACGAGCTG AACCTGGGCAGAAGGGAAGAGTACGACGTCCTGGATAAGCGG AGAGGCCGGGACCCTGAGATGGGCGGCAAGCCTCGGCGGAAG AACCCCCAGGAAGGCCTGTATAACGAACTGCAGAAAGACAAG ATGGCCGAGGCCTACAGCGAGATCGGCATGAAGGGCGAGCGG AGGCGGGGCAAGGGCCACGACGGCCTGTATCAGGGCCTGTCC ACCGCCACCAAGGATACCTACGACGCCCTGCACATGCAGGCCC TGCCCCCAAGGGGC |
| 44 | SS-scFvCD19-DmrA-fuP2A-FRB-TM-41BB-CD3z protein | METDTLLLWVLLLWVPGSTGDYKDEGSDIQMTQTTSSLSASLGD RVTISCRASQDISKYLNWYQQKPDGTVKLLIYHTSRLHSGVPSRFS GSGSGTDYSLTISNLEQEDIATYFCQQGNTLPYTFGGGTKLEITGS TSGSGKPGSGEGSTKGEVKLQESGPGLVAPSQSLSVTCTVSGVSL PDYGVSWIRQPPRKGLEWLGVIWGSE |
| 45 | SS-scFvCD19-DmrA-fuP2A-FRB-TM-41BB-CD3z DNA | ATGGAGACAGACACACTCCTGCTATGGGTACTGCTGCTCTGGG TTCCAGGTTCCACTGGTGACTACAAGGACGAGGGATCCGATAT CCAGATGACCCAGACCACCAGCAGCCTGAGCGCCAGCCTGGG CGATAGAGTGACCATCAGCTGCAGAGCCAGCCAGGACATCAG CAAGTACCTGAACTGGTATCAGCAGAAACCCGACGGCACCGT GAAGCTGCTGATCTACCACACCAGCAGACTGCACAGCGGCGT GCCCAGCAGATTTTCTGGCAGCGGCTCCGGCACCGACTACAGC CTGACCATCTCCAACCTGGAACAGGAAGATATCGCTACCTACT TCTGTCAGCAAGGCAACACCCTGCCCTACACCTTCGGCGGAGG CACCAAGCTGGAAATCACCGGCAGCACAAGCGGCAGCGGCAA GCCTGGATCTGGCGAGGGAAGCACCAAGGGCGAAGTGAAACT GCAGGAAAGCGGCCCTGGACTGGTGGCCCCAAGCCAGTCTCT GAGCGTGACCTGTACCGTGTCCGGCGTGTCCCTGCCTGACTAT GGCGTGTCCTGGATCAGACAGCCACCCAGAAAGGGCCTGGAA TGGCTGGGAGTGATCTGGGGCAGCGAGACAACCTACTACAAC AGCGCCCTGAAGTCCCGGCTGACCATCATCAAGGACAACTCCA AGAGCCAGGTGTTCCTGAAGATGAACAGCCTGCAGACCGACG ACACCGCCATCTACTACTGCGCCAAGCACTACTACTACGGCGG CAGCTACGCCATGGACTACTGGGGCCAGGGCACAAGCGTGAC CGTGTCCAGCGCTAGCGGCTCAGGAGGAGTGCAGGTTGAAAC CATCTCCCCAGGAGACGGGCGCACCTTCCCGAAGCGCGGACA GACATGCGTGGTGCACTACACCGGGATGCTTGAAGATGGAAA GAAATTCGATTCATCGCGGGACAGAAACAAGCCCTTTAAGTTT ATGCTGGGCAAGCAGGAGGTCATCCGAGGCTGGGAAGAAGGG GTTGCCCAGATGAGTGTCGGCCAGAGAGCCAAACTGACTATAT CACCTGACTACGCCTATGGGGCCACTGGGCACCCTGGCATAAT TCCGCCACACGCCACTCTCGTCTTCGATGTGGAGCTTCTAAAA CTGGAAGGCGGCCGCGCTCGTTACAAGCGAAGTGTCTCAGGAT CTGGCGCCACGAACTTCTCTCTGTTAAAGCAAGCAGGAGATGT TGAAGAAAACCCCGGGCCTTCAAGATCCATCCTCTGGCATGAG ATGTGGCATGAAGGCCTGGAAGAGGCATCTCGTTTGTACTTTG GGGAAAGGAACGTGAAAGGCATGTTTGAGGTGCTGGAGCCCT TGCATGCTATGATGGAACGGGGCCCCCAGACTCTGAAGGAAA CATCCTTTAATCAGGCCTATGGTCGAGATTTAATGGAGGCCCA AGAGTGGTGCAGGAAGTACATGAAATCAGGGAATGTCAAGGA CCTCACCCAAGCCTGGGACCTCTATTATCATGTGTTCCGACGA ATCTCAAAGGCTAGCGCCAAGCCTACCACCACCCCTGCCCCTA GACCTCCAACACCCGCCCCAACAATCGCCAGCCAGCCTCTGTC TCTGAGGCCCGAGGCTTGTAGACCAGCTGCTGGCGGAGCCGTA CACACCAGAGGACTGGATTTCGCCTGCGACATCTACATCTGG CCCCTCTGGCCGGCACATGTGGCGTGCTGCTGCTGAGCCTCGT GATCACCATGCATAAACGGGGCAGAAAGAAACTCCTGTATAT ATTCAAACAACCATTTATGAGACCAGTACAAACTACTCAAGAG GAAGATGGCTGTAGCTGCCGATTTCCAGAAGAAGAAGAAGGA GGATGTGAACTGCGGGTGAAGTTCAGCAGAAGCGCCGACGCC CCTGCCTACCAGCAGGGCCAGAATCAGCTGTACAACGAGCTG AACCTGGGCAGAAGGGAAGAGTACGACGTCCTGGATAAGCGG AGAGGCCGGGACCCTGAGATGGGCGGCAAGCCTCGGCGGAAG AACCCCCAGGAAGGCCTGTATAACGAACTGCAGAAAGACAAG ATGGCCGAGGCCTACAGCGAGATCGGCATGAAGGGCGAGCGG AGGCGGGGCAAGGGCCACGACGGCCTGTATCAGGGCCTGTCC ACCGCCACCAAGGATACCTACGACGCCCTGCACATGCAGGCCC TGCCCCCAAGGGGC |

TABLE 1-continued

Exemplary DARIC Binding and Signaling Components

| SEQ ID NO. | Construct | Sequence |
| --- | --- | --- |
| 47 | SS-scFvCD19-DmrA-fuP2A-2xDmrB-DmrC-TM-41BB-CD3z protein | METDTLLLWVLLLWVPGSTGDYKDEGSDIQMTQTTSSLSASLGD RVTISCRASQDISKYLNWYQQKPDGTVKLLIYHTSRLHSGVPSRFS GSGSGTDYSLTISNLEQEDIATYFCQQGNTLPYTFGGGTKLEITGS TSGSGKPGSGEGSTKGEVKLQESGPGLVAPSQSLSVTCTVSGVSL PDYGVSWIRQPPRKGLEWLGVIWGSE |
| 48 | SS-scFvCD19-DmrA-fuP2A-2xDmrB-DmrC-TM-41BB-CD3z DNA | ATGGAGACAGACACACTCCTGCTATGGGTACTGCTGCTCTGGG TTCCAGGTTCCACTGGTGACTACAAGGACGAGGGATCCGATAT CCAGATGACCCAGACCACCAGCAGCCTGAGCGCCAGCCTGGG CGATAGAGTGACCATCAGCTGCAGAGCCAGCCAGGACATCAG CAAGTACCTGAACTGGTATCAGCAGAAACCCGACGGCACCGT GAAGCTGCTGATCTACCACACCAGCAGACTGCACAGCGGCGT GCCCAGCAGATTTTCTGGCAGCGGCTCCGGCACCGACTACAGC CTGACCATCTCCAACCTGGAACAGGAAGATATCGCTACCTACT TCTGTCAGCAAGGCAACACCCTGCCCTACACCTTCGGCGGAGG CACCAAGCTGGAAATCACCGGCAGCACAAGCGGCAGCGGCAA GCCTGGATCTGGCGAGGGAAGCACCAAGGGCGAAGTGAAACT GCAGGAAAGCGGCCCTGGACTGGTGGCCCCAAGCCAGTCTCT GAGCGTGACCTGTACCGTGTCCGGCGTGTCCCTGCCTGACTAT GGCGTGTCCTGGATCAGACAGCCACCCAGAAAGGGCCTGGAA TGGCTGGGAGTGATCTGGGGCAGCGAGACAACCTACTACAAC AGCGCCCTGAAGTCCCGGCTGACCATCATCAAGGACAACTCCA AGAGCCAGGTGTTCCTGAAGATGAACAGCCTGCAGACCGACG ACACCGCCATCTACTACTGCGCCAAGCACTACTACTACGGCGG CAGCTACGCCATGGACTACTGGGGCCAGGGCACAAGCGTGAC CGTGTCCAGCGCTAGCGGCTCAGGAGGAGTGCAGGTTGAAAC CATCTCCCCAGGAGACGGGCGCACCTTCCCGAAGCGCGGACA GACATGCGTGGTGCACTACACCGGGATGCTTGAAGATGGAAA GAAATTCGATTCATCGCGGGACAGAAACAAGCCCTTTAAGTTT ATGCTGGGCAAGCAGGAGGTCATCCGAGGCTGGGAAGAAGGG GTTGCCCAGATGAGTGTCGGCCAGAGAGCCAAACTGACTATAT CACCTGACTACGCCTATGGGGCCACTGGGCACCCTGGCATAAT TCCGCCACACGCCACTCTCGTCTTCGATGTGGAGCTTCTAAAA CTGGAAGGCGGCCGCGCTCGTTACAAGCGAAGTGTCTCAGGAT CTGGCGCCACGAACTTCTCTCTGTTAAAGCAAGCAGGAGATGT TGAAGAAAACCCCGGGCCTTCAAGATCCGGCGGTGTCCAAGTC GAAACTATATCGCCTGGCGATGGCAGAACGTTTCCCAAACGTG GCCAGACCTGTGTCGTACACTATACCGGCATGCTAGAGGATGG GAAAAAGGTTGATTCCAGTCGCGATCGGAACAAACCGTTTAA ATTCATGTTGGGGAAGCAAGAGGTTATCAGGGGATGGGAAGA GGGTGTCGCGCAAATGTCGGTTGGGCAACGTGCGAAACTCAC AATTTCCCCGGATTACGCATACGGAGCTACCGGACACCCTGGG ATTATCCCACCGCATGCGACGCTAGTGTTTGACGTAGAGTTCT TGAAGCTCGAATCAGGTACAAGCGGCACTTCTGGCGTACAGGT TGAGACAATTAGTCCCGGAGACGGACGTACATTCCCAAAGAG AGGGCAAACTTGCGTAGTCCATTACACTGGAATGTTGGAAGAC GGCAAGAAAGTGGACAGTTCAAGAGACCGCAATAAGCCTTTC AAGTTTATGCTCGGAAAACAGGAAGTCATACGCGGTTGGGAG GAAGGCGTGGCTCAGATGAGCGTCGGACAGAGGGCAAAGTTG ACCATCAGTCCCGACTATGCGTATGGCGCGACAGGCCATCCCG GAATCATACCTCCCCACGCAACCTTGGTATTCGATGTCGAACT GCTCAAATTAGAGGGTAGTAGATCCATCCTCTGGCATGAGATG TGGCATGAAGGCCTGGAAGAGGCATCTCGTTTGTACTTTGGGG AAAGGAACGTGAAAGGCATGTTTGAGGTGCTGGAGCCCTTGC ATGCTATGATGGAACGGGGCCCCCAGACTCTGAAGGAAACAT CCTTTAATCAGGCCTATGGTCGAGATTTAATGGAGGCCCAAGA GTGGTGCAGGAAGTACATGAAATCAGGGAATGTCAAGGACCT CCTCCAAGCCTGGGACCTCTATTATCATGTGTTCCGACGAATCT CAAAGGCTAGCGCCAAGCCTACCACCACCCCTGCCCCTAGACC TCCAACACCCGCCCCAACAATCGCCAGCCAGCCTCTGTCTCTG AGGCCCGAGGCTTGTAGACCAGCTGCTGGCGGAGCCGTACAC ACCAGAGGACTGGATTTCGCCTGCGACATCTACATCTGGGCCC CTCTGGCCGGCACATGTGGCGTGCTGCTGCTGAGCCTCGTGAT CACCATGCATAAACGGGGCAGAAAGAAACTCCTGTATATATTC AAACAACCATTTATGAGACCAGTACAAACTACTCAAGAGGAA GATGGCTGTAGCTGCCGATTTCCAGAAGAAGAAGAAGGAGGA TGTGAACTGCGGGTGAAGTTCAGCAGAAGCGCCGACGCCCCT GCCTACCAGCAGGGCCAGAATCAGCTGTACAACGAGCTGAAC CTGGGCAGAAGGGAAGAGTACGACGTCCTGGATAAGCGGAGA GGCCGGGACCCTGAGATGGGCGGCAAGCCTCGGCGGAAGAAC CCCCAGGAAGGCCTGTATAACGAACTGCAGAAAGACAAGATG GCCGAGGCCTACAGCGAGATCGGCATGAAGGGCGAGCGGAGG CGGGGCAAGGGCCACGACGGCCTGTATCAGGGCCTGTCCACC |

TABLE 1-continued

Exemplary DARIC Binding and Signaling Components

| SEQ ID NO. | Construct | Sequence |
|---|---|---|
| | | GCCACCAAGGATACCTACGACGCCCTGCACATGCAGGCCCTGC CCCCAAGGGGC |
| 50 | SS-CD19scFv-DmrA-CD4TM protein | MPLGLLWLGLALLGALHAQAGSDIQMTQTTSSLSASLGDRVTISC RASQDISKYLNWYQQKPDGTVKLLIYHTSRLHSGVPSRFSGSGSG TDYSLTISNLEQEDIATYFCQQGNTLPYTFGGGTKLEITGSTSGSG KPGSGEGSTKGEVKLQESGPGLVAPSQSLSVTCTVSGVSLPDYGV SWIRQPPRKGLEWLGVIWGSETTYYN |
| 51 | SS-CD19scFv-DmrA-CD4TM DNA | ATGCCCCTGGGCCTGCTGTGGCTGGGCCTGGCCCTGCTGGGCG CCCTGCACGCCCAGGCCGGATCCGATATCCAGATGACCCAGAC CACCAGCAGCCTGAGCGCCAGCCTGGGCGATAGAGTGACCAT CAGCTGCAGAGCCAGCCAGGACATCAGCAAGTACCTGAACTG GTATCAGCAGAAACCCGACGGCACCGTGAAGCTGCTGATCTAC CACACCAGCAGACTGCACAGCGGCGTGCCCAGCAGATTTTCTG GCAGCGGCTCCGGCACCGACTACAGCCTGACCATCTCCAACCT GGAACAGGAAGATATCGCTACCTACTTCTGTCAGCAAGGCAAC ACCCTGCCCTACACCTTCGGCGGAGGCACCAAGCTGGAAATCA CCGGCAGCACAAGCGGCAGCGGCAAGCCTGGATCTGGCGAGG GAAGCACCAAGGGCGAAGTGAAACTGCAGGAAAGCGGCCCTG GACTGGTGGCCCCAAGCCAGTCTCTGAGCGTGACCTGTACCGT GTCCGGCGTGTCCCTGCCTGACTATGGCGTGTCCTGGATCAGA CAGCCACCCAGAAAGGGCCTGGAATGGCTGGGAGTGATCTGG GGCAGCGAGACAACCTACTACAACAGCGCCCTGAAGTCCCGG CTGACCATCATCAAGGACAACTCCAAGAGCCAGGTGTTCCTGA AGATGAACAGCCTGCAGACCGACGACACCGCCATCTACTACTG CGCCAAGCACTACTACTACGGCGGCAGCTACGCCATGGACTAC TGGGGCCAGGGCACAAGCGTGACCGTGTCCAGCGCTAGCGGC GGAGGTGGGAGCGGAGTGCAGGTGGAAACCATCTCCCCAGGA GACGGGCGCACCTTCCCCAAGCGCGGCCAGACCTGCGTGGTGC ACTACACCGGGATGCTTGAAGATGGAAAGAAATTTGATTCCTC CCGGGACAGAAACAAGCCCTTTAAGTTTATGCTAGGCAAGCA GGAGGTGATCCGAGGCTGGGAAGAAGGGGTTGCCCAGATGAG TGTGGGTCAGAGAGCCAAACTGACTATATCTCCAGATTATGCC TATGGTGCCACTGGGCACCCAGGCATCATCCCACCACATGCCA CTCTCGTCTTCGATGTGGAGCTTCTAAAACTGGAAGGCGGCCG CATGGCCCTGATTGTGCTGGGGGGCGTCGCCGGCCTCCTGCTT TTCATTGGGCTAGGCATCTTCTTC |
| 53 | SS-CD19scFv-DmrA-CD8hingeTM protein | MPLGLLWLGLALLGALHAQAGSDIQMTQTTSSLSASLGDRVTISC RASQDISKYLNWYQQKPDGTVKLLIYHTSRLHSGVPSRFSGSGSG TDYSLTISNLEQEDIATYFCQQGNTLPYTFGGGTKLEITGSTSGSG KPGSGEGSTKGEVKLQESGPGLVAPSQSLSVTCTVSGVSLPDYGV SWIRQPPRKGLEWLGVIWGSETTYYN |
| 54 | SS-CD19scFv-DmrA-CD8hingeTM DNA | ATGCCCCTGGGCCTGCTGTGGCTGGGCCTGGCCCTGCTGGGCG CCCTGCACGCCCAGGCCGGATCCGATATCCAGATGACCCAGAC CACCAGCAGCCTGAGCGCCAGCCTGGGCGATAGAGTGACCAT CAGCTGCAGAGCCAGCCAGGACATCAGCAAGTACCTGAACTG GTATCAGCAGAAACCCGACGGCACCGTGAAGCTGCTGATCTAC CACACCAGCAGACTGCACAGCGGCGTGCCCAGCAGATTTTCTG GCAGCGGCTCCGGCACCGACTACAGCCTGACCATCTCCAACCT GGAACAGGAAGATATCGCTACCTACTTCTGTCAGCAAGGCAAC ACCCTGCCCTACACCTTCGGCGGAGGCACCAAGCTGGAAATCA CCGGCAGCACAAGCGGCAGCGGCAAGCCTGGATCTGGCGAGG GAAGCACCAAGGGCGAAGTGAAACTGCAGGAAAGCGGCCCTG GACTGGTGGCCCCAAGCCAGTCTCTGAGCGTGACCTGTACCGT GTCCGGCGTGTCCCTGCCTGACTATGGCGTGTCCTGGATCAGA CAGCCACCCAGAAAGGGCCTGGAATGGCTGGGAGTGATCTGG GGCAGCGAGACAACCTACTACAACAGCGCCCTGAAGTCCCGG CTGACCATCATCAAGGACAACTCCAAGAGCCAGGTGTTCCTGA AGATGAACAGCCTGCAGACCGACGACACCGCCATCTACTACTG CGCCAAGCACTACTACTACGGCGGCAGCTACGCCATGGACTAC TGGGGCCAGGGCACAAGCGTGACCGTGTCCAGCGCTAGCGGC GGAGGTGGGAGCGGAGTGCAGGTGGAAACCATCTCCCCAGGA GACGGGCGCACCTTCCCCAAGCGCGGCCAGACCTGCGTGGTGC ACTACACCGGGATGCTTGAAGATGGAAAGAAATTTGATTCCTC CCGGGACAGAAACAAGCCCTTTAAGTTTATGCTAGGCAAGCA GGAGGTGATCCGAGGCTGGGAAGAAGGGGTTGCCCAGATGAG TGTGGGTCAGAGAGCCAAACTGACTATATCTCCAGATTATGCC TATGGTGCCACTGGGCACCCAGGCATCATCCCACCACATGCCA CTCTCGTCTTCGATGTGGAGCTTCTAAAACTGGAAGGCGGCCG CGCCAAGCCTACCACCACCCCTGCCCCTAGACCTCCAACACCC GCCCCAACAATCGCCAGCCAGCCTCTGTCTCTGAGGCCCGAGG |

TABLE 1-continued

Exemplary DARIC Binding and Signaling Components

| SEQ ID NO. | Construct | Sequence |
|---|---|---|
| | | CTTGTAGACCAGCTGCTGGCGGAGCCGTGCACACCAGAGGACT GGATTTCGCCTGCGACATCTACATCTGGGCCCCTCTGGCCGGC ACATGTGGCGTGCTGCTGCTGAGCCTCGTGATCACC |
| 56 | SS-CD19scFv-DmrA-Spacer-CD4TM protein | MPLGLLWLGLALLGALHAQAGSDIQMTQTTSSLSASLGDRVTISC RASQDISKYLNWYQQKPDGTVKLLIYHTSRLHSGVPSRFSGSGSG TDYSLTISNLEQEDIATYFCQQGNTLPYTFGGGTKLEITGSTSGSG KPGSGEGSTKGEVKLQESGPGLVAPSQSLSVTCTVSGVSLPDYGV SWIRQPPRKGLEWLGVIWGSETTYYN |
| 57 | SS-CD19scFv-DmrA-Spacer-CD4TM DNA | ATGCCCCTGGGCCTGCTGTGGCTGGGCCTGGCCCTGCTGGGCG CCCTGCACGCCCAGGCCGGATCCGATATCCAGATGACCCAGAC CACCAGCAGCCTGAGCGCCAGCCTGGGCGATAGAGTGACCAT CAGCTGCAGAGCCAGCCAGGACATCAGCAAGTACCTGAACTG GTATCAGCAGAAACCCGACGGCACCGTGAAGCTGCTGATCTAC CACACCAGCAGACTGCACAGCGGCGTGCCCAGCAGATTTTCTG GCAGCGGCTCCGGCACCGACTACAGCCTGACCATCTCCAACCT GGAACAGGAAGATATCGCTACCTACTTCTGTCAGCAAGGCAAC ACCCTGCCCTACACCTTCGGCGGAGGCACCAAGCTGGAAATCA CCGGCAGCACAAGCGGCAGCGGCAAGCCTGGATCTGGCGAGG GAAGCACCAAGGGCGAAGTGAAACTGCAGGAAAGCGGCCCTG GACTGGTGGCCCCAAGCCAGTCTCTGAGCGTGACCTGTACCGT GTCCGGCGTGTCCCTGCCTGACTATGGCGTGTCCTGGATCAGA CAGCCACCCAGAAAGGGCCTGGAATGGCTGGGAGTGATCTGG GGCAGCGAGACAACCTACTACAACAGCGCCCTGAAGTCCCGG CTGACCATCATCAAGGACAACTCCAAGAGCCAGGTGTTCCTGA AGATGAACAGCCTGCAGACCGACGACACCGCCATCTACTACTG CGCCAAGCACTACTACTACGGCGGCAGCTACGCCATGGACTAC TGGGGCCAGGGCACAAGCGTGACCGTGTCCAGCGCTAGCGGC GGAGGTGGGAGCGGAGTGCAGGTGGAAACCATCTCCCCAGGA GACGGGCGCACCTTCCCCAAGCGCGGCCAGACCTGCGTGGTGC ACTACACCGGGATGCTTGAAGATGGAAAGAAATTTGATTCCTC CCGGGACAGAAACAAGCCCTTTAAGTTTATGCTAGGCAAGCA GGAGGTGATCCGAGGCTGGGAAGAAGGGGTTGCCCAGATGAG TGTGGGTCAGAGAGCCAAACTGACTATATCTCCAGATTATGCC TATGGTGCCACTGGGCACCCAGGCATCATCCCACCACATGCCA CTCTCGTCTTCGATGTGGAGCTTCTAAAACTGGAAGGCGGCCG CGAGAGCAAGTACGGACCGCCCTGCCCACCTTGCCCTGCCCCC GAGTTCCTGGGCGGACCCAGCGTGTTCCTGTTCCCACCCAAGC CCAAGGACACCCTGATGATCAGCCGGACCCCCGAGGTGACCT GCGTGGTGGTGGACGTGAGCCAGGAAGATCCCGAGGTCCAGT TCAATTGGTACGTGGACGGCGTGGAAGTGCACAACGCCAAGA CCAAGCCCAGAGAGGAACAGTTCAACAGCACCTACCGGGTGG TGTCTGTGCTGACCGTGCTGCACCAGGACTGGCTGAACGGCAA AGAATACAAGTGCAAGGTGTCCAACAAGGGCCTGCCCAGCAG CATCGAAAAGACCATCAGCAAGGCCAAGGGCCAGCCTCGCGA GCCCCAGGTGTACACCCTGCCTCCCTCCCAGGAAGAGATGACC AAGAACCAGGTGTCCCTGACCTGCCTGGTGAAGGGCTTCTACC CCAGCGACATCGCCGTGGAGTGGGAGAGCAACGGCCAGCCTG AGAACAACTACAAGACCACCCCTCCCGTGCTGGACAGCGACG GCAGCTTCTTCCTGTACAGCCGGCTGACCGTGGACAAGAGCCG GTGGCAGGAAGGCAACGTCTTTAGCTGCAGCGTGATGCACGA GGCCCTGCACAACCACTACACCCAGAAGAGCCTGAGCCTGTCC CTGGGCAAGATGGCCCTGATTGTGCTGGGGGGCGTCGCCGGCC TCCTGCTTTTCATTGGGCTAGGCATCTTCTTC |
| 59 | SS-CD19scFv-DmrA-CD52 GPI anchor protein | MPLGLLWLGLALLGALHAQAGSDIQMTQTTSSLSASLGDRVTISC RASQDISKYLNWYQQKPDGTVKLLIYHTSRLHSGVPSRFSGSGSG TDYSLTISNLEQEDIATYFCQQGNTLPYTFGGGTKLEITGSTSGSG KPGSGEGSTKGEVKLQESGPGLVAPSQSLSVTCTVSGVSLPDYGV SWIRQPPRKGLEWLGVIWGSETTYYN |
| 60 | SS-CD19scFv-DmrA-CD52 GPI anchor DNA | ATGCCCCTGGGCCTGCTGTGGCTGGGCCTGGCCCTGCTGGGCG CCCTGCACGCCCAGGCCGGATCCGATATCCAGATGACCCAGAC CACCAGCAGCCTGAGCGCCAGCCTGGGCGATAGAGTGACCAT CAGCTGCAGAGCCAGCCAGGACATCAGCAAGTACCTGAACTG GTATCAGCAGAAACCCGACGGCACCGTGAAGCTGCTGATCTAC CACACCAGCAGACTGCACAGCGGCGTGCCCAGCAGATTTTCTG GCAGCGGCTCCGGCACCGACTACAGCCTGACCATCTCCAACCT GGAACAGGAAGATATCGCTACCTACTTCTGTCAGCAAGGCAAC ACCCTGCCCTACACCTTCGGCGGAGGCACCAAGCTGGAAATCA CCGGCAGCACAAGCGGCAGCGGCAAGCCTGGATCTGGCGAGG GAAGCACCAAGGGCGAAGTGAAACTGCAGGAAAGCGGCCCTG GACTGGTGGCCCCAAGCCAGTCTCTGAGCGTGACCTGTACCGT |

TABLE 1-continued

Exemplary DARIC Binding and Signaling Components

| SEQ ID NO. | Construct | Sequence |
|---|---|---|
| | | GTCCGGCGTGTCCCTGCCTGACTATGGCGTGTCCTGGATCAGA<br>CAGCCACCCAGAAAGGGCCTGGAATGGCTGGGAGTGATCTGG<br>GGCAGCGAGACAACCTACTACAACAGCGCCCTGAAGTCCCGG<br>CTGACCATCATCAAGGACAACTCCAAGAGCCAGGTGTTCCTGA<br>AGATGAACAGCCTGCAGACCGACGACACCGCCATCTACTACTG<br>CGCCAAGCACTACTACTACGGCGGCAGCTACGCCATGGACTAC<br>TGGGGCCAGGGCACAAGCGTGACCGTGTCCAGCGCTAGCGGC<br>GGAGGTGGGAGCGGAGTGCAGGTGGAAACCATCTCCCCAGGA<br>GACGGGCGCACCTTCCCCAAGCGCGGCCAGACCTGCGTGGTGC<br>ACTACACCGGGATGCTTGAAGATGGAAAGAAATTTGATTCCTC<br>CCGGGACAGAAACAAGCCCTTTAAGTTTATGCTAGGCAAGCA<br>GGAGGTGATCCGAGGCTGGGAAGAAGGGGTTGCCCAGATGAG<br>TGTGGGTCAGAGAGCCAAACTGACTATATCTCCAGATTATGCC<br>TATGGTGCCACTGGGCACCCAGGCATCATCCCACCACATGCCA<br>CTCTCGTCTTCGATGTGGAGCTTCTAAAACTGGAAGGCGGCCG<br>CACCAGCCAAACCAGCAGCCCCTCAGCATCCAGCAACATAAG<br>CGGAGGCATTTTCCTTTTCTTCGTGGCCAATGCCATAATCCACC<br>TCTTCTGCTTCAGT |
| 64 | CD8ss-DmrC-CD8TM-<br>41BB-CD3z-P2A-<br>IgKss-CD19scFv-<br>DmrA-CD4TM protein | MALPVTALLLPLALLLHAARPGSILWHEMWHEGLEEASRLYFGE<br>RNVKGMFEVLEPLHAMMERGPQTLKETSFNQAYGRDLMEAQE<br>WCRKYMKSGNVKDLLQAWDLYYHVFRRISKASAGTGSDIYIWA<br>PLAGTCGVLLLSLVITMHKRGRKKLLYIFKQPFMRPVQTTQEEDG<br>CSCRFPEEEEGGCELRVKFSRSADAPAYQQGQNQLYNELNLGRR<br>EEYDVLDKRRGRDPEMGGKPRRKNPQEGLYNELQKDKMAEAYS<br>EIGMKGERRRGKGHDGLYQGLSTATKDTYDALHMQALPPRSGS<br>GATNFSLLKQAGDVEENPGPSMETDTLLLWVLLLWVPGSTGSDI<br>QMTQTTSSLSASLGDRVTISCRASQDISKYLNWYQQKPDGTVKLL<br>IYHTSRLHSGVPSRFSGSGSGTDYSLTISNLEQEDIATYFCQQGNTL<br>PYTFGGGTKLEITGSTSGSGKPGSGEGSTKGEVKLQESGPGLVAPS<br>QSLSVTCTVSGVSLPDYGVSWIRQPPRKGLEWLGVIWGSETTYY<br>NSALKSRLTIIKDNSKSQVFLKMNSLQTDDTAIYYCAKHYYYGGS<br>YAMDYWGQGTSVTVSSASGGGGSGVQVETISPGDGRTFPKRGQT<br>CVVHYTGMLEDGKKFDSSRDRNKPFKFMLGKQEVIRGWEEGVA<br>QMSVGQRAKLTISPDYAYGATGHPGIIPPHATLVFDVELLKLEGG<br>RMALIVLGGVAGLLLFIGLGIFFCVRCRHRRRQ |
| 65 | CD8ss-DmrC-CD8TM-<br>41BB-CD3z-P2A-<br>IgKss-CD19scFv-<br>DmrA-CD4TM DNA | ATGGCTCTGCCTGTGACAGCTCTGCTGCTGCCTCTGGCCCTGCT<br>GCTCCATGCCGCCAGACCCGGATCCATCCTCTGGCATGAGATG<br>TGGCATGAAGGCCTGGAAGAGGCATCTCGTTTGTACTTTGGGG<br>AAAGGAACGTGAAAGGCATGTTTGAGGTGCTGGAGCCCTTGC<br>ATGCTATGATGGAACGGGGCCCCCAGACTCTGAAGGAAACAT<br>CCTTTAATCAGGCCTATGGTCGAGATTTAATGGAGGCCCAAGA<br>GTGGTGCAGGAAGTACATGAAATCAGGGAATGTCAAGGACCT<br>CCTCCAAGCCTGGGACCTCTATTATCATGTGTTCCGACGAATCT<br>CAAAGGCTAGCGCCGGCACTGGTTCCGACATCTACATCTGGGC<br>CCCTCTGGCCGGCACATGTGGCGTGCTGCTGCTGAGCCTCGTG<br>ATCACCATGCATAAACGGGGCAGAAAGAAACTCCTGTATATAT<br>TCAAACAACCATTTATGAGACCAGTACAAACTACTCAAGAGG<br>AAGATGGCTGTAGCTGCCGATTTCCAGAAGAAGAAGAAGGAG<br>GATGTGAACTGCGGGTGAAGTTCAGCAGAAGCGCCGACGCCC<br>CTGCCTACCAGCAGGGCCAGAATCAGCTGTACAACGAGCTGA<br>ACCTGGGCAGAAGGGAAGAGTACGACGTCCTGGATAAGCGGA<br>GAGGCCGGGACCCTGAGATGGGCGGCAAGCCTCGGCGGAAGA<br>ACCCCCAGGAAGGCCTGTATAACGAACTGCAGAAAGACAAGA<br>TGGCCGAGGCCTACAGCGAGATCGGCATGAAGGGCGAGCGGA<br>GGCGGGGCAAGGGCCACGACGGCCTGTATCAGGGCCTGTCCA<br>CCGCCACCAAGGATACCTACGACGCCCTGCACATGCAGGCCCT<br>GCCCCCAAGGTCAGGATCTGGCGCCACGAACTTCTCTCTGTTA<br>AAGCAAGCAGGAGATGTTGAAGAAAACCCCGGGCCTTCAATG<br>GAGACAGACACACTCCTGCTATGGGTACTGCTGCTCTGGGTTC<br>CAGGTTCCACTGGTTCCGATATCCAGATGACCCAGACCACCAG<br>CAGCCTGAGCGCCAGCCTGGGCGATAGAGTGACCATCAGCTG<br>CAGAGCCAGCCAGGACATCAGCAAGTACCTGAACTGGTATCA<br>GCAGAAACCCGACGGCACCGTGAAGCTGCTGATCTACCACAC<br>CAGCAGACTGCACAGCGGCGTGCCCAGCAGATTTTCTGGCAGC<br>GGCTCCGGCACCGACTACAGCCTGACCATCTCCAACCTGGAAC<br>AGGAAGATATCGCTACCTACTTCTGTCAGCAAGGCAACACCCT<br>GCCCTACACCTTCGGCGGAGGCACCAAGCTGGAAATCACCGG<br>CAGCACAAGCGGCAGCGGCAAGCCTGGATCTGGCGAGGGAAG<br>CACCAAGGGCGAAGTGAAACTGCAGGAAAGCGGCCCTGGACT<br>GGTGGCCCCAAGCCAGTCTCTGAGCGTGACCTGTACCGTGTCC<br>GGCGTGTCCCTGCCTGACTATGGCGTGTCCTGGATCAGACAGC<br>CACCCAGAAAGGGCCTGGAATGGCTGGGAGTGATCTGGGGCA |

TABLE 1-continued

| Exemplary DARIC Binding and Signaling Components | | |
|---|---|---|
| SEQ ID NO. | Construct | Sequence |
| | | GCGAGACAACCTACTACAACAGCGCCCTGAAGTCCCGGCTGA CCATCATCAAGGACAACTCCAAGAGCCAGGTGTTCCTGAAGAT GAACAGCCTGCAGACCGACGACACCGCCATCTACTACTGCGCC AAGCACTACTACTACGGCGGCAGCTACGCCATGGACTACTGGG GCCAGGGCACAAGCGTGACCGTGTCCAGCGCTAGCGGCGGAG GTGGGAGCGGAGTGCAGGTGGAAACCATCTCCCCAGGAGACG GGCGCACCTTCCCCAAGCGCGGCCAGACCTGCGTGGTGCACTA CACCGGGATGCTTGAAGATGGAAAGAAATTTGATTCCTCCCGG GACAGAAACAAGCCCTTTAAGTTTATGCTAGGCAAGCAGGAG GTGATCCGAGGCTGGGAAGAAGGGGTTGCCCAGATGAGTGTG GGTCAGAGAGCCAAACTGACTATATCTCCAGATTATGCCTATG GTGCCACTGGGCACCCAGGCATCATCCCACCACATGCCACTCT CGTCTTCGATGTGGAGCTTCTAAAACTGGAAGGCGGCCGCATG GCCCTGATTGTGCTGGGGGGCGTCGCCGGCCTCCTGCTTTTCAT TGGGCTAGGCATCTTCTTCTGTGTCAGGTGCCGGCACCGAAGG CGCCAATAA |
| 67 | CD8ss-DmrC-CD8TM-41BB-CD3z-P2A-IgKss-CD19scFv-DmrA-CD4TM codon optimized protein | MALPVTALLLPLALLLHAARPGSILWHEMWHEGLEEASRLYFGE RNVKGMFEVLEPLHAMMERGPQTLKETSFNQAYGRDLMEAQE WCRKYMKSGNVKDLLQAWDLYYHVFRRISKASAGTGSDIYIWA PLAGTCGVLLLSLVITMHKRGRKKLLYIFKQPFMRPVQTTQEEDG CSCRFPEEEEGGCELRVKFSRSADAPAYQQGQNQLYNELNLGRR EEYDVLDKRRGRDPEMGGKPRRKNPQEGLYNELQKDKMAEAYS EIGMKGERRRGKGHDGLYQGLSTATKDTYDALHMQALPPRSGS GATNFSLLKQAGDVEENPGPSMETDTLLLWVLLLWVPGSTGDIQ MTQTTSSLSASLGDRVTISCRASQDISKYLNWYQQKPDGTVKLLI YHTSRLHSGVPSRFSGSGSGTDYSLTISNLEQEDIATYFCQQGNTL PYTFGGGTKLEITGSTSGSGKPGSGEGSTKGEVKLQESGPGLVAPS QSLSVTCTVSGVSLPDYGVSWIRQPPRKGLEWLGVIWGSETTYY NSALKSRLTIIKDNSKSQVFLKMNSLQTDDTAIYYCAKHYYYGGS YAMDYWGQGTSVTVSSPRGGGGSGVQVETISPGDGRTFPKRGQT CVVHYTGMLEDGKKFDSSRDRNKPFKFMLGKQEVIRGWEEGVA QMSVGQRAKLTISPDYAYGATGHPGIIPPHATLVFDVELLKLEGG RMALIVLGGVAGLLLFIGLGIFFCVRCRHRRRQ |
| 68 | CD8ss-DmrC-CD8TM-41BB-CD3z-P2A-IgKss-CD19scFv-DmrA-CD4TM codon optimized DNA | ATGGCCCTCCCTGTGACCGCCCTGCTGCTCCCCCTCGCCCTGTT GCTCCATGCTGCCCGACCTGGATCCATCCTTTGGCACGAGATG TGGCACGAGGGACTCGAAGAAGCGTCCCGGCTGTACTTCGGA GAGCGGAACGTGAAGGGGATGTTCGAAGTGCTGGAACCCCTG CACGCCATGATGGAGCGGGGTCCTCAGACCCTTAAAGAAACA AGCTTCAACCAGGCGTACGGGCGCGACCTGATGGAAGCCCAG GAGTGGTGCCGCAAGTACATGAAGTCCGGAAACGTGAAGGAT CTGCTGCAAGCCTGGGATCTGTACTACCACGTGTTCAGAAGGA TCTCAAAGGCTAGCGCCGGCACTGGTTCGGATATCTACATTTG GGCACCGCTCGCCGGCACTTGTGGAGTGCTGTTGCTGTCCCTC GTGATCACCATGCATAAGAGGGGACGGAAGAAGCTGCTGTAC ATTTTCAAGCAGCCATTCATGCGGCCTGTGCAAACCACCCAGG AGGAGGACGGGTGCAGCTGCCGGTTCCCTGAGGAAGAGGAGG GCGGATGCGAACTGCGCGTGAAGTTCAGCCGGAGCGCAGATG CTCCCGCATACCAACAGGGACAGAACCAGCTGTATAACGAGC TGAACCTGGGCAGAAGGGAAGAGTACGACGTCCTCGACAAGC GGCGGGGACGCGACCCAGAAATGGGAGGAAAGCCCCGCCGGA AGAACCCGCAGGAAGGCCTGTACAACGAGTTGCAGAAAGACA AGATGGCTGAAGCTTACTCGGAGATTGGCATGAAGGGGGAGA GAAGAAGAGGGAAGGGCCACGACGGCCTTTACCAAGGACTGA GCACTGCCACCAAGGACACCTACGATGCGCTGCACATGCAGG CCCTGCCCCCGCGGTCCGGTTCGGGCGCGACTAACTTCAGCCT GCTGAAGCAGGCCGGAGATGTGGAGGAAAACCCTGGACCGTC CATGGAGACTGATACCCTGCTTCTGTGGGTCCTGCTCCTCTGG GTGCCGGGCTCCACCGGTGACATCCAGATGACCCAGACCACCT CATCCCTGAGCGCCTCTCTGGGTGATCGCGTGACTATCTCCTGC CGGGCGTCGCAGGATATCTCCAAGTACCTGAACTGGTACCAGC AAAAACCGGACGGGACCGTGAAACTGCTGATCTACCATACTTC CCGCCTTCATTCCGGAGTGCCCTCCCGGTTTTCCGGCTCGGGTT CAGGGACTGATTATTCGCTGACCATTTCCAACCTGGAGCAGGA GGACATTGCGACCTACTTCTGCCAACAAGGAAACACCCTGCCC TACACTTTCGGTGGTGGAACCAAGCTCGAGATCACCGGATCAA CCTCGGGCAGCGGGAAGCCGGGCAGCGGAGAGGGATCGACGA AAGGAGAAGTCAAGCTGCAGGAATCCGGCCCGGGACTGGTGG CCCCGAGCCAGTCGCTCTCCGTCACTTGCACCGTGTCGGGAGT GTCCTTGCCCGACTACGGAGTGTCATGGATTCGGCAGCCACCT CGCAAGGGCCTGGAATGGCTCGGCGTGATTTGGGGCTCAGAA ACCACATACTACAACAGCGCCCTGAAGTCTCGGCTCACCATCA TCAAGGACAATTCCAAGTCCCAAGTGTTCCTGAAGATGAATAG |

TABLE 1-continued

Exemplary DARIC Binding and Signaling Components

| SEQ ID NO. | Construct | Sequence |
|---|---|---|
| | | CTTGCAGACTGACGACACCGCGATCTACTACTGTGCCAAGCAC TACTACTACGGCGGTTCCTACGCCATGGACTACTGGGGACAAG GAACTTCCGTGACTGTCTCCTCCCCTAGGGGGGGTGGTGGTTC GGGGGTCCAGGTGGAAACCATTTCCCCCGGCGACGGGCGCAC CTTCCCGAAGCGCGGACAGACCTGTGTGGTGCACTATACCGGA ATGCTCGAAGATGGAAAGAAGTTTGACAGCTCCAGGGACCGC AACAAGCCTTTCAAGTTTATGCTTGGAAAGCAGGAAGTCATCC GGGGCTGGGAAGAGGGAGTCGCCCAGATGAGCGTCGGCCAGC GGGCCAAGCTGACGATCTCCCCTGACTATGCCTACGGCGCTAC CGGCCATCCCGGAATCATTCCGCCGCACGCAACCCTCGTGTTC GACGTGGAATTGCTCAAGCTGGAAGGCGGCCGCATGGCGCTG ATAGTGCTCGGCGGAGTGGCCGGACTGCTGCTGTTCATCGGCC TGGGCATCTTCTTCTGCGTGAGATGCCGCCATAGAAGGCGGCA ATGA |
| 70 | SS-DmrC-CD8TM-41BB-CD3z-P2A-SS-CD123scFv-DmrA-CD4TM protein | MRPTWAWWLFLVLLLALWAPARGGSILWHEMWHEGLEEASRL YFGERNVKGMFEVLEPLHAMMERGPQTLKETSFNQAYGRDLME AQEWCRKYMKSGNVKDLLQAWDLYYHVFRRISKASAGTGSDIY IWAPLAGTCGVLLLSLVITMHKRGRKKLLYIFKQPFMRPVQTTQE EDGCSCRFPEEEEGGCELRVKFSRSADAPAYQQGQNQLYNELNL GRREEYDVLDKRRGRDPEMGGKPRRKNPQEGLYNELQKDKMAE AYSEIGMKGERRRGKGHDGLYQGLSTATKDTYDALHMQALPPR GGRSGSGATNFSLLKQAGDVEENPGPSLWWRLWWLLLLLLLLW PMVWAPRADYKDIVMTQSHKFMSTSVGDRVNITCKASQNVDSA VAWYQQKPGQSPKALIYSASYRYSGVPDRFTGRGSGTDFTLTISS VQAEDLAVYYCQQYYSTPWTFGGGTKLEIKRGGGGSGGGGSGG GGSGGGGSEVKLVESGGGLVQPGGSLSLSCAASGFTFTDYYMSW VRQPPGKALEWLALIRSKADGYTTEYSASVKGRFTLSRDDSQSIL YLQMNALRPEDSATYYCARDAAYYSYYSPEGAMDYWGQGTSV TVSSSASGGGGSGVQVETISPGDGRTFPKRGQTCVVHYTGMLED GKKFDSSRDRNKPFKFMLGKQEVIRGWEEGVAQMSVGQRAKLTI SPDYAYGATGHPGIIPPHATLVFDVELLKLEGGRMALIVLGGVAG LLLFIGLGIFFCVRCRHRRRQ |
| 71 | SS-DmrC-CD8TM-41BB-CD3z-P2A-SS-CD123scFv-DmrA-CD4TM DNA | ATGCGCCCCACCTGGGCCTGGTGGCTGTTCCTGGTGCTGCTGC TGGCCCTGTGGGCACCCGCTCGCGGCGGATCCATCCTCTGGCA TGAGATGTGGCATGAAGGCCTGGAAGAGGCATCTCGTTTGTAC TTTGGGGAAAGGAACGTGAAAGGCATGTTTGAGGTGCTGGAG CCCTTGCATGCTATGATGGAACGGGGCCCCCAGACTCTGAAGG AAACATCCTTTAATCAGGCCTATGGTCGAGATTTAATGGAGGC CCAAGAGTGGTGCAGGAAGTACATGAAATCAGGGAATGTCAA GGACCTCCTCCAAGCCTGGGACCTCTATTATCATGTGTTCCGA CGAATCTCAAAGGCTAGCGCCGGCACTGGTTCCGACATCTACA TCTGGGCCCCTCTGGCCGGCACATGTGGCGTGCTGCTGCTGAG CCTCGTGATCACCATGCATAAACGGGGCAGAAAGAAACTCCT GTATATATTCAAACAACCATTTATGAGACCAGTACAAACTACT CAAGAGGAAGATGGCTGTAGCTGCCGATTTCCAGAAGAAGAA GAAGGAGGATGTGAACTGCGGGTGAAGTTCAGCAGAAGCGCC GACGCCCCTGCCTACCAGCAGGGCCAGAATCAGCTGTACAAC GAGCTGAACCTGGGCAGAAGGGAAGAGTACGACGTCCTGGAT AAGCGGAGAGGCCGGGACCCTGAGATGGGCGGCAAGCCTCGG CGGAAGAACCCCCAGGAAGGCCTGTATAACGAACTGCAGAAA GACAAGATGGCCGAGGCCTACAGCGAGATCGGCATGAAGGGC GAGCGGAGGCGGGGCAAGGGCCACGACGGCCTGTATCAGGGC CTGTCCACCGCCACCAAGGATACCTACGACGCCCTGCACATGC AGGCCCTGCCCCCAAGGGGCGGCCGCTCAGGATCTGGCGCCA CGAACTTCTCTCTGTTAAAGCAAGCAGGAGATGTTGAAGAAAA CCCCGGGCCTTCACTGTGGTGGCGCCTGTGGTGGCTGCTCCTG CTTCTGTTGCTCCTGTGGCCCATGGTGTGGGCCCCTAGGGCGG ACTACAAAGATATTGTGATGACCCAGTCTCACAAATTCATGTC CACATCAGTAGGAGACAGGGTCAACATCACCTGCAAGGCCAG TCAGAATGTGGATAGTGCTGTAGCCTGGTATCAACAGAAACCA GGGCAATCTCCTAAAGCACTGATTTACTCGGCATCCTACCGGT ACAGTGGAGTCCCTGATCGCTTCACAGGCAGGGGATCTGGGAC AGATTTCACTCTCACCATCAGCAGTGTGCAGGCTGAAGACCTG GCAGTTTATTACTGTCAGCAATATTATAGCACTCCGTGGACGT TCGGTGGAGGCACCAAGCTGGAAATCAAACGTGGTGGTGGTG GTTCTGGTGGTGGTGGTTCTGGCGGCGGCGGCTCCGGTGGTGG TGGATCCGAGGTGAAGCTGGTGGAGTCTGGAGGAGGCTTGGT ACAGCCTGGGGGTTCTCTGAGTCTCTCCTGTGCAGCTTCTGGAT TCACCTTCACTGATTACTACATGAGCTGGGTCCGCCAGCCTCC AGGGAAGGCACTTGAGTGGTTGGCTTTGATTAGAAGCAAAGCT GATGGTTACACAACAGAATACAGTGCATCTGTGAAGGGTCGGT TCACCCTCTCCAGAGATGATTCCCAAAGCATCCTCTATCTTCAA |

TABLE 1-continued

| Exemplary DARIC Binding and Signaling Components | | |
|---|---|---|
| SEQ ID NO. | Construct | Sequence |
| | | ATGAATGCCCTGAGACCTGAAGACAGTGCCACTTATTACTGTG<br>CAAGAGATGCGGCCTACTATAGTTACTATAGTCCCGAGGGGGC<br>TATGGACTACTGGGGTCAAGGAACCTCAGTCACCGTCTCCTCG<br>AGCGCTAGCGGCGGAGGTGGGAGCGGAGTGCAGGTGGAAACC<br>ATCTCCCCAGGAGACGGGCGCACCTTCCCCAAGCGCGGCCAG<br>ACCTGCGTGGTGCACTACACCGGGATGCTTGAAGATGGAAAG<br>AAATTTGATTCCTCCCGGGACAGAAACAAGCCCTTTAAGTTTA<br>TGCTAGGCAAGCAGGAGGTGATCCGAGGCTGGGAAGAAGGGG<br>TTGCCCAGATGAGTGTGGGTCAGAGAGCCAAACTGACTATATC<br>TCCAGATTATGCCTATGGTGCCACTGGGCACCCAGGCATCATC<br>CCACCACATGCCACTCTCGTCTTCGATGTGGAGCTTCTAAAAC<br>TGGAAGGCGGCCGCATGGCCCTGATTGTGCTGGGGGGCGTCGC<br>CGGCCTCCTGCTTTTCATTGGGCTAGGCATCTTCTTCTGTGTCA<br>GGTGCCGGCACCGAAGGCGCCAATAA |

EXAMPLES

Example 1

Construction of Daric Binding and Signaling Components

The DARIC binding and signaling components were each separately cloned into a plasmid vector containing a T7 promoter, a hScn or hCD8 secretion signal, respectively, and a downstream linearization site. Linearized plasmids were then used as templates for in vitro transcription reactions, followed by 3'-polyadenylation and 5'-capping steps to create mature in vitro transcribed mRNA (IVT-mRNA) to be electroporated into primary human T cells.

Human T cells were isolated from PBMCs by negative selection using paramagnetic beads and expanded with anti-CD3/anti-CD28 beads for 48 hours prior to electroporation. Control electroporations using IVT-mRNA encoding fluorescent proteins were performed in parallel to confirm transfection efficiency, or 2A protein-linked fluorescent proteins were incorporated directly into the DARIC component mRNA species.

Exemplary IVT-mRNA encoding binding components (scFv specific for CD19 and multimerization domain FKBP12 ("DmrA"), FKBP12 F36V ("DmrB"), FRB (2021-2113) T2098L ("DmrC")) are provided in SEQ ID NOs.: 2, 5, and 8 (scFv specific for CD19 and multimerization domain FKBP12, FKBP12 F36V, or FRB (2021-2113) T2098L, respectively). Exemplary IVT-mRNA encoding signaling components are provided in SEQ ID NOs.:16, 20, and 24 (multimerization domain FRB (2021-2113) T2098L, FKBP12 F36V, or FKBP12, respectively, transmembrane domain, 4-1BB, and CD3ζ).

Multimerization is promoted with a bridging factor, such as rapamycin or rapalogs thereof, or gibberellin or derivatives thereof. Rapamycin and its derivatives (e.g., AP21967, also known as C-16-(S)-7-methylindolerapamycin, $IC_{50}$=10 nM, a chemically modified non-immunosuppressive rapamycin analogue) can induce heterodimerization of FKBP12 and FRB-containing fusion proteins. AP1903 or AP20187 are homo-bivalent drugs based on the FKBP12-interacting component of rapamycin, which can be used in homodimerization scenarios described herein.

Example 2

Cytotoxicity of T Cells Encoding Daric Components

Recombinant T cells expressing the two DARIC components were incubated with K562 target cells (a human myeloid leukemia cell line), which were modified to express either CD19 or CD20 antigen, to examine target cell lysis. Briefly, T cells were co-incubated with a 50:50 mixture of K562-CD19 and K562-CD20 target cell lines, at 3:1 or 10:1 T cell to target cell ratios. In experimental samples, 500 nM final concentration of the hetero-bivalent rapalog AP21967 was added. The relative percentage of each of the target cell lines was monitored by flow cytometry staining for the CD19 and CD20 antigens to evaluate cell lysis (see FIG. 3).

Figure 3A:
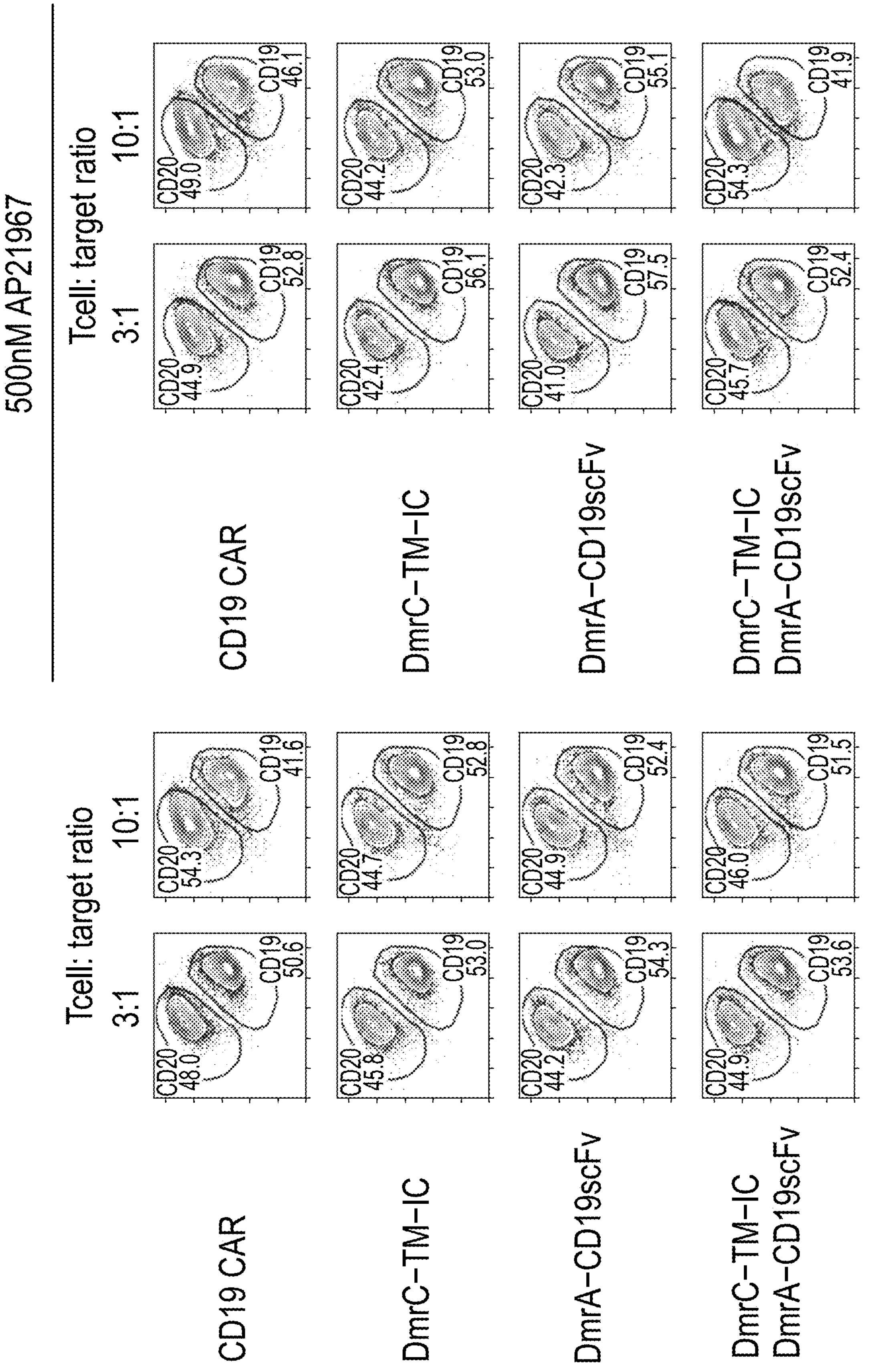
FIGS. 3A and 3B show the cytotoxic properties of human T cells expressing a multipartite signaling complex of this disclosure.

Four samples of primary human T cells were prepared by electroporation with IVT-mRNA encoding (i) an extensively validated single-chain chimeric antigen receptor (CAR) (CD19-CAR, SEQ ID NO.:14, positive control); (ii) the DARIC signaling component only (DSC, SEQ ID NO.:16, negative control); iii) the DARIC binding component only (DBC-CD19, SEQ ID NO.:2, negative control); and (iv) both DARIC binding and signaling components (DSC, SEQ ID NO.:16 plus DBC-CD19, SEQ ID NO.:2). The relative percentages of each of the target cell lines were monitored by flow cytometry staining for the CD19 and CD20 antigens (FIG. 3A).

Figure 3B:
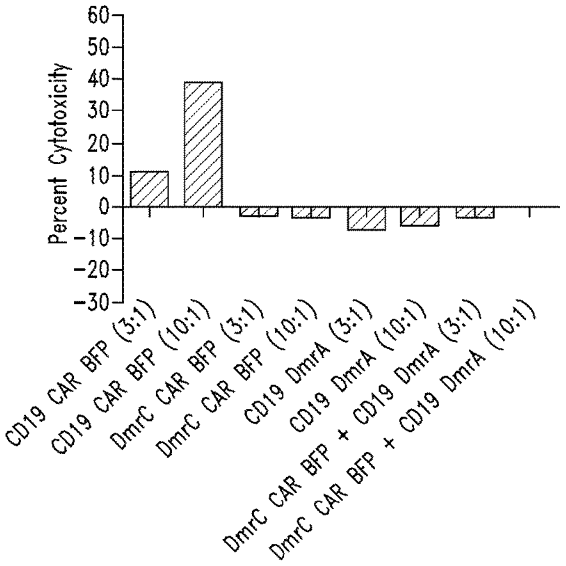
Figure 3B:
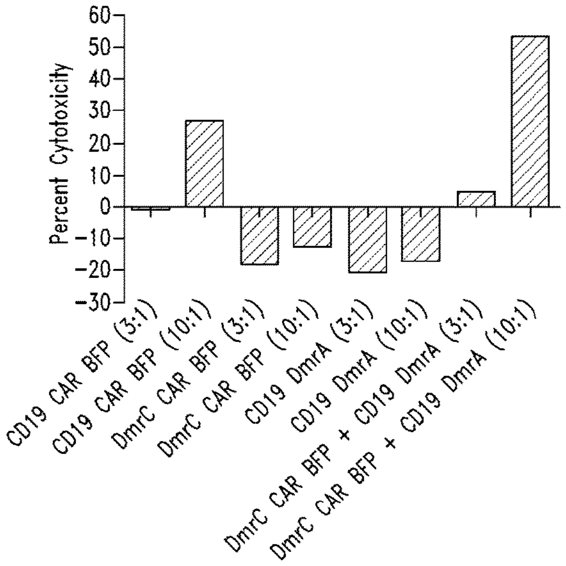

The percent specific cytotoxicity was calculated for each condition as the percentage change relative the input K562-CD19:K562-CD20 ratio. T cells expressing the validated CD19-CAR (SEQ ID NO.:14) showed substantial cytotoxicity and skewing of the ratio of CD19 versus CD20 cells in the live cell gate, particularly at a 10:1 T cell to target cell ratio. The T cells expressing the DARIC binding component alone, DARIC signaling component alone, or both DARIC components but without the addition of the hetero-bivalent rapalog AP21967, showed no significant cytotoxicity. In the presence of AP21967, a substantial specific cytoxicity and loss of the K562-CD19 target cells was observed upon co-incubation with T cells expressing both DARIC components (FIG. 3B).

These results indicate that the DARIC mechanism can reconstitute antigen-specific target cell lysis. Furthermore, the DARIC design enables pharmacological control of antigen-specific T cell cytotoxicity.

Example 3

Cytokine Secretion Profile of T Cells Encoding Daric Components

Figure 4:
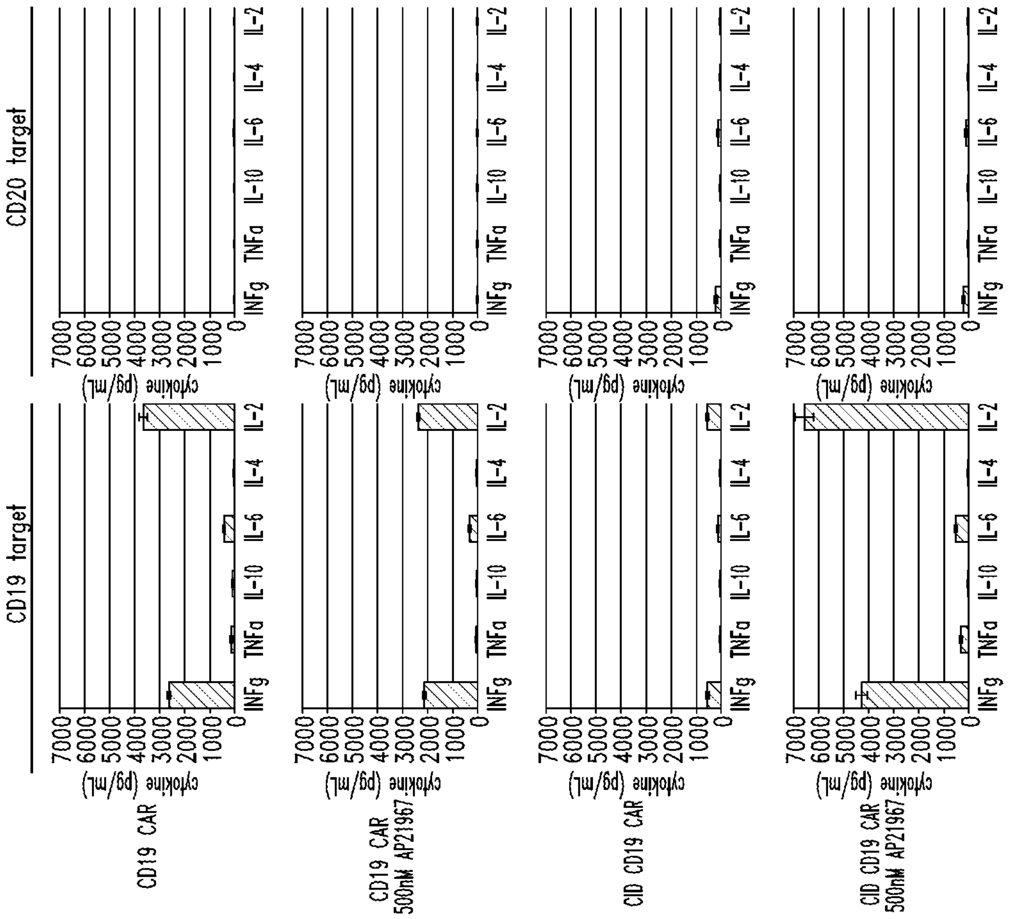
FIG. 4 shows the cytokine secretion profile of human T cells expressing a multipartite signaling complex of this disclosure.

Recombinant T cells expressing the two DARIC components were incubated with K562 target cells (a human myeloid leukemia cell line), which were modified to express either CD19 or CD20 antigen, to examine cytokine expression. Briefly, IVT-mRNA transfected T cells were co-incubated with either the K562-CD19 or K562-CD20 cell lines using T cell to target ratios of 1:1, with or without the addition of 500 nM AP21967. Supernatants were isolated for analysis of cytokine production (see FIG. 4).

Two samples of primary human T cells were isolated, expanded, and then prepared by electroporation with IVT-mRNA encoding either (i) the validated single-chain CAR (CD19-CAR, SEQ ID NO.:13, positive control); or (ii) both DARIC binding and signaling components (DSC, SEQ ID NO.:16 plus DBC-CD19, SEQ ID NO.:2). After extensively washing the expanded and electroporated T cells to remove residual cytokines from the growth media, the T cells were co-incubated with K562 cell lines expressing either the human CD19 antigen (left panels) or the CD20 antigen (right panels) at 1:1 T cell to target cell ratios and in the presence or absence of the AP21967 rapalog. The supernatants were then collected and assayed for analyte concentrations using cytokine capture antibody-labeled beads (Becton Dickenson Cytokine Bead Array, human Th1/Th2 kit). Comparison with recombinant protein standards enabled calculation of absolute concentrations of each of the six cytokines encompassed by the bead array.

Consistent with previous cytotoxicity findings, T cells expressing the positive control CD19-CAR produced substantial amounts of interferon-gamma (IFNγ) and interleukin-2 (IL-2) when co-incubated with CD19 expressing K562 target cells. T cells expressing the DARIC components in the absence of bridging factor AP21967 showed no significant cytokine production, but in the presence of AP21967 produced IFNγ and IL-2 at levels equivalent, or superior, to the single chain CD19-CAR positive control.

Example 4

Lentiviral Delivery of Daric Components

Primary human T cells were isolated, activated, and then transduced with lentiviral vectors encoding DARIC binding and signaling components (SEQ ID NOS.:44 and 47). The transduced T cells were then co-incubated with about a 50:50 mixture of the K562 target cells expressing either CD19 (K562-CD19) or CD20 (K562-CD20) to evaluate antigen-specific cytotoxicity. The overall ratio of T cells to K562 cells was 5:1 in all samples. In control samples, no bridging factor was added, whereas in experimental samples either rapamycin (10 nM) or AP21967 (100 nM) were applied as the bridging factor for the secreted antigen binding component and the signaling component (see, e.g., FIG. 1B). The DARIC antigen binding component includes a CD19 antigen binding scFv domain and a FKBP12 multimerization domain, which was linked to a mCherry fluorescent protein. Two independent multimerization domains having different specificities for bridging components were tested on the DARIC signaling component: FRB, which is responsive to rapamycin, and the FRB (2021-2113) T2098L variant, which is responsive to both rapamycin and AP21967, each linked to the blue fluorescent protein (BFP).

Flow cytometric analysis of the lentivirus-transduced T cells demonstrated expression of both mCherry and BFP proteins simultaneously, indicating both DARIC components were being expressed within the same cells (see FIG. 5, first column for each treatment). Flow cytometric analysis of the K562 cells demonstrated rapamycin and AP21967-dependent elimination of the CD19 expressing K562 cells in the sample expressing variant FRB (2021-2113) T2098L multimerization domain, whereas no addition of a bridging factor had no effect on cell survival (see FIG. 5, top row of second column for each treatment). But, only rapamycin was able to activate the elimination of the K562-CD19 cells by T cells expressing the FRB dimerization domain, while AP21967 or no addition of a bridging factor had no effect on cell survival (see FIG. 5, second row of second column for each treatment). These data show the specificity of cytotoxic activity that can be achieved with the DARIC multipartite component system.

In addition, two distinct T cell populations were mixed, wherein one population was expressing a DARIC antigen binding component and the other population was expressing a DARIC signaling component. This mixed cell population, when co-cultured with the CD19 and CD20 expressing K562 cells, showed a rapamycin-dependent cytotoxicity response against K562-CD19 cells, while the absence of a bridging factor had no effect on target cell survival (see FIG. 5, bottom row). These data indicate that a DARIC antigen binding component expressed by one T cell population can act in trans with a different population of T cells that express a DARIC signaling component and attack the target cells.

The flexibility of the DARIC system was validated by swapping the multimerization domains such that the DARIC binding component targeting CD19 comprised the FRB based DmrC domain and the DARIC signaling component comprised the FKBP12 based DmrA domain (SEQ ID NOs.:12, 31). Primary human T cells were made to express the 'swapped' DARIC components and then co-incubated with 50:50 mixtures of the K562-CD19 and C562-CD20 target cells either in the absence or presence of the indicated concentrations of rapamycin (FIG. 10). Antigen specific cytotoxicity was observed in the experimental samples containing the bridging factor, but absent from the control sample lacking rapamycin. These data demonstrate that the architecture of the DARIC system is flexible and amenable to a variety of multimerization domain orientations.

Example 5

Titration of Bridging Factors to Sub-Therapeutic Levels

A broad range of bridging factor (rapamycin and everolimus) concentrations were tested to determine whether a DARIC system can function at clinically relevant concentrations. As in the Example 4, primary human T cells were isolated, activated, and then transduced with lentiviral vectors expressing a DARIC binding component (SEQ ID NOS.:1, 4, 7) and a DARIC signaling component (SEQ ID NOS.:15, 19, 23). The DARIC expressing T cells were then co-incubated with 50:50 mixtures of the K562-CD19 and K562-CD20 target cells to evaluate antigen-specific cytotoxicity. The overall ratio of T cells to K562 cells was 5:1 in all samples.

The indicated concentrations of rapamycin and everolimus were added to the co-culture samples and then the cytotoxicity responses were evaluated by flow cytometry (FIG. 6). Cytotoxicity responses were maintained to sub-nanomolar drug concentrations, well below the steady state concentrations of rapamycin and everolimus that are presently achieved when these drugs are administered to patients in the clinic.

Example 6

Use of a Tethered Daric Binding Component

Figure 1A:
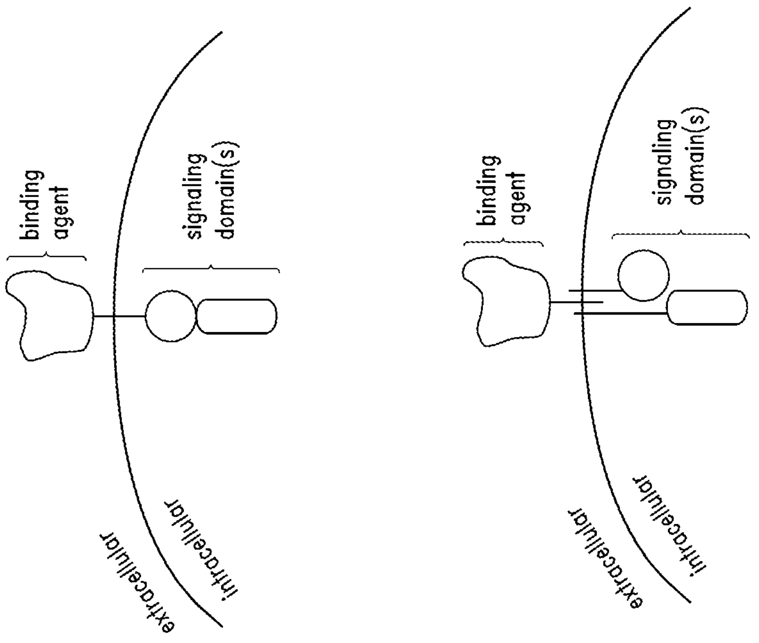
Figure 1B:
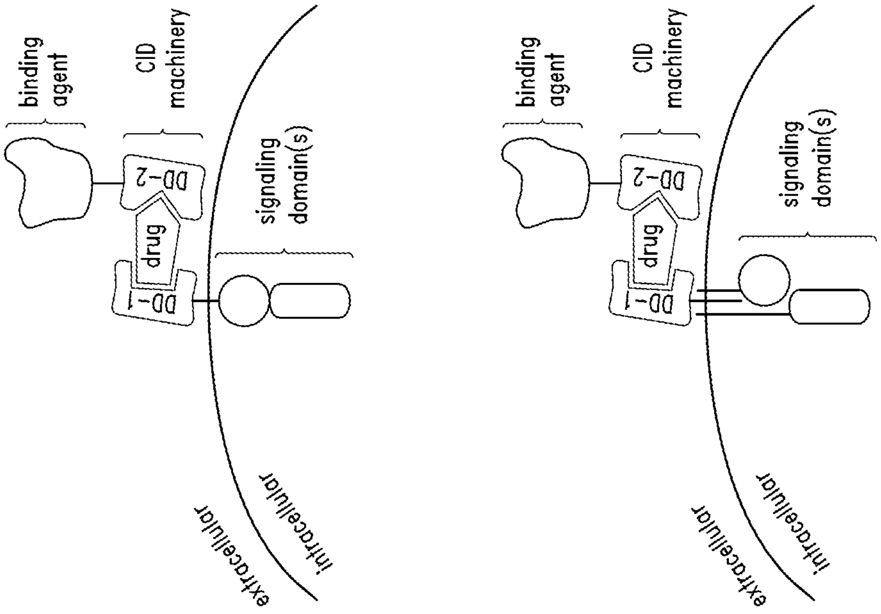
Figure 1C:
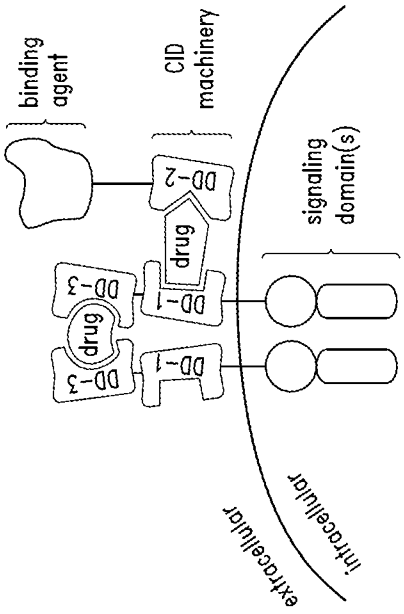
Figure 1D:
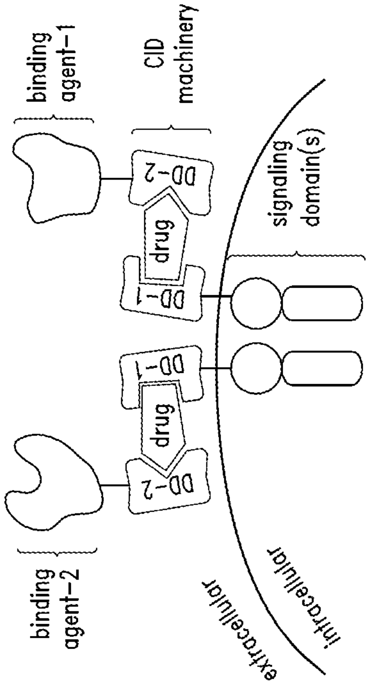
Figure 1E:
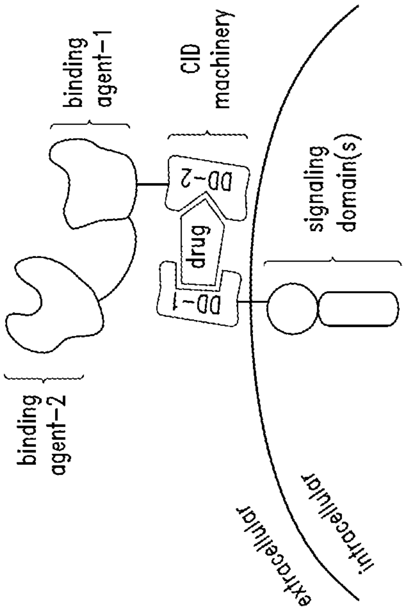
Figure 1F:
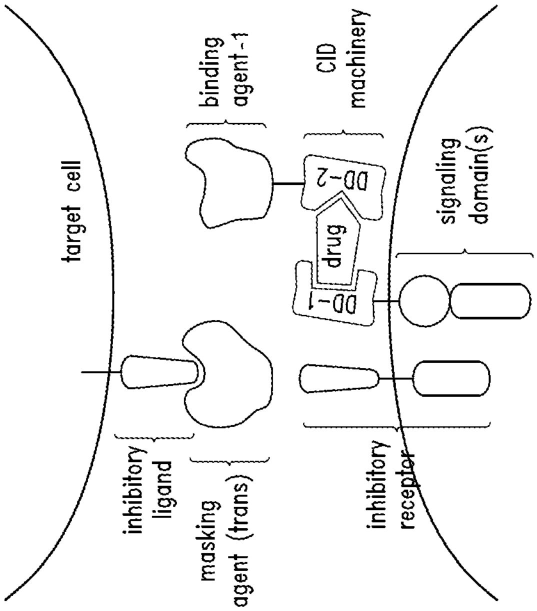
Figure 1G:
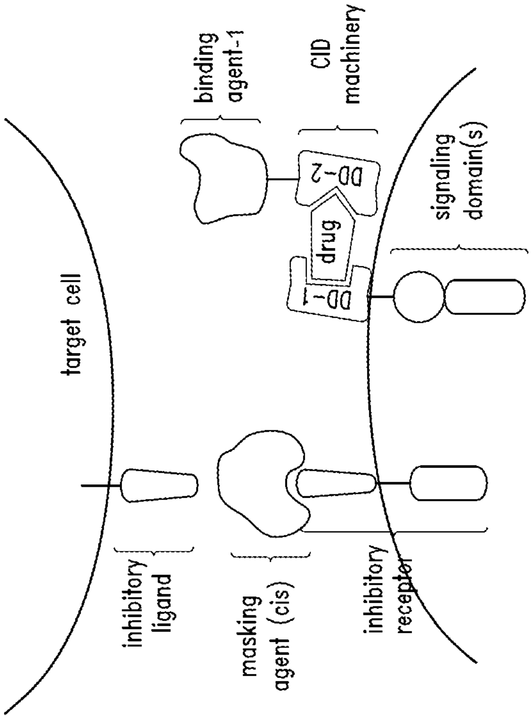
Figure 1H:
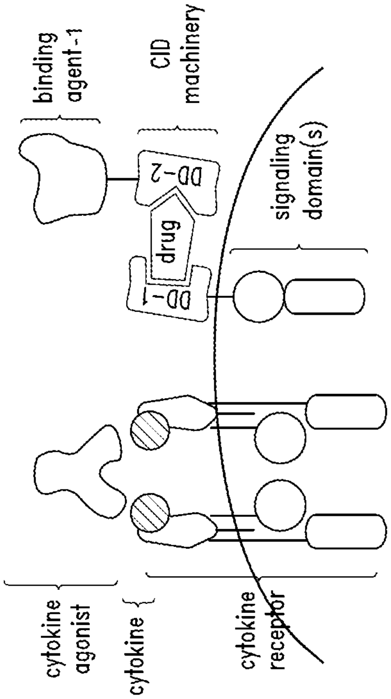
Figure 1J:
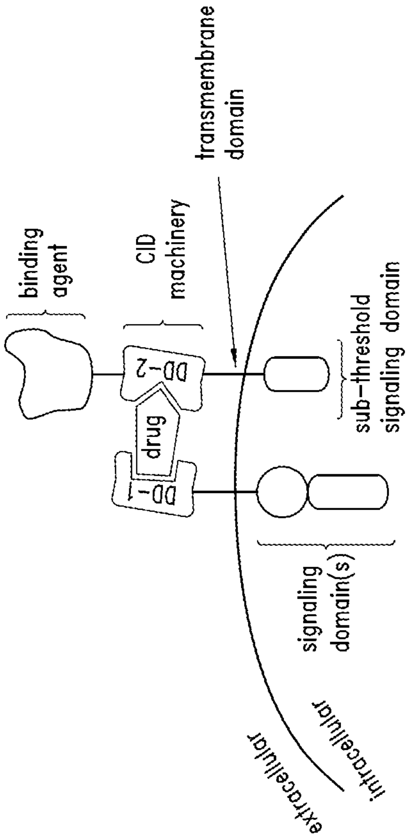
Figure 1K:
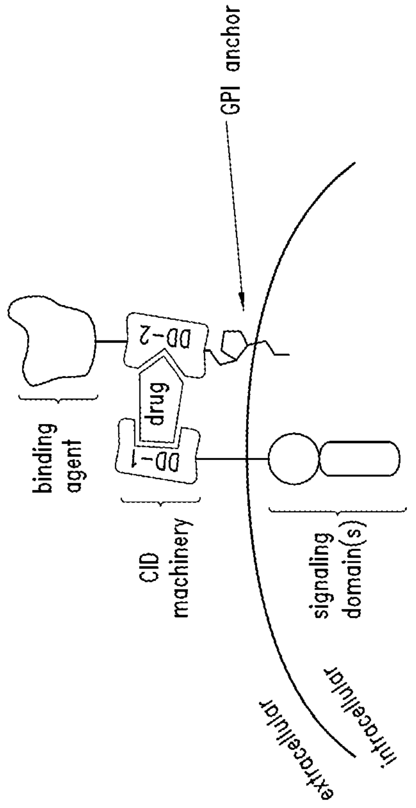
Figure 1L:
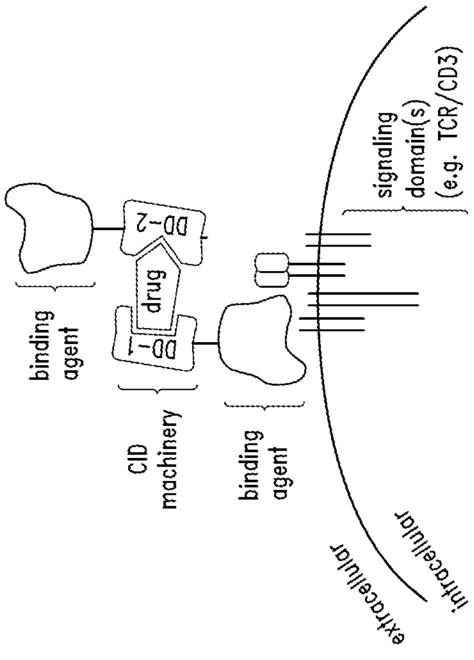
Figure 1M:
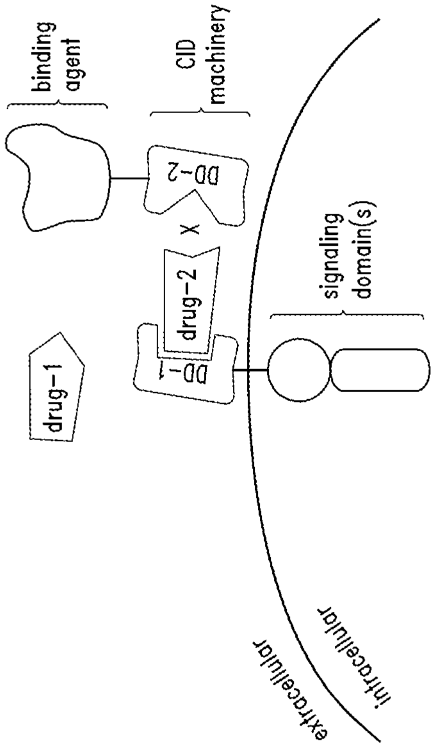
Figure 2:
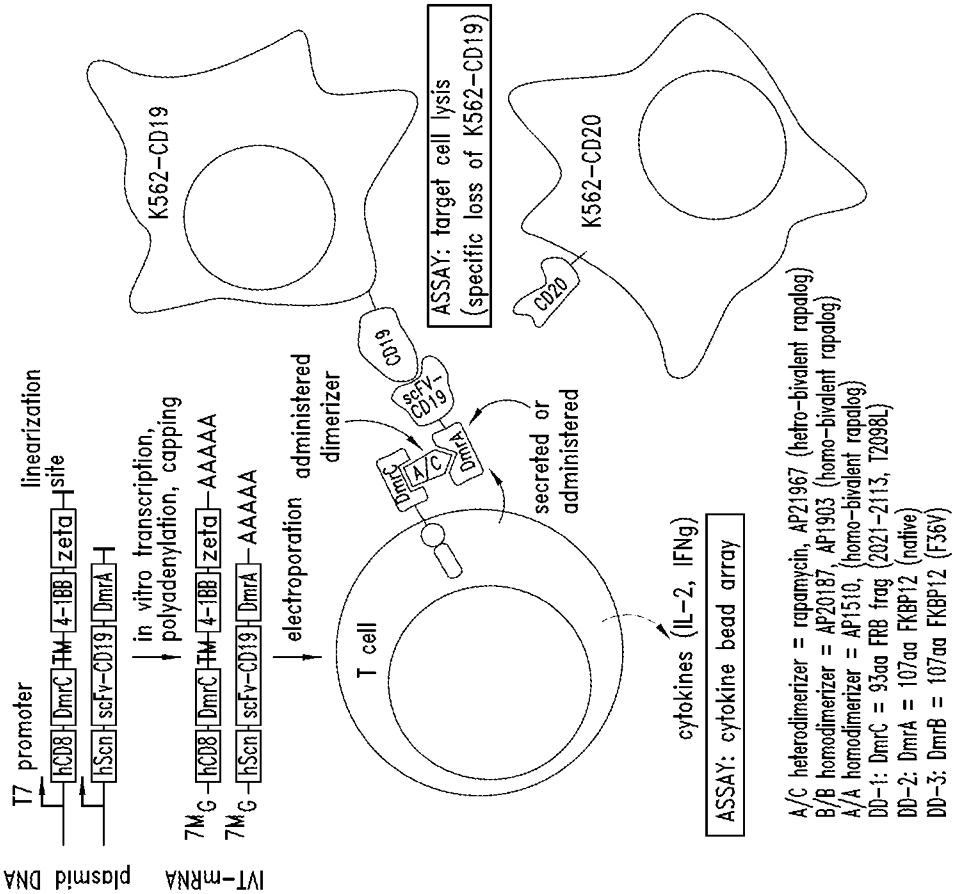
FIG. 2 shows a schematic of an assay to detect specific cell killing and cytokine secretion with a particular multipartite signaling complex of this disclosure.

A series of additional DARIC molecules, in which the antigen binding component was maintained on the T cell surface rather than released into the extracellular space, were tested (see, e.g., FIG. 1I). Several protein regions and transmembrane domains were used to anchor the binding domain to the T cell surface (SEQ ID NOS.:50, 53, 56, 59), each altering the spacing or steric parameters governing multimerization of the DARIC binding and signaling components. As in the previous examples, antigen-specific cytotoxicity responses using lentivirus-transduced T cells and 50:50 mixtures of the K562-CD19 and K562-CD20 target cells were used to evaluate the tethered DARIC binding component. The overall ratio of T cells to K562 cells was 5:1 in all samples, with the indicated concentrations of a bridging factor used in experimental samples.

Each design had the property of bridging factor-responsive, antigen-specific cytotoxicity against the K562-CD19 cells. The tethered DARIC binding component containing the CD8 hinge/CD8 transmembrane domain (SEQ ID NO.: 53) showed a measurable level of activity in the absence of a bridging factor. The tethered DARIC binding component comprising the IgG4 CH2CH3 spacer with CD4 transmembrane domain (SEQ ID NO.:56) provided the strongest cytotoxic response upon addition of the rapamycin (bridging factor), while the tethered DARIC binding component comprising only the CD4 transmembrane domain (SEQ ID NO.:50) were moderately active (FIG. 7). A DARIC binding components comprising a GPI signal sequence from the CD52 protein (see schematic in FIG. 1K) were also tested. The GPI anchored DARIC produced an antigen specific cytotoxicity response only in the presence of an appropriate bridging factor (FIG. 8). These data demonstrate that a DARIC binding component can be either released or tethered to the cell surface and still function with a DARIC signaling component.

Additional lentiviral constructs comprising tethered DARIC binding components were generated and similarly tested in human T cells, including a modified CD4 transmembrane domain with improved activity over other transmembrane tethered DARIC binding components (SEQ ID NOs.:64-69). Additionally, the DARIC signaling and binding components were integrated into a single open reading frame comprising a 2A peptide situated between the two components (such as that used in FIG. 11), thus validating a simplified DARIC delivery scheme using a single lentiviral vector (SEQ ID NOs.:66, 69, 72).

For any of the DARIC componentry designs, similar results are expected using a variety of lentiviral vector designs, such as those comprising bi-directional promoters (SEQ ID NO.:73) for example, or using alternative transgene delivery vectors (e.g., adenovirus or AAV) and schemes such as including the targeted integration of transgenes via homologous recombination, a process that can be stimulated to high efficiency using gene-specific nucleases.

Example 7

Daric Targeting of Additional Model Antigens

The DARIC system was extended to an additional model antigen to show the broad applicability of artificial cells expressing drug regulated multipartite receptors templated herein. K562 target cell lines were generated to express the CD123 antigen by sub-cloning this antigen into a lentiviral vector comprising a puromycin selection cassette (SEQ ID NO.:74), lentiviral particles were produced, and K562 cells were infected and selected with puromycin. Primary human T cells were isolated, activated, and then transduced with lentiviral vectors encoding a CD123 targeting DARIC binding component along with the DARIC signaling component (SEQ ID NOs.:70-72). Antigen-specific cytotoxicity responses were evaluated using lentivirus-transduced T cells co-cultured with 50:50 mixtures of the K562-CD19 and K562-CD123 target cells, using a traditional CD123 targeting chimeric antigen receptor (CAR) as a positive control. The overall ratio of T cells to K562 cells was 5:1 in all samples, with the indicated concentrations of a bridging factor used in experimental samples. Cytotoxicity was observed in the positive control sample and in the CD123 DARIC sample containing rapamycin. The results demonstrated that bridging factor dependent cytotoxic activity could be achieved with the DARIC system targeting diverse antigens (FIG. 9).

Example 8

Deactivation of Daric Using an Anti-Bridging Factor

Deactivation of the DARIC system by the addition of a pharmacological agent that competes for binding to one of the multimerization domains was tested. Primary human T cells expressing either a traditional CD19 targeting CAR or primary human T cells expressing the CD19 targeting DARIC components (SEQ ID NO.:66) were co-incubated with 50:50 mixtures of K562-CD19 and K562-CD20 cells. For the T cells expressing the CD19 targeting CAR (SEQ ID NO.:14), cytotoxicity was observed both in the presence or absence of rapamycin. In contrast, CD19 targeting DARIC T cells, showed efficient antigen-specific cytotoxicity in the presence of sub-nanomolar levels of rapamycin, but showed no cytotoxicity in the absence of the bridging factor (FIG. 11). However, when FK506 was added, a marked reduction in antigen specific cytotoxicity was observed for the DARIC T cells while a minimal reduction was observed for the CAR T cells, indicating that FK506 disrupted the coupling of the DARIC componentry and deactivated the antigen-driven cytotoxicity response.

This example shows that a competitive inhibitor of a bridging factor substantially inhibited DARIC antigen receptors and therefore is suitable for clinical use to limit pathology that can arise as a result of excessive proliferation or activation of administered cells. Without wishing to be bound to any particular theory, this strategy may be particularly effective if the inhibitor has additional immunosuppressive mechanisms of action involving native proteins that contribute in cellular responses, as is true of FK506 inhibiting intracellular cyclophilins that promote T cell proliferative responses.

Example 9

Daric System Leveraging an Endogenous Signaling Receptor

A DARIC system was designed to provide two secreted DARIC components (SEQ ID NO.:75). The DARIC binding component comprises a binding domain that binds CD19 and the DARIC signaling component comprises a binding domain that binds CD3 and a multimerization domain. This system will be tested using a modified co-culture cytotoxicity experiment. Supernatants from T cells transduced with lentiviral particles encoding the two secreted DARIC components will be transferred to a 50:50 mix of K562-CD19 and K562-CD20 target cells also containing non-transduced T cells. Cytotoxicity will be measured in the presence and absence of bridging factor. Control samples comprising the supernatant that is kept in a decoupled state by not providing the bridging factor are not expected to show any antigen specific cytotoxicity. However, samples in which the supernatant and bridging factor are added are expected to initiate the antigen specific cytotoxicity response. This result will demonstrate that artificial cells can be made to express a soluble DARIC system that can systemically initiate cytotoxicity responses in a drug regulated fashion.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated polynucleotide encoding from 5' to 3':

(a) a first fusion polypeptide comprising a first multimerization domain, a first transmembrane domain, and an actuator domain;

(b) a second fusion polypeptide comprising a binding agent; a second multimerization domain; and a second transmembrane domain.

2. The polynucleotide of claim 1, further encoding a viral polypeptide.

3. The polynucleotide of claim 2, wherein the viral polypeptide is selected from the group consisting of: a foot-and-mouth disease virus (FMDV) 2A peptide, an equine rhinitis A virus (ERAV) 2A peptide, a *Thosea asigna* virus (TaV) 2A peptide, a porcine teschovirus-1 (PTV-1) 2A peptide, a Theilovirus 2A peptide, an encephalomyocarditis virus 2A peptide, an aphthovirus 2A peptide, a potyvirus 2A peptide, and a cardiovirus 2A peptide.

4. The polynucleotide of claim 1, further encoding a first secretion signal and a second secretion signal, wherein the first and second secretion signals are the same or different.

5. The polynucleotide of claim 1, wherein the first and second multimerization domains are the same or different.

6. The polynucleotide of claim 1, wherein the multimerization domains of the first and second polypeptides associate with a bridging factor selected from the group consisting of: rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FK506/cyclosporin A (FKCsA) or a derivative thereof, trimethoprim (Tmp)-synthetic ligand for FK506 binding protein (FKBP) (SLF) or a derivative thereof, AP21967, sirolimus, everolimus, novolimus, pimecrolimus, ridaforolimus, tacrolimus, temsirolimus, umirolimus, and zotarolimus.

7. The polynucleotide of claim 6, wherein the first and second multimerization domains are a pair selected from the group consisting of: FKBP and FKBP12-rapamycin binding (FRB), FKBP and calcineurin, FKBP and cyclophilin, FKBP and bacterial dihydrofolate reductase (DHFR), calcineurin and cyclophilin, and PYR1-like 1 (PYL1) and abscisic acid insensitive 1 (ABI1).

8. The polynucleotide of claim 1, wherein the first multimerization domain comprises a first FKBP polypeptide or variant thereof, and the second multimerization domain comprises a first FRB polypeptide or variant thereof.

9. The polynucleotide of claim 1, wherein the first multimerization domain comprises a first FRB polypeptide or variant thereof, and the second multimerization domain comprises a first FKBP polypeptide or variant thereof.

10. The polynucleotide of claim 1, wherein the first transmembrane domain is a CD4, CD8 or CD28 transmembrane domain.

11. The polynucleotide of claim 1, wherein the second transmembrane domain is a CD4, CD8 or CD28 transmembrane domain.

12. The polynucleotide of claim 1, wherein the actuator domain comprises one or a plurality of immunoreceptor tyrosine-based activation motifs (ITAMs).

13. The polynucleotide of claim 1, wherein the actuator domain comprises a lymphocyte receptor signaling domain of a polypeptide selected from the group consisting of: CD3ε, CD3δ, CD3ζ, pre-T cell receptor α (pTα), T cell receptor α (TCRα), T cell receptor β (TCRβ), Fc receptor α (FcR α), Fc receptor β (FcR β), Fc receptor γ (FcRγ), natural-killer group 2, member D (NKG2D), CD79A, CD79B, and any combination thereof.

14. The polynucleotide of claim 1, wherein the first fusion protein further comprises a different actuator domain, a costimulatory domain, an adhesion factor, or any combination thereof.

15. The polynucleotide of claim 14, wherein the costimulatory domain is from a polypeptide selected from the group consisting of: CD27, CD28, CD30, CD40, linker for activation of T-cells (LAT), zeta-chain-associated protein kinase 70 (Zap70), inducible T-cell costimulator (ICOS), DNAX-activation protein 10 (DAP10), 4-1BB, caspase recruitment domain family member 11 (CARD11), herpesvirus entry mediator (HVEM), lymphocyte activating gene 3 (LAG3), signaling lymphocytic activation molecule family member 1 (SLAMF1), lymphocyte-specific protein tyrosine kinase (Lck), fyn oncogene related to src, fgr, yes (Fyn), SH2 domain-containing leukocyte protein of 76 KDa (Slp76), OX40, and any combination thereof.

16. The polynucleotide of claim 1, wherein the actuator domain comprises a cytoplasmic portion that associates with a cytoplasmic signaling protein that is a lymphocyte receptor or signaling domain thereof, a protein comprising a plurality of immunoreceptor tyrosine-based activation motifs (ITAMs), a costimulatory domain, an adhesion factor, or any combination thereof.

17. The polynucleotide of claim 1, further encoding a third exogenous polynucleotide encoding a costimulatory factor, an immunomodulatory factor, an agonist for a costimulatory factor, an agonist for an immunomodulatory factor, or any combination thereof.

18. The polynucleotide of claim 1, wherein the binding agent specifically binds to a target on a target cell surface.

19. The polynucleotide of claim 1, wherein the binding agent comprises an antibody, a single chain variable fragment (scFv), an antigen binding fragment (Fab), a receptor ectodomain, or a ligand.

20. The polynucleotide of claim 1, wherein the second polypeptide further comprises a sequence encoding a linker disposed between the binding agent and the second multimerization domain.

21. The polynucleotide of claim 18, wherein the binding agent specifically binds to a target selected from the group consisting of: α-folate receptor, αvβ6 integrin, B cell maturation antigen (BCMA), B7 homolog 3 (B7-H3), B7 homolog 6 (B7-H6), Carbonic anhydrase IX (CAIX), CD19, CD20, CD22, CD30, CD33, CD3γ, CD44, CD44v6, CD44v7/8, CD70, CD123, CD138, CD171, carcinoembryonic antigen (CEA), delta like canonical Notch ligand 4 (DLL4), epithelial glycoprotein 2 (EGP-2), epithelial glycoprotein 40 (EGP-40), chondroitin sulfate proteoglycan 4 (CSPG4), epidermal growth factor receptor (EGFR), EGFR family including ErbB2 (HER2), EGFR variant III (EGFRvIII), epithelial cellular adhesion molecule (EPCAM), ephrin type-A receptor 2 (EphA2), fibroblast activation protein alpha (FAP), fetal acetylcholine receptor, frizzled class receptor 7 (Fzd7), ganglioside GD2 (GD2), ganglioside GD3 (GD3), Glypican-3 (GPC3), human oncofetal antigen 5T4 (h5T4), interleukin 11 receptor alpha (IL-11Rα), interleukin 13 receptor alpha 2 (IL13R-α2), κ light chain, λ light chain, Lewis Y antigen (LeY), L1 cell adhesion molecule (L1CAM), melanoma antigen gene family member A1 (MAGE-A1), mesothelin, major histocompatibility complex (MHC) presented peptides, mucin 1, cell surface associated (MUC1), mucin 16, cell surface associated (MUC16), neural cell adhesion molecule (NCAM), NKG2D ligands, Notch1, Notch2/3, New York esophageal squamous cell carcinoma 1 (NY-ESO-1), preferentially expressed antigen of melanoma (PRAME), prostate stem cell antigen (PSCA), prostate-specific membrane antigen (PSMA), Survivin, tumor associate glycoprotein 72 (TAG-72), telomerase reverse transcriptase (TERT), vascular endothelial growth factor receptor 2 (VEGFR2), and receptor tyrosine kinase-like orphan receptor 1 (ROR1).

22. The polynucleotide of claim 4, wherein the first polypeptide comprises a FRB T2098L multimerization domain, a CD8α transmembrane domain, a 4-1BB costimulatory domain, and a CD3ζ actuator domain; and wherein the second polypeptide comprises a binding agent, an FKBP12 multimerization domain, and a CD4 transmembrane domain.

23. The polynucleotide of claim 22, wherein the binding agent comprises an anti-CD19 scFv domain or an anti-BCMA scFv domain.

24. The polynucleotide of claim 1, wherein the second polypeptide further comprises an anchor domain.

25. The polynucleotide of claim 24, wherein the anchor domain is a transmembrane domain or a GPI signal sequence.

26. A vector comprising the polynucleotide of claim 1.

27. The vector of claim 26, wherein the vector is a viral vector, a retroviral vector, or a lentiviral vector.

28. A non-natural cell comprising the vector of claim 26.

* * * * *